(12) United States Patent
Guckian et al.

(10) Patent No.: US 10,017,506 B2
(45) Date of Patent: Jul. 10, 2018

(54) ATX MODULATING AGENTS

(71) Applicant: BIOGEN MA INC., Cambridge, MA (US)

(72) Inventors: Kevin M. Guckian, Northborough, MA (US); Gnanasambandam Kumaravel, Lexington, MA (US); Bin Ma, Arlington, MA (US); Sha Mi, Belmont, MA (US); Hairuo Peng, Needham, MA (US); Zhaohui Shao, Brookline, MA (US); Lihong Sun, Lexington, MA (US); Arthur G. Taveras, Boston, MA (US); Deping Wang, Furlong, PA (US); Zhili Xin, Lexington, MA (US); Lei Zhang, Westford, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 15/296,601

(22) Filed: Oct. 18, 2016

(65) Prior Publication Data

US 2017/0158687 A1 Jun. 8, 2017

Related U.S. Application Data

(62) Division of application No. 14/417,300, filed as application No. PCT/US2013/052316 on Jul. 26, 2013, now Pat. No. 9,522,889.

(60) Provisional application No. 61/676,705, filed on Jul. 27, 2012.

(51) Int. Cl.
| | |
|---|---|
| *A61K 31/015* | (2006.01) |
| *A61K 31/4375* | (2006.01) |
| *A61K 31/44* | (2006.01) |
| *C07D 451/02* | (2006.01) |
| *C07D 217/22* | (2006.01) |
| *A61K 31/472* | (2006.01) |
| *A61K 45/06* | (2006.01) |
| *A61K 31/4725* | (2006.01) |
| *C07D 401/06* | (2006.01) |

(52) U.S. Cl.
CPC .......... *C07D 451/02* (2013.01); *A61K 31/472* (2013.01); *A61K 31/4725* (2013.01); *A61K 45/06* (2013.01); *C07D 217/22* (2013.01); *C07D 401/06* (2013.01)

(58) Field of Classification Search
CPC .. C07D 223/06; C07D 209/52; C07D 211/34; C07D 211/62; C07D 217/22; A61K 31/136; A61K 31/196; A61K 31/439; A61K 31/445; A61K 31/46; A61K 31/5375; A61K 31/55; A61K 45/06; C07C 217/22; C07C 229/46; C07C 229/48; C07C 255/59

USPC ......................................................... 514/171
See application file for complete search history.

(56) References Cited

U.S. PATENT DOCUMENTS

| | | | |
|---|---|---|---|
| 5,719,164 A | 2/1998 | Weidmann et al. | |
| 7,629,468 B2 | 12/2009 | Mabire et al. | |
| 8,802,659 B2 | 8/2014 | Thomas et al. | |
| 9,186,367 B2 | 11/2015 | Thomas et al. | |
| 9,522,889 B2* | 12/2016 | Guckian | C07D 217/22 |
| 9,550,798 B2* | 1/2017 | Guckian | A61K 45/06 |
| 2004/0254215 A1 | 12/2004 | Arend et al. | |
| 2006/0241115 A1 | 10/2006 | Potashman et al. | |
| 2007/0298104 A1 | 12/2007 | Arend et al. | |
| 2010/0056506 A1 | 3/2010 | Huang et al. | |
| 2010/0160258 A1 | 6/2010 | Caldwell et al. | |
| 2010/0160357 A1 | 6/2010 | Caldwell et al. | |
| 2010/0240617 A1 | 9/2010 | Lynch et al. | |
| 2013/0324526 A1 | 12/2013 | He et al. | |
| 2014/0066453 A1 | 3/2014 | Blake et al. | |
| 2014/0371209 A1 | 12/2014 | Thomas et al. | |
| 2015/0183741 A1 | 7/2015 | Guckian et al. | |
| 2015/0203493 A1 | 7/2015 | Guckian et al. | |
| 2015/0203515 A1 | 7/2015 | Guckian et al. | |
| 2015/0246063 A1 | 9/2015 | Guckian et al. | |
| 2015/0299123 A1 | 10/2015 | Peng et al. | |
| 2017/0174710 A1* | 6/2017 | Guckian | C07F 7/0818 |

FOREIGN PATENT DOCUMENTS

| | | |
|---|---|---|
| WO | 2003/082350 A2 | 10/2003 |
| WO | 2006/064757 A1 | 6/2006 |
| WO | 2007/067444 A1 | 6/2007 |
| WO | 2010/093704 A1 | 8/2010 |
| WO | 2011/017561 A1 | 2/2011 |
| WO | 2011/151461 A2 | 12/2011 |
| WO | 2012/109108 A1 | 8/2012 |
| WO | 2014/120764 A1 | 8/2014 |

OTHER PUBLICATIONS

Federico et al.; "Therapeutic Potential of Autotaxin/Lysophospholipase D Inhibitors"; Current Drug Targets; 9 (8):698-708 (Aug. 2008).
Gray et al.; "The Preparation of 4- and 5-n-Alkoxy-1-naphthoic and 6- and 7-n-Alkoxy-2-naphthoic Acids"; Journal of the Chemical Society; pp. 678-683 (1954).
Inoue et al.; "Autotaxin, a synthetic enzyme of lysophosphatidic acid (LPA), mediates the induction of nerve-injured neuropathic pain"; Molecular Pain; 4(6):1-5 (2008).
Kasai et al.; "Guest-Dependent Flexible Coordination Networks with Fluorinated Ligands"; Chem. Eur. J.; 13:3089-3105 (2007).
Liu et al.; "ATX-LPA receptor axis in inflammation and cancer"; Cell Cycle; 8(22):3695-3701 (2009).

(Continued)

*Primary Examiner* — Daniel R Carcanague
(74) *Attorney, Agent, or Firm* — McCarter & English, LLP; Steven G. Davis; Xia Zhang

(57) ABSTRACT

Disclosed are bicyclic aryl compounds of formula (I), that can modulate the activity of the autotaxin (ATX) enzyme. This invention further relates to compounds that are ATX inhibitors, and methods of making and using such compounds in the treatment of demyelination due to injury or disease, as well as for treating proliferative disorders such as cancer.

21 Claims, No Drawings

(56) References Cited

OTHER PUBLICATIONS

Nakanaga et al.; "Autotaxin—an LPA producing enzyme with diverse functions"; J. Biochem.; 148(1):13-24 (2010).
Parrill et al.; "Autotaxin inhibitors: a perspective on initial medicinal chemistry efforts"; Expert Opinion on Therapeutic Patents; 20(12):1619-1625 (2010).
Tager; "Autotaxin Emerges as a Therapeutic Target for Idiopathic Pulmonary Fibrosis: Limiting Fibrosis by Limiting Lysophosphatidic Acid Synthesis"; American Journal of Respiratory Cell and Molecular Biology—Editorial; 47 (5):563-565 (Nov. 2012).

* cited by examiner

ATX MODULATING AGENTS

CLAIM OF PRIORITY

This application is a divisional application of U.S. Ser. No. 14/417,300, filed Jan. 26, 2015, which is a 35 U.S.C. § 371 national stage filing of International Application No. PCT/US2013/052316, filed Jul. 26, 2013, which claims priority to U.S. Provisional Application No. 61/676,705, filed Jul. 27, 2012. Each of the above-referenced applications is hereby incorporated by reference in its entirety.

TECHNICAL FIELD

This invention relates to compounds that are ATX modulating agents, especially ATX inhibitors, and methods of making and using such compounds.

BACKGROUND

Autotaxin (ATX, ENPP2) is a secreted glycoprotein widely present in biological fluids, including blood, cancer ascites, synovial, pleural and cerebrospinal fluids, originally isolated from the supernatant of melanoma cells as an autocrine motility stimulation factor (Stracke, M. L., et al. Identification, purification, and partial sequence analysis of autotaxin, a novel motility-stimulating protein. J Biol Chem 267, 2524-2529 (1992), which is incorporated by reference in its entirety). ATX is encoded by a single gene on human chromosome 8 (mouse chromosome 15) whose transcription, regulated by diverse transcription factors (Hoxa13, NFAT-1 and v-jun), results in four alternatively spliced isoforms (α, β, γ and δ). See, for example, Giganti, A., et al Murine and Human Autotaxin alpha, beta, and gamma Isoforms: Gene organization, tissue distribution and biochemical characterization. J Biol Chem 283, 7776-7789 (2008); and van Meeteren, L. A. & Moolenaar, W. H. Regulation and biological activities of the autotaxin-LPA axis. Prog Lipid Res 46, 145-160 (2007); Hashimoto, et al, "Identification and Biochemical Characterization of a Novel Autotaxin Isoform, ATXδ," J. of Biochemistry Advance Access (Oct. 11, 2011); each of which is incorporated by reference in its entirety.

ATX is synthesized as a prepro-enzyme, secreted into the extracellular space after the proteolytic removal of its N-terminal signal peptide (Jansen, S., el al Proteolytic maturation and activation of autotaxin (NPP2), a secreted metastasis-enhancing lysophospho lipase D. J Cell Sci 118, 3081-3089 (2005), which is incorporated by reference in its entirety). ATX is a member of the ectonucleotide pyrophosphatase/ phosphodiesterase family of ectoenzymes (E-NPP) that hydrolyze phosphodiesterase (PDE) bonds of various nucleotides and derivatives (Stefan, C, Jansen, S. & Bollen, M. NPP-type ectophosphodiesterases: unity in diversity. Trends Biochem Sci 30, 542-550 (2005), which is incorporated by reference in its entirety). The enzymatic activity of ATX was enigmatic, until it was shown to be identical to lysophospholipase D (lysoPLD) (Umezu-Goto, M., et al. Autotaxin has lysophospholipase D activity leading to tumor cell growth and motility by lysophosphatidic acid production. J Cell Biol 158, 227-233 (2002), which is incorporated by reference in its entirety), which is widely present in biological fluids. Since ATX is a constitutively active enzyme, the biological outcome of ATX action will largely depend on its expression levels and the local availability of its substrates. The major lysophospholipid substrate for ATX, lysophosphatidylcholine (LPC), is secreted by the liver and is abundantly present in plasma (at about 100 μM) as a predominantly albumin bound form (Croset, M., Brossard, N., Polette, A. & Lagarde, M. Characterization of plasma unsaturated lysophosphatidylcholines in human and rat Biochem J 345 Pt 1, 61-67 (2000), which is incorporated by reference in its entirety). LPC is also detected in tumor-cell conditioned media (Umezu-Goto, M., et al.), presumably as a constituent of shed microvesicles. ATX, through its lysoPLD activity converts LPC to lysophosphatidic acid (LPA).

LPC is an important inflammatory mediator with recognized effects in multiple cell types and pathophysiological processes. It is a major component of oxidized low density lipoprotein (oxLDL) and it can exist in several other forms including free, micellar, bound to hydrophobic proteins such as albumin and incorporated in plasma membranes. It is produced by the hydrolysis of phosphatidylcholine (PC) by PLA2 with concurrent release of arachidonic acid and in turn of other pro-inflammatory mediators (prostaglandins and leukotrienes). Moreover, LPC externalization constitutes a chemotactic signal to phagocytic cells, while interaction with its receptors can also stimulate lymphocytic responses. LPC has been shown to have therapeutic effects in experimental sepsis, possibly by suppressing endotoxin-induced HMGB1 release from macrophages/monocytes.

LPA, the product of ATX action on LPC, is a bioactive phospholipid with diverse functions in almost every mammalian cell line (Moolenaar, W. H., van Meeteren, L. A. & Giepmans, B. N. The ins and outs of lysophosphatidic acid signaling. Bioessays 28, 870-881 (2004), which is incorporated by reference in its entirety). LPA is a major constituent of serum bound tightly to albumin, gelsolin and possibly other as yet unidentified proteins. (See, e.g., Goetzl, E. J., et al Gelsolin binding and. cellular presentation of lysophosphatidic acid. J Biol Chem 275, 14573-14578 (2000); and Tigyi, G. & Miledi, R, Lysophosphatidates bound to serum albumin activate membrane currents in Xenopus oocytes and neurite retraction in PC 12 pheochromocytoma cells. J Biol Chem 267, 21360-21367 (1992); each of which is incorporated by reference in its entirety.)

LPA is also found in other biofluids, such as saliva and follicular fluid, and has been implicated in a wide array of functions, such as wound healing, tumor invasion and metastasis, neurogenesis, myelination, astrocytes outgrowth and neurite retraction. The long list of LPA functions was also explained with the discovery that it signals through G-protein coupled receptors (GPCRs), via classical second messenger pathways. Five mammalian cell-surface LPA receptors have been identified so far. The best known are LPA1-3 (namely Edg-2, Edg-4 and Edg7) which are all members of the so-called 'endothelial differentiation gene' (EDG) family of GPCRs (Contos, J. J., Ishii, I. & Chun, J. Lysophosphatidic acid receptors. Mol Pharmacol 58, 1188-1196 (2000), which is incorporated by reference in its entirety). LPA receptors can couple to at least three distinct G proteins ($G_q$, $G_i$ and $G_{12/13}$), which, in turn, feed into multiple effector systems. LPA activates $G_q$ and thereby stimulates phospholipase C (PLC), with subsequent phosphatidylinositol-bisphosphate hydrolysis and generation of multiple second messengers leading to protein kinase C activation and changes in cytosolic calcium. LPA also activates $G_i$, which leads to at least three distinct signaling routes: inhibition of adenylyl cyclase with inhibition of cyclic AMP accumulation; stimulation of the mitogenic RAS-MAPK (mitogen-activated protein kinase) cascade; and activation of phosphatidylinositol 3-kinase (PI3K), leading to activation of the guanosine diphosphate/guanosine triphosphate (GDP/GTP) exchange factor TIAM1 and the downstream RAC GTPase, as well as to activation of the AKT/PKB antiapoptotic pathway. Finally, LPA activates $G_{12/13}$, leading to activation of the small GTPase RhoA, which drives cytoskeletal contraction and cell rounding. So, LPA not only signals via classic second messengers such as calcium, diacylglycerol and cAMP, but it also activates RAS- and RHO-family GTPases, the master switches that control cell proliferation, migration and morphogenesis.

LPA signaling through the RhoA-Rho kinase pathway mediates neurite retraction and inhibition of axon growth. Interfering with LPA signaling has been shown to promote axonal regeneration and functional recovery after CNS injury or cerebral ischemia. (See Broggini, et al., *Molecular Biology of the Cell* (2010), 21:521-537.) It has been reported that addition of LPA to dorsal root fibers in ex vivo culture causes demyelination, whereas LPC fails to cause significant demyelination of nerve fibers in ex vivo cultures without further addition of recombinant ATX to the culture which when added caused significant demyelination at equivalent levels to LPA presumable due to conversion of LPC to LPA through the enzymatic activity of ATX. Moreover, injury induced demyelination was attenuated by about 50% in $atx^{+/-}$ mice (Nagai, et al., *Molecular Pain* (2010), 6:78).

A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve (e.g. in Bell's palsy)), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes dorsalis due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency and copper deficiency. Other demyelination disorders may have unknown causes or multiple causes such as trigeminal neuralgia, Marchiafava-Bignami disease and Bell's palsy. One particularly successful approach to treating demyelination disorders which are caused by autoimmune dysfunction has been to attempt to limit the extent of demyelination by treating the patient with immunoregulatory drugs. However, typically this approach has merely postponed but not avoided the onset of disability in these patients. Patients with demyelination due to other causes have even fewer treatment options. Therefore, the need exists to develop new treatments for patients with demyelination diseases or disorders.

SUMMARY

The present invention relates to compounds which inhibit ATX. Without wishing to be bound by any theory, it is believed that LPA inhibits remyelination of neurons that have suffered demyelination due to injury or disease and that inhibition of ATX will prevent the conversion of LPC to LPA and thus allow remyelination to occur. In addition, activation of PLC, ERK and Rho via LPA receptors results in cell proliferation, cell survival and changes in cell morphology. Therefore, inhibition of ATX is expected to be useful for treating demyclination due to injury or disease, as well as for treating proliferative disorders such as cancer.

In one aspect, a compound, or a pharmaceutically acceptable salt thereof, is represented by structural formula (I):

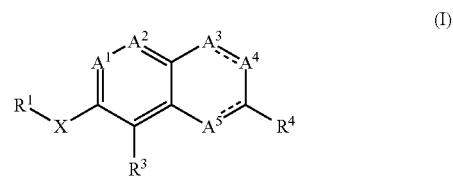

In formula (I), X can be O, $S(O)_r$, $NR^{12}$, $C(O)$ or $CH_2$.
$A^1$ and $A^2$ can each independently be $CR^2$ or N.
$A^3$, $A^4$ and $A^5$ can each independently be $CR^2$, $C(R^2)_2$, N, or $NR^{19}$, provided that at least three of $A^1$, $A^2$, $A^3$, $A^4$, $A^5$, and $A^6$ are independently $CR^2$ or $C(R^2)_2$.

"------" indicates a double or a single bond.

$R^1$ can be a $C_{6-20}$alkyl, a $C_{3-14}$carbocyclyl, a 3- to 15-membered heterocyclyl, a $C_{6-10}$aryl, or a five- to 14-membered heteroaryl, wherein the heterocyclyl and the heteroaryl comprising from 1 to 10 heteroatoms independently selected from N, S or O, and wherein $R^1$ may be optionally substituted with from one to six independently selected $R^6$.

$R^2$, for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido.

$R^3$ can be hydrogen, a halo, $C_{1-6}$haloalkyl or cyano, provided that when $R^3$ is hydrogen, $R^1$ is a $C_{3-8}$cycloalkyl which is optionally substituted with from 1 to 6.

R4 is a carboxylic acid or a group represented by the following formula:

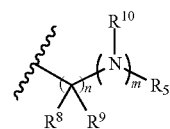

wherein ⟨ represents the point of attachment; provided that when R4 is a carboxylic acid, A1 is N and R1 is a $C_{3-8}$cycloalkyl which is optionally substituted with from 1 to 6.

$R^5$ can be a $C_{1-6}$alkylene, $C_{3-8}$carbocyclyl, a 3- to 8-membered heterocyclyl, $C_{6-10}$aryl, a 5- to 10-membered heteroaryl, a bridged ring system comprising from 6 to 12 ring members, a spiro ring system comprising from 5-14 ring members, or a bicyclic ring system represented by the following formula:

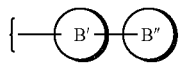

wherein B' and B" are independently selected from the group consisting of monocyclic $C_{3-8}$carbocyclyl, a monocyclic 3- to 8-membered heterocyclyl, phenyl or a 5- to 6-membered heteroaryl; wherein $R^5$ may be optionally substituted with from 1 to 4 independently selected $R^{11}$.

$R^6$, for each occurrence, can be independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom may form $C_{3-8}$spirocycloalkyl or 3- to 8-membered spiroheterocycloalkyl.

$R^7$ can be —OH, —C(O)OR$^{15}$, —C(O)N(R$^{16}$)$_2$, —C(O)N(R$^{15}$)—S(O)$_2$R$^{15}$, —S(O)$_2$R$^{15}$, —C(O)NHC(O)R$^5$, —Si(O)OH, —B(OH)$_2$, —N(R$^{15}$)S(O)$_2$R$^{15}$, —S(O)$_2$N(R$^{15}$)$_2$, —O—P(O)(OR$^{15}$)$_2$, —P(O)(OR$^{15}$)$_2$, —CN, —S(O)$_2$NHC(O)R$^{15}$, —C(O)NHS(O)$_2$R$^{15}$, —C(O)NHOH, —C(O)NHCN, or a heteroaryl or a heterocyclyl selected from the group consisting of formulae (a)-(i'):

(a) 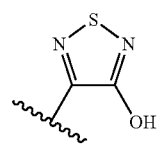

(b) 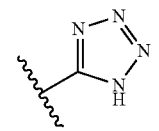

(c) 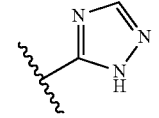

(d) 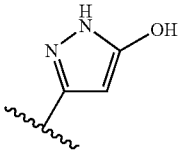

(e) 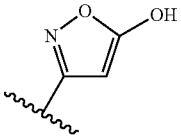

(f) 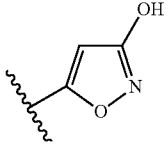

-continued (g) 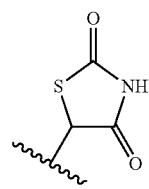

(h) 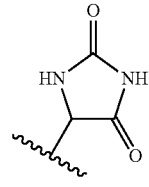

(i) 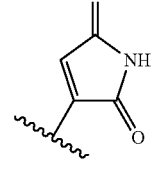

(j) 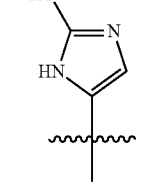

(k) 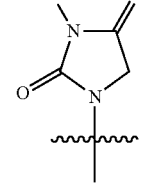

(l) 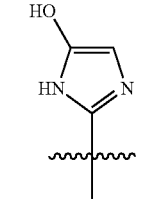

(m) 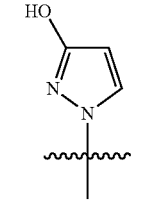

(n) 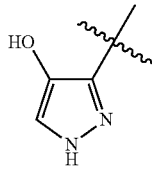

-continued
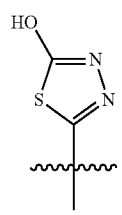 (o)
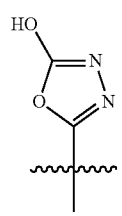 (p)
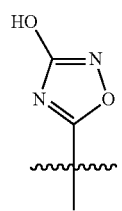 (q)
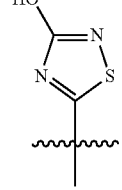 (r)
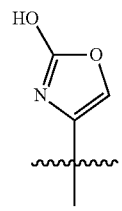 (s)
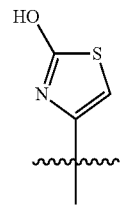 (t)
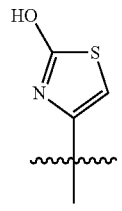 (u)
-continued
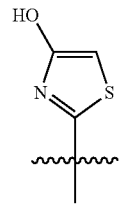 (v)
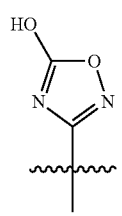 (w)
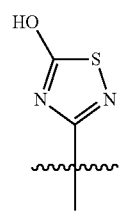 (x)
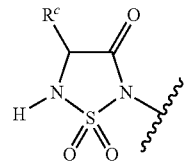 (y)
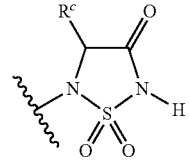 (z)
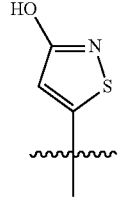 (a′)
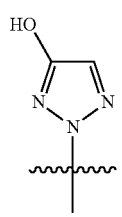 (b′)
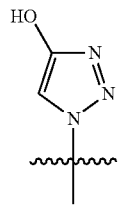 (c′)

(d') 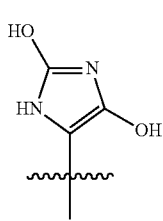

(e') 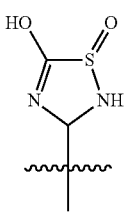

(f') 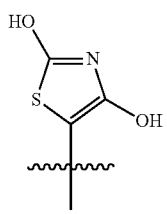

(g') 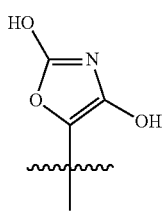

(h') 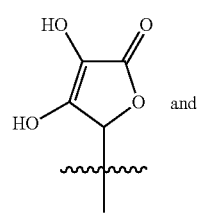

and (i') 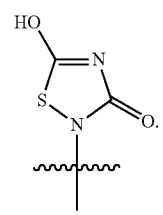

$R^8$ and $R^9$ can each independently be hydrogen, a carboxy, $C_{1-6}$alkyl, or a $C_{2-6}$alkenyl; or $R^8$ and $R^9$ together with the carbon to which they are attached can be —C(=O)—, a $C_{3-8}$spirocycloalkyl, or a 3- to 8-membered spiroheterocycloalkyl.

$R^{10}$ and $R^{12}$ can each independently be hydrogen or a $C_{1-6}$alkyl.

$R^{11}$, for each occurrence, can be independently halo, hydroxyl, nitro, cyano, $C_{1-6}$alkyl, $C_{1-6}$haloalkyl, $C_{1-6}$alkoxy, —$(CR^{17}R^{18})_p$—$R^7$, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —$C(O)NR^aR^b$, —$N(R^a)C(O)R^b$, —$C(O)R^a$, —$S(O)_rR^a$, or —$N(R^a)S(O)_2R^b$.

$R^{15}$ for each occurrence can be independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

$R^{16}$ can be $R^{15}$; or two $R^{16}$ together with the nitrogen atom to which they are attached can form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl.

$R^{17}$ and $R^{18}$, for each occurrence, can be each independently hydrogen, a halo, or a $C_{1-4}$haloalkyl.

$R^{19}$ for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, ($C_{1-6}$alkoxycarbonyl, carbamoyl, N—($C_{1-6}$alkyl)carbamoyl, N,N-di-(($C_{1-6}$alkyl)carbamoyl, $C_{1-6}$alkylsulfonyl, sulfamoyl, N—($C_{1-6}$alkyl)sulfamoyl, and N,N-di-($C_{1-6}$alkyl)sulfamoyl.

$R^a$ and $R^b$, for each occurrence, can be independently hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl.

$R^c$ is hydrogen or a $C_{1-4}$alkyl.

m can be 0 or 1, provided that when m is 0, $R^5$ comprises at least one nitrogen.

n can be an integer from 1 to 6.

p can be 0 or an integer from 1 to 6.

r, for each occurrence, can be independently 0, 1, or 2.

The compound is not 4,4'-((perfluoronaphthalene-2,7-diyl)bis(methylene))dipyridine, 3-(1,4-dioxaspiro[4.5]decan-8-ylamino)-8-methylisoquinoline-6-carboxylic acid, or (2-methoxy-3-(morpholinomethyl)quinolin-6-yl)(4-methoxycyclohexyl)methanone.

In one aspect, a compound, or a pharmaceutically acceptable salt thereof, is represented by structural formula (Ia):

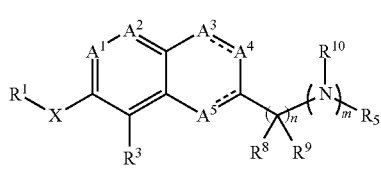

(Ia)

In formula (Ia), X can be O, $S(O)_r$, $NR^{12}$, C(O) or $CH_2$.

$A^1$ and $A^2$ can each independently be $CR^2$ or N.

$A^3$, $A^4$ and $A^5$ can each independently be $CR^2$, $C(R^2)_2$, N, or $NR^{19}$, provided that at least three of $A^1$, $A^2$, $A^3$, $A^4$, $A^5$, and $A^6$ are independently $CR^2$ or $C(R^2)_2$.

"------" indicates a double or a single bond.

$R^1$ can be a $C_{6-20}$alkyl, a $C_{3-14}$carbocyclyl, a 3- to 15-membered heterocyclyl, a $C_{6-10}$aryl, or a five- to 14-membered heteroaryl, wherein the heterocyclyl and the heteroaryl comprising from 1 to 10 heteroatoms independently selected from N, S or O, and wherein $R^1$ may be optionally substituted with from one to six independently selected $R^6$.

$R^2$, for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido.

$R^3$ can be a halo, $C_{1-6}$haloalkyl or cyano.

$R^5$ can be a $C_{1-6}$alkylene, $C_{3-8}$carbocyclyl, a 3- to 8-membered heterocyclyl, $C_{6-10}$aryl, a 5- to 10-membered heteroaryl, a bridged ring system comprising from 6 to 12 ring members, a spiro ring system comprising from 5-14 ring members, or a bicyclic ring system represented by the following formula:

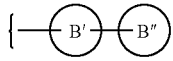

wherein B' and B" are independently selected from the group consisting of monocyclic $C_{3-8}$carbocyclyl, a monocyclic 3- to 8-membered heterocyclyl, phenyl or a 5- to 6-membered heteroaryl; wherein $R^5$ may be optionally substituted with from 1 to 4 independently selected $R^{11}$.

$R^6$, for each occurrence, can be independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom may form $C_{3-8}$spirocycloalkyl or 3- to 8-membered spiroheterocycloalkyl.

$R^7$ can be —OH, —C(O)OR$^{15}$, —C(O)N(R$^{16}$)$_2$, —C(O)N(R$^{15}$)—S(O)$_2$R$^{15}$, —S(O)$_2$OR$^{15}$, —C(O)NHC(O)R$^{15}$, —Si(O)OH, —B(OH)$_2$, —N(R$^{15}$)S(O)$_2$R$^{15}$, —S(O)$_2$N(R$^{15}$)$_2$, —O—P(O)(OR$^{15}$)$_2$, —P(O)(OR$^{15}$)$_2$, —CN, —S(O)$_2$NHC(O)R$^{15}$, —C(O)NHS(O)$_2$R$^{15}$, —C(O)NHOH, —C(O)NHCN, or a heteroaryl or a heterocyclyl selected from the group consisting of formulae (a)-(i'):

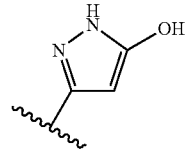
(a)

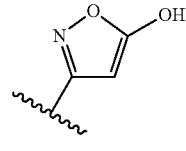
(b)

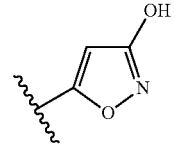
(c)

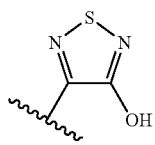
(d)

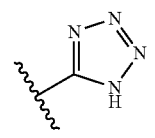
(e)

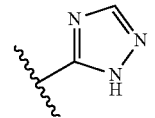
(f)

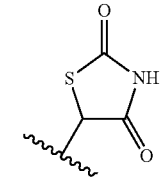
(g)

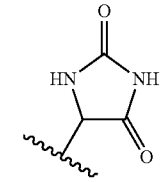
(h)

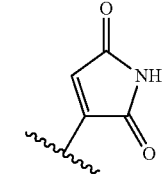
(i)

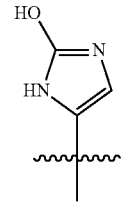
(j)

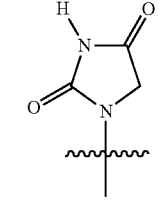
(k)

-continued
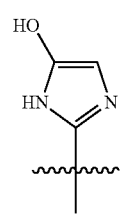 (l)
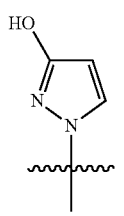 (m)
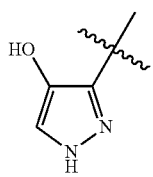 (n)
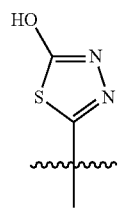 (o)
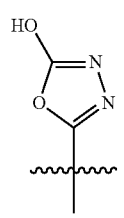 (p)
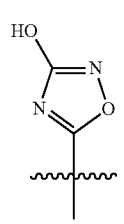 (q)
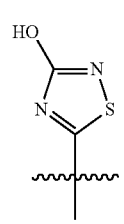 (r)
-continued
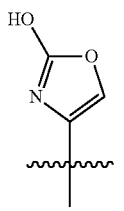 (s)
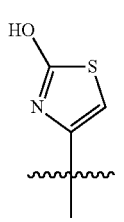 (t)
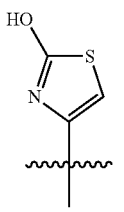 (u)
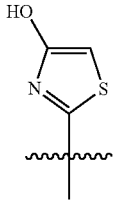 (v)
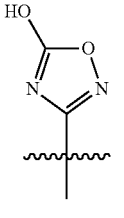 (w)
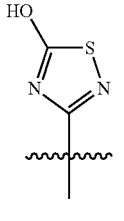 (x)
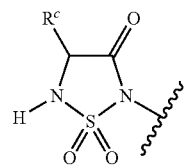 (y)
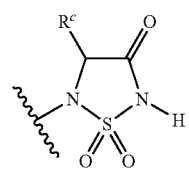 (z)

-continued (a') 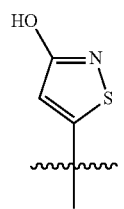

(b') 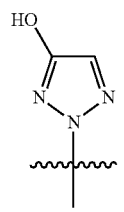

(c') 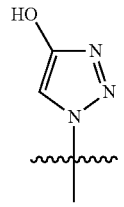

(d') 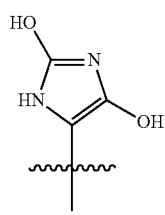

(e') 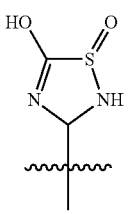

(f') 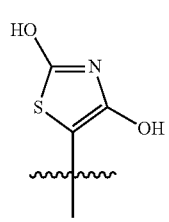

(g') 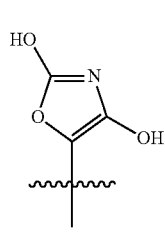

-continued (h') 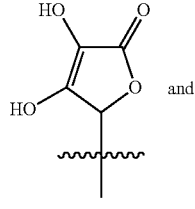 and (i') 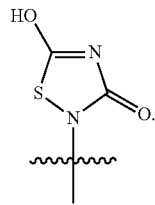

$R^8$ and $R^9$ can each independently be hydrogen, a carboxy, $C_{1-6}$alkyl, or a $C_{2-6}$alkenyl; or $R^8$ and $R^9$ together with the carbon to which they are attached can be —C(=O)—, a $C_{3-8}$spirocycloalkyl, or a 3- to 8-membered spiroheterocycloalkyl.

$R^{10}$ and $R^{12}$ can each independently be hydrogen or a $C_{1-6}$alkyl.

$R^{11}$, for each occurrence, can be independently halo, hydroxyl, nitro, cyano, $C_{1-6}$alkyl, $C_{1-6}$haloalkyl, $C_{1-6}$alkoxy, —(CR$^{17}$R$^{18}$)$_p$—R$^7$, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —NR$^a$R$^b$, —C(O)NR$^a$R$^b$, —N(R$^a$)C(O)R$^b$, —C(O)R$^a$, —S(O)$_r$R$^a$, or —N(R$^a$)S(O)$_2$R$^b$.

$R^{15}$ for each occurrence can be independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

$R^{16}$ can be $R^{15}$; or two $R^{16}$ together with the nitrogen atom to which they are attached can form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl.

$R^{17}$ and $R^{18}$, for each occurrence, can be each independently hydrogen, a halo, or a $C_{1-4}$haloalkyl.

$R^{19}$ for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $C_{1-6}$alkoxycarbonyl, carbamoyl, N—($C_{1-6}$alkyl)carbamoyl, N,N-di-($C_{1-6}$alkyl)carbamoyl, $C_{1-6}$alkylsulfonyl, sulfamoyl, N—($C_{1-6}$alkyl)sulfamoyl, and N,N-di-($C_{1-6}$alkyl)sulfamoyl.

$R^a$ and $R^b$, for each occurrence, can be independently hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl.

$R^c$ is hydrogen or a $C_{1-4}$alkyl.

m can be 0 or 1, provided that when m is 0, $R^5$ comprises at least one nitrogen.

n can be an integer from 1 to 6.

p can be 0 or an integer from 1 to 6.

r, for each occurrence, can be independently 0, 1, or 2.

The compound is not 4,4'-((perfluoronaphthalene-2,7-diyl)bis(methylene))dipyridine.

In some cases, $A^1$ and $A^2$ can each independently be $CR^2$. In some cases, $A^1$ and $A^2$ can each independently be $CR^2$, and one of $A^3$, $A^4$, and $A^5$ can be N. In some cases, $A^1$ and $A^2$ can each independently be $CR^2$, and one of $A^3$, $A^4$, and $A^5$ can be N, and the others of $A^3$, $A^4$, and $A^5$ can each independently be $CR^2$. In some embodiments, $A^1$, $A^2$, $A^3$, $A^4$, and $A^5$ are all $CR^2$ and each occurrence of "------" is a double bond. In some embodiments, $A^1$ is N and $A^2$, $A^3$, $A^4$, and $A^5$ are all $CR^2$ and each occurrence of "------" is a double bond.

In some embodiments, $R^1$ is a $C_{3-8}$cycloalkyl which is optionally substituted by one or two independently selected $R^6$.

In some embodiments, X is O.

In some embodiments, X is NH.

The compound, or a pharmaceutically acceptable salt thereof, can be represented by formula (II):

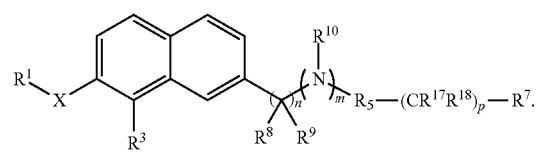

(II)

The compound, or a pharmaceutically acceptable salt thereof, can be represented by formula (III):

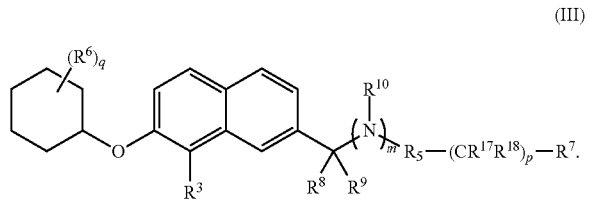

(III)

In formula (III), q can be 0, 1, 2, or 3.

In some embodiments, m can be 0; and $R^5$ can be selected from the group consisting of:

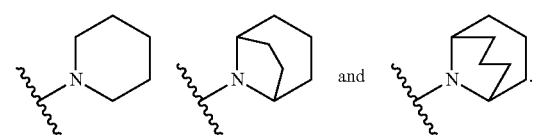

In some embodiments, m can be 1; and $R^5$ can be cyclobutyl, cyclopentyl, or cyclohexyl, each of which may be optionally substituted with from 1 to 3 independently selected $R^{11}$.

In some embodiments, $R^7$ can be —COOH.

In some embodiments, n can be 1.

In some embodiments, $R^8$ can be hydrogen, and $R^9$ can be $C_{1-6}$alkyl; or n can be 1, and $R^8$ and $R^9$ together with the carbon to which they are attached are —C(=O)—.

In some embodiments, $R^8$ and $R^9$ can each independently be hydrogen.

In some embodiments, $R^3$ can be trifluoromethyl.

In some embodiments, q is 1 and $R^6$ is $C_{1-6}$alkyl.

In some embodiments, q is 1 and $R^6$ is t-butyl.

In some embodiments, q is 1 and $R^6$ is methyl, ethyl or isopropyl.

In some embodiments, $R^6$ is trifluoromethyl, difluoromethyl or monofluoromethyl.

In some embodiments, q is 1 and $R^1$ is

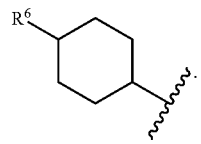

In some embodiments, the compound is selected from the group consisting of:

4-((7-((cis-4-methylcyclohexyl)oxy)-8-(trifluoromethyl)naphthalen-2-yl)methyl)morpholine;

9-[7-(cis-4-methyl-cyclohexyloxy-8-trifluoromethyl-naphthalen-2-ylmethyl]-9-aza-bicyclo[3.3.1]nonane-3-carboxylic acid;

8-[7-(cis-4-methyl-cyclohexyloxy)-8-trifluoromethyl-naphthalen-2-ylmethyl]-8-aza-bicyclo[3.2.1]octane-3-carboxylic acid;

1-[7-(cis-4-Methyl-cyclohexyloxy)-8-trifluoromethyl-naphthalen-2-ylmethyl]-piperidine-4-carboxylic acid;

9-{1-[7-(cis-4-methyl-cyclohexyloxy)-8-trifluoromethyl-naphthalen-2-yl]-ethyl}-9-aza-bicyclo[3.3.1]nonane-3-carboxylic acid;

9-{(S)-1-[7-(cis-4-methyl-cyclohexyloxy)-8-trifluoromethyl-naphthalen-2-yl]-ethyl}-9-aza-bicyclo[3.3.1]nonane-3-carboxylic acid;

9-{(R)-1-[7-(cis-4-methyl-cyclohexyloxy)-8-trifluoromethyl-naphthalen-2-yl]-ethyl}-9-aza-bicyclo[3.3.1]nonane-3-carboxylic acid;

8-{1-[7-(cis-4-methyl-cyclohexyloxy)-8-trifluoromethyl-naphthalen-2-yl]-ethyl}-8-aza-bicyclo[3.2.1]octane-3-carboxylic acid;

8-{(R)-1-[7-(cis-4-methyl-cyclohexyloxy)-8-trifluoromethyl-naphthalen-2-yl]-ethyl}-8-aza-bicyclo[3.2.1]octane-3-carboxylic acid;

8-{(S)-1-[7-(cis-4-methyl-cyclohexyloxy)-8-trifluoromethyl-naphthalen-2-yl]-ethyl}-8-aza-bicyclo[3.2.1]octane-3-carboxylic acid;

2-((R)-1-((8-(trifluoromethyl)-7-((cis-4-(trifluoromethyl)cyclohexyl)oxy)naphthalen-2-yl)methyl)piperidin-3-yl)acetic acid;

2,2-dimethyl-3-(((8-(trifluoromethyl)-7-((cis-4-(trifluoromethyl)cyclohexyl)oxy)-naphthalen-2-yl)methyl)amino)cyclobutanecarboxylic acid;

9-[8-trifluoromethyl-7-(cis-4-trifluoromethyl-cyclohexyloxy)-naphthalen-2-ylmethyl]-9-aza-bicyclo[3.3.1]nonane-3-carboxylic acid;

9-{1-[7-(cis-4-trifluoromethyl-cyclohexyloxy)-8-trifluoromethyl-naphthalen-2-yl]-ethyl}-9-aza-bicyclo[3.3.1]nonane-3-carboxylic acid;

((R)-1-{1-[8-trifluoromethyl-7-(4-trifluoromethyl-cyclohexyloxy)-naphthalen-2-yl]-ethyl}-piperidin-3-yl)-acetic acid;

8-{1-[7-(cis-4-trifluoromethyl-cyclohexyloxy)-8-trifluoromethyl-naphthalen-2-yl]-ethyl}-8-aza-bicyclo[3.2.1]octane-3-carboxylic acid;

8-{(S)-1-[7-(cis-4-trifluoromethyl-cyclohexyloxy)-8-trifluoromethyl-naphthalen-2-yl]-ethyl}-8-aza-bicyclo[3.2.1]octane-3-carboxylic acid;

8-{(R)-1-[7-(cis-4-trifluoromethyl-cyclohexyloxy)-8-trifluoromethyl-naphthalen-2-yl]-ethyl}-8-aza-bicyclo[3.2.1]octane-3-carboxylic acid;

9-[7-(4-methyl-cyclohexyloxy)-8-trifluoromethyl-naphthalene-2-carbonyl]-9-aza-bicyclo[3.3.1]nonane-3-carboxylic acid;

9-[8-trifluoromethyl-7-(4-trifluoromethyl-cyclohexyloxy)-naphthalene-2-carbonyl]-9-aza-bicyclo[3.3.1]nonane-3-carboxylic acid;

9-[8-Chloro-7-(4-methyl-cyclohexyloxy)-naphthalen-2-ylmethyl]-9-aza-bicyclo[3.3.1]nonane-3-carboxylic acid;

9-[1-(8-trifluoromethyl-7-(cis-4-methylcyclohexyloxy)-naphthalen-2-yl)ethyl]-9-aza-bicyclo[3.3.1]nonane;

12-(1-(8-trifluoromethyl-7-(cis-4-methylcyclohexyloxy)naphthalene-2-yl)ethyl)-4,6,12-triaza-tricyclo[7.2.1.0(2,7)]dodeca-2(7),3,5-triene;

8-(1-(7-((cis-4-methylcyclohexyl)oxy)-8-(trifluoromethyl)naphthalen-2-yl)propyl)-8-azabicyclo[3.2.1]octane-3-carboxylic acid;

1-(1-(7-((cis-4-methylcyclohexyl)oxy)-8-(trifluoromethyl)naphthalen-2-yl)propyl)piperidine-4-carboxylic acid;

2-((3R)-1-(1-(7-((cis-4-methylcyclohexyl)oxy)-8-(trifluoromethyl)naphthalen-2-yl)propyl)piperidin-3-yl)acetic acid;

((R)-1-{1-[8-trifluoromethyl-7-(4-trifluoromethyl-cyclohexyloxy)-naphthalen-2-yl]-ethyl}-piperidin-3-yl)-acetic acid;

2-((S)-1-((8-(trifluoromethyl)-7-((cis-4-(trifluoromethyl)cyclohexyl)oxy)naphthalen-2-yl)methyl)piperidin-3-yl)acetic acid;

8-(8-(trifluoromethyl)-7-((cis-4-(trifluoromethyl)cyclohexyl)oxy)-2-naphthoyl)-8-azabicyclo[3.2.1]octane-3-carboxylic acid; and 8-[7-(cis-4-methyl-cyclohexyloxy)-8-trifluoromethyl-naphthalene-2-carbonyl]-8-azabicyclo[3.2.1]octane-3-carboxylic acid;

or a pharmaceutically acceptable salt thereof.

In some embodiments, the compound is selected from the group consisting of:

1-((8-chloro-7-((cis-4-(trifluoromethyl)cyclohexyl)oxy)naphthalen-2-yl)methyl)piperidine-4-carboxylic acid;

9-((8-chloro-7-((cis-4-(trifluoromethyl)cyclohexyl)oxy)naphthalen-2-yl)methyl)-9-azabicyclo[3.3.1]nonane-3-carboxylic acid;

1-(1-(8-chloro-7-((cis-4-(trifluoromethyl)cyclohexyl)oxy)naphthalen-2-yl)ethyl)piperidine-4-carboxylic acid;

8-(1-(8-chloro-7-((cis-4-(trifluoromethyl)cyclohexyl)oxy)naphthalen-2-yl)ethyl)-8-azabicyclo[3.2.1]octane-3-carboxylic acid;

9-(1-(8-chloro-7-((cis-4-(trifluoromethyl)cyclohexyl)oxy)naphthalen-2-yl)ethyl)-9-azabicyclo[3.3.1]nonane-3-carboxylic acid;

1-(1-(8-chloro-7-((cis-4-(trifluoromethyl)cyclohexyl)oxy)naphthalen-2-yl)propyl)piperidine-4-carboxylic acid;

(1R,3S)-3-((1-(8-chloro-7-((cis-4-(trifluoromethyl)cyclohexyl)oxy)naphthalen-2-yl)propyl)amino)-2,2-dimethylcyclobutanecarboxylic acid;

1-((8-cyano-7-((cis-4-(trifluoromethyl)cyclohexyl)oxy)naphthalen-2-yl)methyl)piperidine-4-carboxylic acid;

8-((8-cyano-7-((cis-4-(trifluoromethyl)cyclohexyl)oxy)naphthalen-2-yl)methyl)-8-azabicyclo[3.2.1]octane-3-carboxylic acid;

9-((8-cyano-7-((cis-4-(trifluoromethyl)cyclohexyl)oxy)naphthalen-2-yl)methyl)-9-azabicyclo[3.3.1]nonane-3-carboxylic acid;

1-(1-(8-cyano-7-((cis-4-(trifluoromethyl)cyclohexyl)oxy)naphthalen-2-yl)ethyl)piperidine-4-carboxylic acid;

8-(1-(8-cyano-7-((cis-4-(trifluoromethyl)cyclohexyl)oxy)naphthalen-2-yl)ethyl)-8-azabicyclo[3.2.1]octane-3-carboxylic acid;

9-(1-(8-cyano-7-((cis-4-(trifluoromethyl)cyclohexyl)oxy)naphthalen-2-yl)ethyl)-9-azabicyclo[3.3.1]nonane-3-carboxylic acid;

1-(1-(8-cyano-7-((cis-4-(trifluoromethyl)cyclohexyl)oxy)naphthalen-2-yl)propyl)piperidine-4-carboxylic acid;

8-(1-(8-cyano-7-((cis-4-(trifluoromethyl)cyclohexyl)oxy)naphthalen-2-yl)propyl)-8-azabicyclo[3.2.1]octane-3-carboxylic acid;

9-(1-(8-cyano-7-((cis-4-(trifluoromethyl)cyclohexyl)oxy)naphthalen-2-yl)propyl)-9-azabicyclo[3.3.1]nonane-3-carboxylic acid;

8-(1-(8-(difluoromethyl)-7-((cis-4-(trifluoromethyl)cyclohexyl)oxy)naphthalen-2-yl)ethyl)-8-azabicyclo[3.2.1]octane-3-carboxylic acid;

1-((8-(trifluoromethyl)-7-((cis-4-(trifluoromethyl)cyclohexyl)oxy)naphthalen-2-yl)methyl)piperidine-4-carboxylic acid;

1-(1-(8-(trifluoromethyl)-7-((cis-4-(trifluoromethyl)cyclohexyl)oxy) naphthalen-2-yl)ethyl)piperidine-4-carboxylic acid;

1-(1-(8-(trifluoromethyl)-7-((cis-4-(trifluoromethyl)cyclohexyl)oxy) naphthalene-2-yl)propyl)piperidine-4-carboxylic acid;

8-((S)-1-(8-(trifluoromethyl)-7-((cis-4-(trifluoromethyl)cyclohexyl)oxy)naphthalen-2-yl)-2,2,2-trideuteroethyl)-8-azabicyclo[3.2.1]octane-3-carboxylic acid;

1-((8-chloro-7-((cis-4-ethylcyclohexyl)oxy)naphthalen-2-yl)methyl)piperidine-4-carboxylic acid;

8-((8-chloro-7-((cis-4-ethylcyclohexyl)oxy)naphthalen-2-yl)methyl)-8-azabicyclo[3.2.1]octane-3-carboxylic acid;

9-((8-chloro-7-((cis-4-ethylcyclohexyl)oxy)naphthalen-2-yl)methyl)-9-azabicyclo[3.3.1]nonane-3-carboxylic acid;

1-((7-((cis-4-ethylcyclohexyl)oxy)-8-(trifluoromethyl)naphthalen-2-yl)methyl)piperidine-4-carboxylic acid;

8-((7-((cis-4-ethylcyclohexyl)oxy)-8-(trifluoromethyl)naphthalen-2-yl)methyl)-8-azabicyclo[3.2.1]octane-3-carboxylic acid;

9-((7-((cis-4-ethylcyclohexyl)oxy)-8-(trifluoromethyl)naphthalen-2-yl)methyl)-9-azabicyclo[3.3.1]nonane-3-carboxylic acid;

2-((R)-1-((7-((cis-4-ethylcyclohexyl)oxy)-8-(trifluoromethyl)naphthalen-2-yl)methyl) piperidin-3-yl)acetic acid;

3-(((7-((cis-4-ethylcyclohexyl)oxy)-8-(trifluoromethyl)naphthalen-2-yl)methyl)amino)-2,2-dimethylcyclobutanecarboxylic acid;

8-(1-(7-((cis-4-ethylcyclohexyl)oxy)-8-(trifluoromethyl)naphthalen-2-yl)ethyl)-8-azabicyclo[3.2.1]octane-3-carboxylic acid;

9-(1-(7-((cis-4-ethylcyclohexyl)oxy)-8-(trifluoromethyl)naphthalen-2-yl)ethyl)-9-azabicyclo[3.3.1]nonane-3-carboxylic acid;

1-(1-(7-((cis-4-ethylcyclohexyl)oxy)-8-(trifluoromethyl) naphthalen-2-yl)ethyl)piperidine-4-carboxylic acid;
2-((3R)-1-(1-(7-((cis-4-ethylcyclohexyl)oxy)-8-(trifluoromethyl)naphthalen-2-yl)ethyl)piperidin-3-yl)acetic acid;
3-((1-(7-((cis-4-ethylcyclohexyl)oxy)-8-(trifluoromethyl) naphthalen-2-yl)ethyl)amino)-2,2-dimethylcyclobutanecarboxylic acid;
1-(1-(7-((cis-4-ethylcyclohexyl)oxy)-8-(trifluoromethyl) naphthalen-2-yl)propyl)piperidine-4-carboxylic acid;
2-((3R)-1-(1-(7-((cis-4-ethylcyclohexyl)oxy)-8-(trifluoromethyl)naphthalen-2-yl)propyl)piperidin-3-yl)acetic acid;
2-((R)-1-((8-chloro-7-((cis-4-ethylcyclohexyl)oxy)naphthalen-2-yl)methyl)piperidin-3-yl)acetic acid;
8-(1-(8-(difluoromethyl)-7-((cis-4-ethylcyclohexyl)oxy) naphthalen-2-yl)ethyl)-8-azabicyclo[3.2.1]octane-3-carboxylic acid;
1-(1-(8-chloro-7-((cis-4-ethylcyclohexyl)oxy)naphthalen-2-yl)ethyl)piperidine-4-carboxylic acid;
8-(1-(8-chloro-7-((cis-4-ethylcyclohexyl)oxy)naphthalen-2-yl)ethyl)-8-azabicyclo[3.2.1]octane-3-carboxylic acid;
9-(1-(8-chloro-7-((cis-4-ethylcyclohexyl)oxy)naphthalen-2-yl)ethyl)-9-azabicyclo[3.3.1]nonane-3-carboxylic acid;
(1R,3S)-3-((1-(8-chloro-7-((cis-4-ethylcyclohexyl)oxy) naphthalen-2-yl)ethyl)amino)-2,2-dimethylcyclobutanecarboxylic acid;
(1R,3S)-3-(((8-chloro-7-((cis-4-ethylcyclohexyl)oxy)naphthalen-2-yl)methyl)amino)-2,2-dimethylcyclobutanecarboxylic acid;
1-((8-cyano-7-((cis-4-ethylcyclohexyl)oxy)naphthalen-2-yl)methyl)piperidine-4-carboxylic acid;
8-((8-cyano-7-((cis-4-ethylcyclohexyl)oxy)naphthalen-2-yl)methyl)-8-azabicyclo[3.2.1]octane-3-carboxylic acid;
8-((8-cyano-7-((cis-4-ethylcyclohexyl)oxy)naphthalen-2-yl)methyl)-8-azabicyclo[3.2.1]octane-3-carboxylic acid;
9-((8-cyano-7-((cis-4-ethylcyclohexyl)oxy)naphthalen-2-yl)methyl)-9-azabicyclo[3.3.1]nonane-3-carboxylic acid;
1-(1-(8-cyano-7-((cis-4-ethylcyclohexyl)oxy)naphthalen-2-yl)ethyl)piperidine-4-carboxylic acid;
8-(1-(8-cyano-7-((cis-4-ethylcyclohexyl)oxy)naphthalen-2-yl)ethyl)-8-azabicyclo[3.2.1]octane-3-carboxylic acid;
9-(1-(8-cyano-7-((cis-4-ethylcyclohexyl)oxy)naphthalen-2-yl)ethyl)-9-azabicyclo[3.3.1]nonane-3-carboxylic acid;
1-(1-(8-chloro-7-((cis-4-ethylcyclohexyl)oxy)naphthalen-2-yl)propyl)piperidine-4-carboxylic acid;
1-(1-(8-cyano-7-((cis-4-ethylcyclohexyl)oxy)naphthalen-2-yl)propyl)piperidine-4-carboxylic acid;
2-((R)-1-((7-((cis-4-methylcyclohexyl)oxy)-8-(trifluoromethyl)naphthalen-2-yl)methyl)piperidin-3-yl)acetic acid;
2,2-dimethyl-3-(((7-((cis-4-methylcyclohexyl)oxy)-8-(trifluoromethyl)naphthalen-2-yl)methyl)amino)cyclobutanecarboxylic acid;
1-((8-chloro-7-((cis-4-methylcyclohexyl)oxy)naphthalen-2-yl)methyl)piperidine-4-carboxylic acid;
1-(1-(7-((cis-4-methylcyclohexyl)oxy)-8-(trifluoromethyl) naphthalen-2-yl)ethyl)piperidine-4-carboxylic acid;
2-((3R)-1-(1-(7-((cis-4-methylcyclohexyl)oxy)-8-(trifluoromethyl)naphthalen-2-yl)ethyl)piperidin-3-yl)acetic acid;
2,2-dimethyl-3-((1-(7-((cis-4-methylcyclohexyl)oxy)-8-(trifluoromethyl)naphthalen-2-yl)ethyl)amino)cyclobutanecarboxylic acid;
8-((8-chloro-7-((cis-4-methylcyclohexyl)oxy)naphthalen-2-yl)methyl)-8-azabicyclo[3.2.1]octane-3-carboxylic acid;
2-((R)-1-((8-chloro-7-((cis-4-methylcyclohexyl)oxy)naphthalen-2-yl)methyl)piperidin-3-yl)acetic acid;
3-(((8-chloro-7-((cis-4-methylcyclohexyl)oxy)naphthalen-2-yl)methyl)amino)-2,2-dimethylcyclobutanecarboxylic acid;
9-((8-(difluoromethyl)-7-((cis-4-methylcyclohexyl)oxy) naphthalen-2-yl)methyl)-9-azabicyclo[3.3.1]nonane-3-carboxylic acid;
8-(1-(8-(difluoromethyl)-7-((cis-4-methylcyclohexyl)oxy) naphthalen-2-yl)ethyl)-8-azabicyclo[3.2.1]octane-3-carboxylic acid;
9-(1-(8-(difluoromethyl)-7-((cis-4-methylcyclohexyl)oxy) naphthalen-2-yl)ethyl)-9-azabicyclo[3.3.1]nonane-3-carboxylic acid;
1-(1-(8-chloro-7-((cis-4-methylcyclohexyl)oxy)naphthalen-2-yl)ethyl)piperidine-4-carboxylic acid;
8-(1-(8-chloro-7-((cis-4-methylcyclohexyl)oxy)naphthalen-2-yl)ethyl)-8-azabicyclo[3.2.1]octane-3-carboxylic acid;
9-(1-(8-chloro-7-((cis-4-methylcyclohexyl)oxy)naphthalen-2-yl)ethyl)-9-azabicyclo[3.3.1]nonane-3-carboxylic acid;
2-((3R)-1-(1-(8-chloro-7-((cis-4-methylcyclohexyl)oxy) naphthalen-2-yl)ethyl)piperidin-3-yl)acetic acid;
Cis-3-((1-(8-chloro-7-((cis-4-methylcyclohexyl)oxy)naphthalen-2-yl)ethyl)amino)-2, 2-dimethylcyclobutanecarboxylic acid;
1-(1-(8-chloro-7-(cis-4-methylcyclohexyl)oxy)naphthalen-2-yl)propyl)piperidine-4-carboxylic acid;
8-(1-(8-chloro-7-((cis-4-methylcyclohexyl)oxy)naphthalen-2-yl)propyl)-8-azabicyclo [3.2.1]octane-3-carboxylic acid;
8-((8-cyano-7-((cis-4-methylcyclohexyl)oxy)naphthalen-2-yl)methyl)-8-azabicyclo[3.2.1]octane-3-carboxylic acid;
1-((8-cyano-7-((cis-4-methylcyclohexyl)oxy)naphthalen-2-yl)methyl)piperidine-4-carboxylic acid;
9-((8-cyano-7-((cis-4-methylcyclohexyl)oxy)naphthalen-2-yl)methyl)-9-azabicyclo[3.3.1]nonane-3-carboxylic acid;
Cis-3-(((8-cyano-7-((cis-4-methylcyclohexyl)oxy)naphthalen-2-yl)methyl)amino)-2,2-dimethylcyclobutanecarboxylic acid;
1-(1-(8-cyano-7-((cis-4-methylcyclohexyl)oxy)naphthalen-2-yl)ethyl)piperidine-4-carboxylic acid;
8-(1-(8-cyano-7-((cis-4-methylcyclohexyl)oxy)naphthalen-2-yl)ethyl)-8-azabicyclo[3.2.1]octane-3-carboxylic acid;
9-(1-(8-cyano-7-((cis-4-methylcyclohexyl)oxy)naphthalen-2-yl)ethyl)-9-azabicyclo[3.3.1]nonane-3-carboxylic acid;
1-(1-(8-cyano-7-((cis-4-methylcyclohexyl)oxy)naphthalen-2-yl)propyl)piperidine-4-carboxylic acid;
9-(1-(7-((cis-4-methylcyclohexyl)oxy)-8-(trifluoromethyl) naphthalen-2-yl)propyl)-9-azabicyclo[3.3.1]nonane-3-carboxylic acid;
2,2-dimethyl-3-((1-(7-((cis-4-methylcyclohexyl)oxy)-8-(trifluoromethyl)naphthalen-2-yl)propyl)amino)cyclobutanecarboxylic acid;
1-((7-((cis-4-isopropylcyclohexyl)oxy)-8-(trifluoromethyl) naphthalen-2-yl)methyl)piperidine-4-carboxylic acid;
8-((7-((cis-4-isopropylcyclohexyl)oxy)-8-(trifluoromethyl) naphthalen-2-yl)methyl)-8-azabicyclo[3.2.1]octane-3-carboxylic acid;
9-((7-((cis-4-isopropylcyclohexyl)oxy)-8-(trifluoromethyl) naphthalen-2-yl)methyl)-9-azabicyclo[3.3.1]nonane-3-carboxylic acid;
3-(((7-((cis-4-isopropylcyclohexyl)oxy)-8-(trifluoromethyl) naphthalen-2-yl)methyl)amino)-2,2-dimethylcyclobutanecarboxylic acid;
cis-3-((1-(7-((cis-4-methylcyclohexyl)oxy)-8-(trifluoromethyl)naphthalen-2-yl)ethyl) amino)cyclobutanecarboxylic acid;

trans-3-((1-(7-((cis-4-methylcyclohexyl)oxy)-8-(trifluoromethyl)naphthalen-2-yl)ethyl)amino)cyclobutanecarboxylic acid;
(1S,3R)-2,2-dimethyl-3-((1-(7-((cis-4-methylcyclohexyl)oxy)-8-(trifluoromethyl)naphthalen-2-yl)ethyl)amino)cyclobutanecarboxylic acid;
(1R,3S)-2,2-dimethyl-3-((1-(7-((cis-4-methylcyclohexyl)oxy)-8-(trifluoromethyl)naphthalen-2-yl)ethyl)amino)cyclobutanecarboxylic acid;
(1S,3S)-2,2-dimethyl-3-(((S)-1-(7-((cis-4-methylcyclohexyl)oxy)-8-(trifluoromethyl) naphthalen-2-yl)ethyl)amino)cyclobutanecarboxylic acid;
((1R,3S)-2,2-dimethyl-3-(((S)-1-(7-((cis-4-methylcyclohexyl)oxy)-8-(trifluoromethyl)naphthalen-2-yl)ethyl)amino)cyclobutanecarboxylic acid;
(1S,3S)-2,2-dimethyl-3-(((R)-1-(7-((cis-4-methylcyclohexyl)oxy)-8-(trifluoromethyl) naphthalen-2-yl)ethyl)amino)cyclobutanecarboxylic acid;
(1R,3S)-2,2-dimethyl-3-(((R)-1-(7-((cis-4-methylcyclohexyl)oxy)-8-(trifluoromethyl) naphthalen-2-yl)ethyl)amino)cyclobutanecarboxylic acid;
(1S,3R)-3-((1-(7-((cis-4-ethylcyclohexyl)oxy)-8-(trifluoromethyl)naphthalen-2-yl)ethyl)amino)-2,2-dimethylcyclobutanecarboxylic acid;
((1R,3S)-3-((1-(7-((cis-4-ethylcyclohexyl)oxy)-8-(trifluoromethyl)naphthalen-2-yl)ethyl)amino)-2,2-dimethylcyclobutanecarboxylic acid;
((1R,3S)-3-((1-(7-((cis-4-ethylcyclohexyl)oxy)-8-(trifluoromethyl)naphthalen-2-yl)ethyl)amino)-2,2-dimethylcyclobutanecarboxylic acid;
(1R,3R)-3-(((S)-1-(7-((cis-4-ethylcyclohexyl)oxy)-8-(trifluoromethyl)naphthalen-2-yl)ethyl)amino)-2,2-dimethylcyclobutanecarboxylic acid;
(1S,3R)-3-(((S)-1-(7-((cis-4-ethylcyclohexyl)oxy)-8-(trifluoromethyl)naphthalen-2-yl)ethyl)amino)-2,2-dimethyl cyclobutanecarboxylic acid;
(1R,3R)-3-(((R)-1-(7-((cis-4-ethylcyclohexyl)oxy)-8-(trifluoromethyl)naphthalen-2-yl)ethyl)amino)-2,2-dimethylcyclobutanecarboxylic acid;
(1S,3R)-3-(((R)-1-(7-((cis-4-ethylcyclohexyl)oxy)-8-(trifluoromethyl)naphthalen-2-yl)ethyl)amino)-2,2-dimethylcyclobutanecarboxylic acid;
(1S,3S)-3-(((S)-1-(7-((cis-4-ethylcyclohexyl)oxy)-8-(trifluoromethyl)naphthalen-2-yl)ethyl)amino)-2,2-dimethylcyclobutanecarboxylic acid;
(1R,3S)-3-(((S)-1-(7-((cis-4-ethylcyclohexyl)oxy)-8-(trifluoromethyl)naphthalen-2-yl)ethyl)amino)-2,2-dimethylcyclobutanecarboxylic acid;
(1S,3S)-3-(((R)-1-(7-((cis-4-ethylcyclohexyl)oxy)-8-(trifluoromethyl)naphthalen-2-yl)ethyl)amino)-2,2-dimethylcyclobutanecarboxylic acid;
(1R,3S)-3-(((R)-1-(7-((cis-4-ethylcyclohexyl)oxy)-8-(trifluoromethyl)naphthalen-2-yl)ethyl)amino)-2,2-dimethylcyclobutanecarboxylic acid;
(1S,3R)-2,2-dimethyl-3-((1-(8-(trifluoromethyl)-7-((cis-4-(trifluoromethyl) cyclohexyl)oxy)naphthalen-2-yl)ethyl)amino)cyclobutanecarboxylic acid;
(1R,3S)-2,2-dimethyl-3-((1-(8-(trifluoromethyl)-7-((cis-4-(trifluoromethyl) cyclohexyl)oxy)naphthalen-2-yl)ethyl)amino)cyclobutanecarboxylic acid;
(1R,3R)-2,2-dimethyl-3-(((S)-1-(8-(trifluoromethyl)-7-((cis-4-(trifluoromethyl)cyclohexyl)oxy)naphthalen-2-yl)ethyl)amino)cyclobutanecarboxylic acid;
(1S,3R)-2,2-dimethyl-3-(((S)-1-(8-(trifluoromethyl)-7-((cis-4-(trifluoromethyl)cyclohexyl)oxy)naphthalen-2-yl)ethyl)amino)cyclobutanecarboxylic acid;
(1R,3R)-2,2-dimethyl-3-(((R)-1-(8-(trifluoromethyl)-7-((cis-4-(trifluoromethyl)cyclohexyl)oxy)naphthalen-2-yl)ethyl)amino)cyclobutanecarboxylic acid;
(1S,3R)-2,2-dimethyl-3-(((R)-1-(8-(trifluoromethyl)-7-((cis-4-(trifluoromethyl)cyclohexyl)oxy)naphthalen-2-yl)ethyl)amino)cyclobutanecarboxylic acid;
(1R,3S)-2,2-dimethyl-3-(((S)-1-(8-(trifluoromethyl)-7-((cis-4-(trifluoromethyl)cyclohexyl)oxy)naphthalen-2-yl)ethyl)amino)cyclobutanecarboxylic acid;
(1S,3R)-2,2-dimethyl-3-(((S)-1-(8-(trifluoromethyl)-7-((cis-4-(trifluoromethyl)cyclohexyl)oxy)naphthalen-2-yl)ethyl)amino)cyclobutanecarboxylic acid;
(1R,3R)-2,2-dimethyl-3-(((R)-1-(8-(trifluoromethyl)-7-((cis-4-(trifluoromethyl)cyclohexyl)oxy)naphthalen-2-yl)ethyl)amino)cyclobutanecarboxylic acid;
(1S,3R)-2,2-dimethyl-3-(((R)-1-(8-(trifluoromethyl)-7-((cis-4-(trifluoromethyl)cyclohexyl)oxy)naphthalen-2-yl)ethyl)amino)cyclobutanecarboxylic acid;
1-((8-(trifluoromethyl)-7-((cis-4-(trifluoromethyl)cyclohexyl)oxy) naphthalen-2-yl)methyl)azepane-4-carboxylic acid;
cis-4-(((8-(trifluoromethyl)-7-((cis-4-(trifluoromethyl)cyclohexyl)oxy)naphthalen-2-yl)methyl)amino)cyclohexanecarboxylic acid;
trans-4-(((8-(trifluoromethyl)-7-((cis-4-(trifluoromethyl)cyclohexyl)oxy)naphthalen-2-yl)methyl)amino)cyclohexanecarboxylic acid;
2-(4-(((8-(trifluoromethyl)-7-((cis-4-(trifluoromethyl)cyclohexyl)oxy)naphthalen-2-yl)methyl)amino)cyclohexyl)acetic acid;
3-(((8-(trifluoromethyl)-7-((cis-4-(trifluoromethyl)cyclohexyl) oxy)naphthalen-2-yl)methyl)amino)cyclopentanecarboxylic acid;
3-(((8-(trifluoromethyl)-7-((cis-4-(trifluoromethyl)cyclohexyl) oxy)naphthalen-2-yl)methyl)amino)cyclobutanecarboxylic acid;
cis-4-((1-(8-(trifluoromethyl)-7-((cis-4-(trifluoromethyl)cyclohexyl) oxy)naphthalen-2-yl)ethyl)amino)cyclohexanecarboxylic acid;
4-((1-(7-((cis-4-ethylcyclohexyl)oxy)-8-(trifluoromethyl) naphthalen-2-yl)ethyl)amino)bicyclo[2.2.1]heptane-1-carboxylic acid;
3-((1-(7-((cis-4-ethylcyclohexyl)oxy)-8-(trifluoromethyl) naphthalen-2-yl)ethyl)amino)cyclopentanecarboxylic acid;
methyl 9-(1-(7-((cis-4-ethylcyclohexyl)oxy)-8-(trifluoromethyl)naphthalen-2-yl)ethyl)-9-azabicyclo[3.3.1]nonane-3-carboxylate;
9-((S)-1-(7-((cis-4-ethylcyclohexyl)oxy)-8-(trifluoromethyl)naphthalen-2-yl)ethyl)-9-azabicyclo[3.3.1]nonane-3-carboxylic acid;
9-((R)-1-(7-((cis-4-ethylcyclohexyl)oxy)-8-(trifluoromethyl)naphthalen-2-yl)ethyl)-9-azabicyclo[3.3.1]nonane-3-carboxylic acid;
cis-4-((1-(7-((cis-4-ethylcyclohexyl)oxy)-8-(trifluoromethyl)naphthalen-2-yl)ethyl)amino)cyclohexanecarboxylic acid;
cis-4-(((S)-1-(7-((cis-4-ethylcyclohexyl)oxy)-8-(trifluoromethyl)naphthalen-2-yl)ethyl)amino)cyclohexanecarboxylic acid;
cis-4-(((R)-1-(7-((cis-4-ethylcyclohexyl)oxy)-8-(trifluoromethyl)naphthalen-2-yl)ethyl)amino)cyclohexanecarboxylic acid;
cis-4-(((S)-1-(8-(trifluoromethyl)-7-((cis-4-(trifluoromethyl) cyclohexyl)oxy)naphthalen-2-yl)ethyl)amino)cyclohexanecarboxylic acid;

cis-4-(((R)-1-(8-(trifluoromethyl)-7-((cis-4-(trifluoromethyl) cyclohexyl)oxy)naphthalen-2-yl)ethyl)amino)cyclohexanecarboxylic acid;
9-((S)-1-(8-(trifluoromethyl)-7-((cis-4-(trifluoromethyl) cyclohexyl)oxy)naphthalen-2-yl)ethyl)-9-azabicyclo[3.3.1]nonane-3-carboxylic acid;
9-((R)-1-(8-(trifluoromethyl)-7-((cis-4-(trifluoromethyl) cyclohexyl)oxy)naphthalen-2-yl)ethyl)-9-azabicyclo[3.3.1]nonane-3-carboxylic acid;
9-((3-fluoro-7-((cis-4-methylcyclohexyl)oxy)-8-(trifluoromethyl)naphthalen-2-yl)methyl)-9-azabicyclo[3.3.1]nonane-3-carboxylic acid;
8-(1-(3-fluoro-7-((cis-4-methylcyclohexyl)oxy)-8-(trifluoromethyl)naphthalen-2-yl)ethyl)-8-azabicyclo[3.2.1]octane-3-carboxylic acid;
8-(1-(3-fluoro-8-(trifluoromethyl)-7-((cis-4-(trifluoromethyl) cyclohexyl)oxy)naphthalen-2-yl)ethyl)-8-azabicyclo[3.2.1]octane-3-carboxylic acid;
8-((3-fluoro-8-(trifluoromethyl)-7-((cis-4-(trifluoromethyl) cyclohexyl)oxy)naphthalen-2-yl)methyl)-8-azabicyclo[3.2.1]octane-3-carboxylic acid;
cis-4-((1-(7-((cis-4-methylcyclohexyl)oxy)-8-(trifluoromethyl)naphthalen-2-yl)ethyl) amino)cyclohexanecarboxylic acid;
trans-4-((1-(8-(trifluoromethyl)-7-((cis-4-(trifluoromethyl) cyclohexyl)oxy)naphthalen-2-yl)ethyl)amino)cyclohexanecarboxylic acid;
8-((S)-1-(7-((cis-4-ethylcyclohexyl)oxy)-8-(trifluoromethyl)naphthalen-2-yl)ethyl)-8-azabicyclo[3.2.1]octane-3-carboxylic acid;
8-((R)-1-(7-((cis-4-ethylcyclohexyl)oxy)-8-(trifluoromethyl)naphthalen-2-yl)ethyl)-8-azabicyclo[3.2.1]octane-3-carboxylic acid;
cis-4-((1-(7-((cis-4-ethylcyclohexyl)oxy)-8-(trifluoromethyl)naphthalen-2-yl)propyl)amino)cyclohexanecarboxylic acid;
cis-4-((1-(7-((cis-4-methylcyclohex yl)oxy)-8-(trifluoromethyl)naphthalen-2-yl)propyl)amino)cyclohexanecarboxylic acid;
cis-4-((1-(8-(trifluoromethyl)-7-((cis-4-(trifluoromethyl) cyclohexyl)oxy)naphthalen-2-yl)propyl)amino)cyclohexanecarboxylic acid;
Methyl 3-(3-((trans-4-(tert-butyl)cyclohexyl)amino)isoquinoline-6-carboxamido)cyclohexanecarboxylate;
3-(3-((trans-4-(tert-butyl)cyclohexyl)amino)isoquinoline-6-carboxamido)cyclohexane carboxylic acid;
3-((trans-4-(tert-butyl)cyclohexyl)amino)-N-cyclohexyl isoquinoline-6-carboxamide;
4-(3-((trans-4-(tert-butyl)cyclohexyl) amino)isoquinoline-6-carboxamido)bicyclo[2.2.2]octane-1-carboxylic acid;
8-(3-((trans-4-(tert-butyl)cyclohexyl)amino)isoquinoline-6-carbonyl)-8-azabicyclo[3.2.1]octane-3-carboxylic acid;
cis-4-(3-((trans-4-(tert-butyl)cyclohexyl)amino)isoquinoline-6-carboxamido)cyclohexanecarboxylic acid;
trans-4-(3-((trans-4-(tert-butyl)cyclohexyl)amino) isoquinoline-6-carboxamido)cyclohexanecarboxylic acid;
1-(3-((trans-4-(tert-butyl)cyclohexyl)amino)isoquinoline-6-carbonyl)piperidine-4-carboxylic acid;
2-(1-(3-((trans-4-(tert-butyl)cyclohexyl)amino)isoquinoline-6-carbonyl)piperidin-4-yl)acetic acid;
2-(1-(3-((trans-4-(tert-butyl)cyclohexyl)amino)isoquinoline-6-carbonyl)piperidin-4-yl)acetic acid; or
cis-4-(3-((trans-4-(tert-butyl)cyclohexyl)amino)-4-chloroisoquinoline-6-carboxamido)cyclohexanecarboxylic acid,
or a pharmaceutically acceptable salt thereof.

In another aspect, a pharmaceutical composition includes a pharmaceutically acceptable carrier or excipient and a compound represented by structural formula (I):

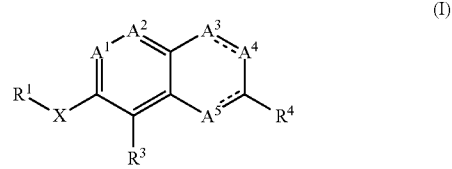

(I)

In formula (I), X can be O, S(O)$_r$, NR$^{12}$, C(O) or CH$_2$.
A$^1$ and A$^2$ can each independently be CR$^2$ or N.
A$^3$, A$^4$ and A$^5$ can each independently be CR$^2$, C(R$^2$)$_2$, N, or NR$^{19}$, provided that at least three of A$^1$, A$^2$, A$^3$, A$^4$, A$^5$, and A$^6$ are independently CR$^2$ or C(R$^2$)$_2$.
"------" indicates a double or a single bond.
R$^1$ can be a C$_{6-20}$alkyl, a C$_{3-14}$carbocyclyl, a 3- to 15-membered heterocyclyl, a C$_{6-10}$aryl, or a five- to 14-membered heteroaryl, wherein the heterocyclyl and the heteroaryl comprising from 1 to 10 heteroatoms independently selected from N, S or O, and wherein R$^1$ may be optionally substituted with from one to six independently selected R$^6$.
R$^2$, for each occurrence, can be independently selected from the group consisting of hydrogen, halo, hydroxyl, nitro, cyano, carboxy, C$_{1-6}$alkyl, C$_{1-6}$haloalkyl, C$_{3-8}$cycloalkyl, C$_{3-8}$halocycloalkyl, C$_{1-6}$alkoxy, C$_{1-6}$haloalkoxy, C$_{3-8}$cycloalkoxy, C$_{3-8}$halocycloalkoxy, C$_{1-6}$alkanoyl, amino, N—(C$_{1-6}$alkyl)amino, N,N-di-(C$_{1-6}$alkyl)amino, C$_{1-6}$alkoxycarbonyl, C$_{1-6}$alkanoyloxy, carbamoyl, N—(C$_{1-6}$alkyl)carbamoyl, N,N-di-(C$_{1-6}$alkyl)carbamoyl, C$_{1-6}$alkylamido, mercapto, C$_{1-6}$alkylthio, C$_{1-6}$alkylsulfonyl, sulfamoyl, N—(C$_{1-6}$alkyl)sulfamoyl, N,N-di-(C$_{1-6}$alkyl)sulfamoyl, and C$_{1-6}$alkylsulfonamido.
R$^3$ can be hydrogen, a halo, C$_{1-6}$haloalkyl or cyano, provided that when R$^3$ is hydrogen, R$^1$ is a C$_{3-8}$cycloalkyl which is optionally substituted with from 1 to 6.
R4 is a carboxylic acid or a group represented by the following formula:

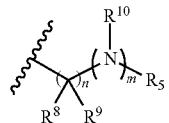

wherein ⁝ represents the point of attachment; provided that when R4 is a carboxylic acid, A1 is N and R1 is a C$_{3-8}$cycloalkyl which is optionally substituted with from 1 to 6.
R$^5$ can be a C$_{1-6}$alkylene, C$_{3-8}$carbocyclyl, a 3- to 8-membered heterocyclyl, C$_{6-10}$aryl, a 5- to 10-membered heteroaryl, a bridged ring system comprising from 6 to 12 ring members, a spiro ring system comprising from 5-14 ring members, or a bicyclic ring system represented by the following formula:

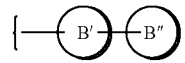

wherein B' and B" are independently selected from the group consisting of monocyclic $C_{3-8}$carbocyclyl, a monocyclic 3- to 8-membered heterocyclyl, phenyl or a 5- to 6-membered heteroaryl; wherein $R^5$ may be optionally substituted with from 1 to 4 independently selected $R^{11}$.

$R^6$, for each occurrence, can be independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom may form $C_{3-8}$spirocycloalkyl or 3- to 8-membered spiroheterocycloalkyl.

$R^7$ can be —OH, —C(O)OR$^{15}$, —C(O)N(R$^{16}$)$_2$, —C(O)N(R$^{15}$)—S(O)$_2$R$^{15}$, —S(O)$_2$OR$^{15}$, —C(O)NHC(O)R$^{15}$, —Si(O)OH, —B(OH)$_2$, —N(R$^{15}$)S(O)$_2$R$^{15}$, —S(O)$_2$N(R$^{15}$)$_2$, —O—P(O)(OR$^{15}$)$_2$, —P(O)(OR$^{15}$)$_2$, —CN, —S(O)$_2$NHC(O)R$^{15}$, —C(O)NHS(O)$_2$R$^{15}$, —C(O)NHOH, —C(O)NHCN, or a heteroaryl or a heterocyclyl selected from the group consisting of formulae (a)-(i'):

(a)
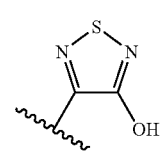

(b)
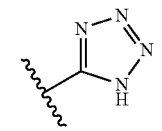

(c)
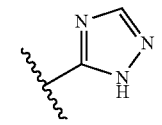

(d)
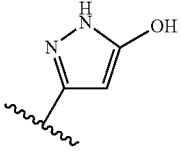

(e)
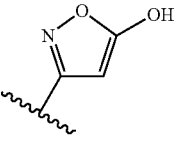

(f)
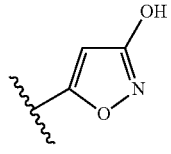

(g)
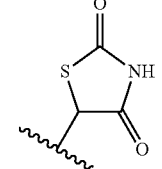

(h)
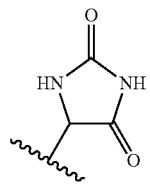

(i)
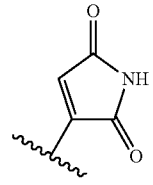

(j)
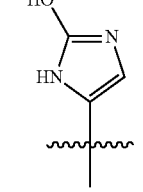

(k)
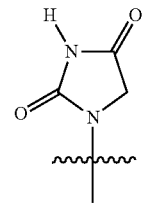

(l)
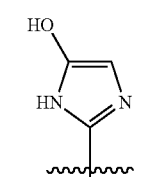

(m)
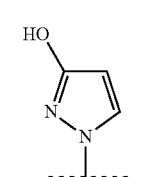

(n)
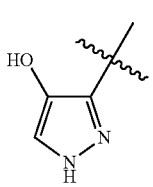

(o)
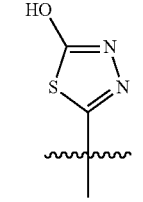

-continued
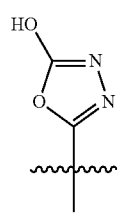 (p)
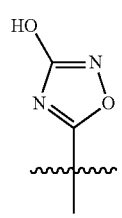 (q)
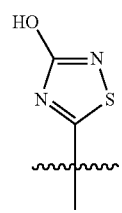 (r)
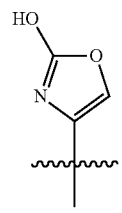 (s)
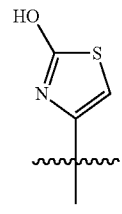 (t)
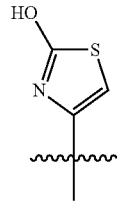 (u)
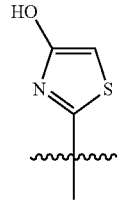 (v)
-continued
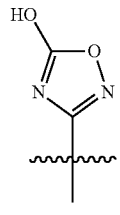 (w)
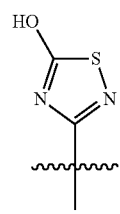 (x)
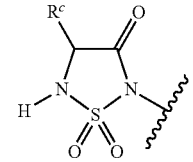 (y)
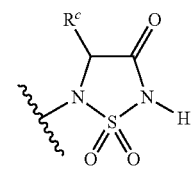 (z)
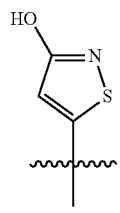 (a′)
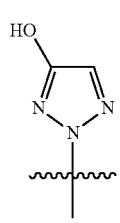 (b′)
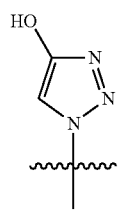 (c′)
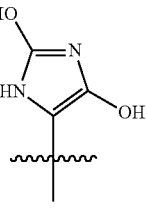 (d′)

-continued

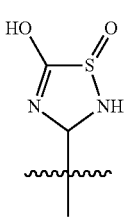
(e')

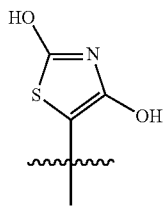
(f')

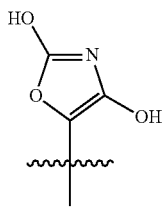
(g')

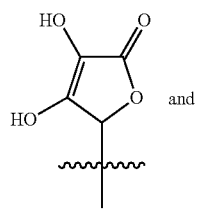
(h')

and

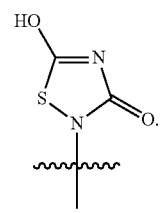
(i')

$R^8$ and $R^9$ can each independently be hydrogen, a carboxy, $C_{1-6}$alkyl, or a $C_{2-6}$alkenyl; or $R^8$ and $R^9$ together with the carbon to which they are attached can be —C(=O)—, a $C_{3-8}$spirocycloalkyl, or a 3- to 8-membered spiroheterocycloalkyl.

$R^{10}$ and $R^{12}$ can each independently be hydrogen or a $C_{1-6}$alkyl.

$R^{11}$, for each occurrence, can be independently halo, hydroxyl, nitro, cyano, $C_{1-6}$alkyl, $C_{1-6}$haloalkyl, $C_{1-6}$alkoxy, —$(CR^{17}R^{18})_p$—$R^7$, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —$C(O)NR^aR^b$, —$N(R^a)C(O)R^b$, —$C(O)R^a$, —$S(O)_rR^a$, or —$N(R^a)S(O)_2R^b$.

$R^{15}$ for each occurrence can be independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—$(C_{1-4}$alkyl)amino, N,N-di-$(C_{1-4}$alkyl)amino, carbamoyl, N—$(C_{1-4}$alkyl)carbamoyl, N,N-di-$(C_{1-4}$alkyl)carbamoyl, $C_{1-4}$alkylamido, $C_{1-4}$alkylsulfonyl, $C_{1-4}$alkylsulfonamido, sulfamoyl, N—$(C_{1-4}$alkyl)sulfamoyl, and N,N—$(C_{1-4}$dialkyl)-sulfamoyl.

$R^{16}$ can be $R^{15}$; or two $R^{16}$ together with the nitrogen atom to which they are attached can form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—$(C_{1-4}$alkyl)amino, N,N-di-$(C_{1-4}$alkyl)amino, carbamoyl, N—$(C_{1-4}$alkyl)carbamoyl, N,N-di-$(C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—$(C_{1-4}$dialkyl)-sulfamoyl.

$R^{17}$ and $R^{18}$, for each occurrence, can be each independently hydrogen, a halo, or a $C_{1-4}$haloalkyl.

$R^{19}$ for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $(C_{1-6}$alkoxycarbonyl, carbamoyl, N—$(C_{1-6}$alkyl)carbamoyl, N,N-di-$((C_{1-6}$alkyl)carbamoyl, $C_{1-6}$alkylsulfonyl, sulfamoyl, N—$(C_{1-6}$alkyl)sulfamoyl, and N,N-di-$(C_{1-6}$alkyl)sulfamoyl.

$R^a$ and $R^b$, for each occurrence, can be independently hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl.

$R^c$ is hydrogen or a $C_{1-4}$alkyl.

m can be 0 or 1, provided that when m is 0, $R^5$ comprises at least one nitrogen.

n can be an integer from 1 to 6.

p can be 0 or an integer from 1 to 6.

r, for each occurrence, can be independently 0, 1, or 2.

The compound is not 4,4'-((perfluoronaphthalene-2,7-diyl)bis(methylene))dipyridine, 3-(1,4-dioxaspiro[4.5]decan-8-ylamino)-8-methylisoquinoline-6-carboxylic acid, or (2-methoxy-3-(morpholinomethyl)quinolin-6-yl)(4-methoxycyclohexyl)methanone.

In another aspect, a pharmaceutical composition includes a pharmaceutically acceptable carrier or excipient and a compound represented by structural formula (Ia):

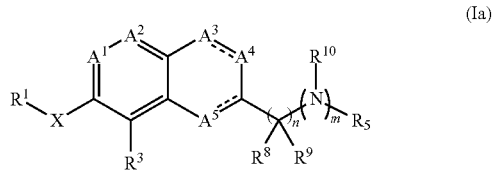
(Ia)

or a pharmaceutically acceptable salt thereof.

In formula (Ia), X can be O, $S(O)_r$, $NR^{12}$, C(O) or $CH_2$.

$A^1$ and $A^2$ can each independently be $CR^2$ or N.

$A^3$, $A^4$ and $A^5$ can each independently be $CR^2$, $C(R^2)_2$, N, or $NR^{19}$, provided that at least three of $A^1$, $A^2$, $A^3$, $A^4$, $A^5$, and $A^6$ are independently $CR^2$ or $C(R^2)_2$.

"------" indicates a double or a single bond.

$R^1$ can be a $C_{6-20}$alkyl, a $C_{3-14}$carbocyclyl, a 3- to 15-membered heterocyclyl, a $C_{6-10}$ aryl, or a five- to 14-membered heteroaryl, wherein the heterocyclyl and the heteroaryl comprising from 1 to 10 heteroatoms independently selected from N, S or O, and wherein R¹ may be optionally substituted with from one to six independently selected R⁶.

R², for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido.

R³ can be a halo, $C_{1-6}$haloalkyl or cyano.

R⁵ can be a $C_{1-6}$alkylene, $C_{3-8}$carbocyclyl, a 3- to 8-membered heterocyclyl, $C_{6-10}$aryl, a 5- to 10-membered heteroaryl, a bridged ring system comprising from 6 to 12 ring members, a spiro ring system comprising from 5-14 ring members, or a bicyclic ring system represented by the following formula:

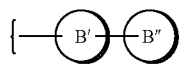

wherein B' and B" are independently selected from the group consisting of monocyclic $C_{3-8}$carbocyclyl, a monocyclic 3- to 8-membered heterocyclyl, phenyl or a 5- to 6-membered heteroaryl; wherein R⁵ may be optionally substituted with from 1 to 4 independently selected R¹¹.

R⁶, for each occurrence, can be independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two R⁶ that are attached to the same carbon atom may form $C_{3-8}$spirocycloalkyl or 3- to 8-membered spiroheterocycloalkyl.

R⁷ can be —OH, —C(O)OR¹⁵, —C(O)N(R¹⁶)₂, —C(O)N(R¹⁵)—S(O)₂R, —S(O)₂OR¹⁵, —C(O)NHC(O)R¹⁵, —Si(O)OH, —B(OH)₂, —N(R¹⁵)S(O)₂R¹⁵, —S(O)₂N(R¹⁵)₂, —O—P(O)(OR¹⁵)₂, —P(O)(OR¹⁵)₂, —CN, —S(O)₂NHC(O)R¹⁵, —C(O)NHS(O)₂R¹⁵, —C(O)NHOH, —C(O)NHCN, or a heteroaryl or a heterocyclyl selected from the group consisting of formulae (a)-(i'):

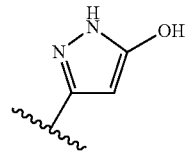 (a)

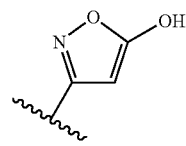 (b)

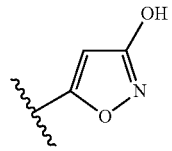 (c)

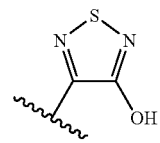 (d)

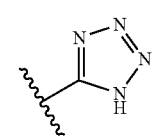 (e)

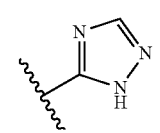 (f)

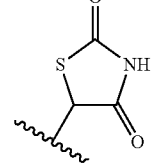 (g)

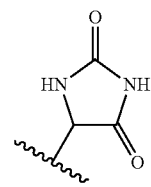 (h)

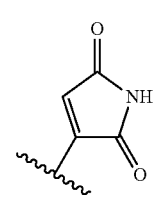 (i)

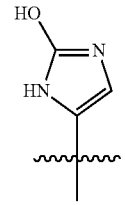 (j)

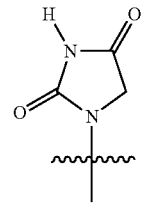 (k)

-continued
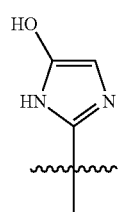
(l)
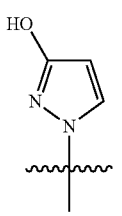
(m)
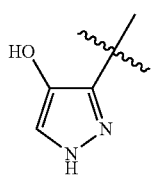
(n)
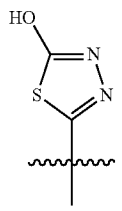
(o)
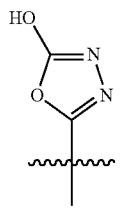
(p)
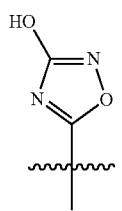
(q)
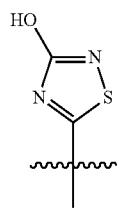
(r)
-continued
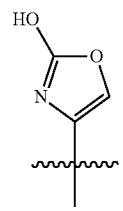
(s)
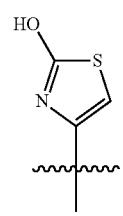
(t)
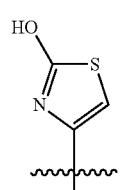
(u)
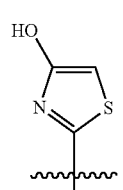
(v)
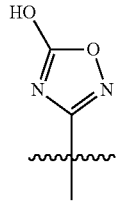
(w)
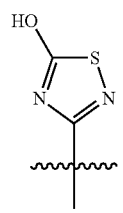
(x)
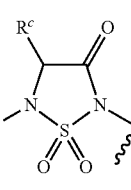
(y)
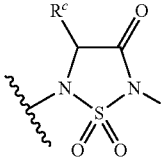
(z)

-continued (a') 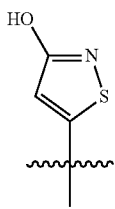

(b') 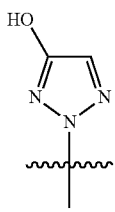

(c') 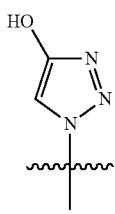

(d') 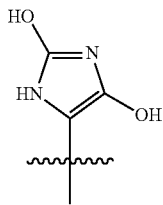

(e') 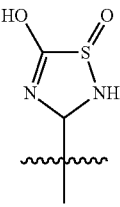

(f') 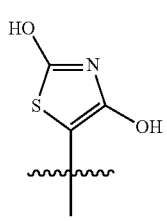

(g') 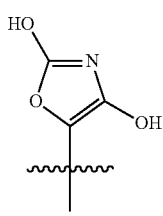

-continued (h') 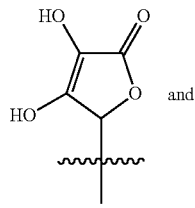 and (i') 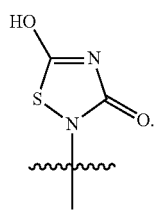.

$R^8$ and $R^9$ can each independently be hydrogen, a carboxy, $C_{1-6}$alkyl, or a $C_{2-6}$alkenyl; or $R^8$ and $R^9$ together with the carbon to which they are attached can be —C(=O)—, a $C_{3-8}$spirocycloalkyl, or a 3- to 8-membered spiroheterocycloalkyl.

$R^{10}$ and $R^{12}$ can each independently be hydrogen or a $C_{1-6}$alkyl.

$R^{11}$, for each occurrence, can be independently halo, hydroxyl, nitro, cyano, $C_{1-6}$alkyl, $C_{1-6}$haloalkyl, $C_{1-6}$alkoxy, —(CR$^{17}$R$^{18}$)$_p$—R$^7$, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —NR$^a$R$^b$, —C(O)NR$^a$R$^b$, —N(R$^a$)C(O)R$^b$, —C(O)R$^a$, —S(O)$_r$R$^a$, or —N(R$^a$)S(O)$_2$R$^b$.

$R^{15}$ for each occurrence can be independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

$R^{16}$ can be $R^{15}$; or two $R^{16}$ together with the nitrogen atom to which they are attached can form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl.

$R^{17}$ and $R^{18}$, for each occurrence, can be each independently hydrogen, a halo, or a $C_{1-4}$haloalkyl.

$R^{19}$ for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $C_{1-6}$alkoxycarbonyl, carbamoyl, N—($C_{1-6}$alkyl)carbamoyl, N,N-di-(C$_{1-6}$alkyl)carbamoyl, C$_{1-6}$alkylsulfonyl, sulfamoyl, N—(C$_{1-6}$alkyl)sulfamoyl, and N,N-di-(C$_{1-6}$alkyl)sulfamoyl.

R$^a$ and R$^b$, for each occurrence, can be independently hydrogen, C$_{1-6}$alkyl, C$_{2-6}$alkenyl, C$_{2-6}$alkynyl, C$_{3-8}$cycloalkyl, C$_{6-10}$aryl, or C$_{3-8}$halocycloalkyl.

R$^c$ is hydrogen or a C$_{1-4}$alkyl.

m can be 0 or 1, provided that when m is 0, R$^5$ comprises at least one nitrogen.

n can be an integer from 1 to 6.

p can be 0 or an integer from 1 to 6.

r, for each occurrence, can be independently 0, 1, or 2.

The compound is not 4,4'-((perfluoronaphthalene-2,7-diyl)bis(methylene))dipyridine.

In another aspect, a method of prevent, treating, or reducing symptoms of a condition mediated by ATX activity in a mammal comprising administering to said mammal an effective amount of a compound represented by structural formula (I):

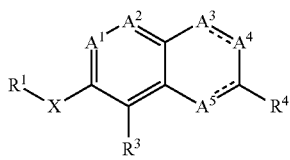

(I)

In formula (I), X can be O, S(O)$_r$, NR$^{12}$, C(O) or CH$_2$.

A$^1$ and A$^2$ can each independently be CR$^2$ or N.

A$^3$, A$^4$ and A$^5$ can each independently be CR$^2$, C(R$^2$)$_2$, N, or NR$^{19}$, provided that at least three of A$^1$, A$^2$, A$^3$, A$^4$, A$^5$, and A$^6$ are independently CR$^2$ or C(R$^2$)$_2$.

"------" indicates a double or a single bond.

R$^1$ can be a C$_{6-20}$alkyl, a C$_{3-14}$carbocyclyl, a 3- to 15-membered heterocyclyl, a C$_{6-10}$aryl, or a five- to 14-membered heteroaryl, wherein the heterocyclyl and the heteroaryl comprising from 1 to 10 heteroatoms independently selected from N, S or O, and wherein R$^1$ may be optionally substituted with from one to six independently selected R$^6$.

R$^2$, for each occurrence, can be independently selected from the group consisting of hydrogen, halo, hydroxyl, nitro, cyano, carboxy, C$_{1-6}$alkyl, C$_{1-6}$haloalkyl, C$_{3-8}$cycloalkyl, C$_{3-8}$halocycloalkyl, C$_{1-6}$alkoxy, C$_{1-6}$haloalkoxy, C$_{3-8}$cycloalkoxy, C$_{3-8}$halocycloalkoxy, C$_{1-6}$alkanoyl, amino, N—(C$_{1-6}$alkyl)amino, N,N-di-(C$_{1-6}$alkyl)amino, C$_{1-6}$alkoxycarbonyl, C$_{1-6}$alkanoyloxy, carbamoyl, N—(C$_{1-6}$alkyl)carbamoyl, N,N-di-(C$_{1-6}$alkyl)carbamoyl, C$_{1-6}$alkylamido, mercapto, C$_{1-6}$alkylthio, C$_{1-6}$alkylsulfonyl, sulfamoyl, N—(C$_{1-6}$alkyl)sulfamoyl, N,N-di-(C$_{1-6}$alkyl)sulfamoyl, and C$_{1-6}$alkylsulfonamido.

R$^3$ can be hydrogen, a halo, C$_{1-6}$haloalkyl or cyano, provided that when R$^3$ is hydrogen, R$^1$ is a C$_{3-8}$cycloalkyl which is optionally substituted with from 1 to 6.

R4 is a carboxylic acid or a group represented by the following formula:

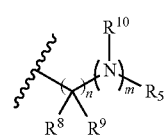

wherein ⌇ represents the point of attachment; provided that when R4 is a carboxylic acid, A1 is N and R1 is a C$_{3-8}$cycloalkyl which is optionally substituted with from 1 to 6.

R$^5$ can be a C$_{1-6}$alkylene, C$_{3-8}$carbocyclyl, a 3- to 8-membered heterocyclyl, C$_{6-10}$aryl, a 5- to 10-membered heteroaryl, a bridged ring system comprising from 6 to 12 ring members, a spiro ring system comprising from 5-14 ring members, or a bicyclic ring system represented by the following formula:

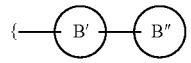

wherein B' and B" are independently selected from the group consisting of monocyclic C$_{3-8}$carbocyclyl, a monocyclic 3- to 8-membered heterocyclyl, phenyl or a 5- to 6-membered heteroaryl; wherein R$^5$ may be optionally substituted with from 1 to 4 independently selected R$^{11}$.

R$^6$, for each occurrence, can be independently selected from the group consisting of halo, C$_{1-6}$alkyl, C$_{1-6}$alkoxy, C$_{1-6}$haloalkyl, C$_{3-8}$cycloalkyl, C$_{6-10}$aryl, C$_{1-6}$alkoxy-C$_{1-6}$alkyl, and tri-(C$_{1-6}$alkyl)silyl; or two R$^6$ that are attached to the same carbon atom may form C$_{3-8}$spirocycloalkyl or 3- to 8-membered spiroheterocycloalkyl.

R$^7$ can be —OH, —C(O)OR$^{15}$, —C(O)N(R$^{16}$)$_2$, —C(O)N(R$^{15}$)—S(O)$_2$R$^{15}$, —S(O)$_2$OR$^{15}$, —C(O)NHC(O)R$^{15}$, —Si(O)OH, —B(OH)$_2$, —N(R$^{15}$)S(O)$_2$R$^{15}$, —S(O)$_2$N(R$^{15}$)$_2$, —O—P(O)(OR$^{15}$)$_2$, —P(O)(OR$^{15}$)$_2$, —CN, —S(O)$_2$NHC(O)R$^{15}$, —C(O)NHS(O)$_2$R$^{15}$, —C(O)NHOH, —C(O)NHCN, or a heteroaryl or a heterocyclyl selected from the group consisting of formulae (a)-(i'):

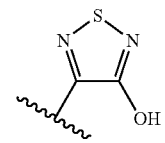

(a)

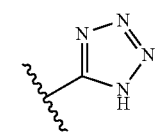

(b)

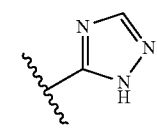

(c)

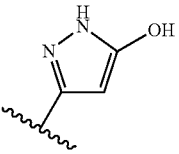

(d)

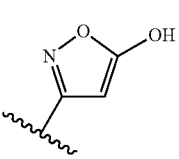

(e)

41
-continued
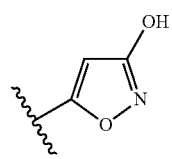 (f)
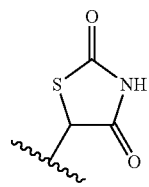 (g)
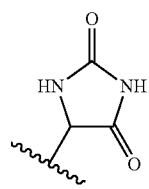 (h)
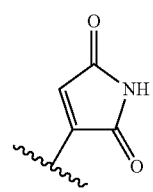 (i)
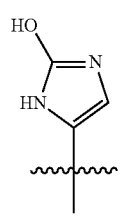 (j)
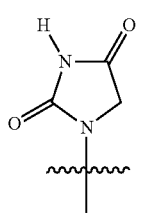 (k)
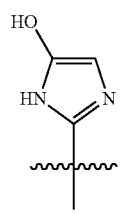 (l)
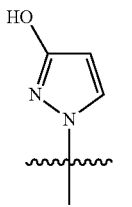 (m)
42
-continued
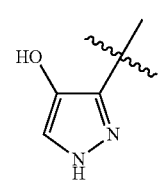 (n)
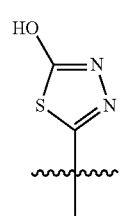 (o)
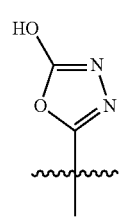 (p)
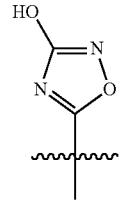 (q)
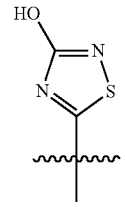 (r)
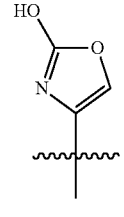 (s)
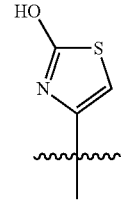 (t)

-continued
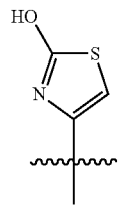 (u)
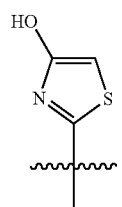 (v)
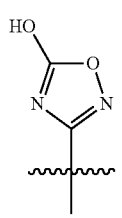 (w)
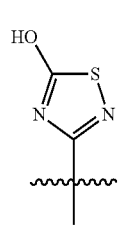 (x)
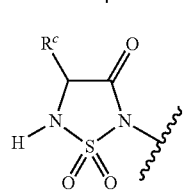 (y)
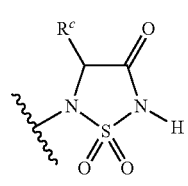 (z)
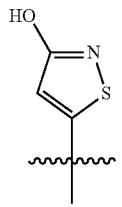 (a')
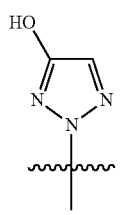 (b')
-continued
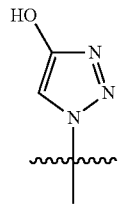 (c')
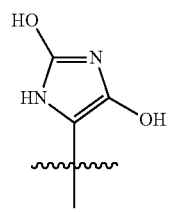 (d')
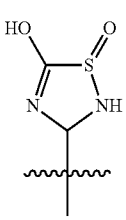 (e')
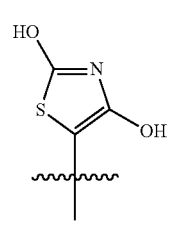 (f')
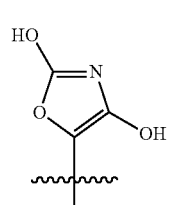 (g')
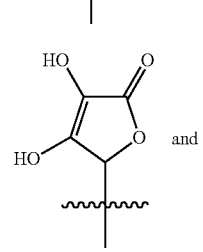 and (h')
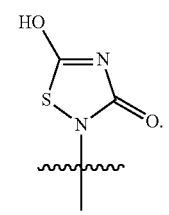 (i')
$R^8$ and $R^9$ can each independently be hydrogen, a carboxy, $C_{1-6}$alkyl, or a $C_{2-6}$alkenyl; or $R^8$ and $R^9$ together with the carbon to which they are attached can be —C(═O)—, a $C_{3-8}$spirocycloalkyl, or a 3- to 8-membered spiroheterocycloalkyl.

$R^{10}$ and $R^{12}$ can each independently be hydrogen or a $C_{1-6}$alkyl.

$R^{11}$, for each occurrence, can be independently halo, hydroxyl, nitro, cyano, $C_{1-6}$alkyl, $C_{1-6}$haloalkyl, $C_{1-6}$alkoxy, —$(CR^{17}R^{18})_p$—$R^7$, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —$C(O)NR^aR^b$, —$N(R^a)C(O)R^b$, —$C(O)R^a$, —$S(O)_rR^a$, or —$N(R^a)S(O)_2R^b$.

$R^{15}$ for each occurrence can be independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

$R^{16}$ can be $R^{15}$; or two $R^{16}$ together with the nitrogen atom to which they are attached can form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

$R^{17}$ and $R^{18}$, for each occurrence, can be each independently hydrogen, a halo, or a $C_{1-4}$haloalkyl.

$R^{19}$ for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, ($C_{1-6}$alkoxycarbonyl, carbamoyl, N—($C_{1-6}$alkyl)carbamoyl, N,N-di-($C_{1-6}$alkyl)carbamoyl, $C_{1-6}$alkylsulfonyl, sulfamoyl, N—($C_{1-6}$alkyl)sulfamoyl, and N,N-di-($C_{1-6}$alkyl)sulfamoyl.

$R^a$ and $R^b$, for each occurrence, can be independently hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl.

$R^c$ is hydrogen or a $C_{1-4}$alkyl.

m can be 0 or 1, provided that when m is 0, $R^5$ comprises at least one nitrogen.

n can be an integer from 1 to 6.

p can be 0 or an integer from 1 to 6.

r, for each occurrence, can be independently 0, 1, or 2.

The compound is not 4,4'-((perfluoronaphthalene-2,7-diyl)bis(methylene))dipyridine, 3-(1,4-dioxaspiro[4.5]decan-8-ylamino)-8-methylisoquinoline-6-carboxylic acid, or (2-methoxy-3-(morpholinomethyl)quinolin-6-yl)(4-methoxycyclohexyl)methanone.

In another aspect, a method of prevent, treating, or reducing symptoms of a condition mediated by ATX activity in a mammal comprising administering to said mammal an effective amount of a compound represented by structural formula (Ia):

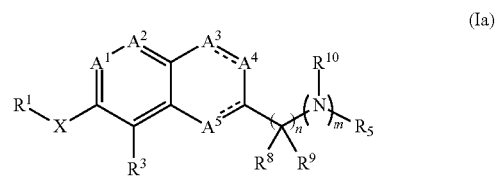

(Ia)

In formula (Ia), X can be O, $S(O)_r$, $NR^{12}$, C(O) or $CH_2$.

$A^1$ and $A^2$ can each independently be $CR^2$ or N.

$A^3$, $A^4$ and $A^5$ can each independently be $CR^2$, $C(R^2)_2$, N, or $NR^{19}$, provided that at least three of $A^1$, $A^2$, $A^3$, $A^4$, $A^5$, and $A^6$ are independently $CR^2$ or $C(R^2)_2$.

"------" indicates a double or a single bond.

$R^1$ can be a $C_{6-20}$alkyl, a $C_{3-14}$carbocyclyl, a 3- to 15-membered heterocyclyl, a $C_{6-10}$aryl, or a five- to 14-membered heteroaryl, wherein the heterocyclyl and the heteroaryl comprising from 1 to 10 heteroatoms independently selected from N, S or O, and wherein $R^1$ may be optionally substituted with from one to six independently selected $R^6$.

$R^2$, for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido.

$R^3$ can be a halo, $C_{1-6}$haloalkyl or cyano.

$R^5$ can be a $C_{1-6}$alkylene, $C_{3-8}$carbocyclyl, a 3- to 8-membered heterocyclyl, $C_{6-10}$aryl, a 5- to 10-membered heteroaryl, a bridged ring system comprising from 6 to 12 ring members, a spiro ring system comprising from 5-14 ring members, or a bicyclic ring system represented by the following formula:

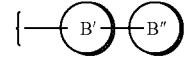

wherein B' and B" are independently selected from the group consisting of monocyclic $C_{3-8}$carbocyclyl, a monocyclic 3- to 8-membered heterocyclyl, phenyl or a 5- to 6-membered heteroaryl; wherein $R^5$ may be optionally substituted with from 1 to 4 independently selected $R^{11}$.

$R^6$, for each occurrence, can be independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom may form $C_{3-8}$spirocycloalkyl or 3- to 8-membered spiroheterocycloalkyl.

$R^7$ can be —OH, —$C(O)OR^{15}$, —$C(O)N(R^{16})_2$, —$C(O)N(R^{15})$—$S(O)_2R^{15}$, —$S(O)_2OR^{15}$, —$C(O)NHC(O)R^{15}$, —$Si(O)OH$, —$B(OH)_2$, —$N(R^{15})S(O)_2R^{15}$, —$S(O)_2N(R^{15})_2$, —O—$P(O)(OR^{15})_2$, —$P(O)(OR^{15})_2$, —CN, —$S(O)_2NHC(O)R^{15}$, —$C(O)NHS(O)_2R^{15}$, —C(O)NHOH, —C(O)NHCN, or a heteroaryl or a heterocyclyl selected from the group consisting of formulae (a)-(i'):

47
(a) 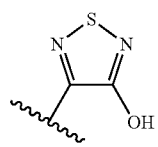
(b) 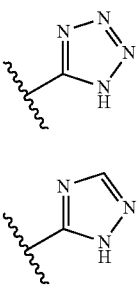
(c) 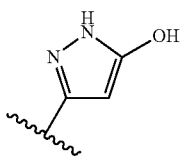
(d) 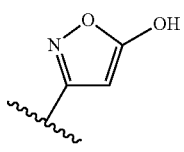
(e) 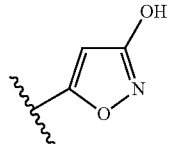
(f) 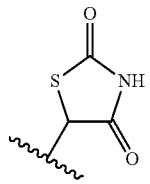
(g) 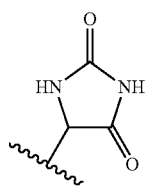
(h) 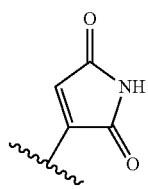
(i)
48
-continued
(j) 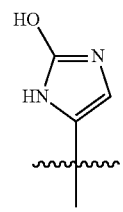
(k) 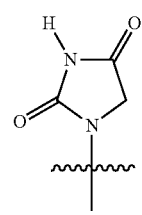
(l) 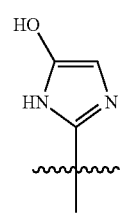
(m) 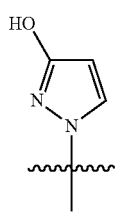
(n) 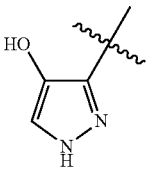
(o) 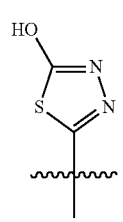
(p) 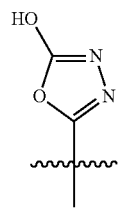

(q) 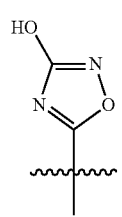
(r) 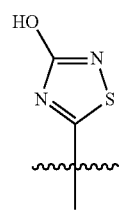
(s) 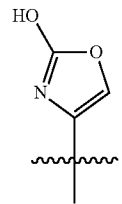
(t) 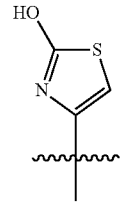
(u) 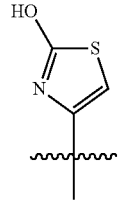
(v) 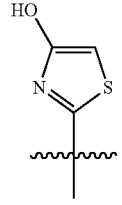
(w) 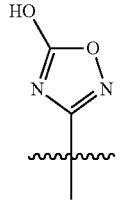
(x) 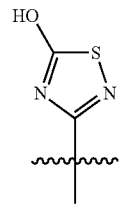
(y) 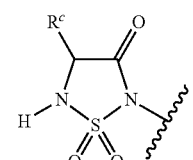
(z) 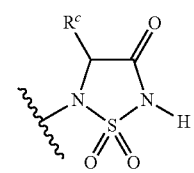
(a') 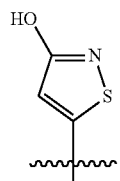
(b') 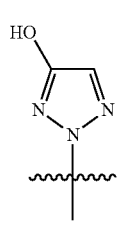
(c') 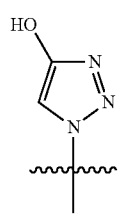
(d') 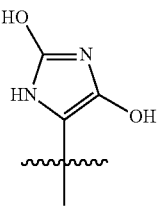
(e') 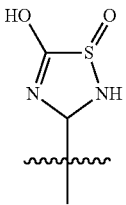

-continued

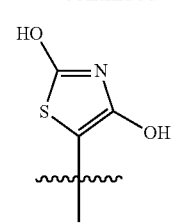
(f')

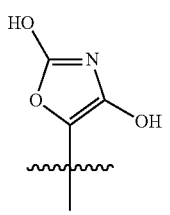
(g')

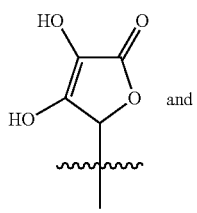 and
(h')

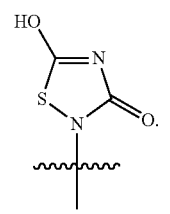
(i')

$R^8$ and $R^9$ can each independently be hydrogen, a carboxy, $C_{1-6}$alkyl, or a $C_{2-6}$alkenyl; or $R^8$ and $R^9$ together with the carbon to which they are attached can be —C(=O)—, a $C_{3-8}$spirocycloalkyl, or a 3- to 8-membered spiroheterocycloalkyl.

$R^{10}$ and $R^{12}$ can each independently be hydrogen or a $C_{1-6}$alkyl.

$R^{11}$, for each occurrence, can be independently halo, hydroxyl, nitro, cyano, $C_{1-6}$alkyl, $C_{1-6}$haloalkyl, $C_{1-6}$alkoxy, —$(CR^{17}R^{18})_p$—$R^7$, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —$C(O)NR^aR^b$, —$N(R^a)C(O)R^b$, —$C(O)R^a$, —$S(O)_rR^a$, or —$N(R^a)S(O)_2R^b$.

$R^{15}$ for each occurrence can be independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—$(C_{1-4}$alkyl)amino, N,N-di-$(C_{1-4}$alkyl)amino, carbamoyl, N—$(C_{1-4}$alkyl)carbamoyl, N,N-di-$(C_{1-4}$alkyl)carbamoyl, $C_{1-4}$alkylamido, $C_{1-4}$alkylsulfonyl, $C_{1-4}$alkylsulfonamido, sulfamoyl, N—$(C_{1-4}$alkyl)sulfamoyl, and N,N—$(C_{1-4}$dialkyl)-sulfamoyl.

$R^{16}$ can be $R^{15}$; or two $R^{16}$ together with the nitrogen atom to which they are attached can form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—$(C_{1-4}$alkyl)amino, N,N-di-$(C_{1-4}$alkyl)amino, carbamoyl, N—$(C_{1-4}$alkyl)carbamoyl, N,N-di-$(C_{1-4}$alkyl)carbamoyl, $C_{1-4}$alkylamido, $C_{1-4}$alkylsulfonyl, $C_{1-4}$alkylsulfonamido, sulfamoyl, N—$(C_{1-4}$alkyl)sulfamoyl, and N,N—$(C_{1-4}$dialkyl)-sulfamoyl.

$R^{17}$ and $R^{18}$, for each occurrence, can be each independently hydrogen, a halo, or a $C_{1-4}$haloalkyl.

$R^{19}$ for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $C_{1-6}$alkoxycarbonyl, carbamoyl, N—$(C_{1-6}$alkyl)carbamoyl, N,N-di-$(C_{1-6}$alkyl)carbamoyl, $C_{1-6}$alkylsulfonyl, sulfamoyl, N—$(C_{1-6}$alkyl)sulfamoyl, and N,N-di-$(C_{1-6}$alkyl)sulfamoyl.

$R^a$ and $R^b$, for each occurrence, can be independently hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl.

$R^c$ is hydrogen or a $C_{1-4}$alkyl.

m can be 0 or 1, provided that when m is 0, $R^5$ comprises at least one nitrogen.

n can be an integer from 1 to 6.

p can be 0 or an integer from 1 to 6.

r, for each occurrence, can be independently 0, 1, or 2.

The compound is not 4,4'-((perfluoronaphthalene-2,7-diyl)bis(methylene))dipyridine.

The condition can be selected from the group consisting of an inflammatory disorder, an autoimmune disorder, a fibrosis of the lung, or a malignancy of the lung. The inflammatory disorder can be rheumatoid arthritis. The autoimmune disorder can be multiple sclerosis. The method can further include administering to said mammal an effective amount of one or more drugs selected from the group consisting of: a corticosteroid, a bronchodilator, an antiasthmatic, an antiinflammatory, an antirheumatic, an immunosuppressant, an antimetabolite, an immunomodulator, an antipsoriatic, and an antidiabetic.

In another aspect, a method of preventing, treating, or reducing chronic pain in a mammal includes administering to said mammal an effective amount of a compound, or a pharmaceutically acceptable salt thereof, represented by formula (I):

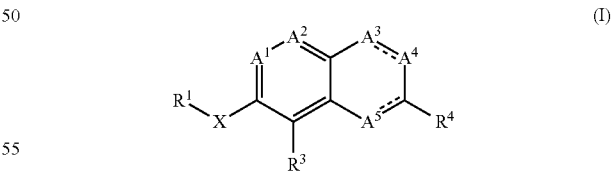
(I)

In formula (I), X can be O, $S(O)_r$, $NR^{12}$, C(O) or $CH_2$.

$A^1$ and $A^2$ can each independently be $CR^2$ or N.

$A^3$, $A^4$ and $A^5$ can each independently be $CR^2$, $C(R^2)_2$, N, or $NR^{19}$, provided that at least three of $A^1$, $A^2$, $A^3$, $A^4$, $A^5$, and $A^6$ are independently $CR^2$ or $C(R^2)_2$.

"------" indicates a double or a single bond.

$R^1$ can be a $C_{6-20}$alkyl, a $C_{3-14}$carbocyclyl, a 3- to 15-membered heterocyclyl, a $C_{6-10}$aryl, or a five- to 14-membered heteroaryl, wherein the heterocyclyl and the heteroaryl comprising from 1 to 10 heteroatoms independently selected from N, S or O, and wherein $R^1$ may be optionally substituted with from one to six independently selected $R^6$.

$R^2$, for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido.

$R^3$ can be hydrogen, a halo, $C_{1-6}$haloalkyl or cyano, provided that when $R^3$ is hydrogen, $R^1$ is a $C_{3-8}$cycloalkyl which is optionally substituted with from 1 to 6.

R4 is a carboxylic acid or a group represented by the following formula:

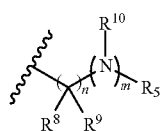

wherein ⸹ represents the point of attachment; provided that when R4 is a carboxylic acid, A1 is N and R1 is a $C_{3-8}$cycloalkyl which is optionally substituted with from 1 to 6.

$R^5$ can be a $C_{1-6}$alkylene, $C_{3-8}$carbocyclyl, a 3- to 8-membered heterocyclyl, $C_{6-10}$aryl, a 5- to 10-membered heteroaryl, a bridged ring system comprising from 6 to 12 ring members, a spiro ring system comprising from 5-14 ring members, or a bicyclic ring system represented by the following formula:

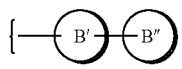

wherein B' and B" are independently selected from the group consisting of monocyclic $C_{3-8}$carbocyclyl, a monocyclic 3- to 8-membered heterocyclyl, phenyl or a 5- to 6-membered heteroaryl; wherein $R^5$ may be optionally substituted with from 1 to 4 independently selected $R^{11}$.

$R^6$, for each occurrence, can be independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom may form $C_{3-8}$spirocycloalkyl or 3- to 8-membered spiroheterocycloalkyl.

$R^7$ can be —OH, —C(O)O$R^{15}$, —C(O)N($R^{16}$)$_2$, —C(O)N($R^{15}$)—S(O)$_2$$R^{15}$, —S(O)$_2$O$R^{15}$, —C(O)NHC(O)$R^{15}$, —Si(O)OH, —B(OH)$_2$, —N($R^{15}$)S(O)$_2$$R^{15}$, —S(O)$_2$N($R^{15}$)$_2$, —O—P(O)(O$R^{15}$)$_2$, —P(O)(O$R^{15}$)$_2$, —CN, —S(O)$_2$NHC(O)$R^{15}$, —C(O)NHS(O)$_2$$R^{15}$, —C(O)NHOH, —C(O)NHCN, or a heteroaryl or a heterocyclyl selected from the group consisting of formulae (a)-(i'):

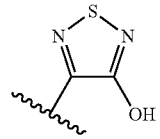

(a)

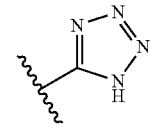

(b)

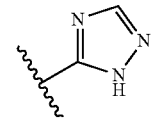

(c)

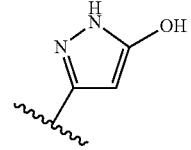

(d)

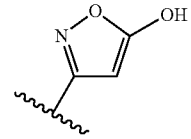

(e)

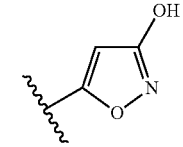

(f)

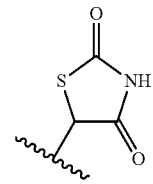

(g)

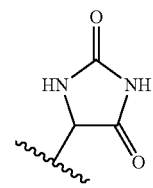

(h)

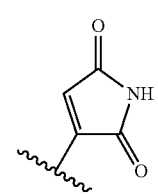

(i)

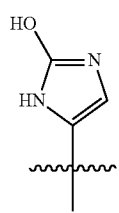 (j)
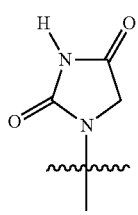 (k)
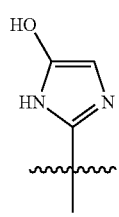 (l)
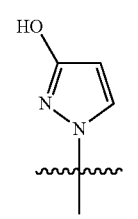 (m)
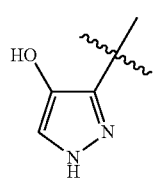 (n)
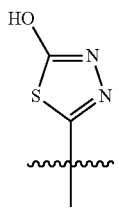 (o)
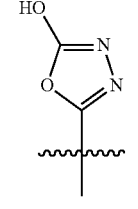 (p)
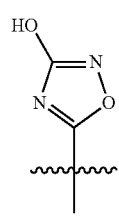 (q)
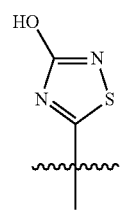 (r)
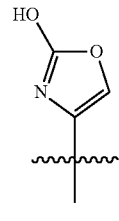 (s)
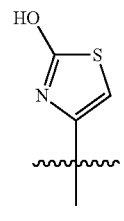 (t)
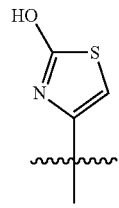 (u)
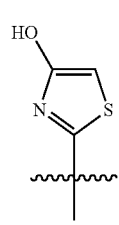 (v)
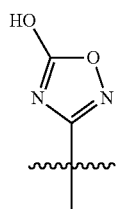 (w)

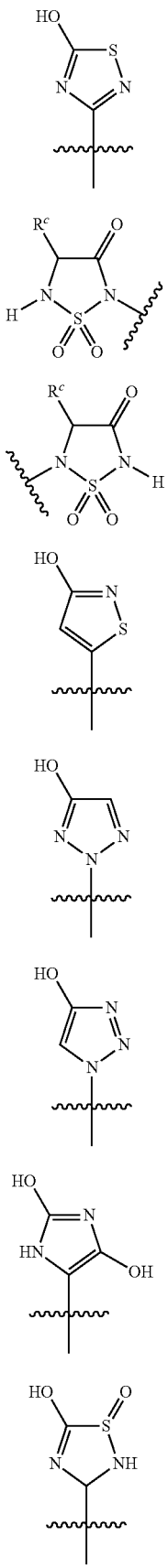
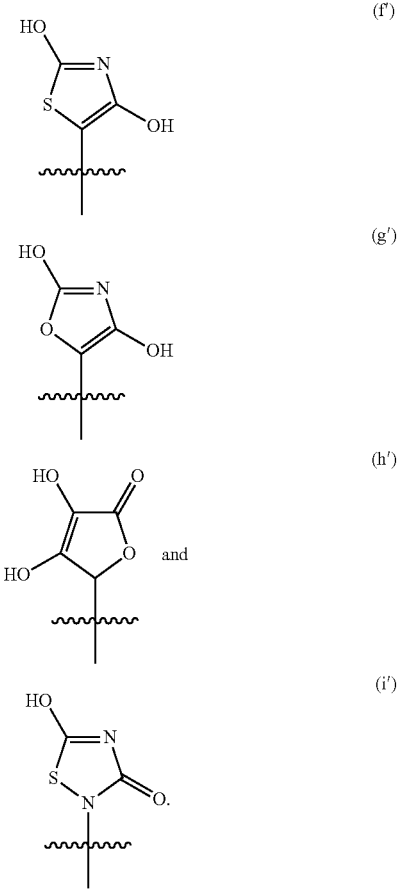

$R^8$ and $R^9$ can each independently be hydrogen, a carboxy, $C_{1-6}$alkyl, or a $C_{2-6}$alkenyl; or $R^8$ and $R^9$ together with the carbon to which they are attached can be —C(=O)—, a $C_{3-8}$spirocycloalkyl, or a 3- to 8-membered spiroheterocycloalkyl.

$R^{10}$ and $R^{12}$ can each independently be hydrogen or a $C_{1-6}$alkyl.

$R^{11}$, for each occurrence, can be independently halo, hydroxyl, nitro, cyano, $C_{1-6}$alkyl, $C_{1-6}$haloalkyl, $C_{1-6}$alkoxy, —$(CR^{17}R^{18})_p$—$R^7$, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —$C(O)NR^aR^b$, —$N(R^a)C(O)R^b$, —$C(O)R^a$, —$S(O)_rR^a$, or —$N(R^a)S(O)_2R^b$.

$R^{15}$ for each occurrence can be independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

$R^{16}$ can be $R^{15}$; or two $R^{16}$ together with the nitrogen atom to which they are attached can form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl.

$R^{17}$ and $R^{18}$, for each occurrence, can be each independently hydrogen, a halo, or a $C_{1-4}$haloalkyl.

$R^{19}$ for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $C_{1-6}$alkoxycarbonyl, carbamoyl, N—($C_{1-6}$alkyl)carbamoyl, N,N-di-($C_{1-6}$alkyl)carbamoyl, $C_{1-6}$alkylsulfonyl, sulfamoyl, N—($C_{1-6}$alkyl)sulfamoyl, and N,N-di-($C_{1-6}$alkyl)sulfamoyl.

$R^a$ and $R^b$, for each occurrence, can be independently hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl.

$R^c$ is hydrogen or a $C_{1-4}$alkyl.

m can be 0 or 1, provided that when m is 0, $R^5$ comprises at least one nitrogen.

n can be an integer from 1 to 6.

p can be 0 or an integer from 1 to 6.

r, for each occurrence, can be independently 0, 1, or 2.

The compound is not 4,4'-((perfluoronaphthalene-2,7-diyl)bis(methylene))dipyridine, 3-(1,4-dioxaspiro[4.5]decan-8-ylamino)-8-methylisoquinoline-6-carboxylic acid, or (2-methoxy-3-(morpholinomethyl)quinolin-6-yl)(4-methoxycyclohexyl)methanone.

In another aspect, a method of preventing, treating, or reducing chronic pain in a mammal includes administering to said mammal an effective amount of a compound, or a pharmaceutically acceptable salt thereof, represented by formula (Ia):

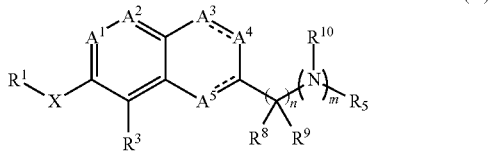

(Ia)

or a pharmaceutically acceptable salt thereof, wherein:

X is O, $S(O)_r$, $NR^{12}$, C(O) or $CH_2$;

$A^1$ and $A^2$ are each independently $CR^2$ or N;

$A^3$, $A^4$ and $A^5$ are each independently $CR^2$, $C(R^2)_2$, N, or $NR^{19}$, provided that at least three of $A^1$, $A^2$, $A^3$, $A^4$, $A^5$, and $A^6$ are independently $CR^2$ or $C(R^2)_2$;

"-----" indicates a double or a single bond;

$R^1$ is a $C_{6-20}$alkyl, a $C_{3-14}$carbocyclyl, a 3- to 15-membered heterocyclyl, a $C_{6-10}$aryl, or a five- to 14-membered heteroaryl, wherein the heterocyclyl and the heteroaryl comprising from 1 to 10 heteroatoms independently selected from N, S or O, and wherein $R^1$ may be optionally substituted with from one to six independently selected $R^6$;

$R^2$, for each occurrence, is independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido;

$R^3$ is a halo, $C_{1-6}$haloalkyl or cyano;

$R^5$ is a $C_{1-6}$alkylene, $C_{3-8}$carbocyclyl, a 3- to 8-membered heterocyclyl, $C_{6-10}$aryl, a 5- to 10-membered heteroaryl, a bridged ring system comprising from 6 to 12 ring members, a spiro ring system comprising from 5-14 ring members, or a bicyclic ring system represented by the following formula:

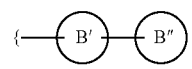

wherein B' and B" are independently selected from the group consisting of monocyclic $C_{3-8}$carbocyclyl, a monocyclic 3- to 8-membered heterocyclyl, phenyl or a 5- to 6-membered heteroaryl; wherein $R^5$ may be optionally substituted with from 1 to 4 independently selected $R^{11}$;

$R^6$, for each occurrence, is independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom may form $C_{3-8}$spirocycloalkyl or 3- to 8-membered spiroheterocycloalkyl;

$R^7$ is —OH, —C(O)O$R^{15}$, —C(O)N($R^{16}$)$_2$, —C(O)N($R^{15}$)—S(O)$_2R^{15}$, —S(O)$_2$O$R^{15}$, —C(O)NHC(O)$R^{15}$, —Si(O)OH, —B(OH)$_2$, —N($R^{15}$)S(O)$_2R^{15}$, —S(O)$_2$N($R^{15}$)$_2$, —O—P(O)(O$R^{15}$)$_2$, —P(O)(O$R^{15}$)$_2$, —CN, —S(O)$_2$NHC(O)$R^{15}$, —C(O)NHS(O)$_2R^{15}$, —C(O)NHOH, —C(O)NHCN, or a heteroaryl or a heterocyclyl selected from the group consisting of formulae (a)-(i'):

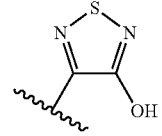

(a)

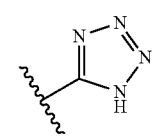

(b)

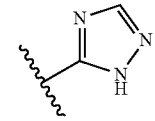

(c)

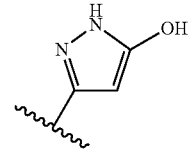

(d)

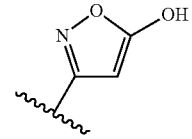

(e)

-continued
(f) 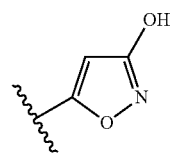
(g) 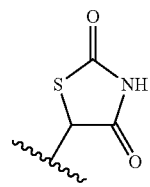
(h) 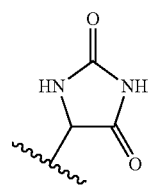
(i) 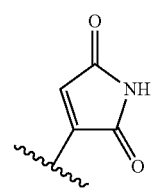
(j) 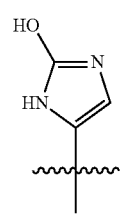
(k) 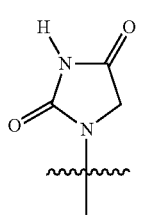
(l) 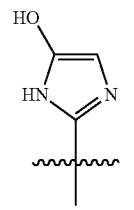
(m) 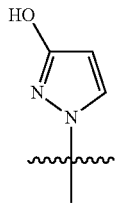
-continued
(n) 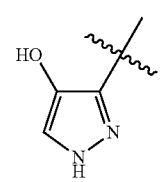
(o) 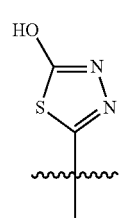
(p) 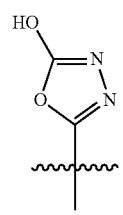
(q) 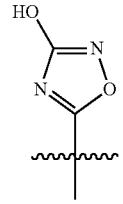
(r) 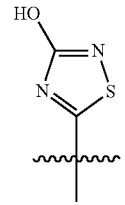
(s) 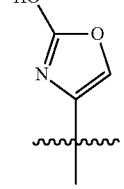
(t) 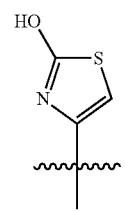

(u) 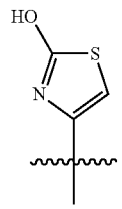
(v) 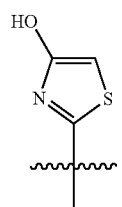
(w) 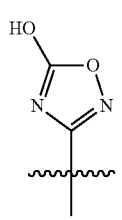
(x) 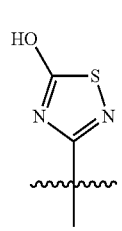
(y) 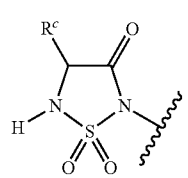
(z) 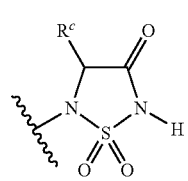
(a') 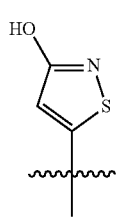
(b') 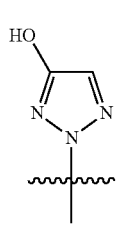
(c') 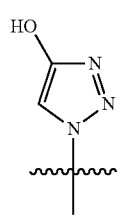
(d') 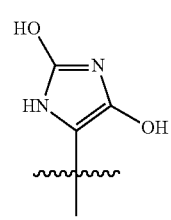
(e') 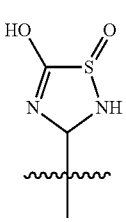
(f') 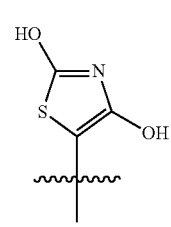
(g') 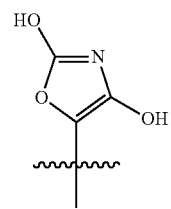
(h') 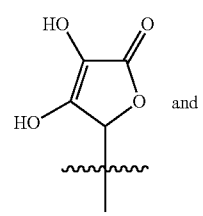
and
(i') 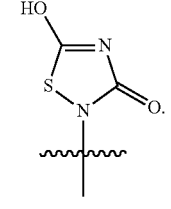
$R^8$ and $R^9$ are each independently hydrogen, a carboxy, $C_{1-6}$alkyl, or a $C_{2-6}$alkenyl; or $R^8$ and $R^9$ together with the carbon to which they are attached are —C(=O)—, a $C_{3-8}$spirocycloalkyl, or a 3- to 8-membered spiroheterocycloalkyl;

$R^{10}$ and $R^{12}$ are each, independently, hydrogen or a $C_{1-6}$alkyl;

$R^{11}$, for each occurrence, is independently halo, hydroxyl, nitro, cyano, $C_{1-6}$alkyl, $C_{1-6}$haloalkyl, $C_{1-6}$alkoxy, $-(CR^{17}R^{18})_p-R^7$, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, $-NR^aR^b$, $-C(O)NR^aR^b$, $-N(R^a)C(O)R^b$, $-C(O)R^a$, $-S(O)_rR^a$, or $-N(R^a)S(O)_2R^b$;

$R^{15}$ for each occurrence is independently selected from the group consisting of hydrogen, $C_{1-6}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, $N-(C_{1-4}$alkyl$)$amino, N,N-di-$(C_{1-4}$alkyl$)$amino, carbamoyl, $N-(C_{1-4}$alkyl$)$carbamoyl, N,N-di-$(C_{1-4}$alkyl$)$carbamoyl, $C_{1-4}$alkylamido, $C_{1-4}$alkylsulfonyl, $C_{1-4}$alkylsulfonamido, sulfamoyl, $N-(C_{1-4}$alkyl$)$sulfamoyl, and N,N—$(C_{1-4}$dialkyl$)$-sulfamoyl;

$R^{16}$ is $R^{15}$; or two $R^{16}$ together with the nitrogen atom to which they are attached form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, $N-(C_{1-4}$alkyl$)$amino, N,N-di-$(C_{1-4}$alkyl$)$amino, carbamoyl, $N-(C_{1-4}$alkyl$)$carbamoyl, N,N-di-$(C_{1-4}$alkyl$)$carbamoyl, $C_{1-4}$alkylamido, $C_{1-4}$alkylsulfonyl, $C_{1-4}$alkylsulfonamido, sulfamoyl, $N-C_{1-4}$alkylsulfamoyl, and N,N—$(C_{1-4}$dialkyl$)$-sulfamoyl;

$R^{17}$ and $R^{18}$, for each occurrence, are each independently hydrogen, a halo, or a $C_{1-4}$haloalkyl;

$R^{19}$ for each occurrence is independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $C_{1-6}$alkoxycarbonyl, carbamoyl, $N-(C_{1-6}$alkyl$)$carbamoyl, N,N-di-$(C_{1-6}$alkyl$)$carbamoyl, $C_{1-6}$alkylsulfonyl, sulfamoyl, $N-(C_{1-6}$alkyl$)$sulfamoyl, and N,N-di-$(C_{1-6}$alkyl$)$sulfamoyl;

$R^a$ and $R^b$, for each occurrence, are independently hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl;

$R^c$ is hydrogen or a $C_{1-4}$alkyl;

m is 0 or 1, provided that when m is 0, $R^5$ comprises at least one nitrogen;

n is an integer from 1 to 6;

p is 0 or an integer from 1 to 6; and r, for each occurrence, is independently 0, 1, or 2;

provided that the compound is not 4,4'-((perfluoronaphthalene-2,7-diyl)bis(methylene))dipyridine.

In some embodiments, the chronic pain can be inflammatory pain or neuropathic pain.

Other features or advantages will be apparent from the following detailed description of several embodiments, and also from the appended claims.

DETAILED DESCRIPTION

The disclosed compounds can have activity as ATX modulators. In particular, the compounds can be ATX inhibitors.

In one embodiment, the invention provides a compound represented by formula (I):

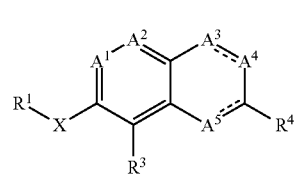

or a pharmaceutically acceptable salt thereof, wherein

X can be O, $S(O)_r$, $NR^{12}$, $C(O)$ or $CH_2$.

$A^1$ and $A^2$ can each independently be $CR^2$ or N.

$A^3$, $A^4$ and $A^5$ can each independently be $CR^2$, $C(R^2)_2$, N, or $NR^{19}$, provided that at least three of $A^1$, $A^2$, $A^3$, $A^4$, $A^5$, and $A^6$ are independently $CR^2$ or $C(R^2)_2$.

"------" indicates a double or a single bond.

$R^1$ can be a $C_{6-20}$alkyl, a $C_{3-14}$carbocyclyl, a 3- to 15-membered heterocyclyl, a $C_{6-10}$aryl, or a five- to 14-membered heteroaryl, wherein the heterocyclyl and the heteroaryl comprising from 1 to 10 heteroatoms independently selected from N, S or O, and wherein $R^1$ may be optionally substituted with from one to six independently selected $R^6$.

$R^2$, for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, $N-(C_{1-6}$alkyl$)$amino, N,N-di-$(C_{1-6}$alkyl$)$amino, $C_{1-6}$alkoxycarbonyl, $C_{1-6}$alkanoyloxy, carbamoyl, $N-(C_{1-6}$alkyl$)$carbamoyl, N,N-di-$(C_{1-6}$alkyl$)$carbamoyl, $C_{1-6}$alkylamido, mercapto, $C_{1-6}$alkylthio, $C_{1-6}$alkylsulfonyl, sulfamoyl, $N-(C_{1-6}$alkyl$)$sulfamoyl, N,N-di-$(C_{1-6}$alkyl$)$sulfamoyl, and $C_{1-6}$alkylsulfonamido.

$R^3$ can be hydrogen, a halo, $C_{1-6}$haloalkyl or cyano, provided that when $R^3$ is hydrogen, $R^1$ is a $C_{3-8}$cycloalkyl which is optionally substituted with from 1 to 6.

R4 is a carboxylic acid or a group represented by the following formula:

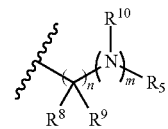

wherein ⸹ represents the point of attachment; provided that when R4 is a carboxylic acid, A1 is N and R1 is a $C_{3-8}$cycloalkyl which is optionally substituted with from 1 to 6.

$R^5$ can be a $C_{1-6}$alkylene, $C_{3-8}$carbocyclyl, a 3- to 8-membered heterocyclyl, $C_{6-10}$aryl, a 5- to 10-membered heteroaryl, a bridged ring system comprising from 6 to 12 ring members, a spiro ring system comprising from 5-14 ring members, or a bicyclic ring system represented by the following formula:

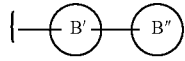

wherein B' and B" are independently selected from the group consisting of monocyclic $C_{3-8}$carbocyclyl, a monocyclic 3- to 8-membered heterocyclyl, phenyl or a 5- to 6-membered heteroaryl; wherein $R^5$ may be optionally substituted with from 1 to 4 independently selected $R^{11}$.

$R^6$, for each occurrence, can be independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom may form $C_{3-8}$spirocycloalkyl or 3- to 8-membered spiroheterocycloalkyl.

$R^7$ can be —OH, —C(O)OR$^{15}$, —C(O)N(R$^{15}$)$_2$, —C(O)N(R$^{15}$)—S(O)$_2$R$^{15}$, —S(O)$_2$OR$^{15}$, —C(O)NHC(O)R$^{15}$, —Si(O)OH, —B(OH)$_2$, —N(R$^{15}$)S(O)$_2$R$^{15}$, —S(O)$_2$N(R$^{15}$)$_2$, —O—P(O)(OR$^{15}$)$_2$, —P(O)(OR$^{15}$)$_2$, —CN, —S(O)$_2$NHC(O)R$^{15}$, —C(O)NHS(O)$_2$R$^{15}$, —C(O)NHOH, —C(O)NHCN, or a heteroaryl or a heterocyclyl selected from the group consisting of formulae (a)-(i'):

(a) 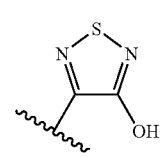

(b) 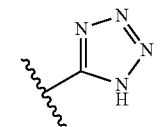

(c) 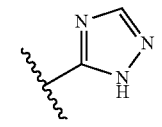

(d) 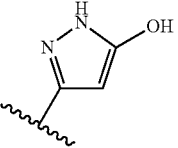

(e) 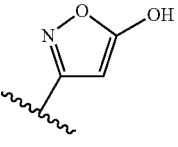

(f) 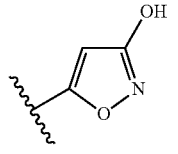

(g) 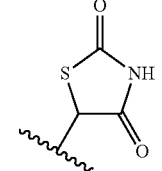

(h) 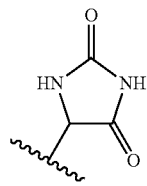

(i) 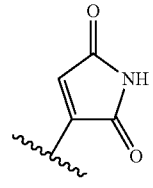

(j) 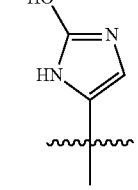

(k) 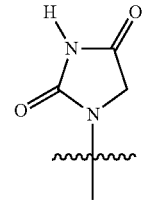

(l) 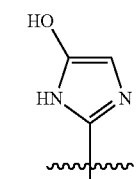

(m) 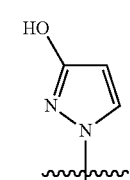

(n) 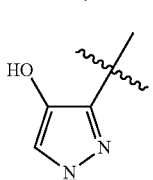

(o) 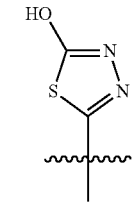

-continued
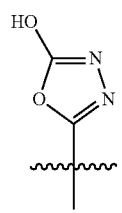 (p)
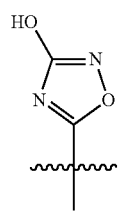 (q)
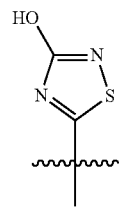 (r)
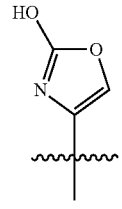 (s)
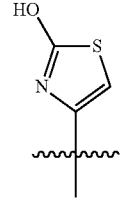 (t)
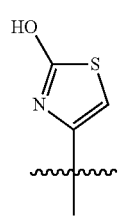 (u)
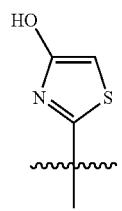 (v)
-continued
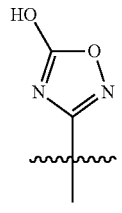 (w)
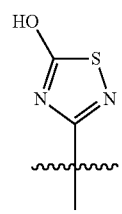 (x)
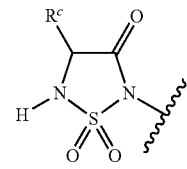 (y)
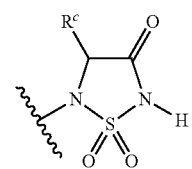 (z)
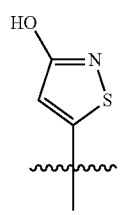 (a′)
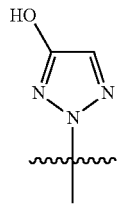 (b′)
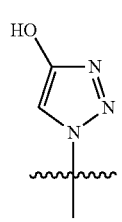 (c′)
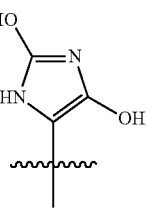 (d′)

-continued

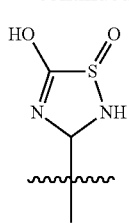
(e')

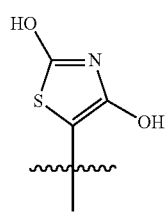
(f')

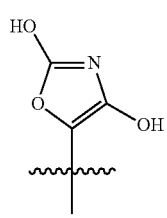
(g')

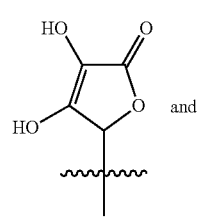
(h')

and

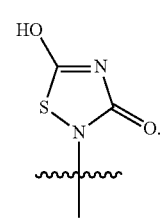
(i')

$R^8$ and $R^9$ can each independently be hydrogen, a carboxy, $C_{1-6}$alkyl, or a $C_{2-6}$alkenyl; or $R^8$ and $R^9$ together with the carbon to which they are attached can be —C(=O)—, a $C_{3-8}$spirocycloalkyl, or a 3- to 8-membered spiroheterocycloalkyl.

$R^{10}$ and $R^{12}$ can each independently be hydrogen or a $C_{1-6}$alkyl.

$R^{11}$, for each occurrence, can be independently halo, hydroxyl, nitro, cyano, $C_{1-6}$alkyl, $C_{1-6}$haloalkyl, $C_{1-6}$alkoxy, —$(CR^{17}R^{18})_p$—$R^7$, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —$C(O)NR^aR^b$, —$N(R^a)C(O)R^b$, —$C(O)R^a$, —$S(O)_rR^a$, or —$N(R^a)S(O)_2R^b$.

$R^{15}$ for each occurrence can be independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

$R^{16}$ can be $R^{15}$; or two $R^{16}$ together with the nitrogen atom to which they are attached can form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, ($C_{1-4}$alkylsulfonyl, ($C_{1-4}$alkylsulfonamido, sulfamoyl, N—($C_{1-4}$alkyl)sulfamoyl, and N,N—($C_{1-4}$dialkyl)-sulfamoyl.

$R^{17}$ and $R^{18}$, for each occurrence, can be each independently hydrogen, a halo, or a $C_{1-4}$haloalkyl.

$R^{19}$ for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $C_{1-6}$alkoxycarbonyl, carbamoyl, N—($C_{1-6}$alkyl)carbamoyl, N,N-di-($C_{1-6}$alkyl)carbamoyl, $C_{1-6}$alkylsulfonyl, sulfamoyl, N—($C_{1-6}$alkyl)sulfamoyl, and N,N-di-($C_{1-6}$alkyl)sulfamoyl.

$R^a$ and $R^b$, for each occurrence, can be independently hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl.

$R^c$ is hydrogen or a $C_{1-4}$alkyl.

m can be 0 or 1, provided that when m is 0, $R^5$ comprises at least one nitrogen.

n can be an integer from 1 to 6.

p can be 0 or an integer from 1 to 6.

r, for each occurrence, can be independently 0, 1, or 2, provided that the compound is not 4,4'-((perfluoronaphthalene-2,7-diyl)bis(methylene))dipyridine, 3-(1,4-dioxaspiro[4.5]decan-8-ylamino)-8-methylisoquinoline-6-carboxylic acid, or (2-methoxy-3-(morpholinomethyl)quinolin-6-yl)(4-methoxycyclohexyl)methanone.

In another embodiment, compounds of the invention can be represented by structural formula (Ia):

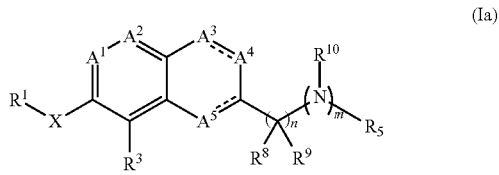
(Ia)

or a pharmaceutically acceptable salt thereof, can be an ATX modulator.

In formula (I), X can be O, $S(O)_r$, $NR^{12}$, C(O) or $CH_2$.

$A^1$ and $A^2$ can each independently be $CR^2$ or N.

$A^3$, $A^4$ and $A^5$ can each independently be $CR^2$, $C(R^2)_2$, N, or $NR^{19}$, provided that at least three of $A^1$, $A^2$, $A^3$, $A^4$, $A^5$, and $A^6$ are independently $CR^2$ or $C(R^2)_2$.

"------" indicates a double or a single bond.

$R^1$ can be a $C_{6-20}$alkyl, a $C_{3-14}$carbocyclyl, a 3- to 15-membered heterocyclyl, a $C_{6-10}$aryl, or a five- to 14-membered heteroaryl, wherein the heterocyclyl and the heteroaryl comprising from 1 to 10 heteroatoms independently selected from N, S or O, and wherein $R^1$ may be optionally substituted with from one to six independently selected $R^6$.

$R^2$, for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido.

$R^3$ can be a halo, $C_{1-6}$haloalkyl or cyano.

$R^5$ can be a $C_{1-6}$alkylene, $C_{3-8}$carbocyclyl, a 3- to 8-membered heterocyclyl, $C_{6-10}$aryl, a 5- to 10-membered heteroaryl, a bridged ring system comprising from 6 to 12 ring members, a spiro ring system comprising from 5-14 ring members, or a bicyclic ring system represented by the following formula:

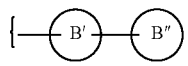

wherein B' and B" are independently selected from the group consisting of monocyclic $C_{3-8}$carbocyclyl, a monocyclic 3- to 8-membered heterocyclyl, phenyl or a 5- to 6-membered heteroaryl; wherein $R^5$ may be optionally substituted with from 1 to 4 independently selected $R^{11}$.

$R^6$, for each occurrence, can be independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom may form $C_{3-8}$spirocycloalkyl or 3- to 8-membered spiroheterocycloalkyl.

$R^7$ can be —OH, —C(O)OR$^{15}$, —C(O)N(R$^{16}$)$_2$, —C(O)N(R$^{15}$)—S(O)$_2$R$^{15}$, —S(O)$_2$OR$^{15}$, —C(O)NHC(O)R$^{15}$, —Si(O)OH, —B(OH)$_2$, —N(R$^{15}$)S(O)$_2$R$^{15}$, —S(O)$_2$N(R$^{15}$)$_2$, —O—P(O)(OR$^{15}$)$_2$, —P(O)(OR$^{15}$)$_2$, —CN, —S(O)$_2$NHC(O)R$^{15}$, —C(O)NHS(O)$_2$R$^{15}$, —C(O)NHOH, —C(O)NHCN, or a heteroaryl or a heterocyclyl selected from the group consisting of formulae (a)-(i'):

(a)
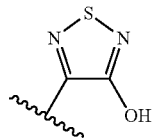

(b)
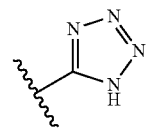

(c)
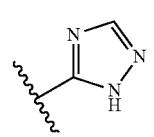

(d)
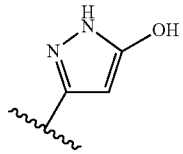

(e)
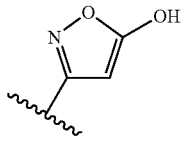

(f)
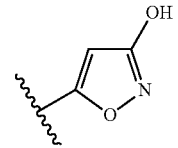

(g)
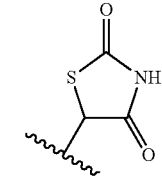

(h)
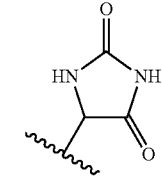

(i)
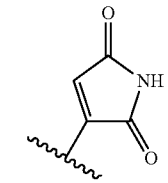

(j)
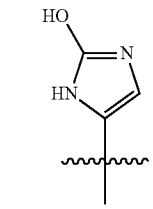

(k)
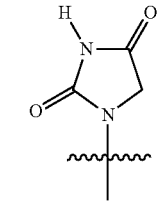

(l) 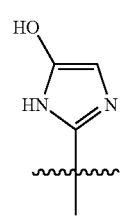
(m) 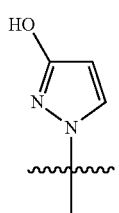
(n) 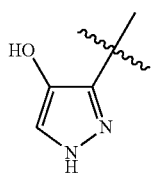
(o) 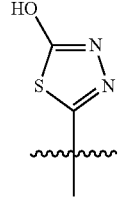
(p) 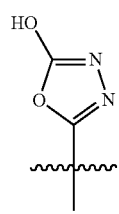
(q) 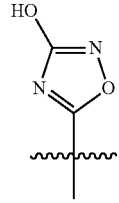
(r) 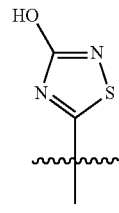
(s) 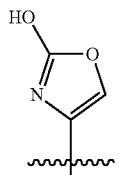
(t) 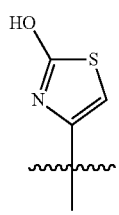
(u) 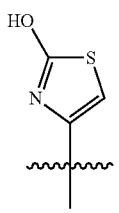
(v) 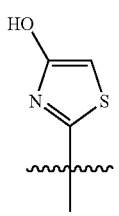
(w) 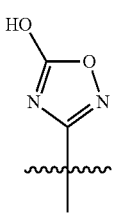
(x) 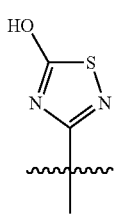
(y) 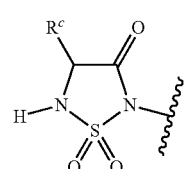
(z) 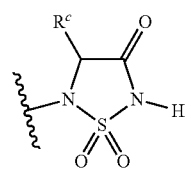

(a') 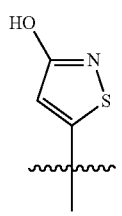

(b') 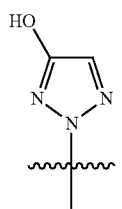

(c') 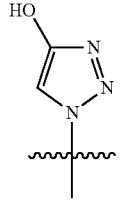

(d') 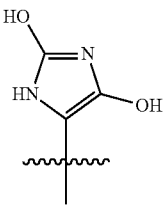

(e') 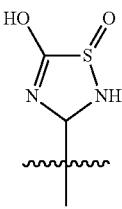

(f') 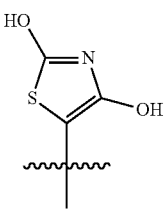

(g') 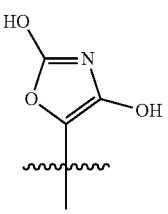

-continued

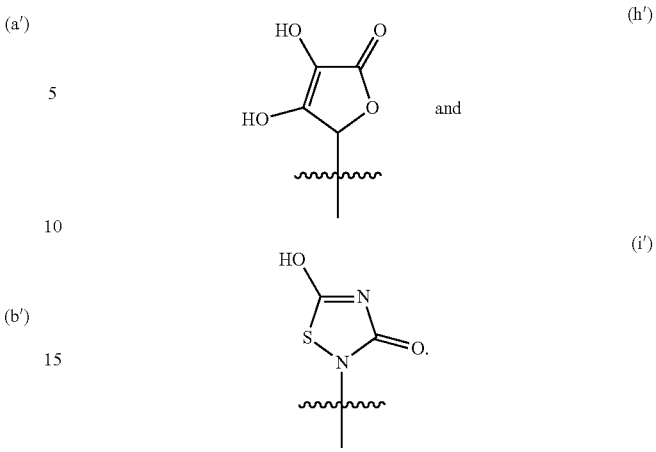

$R^8$ and $R^9$ can each independently be hydrogen, a carboxy, $C_{1-6}$alkyl, or a $C_{2-6}$alkenyl; or $R^8$ and $R^9$ together with the carbon to which they are attached can be —C(=O)—, a $C_{3-8}$spirocycloalkyl, or a 3- to 8-membered spiroheterocycloalkyl.

$R^{10}$ and $R^{12}$ can each independently be hydrogen or a $C_{1-6}$alkyl.

$R^{11}$, for each occurrence, can be independently halo, hydroxyl, nitro, cyano, $C_{1-6}$alkyl, $C_{1-6}$haloalkyl, $C_{1-6}$alkoxy, —$(CR^{17}R^{18})_p$—$R^7$, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —$C(O)NR^aR^b$, —$N(R^a)C(O)R^b$, —$C(O)R^a$, —$S(O)_rR^a$, or —$N(R^a)S(O)_2R^b$.

$R^{15}$ for each occurrence can be independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

$R^{16}$ can be $R^{15}$; or two $R^{16}$ together with the nitrogen atom to which they are attached can form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl.

$R^{17}$ and $R^{18}$, for each occurrence, can be each independently hydrogen, a halo, or a $C_{1-4}$haloalkyl.

$R^{19}$ for each occurrence can be independently selected from the group consisting of hydrogen, carboxy, $C_{1-6}$alkyl, $C_{1-6}$haloalkyl, $C_{3-8}$cycloalkyl, $C_{3-8}$halocycloalkyl, $C_{1-6}$alkanoyl, $C_{1-6}$alkoxycarbonyl, carbamoyl, N—($C_{1-6}$alkyl)carbamoyl, N,N-di-($C_{1-6}$alkyl)carbamoyl, $C_{1-6}$alkylsulfonyl, sulfamoyl, N—($C_{1-6}$alkyl)sulfamoyl, and N,N-di-($C_{1-6}$alkyl)sulfamoyl.

$R^a$ and $R^b$, for each occurrence, can be independently hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl.

$R^c$ is hydrogen or a $C_{1-4}$alkyl.

m can be 0 or 1, provided that when m is 0, $R^5$ comprises at least one nitrogen.

n can be an integer from 1 to 6.

p can be 0 or an integer from 1 to 6.

r, for each occurrence, can be independently 0, 1, or 2, provided that the compound is not the compound is not 4,4'-((perfluoronaphthalene-2,7-diyl)bis(methylene))dipyridine.

In some embodiments, $A^1$ and $A^2$ can each independently be $CR^2$. In some embodiments, $A^1$ and $A^2$ can each independently be $CR^2$, and one of $A^3$, $A^4$, and $A^5$ can be N. In some embodiments, $A^1$ and $A^2$ can each independently be $CR^2$, and one of $A^3$, $A^4$, and $A^5$ can be N, and the others of $A^3$, $A^4$, and $A^5$ can each independently be $CR^2$. In some embodiments, $A^1$, $A^2$, $A^3$, $A^4$, and $A^5$ are all $CR^2$ and each occurrence of "------" is a double bond. In some embodiments, $A^1$ is N and $A^2$, $A^3$, $A^4$, and $A^5$ are all $CR^2$ and each occurrence of "------" is a double bond.

In some embodiments, $R^1$ is a $C_{3-8}$cycloalkyl which is optionally substituted by one or two independently selected $R^6$.

In some embodiments, X is O.

In some embodiments, X is NH.

In some embodiments, the compound, or a pharmaceutically acceptable salt thereof, is represented by formula (II):

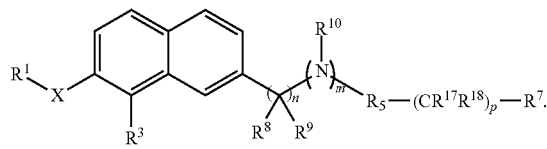

(II)

In some embodiments, the compound, or a pharmaceutically acceptable salt thereof, is represented by formula (III):

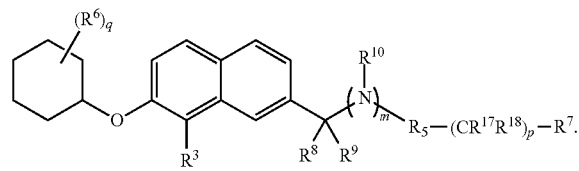

(III)

In formula (III), q can be 0, 1, 2, or 3.

In some embodiments, m can be 0; and $R^5$ can be selected from the group consisting of:

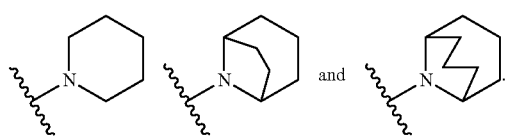

In some embodiments, m can be 1; and $R^5$ can be cyclobutyl, cyclopentyl, or cyclohexyl, each of which may be optionally substituted with from 1 to 3 independently selected $R^{11}$.

In some embodiments, $R^7$ can be —COOH.

In some embodiments, n can be 1.

In some embodiments, $R^8$ can be hydrogen, and $R^9$ can be $C_{1-6}$alkyl; or n can be 1, and $R^8$ and $R^9$ together with the carbon to which they are attached are —C(=O)—.

In some embodiments, $R^8$ and $R^9$ can each independently be hydrogen.

In some embodiments, $R^3$ can be trifluoromethyl.

In some embodiments, q is 1 and $R^6$ is $C_{1-6}$alkyl.

In some embodiments, q is 1 and $R^6$ is t-butyl.

In some embodiments, q is 1 and $R^6$ is methyl or ethyl.

In some embodiments, q is 1 and $R^6$ is trifluoromethyl.

In some embodiments, q is 1 and $R^1$ is

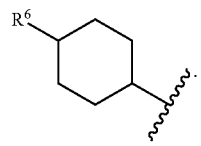

In some embodiments, $R^6$ is trifluoromethyl.

In some embodiments, the compound is selected from the group consisting of:

4-((7-((cis-4-methylcyclohexyl)oxy)-8-(trifluoromethyl) naphthalen-2-yl)methyl)morpholine;

9-[7-(cis-4-methyl-cyclohexyloxy)-8-trifluoromethyl-naphthalen-2-ylmethyl]-9-aza-bicyclo[3.3.1]nonane-3-carboxylic acid;

8-[7-(cis-4-methyl-cyclohexyloxy)-8-trifluoromethyl-naphthalen-2-ylmethyl]-8-aza-bicyclo[3.2.1]octane-3-carboxylic acid;

1-[7-(cis-4-Methyl-cyclohexyloxy)-8-trifluoromethyl-naphthalen-2-ylmethyl]-piperidine-4-carboxylic acid;

9-1{-[7-(cis-4-methyl-cyclohexyloxy)-8-trifluoromethyl-naphthalen-2-yl]-ethyl}-9-aza-bicyclo[3.3.1]nonane-3-carboxylic acid;

9-{(S)-1-[7-(cis-4-methyl-cyclohexyloxy)-8-trifluoromethyl-naphthalen-2-yl]-ethyl}-9-aza-bicyclo[3.3.1]nonane-3-carboxylic acid;

9-{(R)-1-[7-(cis-4-methyl-cyclohexyloxy)-8-trifluoromethyl-naphthalen-2-yl]-ethyl}-9-aza-bicyclo[3.3.1]nonane-3-carboxylic acid;

8-{1-[7-(cis-4-methyl-cyclohexyloxy)-8-trifluoromethyl-naphthalen-2-yl]-ethyl}-8-aza-bicyclo[3.2.1]octane-3-carboxylic acid;

8-{(R)-1-[7-(cis-4-methyl-cyclohexyloxy)-8-trifluoromethyl-naphthalen-2-yl]-ethyl}-8-aza-bicyclo[3.2.1]octane-3-carboxylic acid;

8-{(S)-1-[7-(cis-4-methyl-cyclohexyloxy)-8-trifluoromethyl-naphthalen-2-yl]-ethyl}-8-aza-bicyclo[3.2.1]octane-3-carboxylic acid;

2-((R)-1-((8-(trifluoromethyl)-7-((cis-4-(trifluoromethyl) cyclohexyl)oxy)naphthalen-2-yl)methyl)piperidin-3-yl) acetic acid;

2,2-dimethyl-3-(((8-(trifluoromethyl)-7-((cis-4-(trifluoromethyl)cyclohexyl)oxy)-naphthalen-2-yl)methyl)amino) cyclobutanecarboxylic acid;

9-[8-trifluoromethyl-7-(cis-4-trifluoromethyl-cyclohexyloxy)-naphthalen-2-ylmethyl]-9-aza-bicyclo[13.3.1] nonane-3-carboxylic acid;

9-{1-[7-(cis-4-trifluoromethyl-cyclohexyloxy)-8-trifluoromethyl-naphthalen-2-yl]-ethyl}-9-aza-bicyclo[3.3.1]nonane-3-carboxylic acid;

((R)-1-{1-[8-trifluoromethyl-7-(4-trifluoromethyl-cyclohexyloxy)-naphthalen-2-yl]-ethyl}-piperidin-3-yl)-acetic acid;

8-{1-[7-(cis-4-trifluoromethyl-cyclohexyloxy)-8-trifluoromethyl-naphthalen-2-yl]-ethyl}-8-aza-bicyclo[3.2.1]octane-3-carboxylic acid;

8-{(S)-1-[7-(cis-4-trifluoromethyl-cyclohexyloxy)-8-trifluoromethyl-naphthalen-2-yl]-ethyl}-8-aza-bicyclo[3.2.1]octane-3-carboxylic acid;

8-{(R)-1-[7-(cis-4-trifluoromethyl-cyclohexyloxy)-8-trifluoromethyl-naphthalen-2-yl]-ethyl}-8-aza-bicyclo[3.2.1]octane-3-carboxylic acid;

9-[7-(4-methyl-cyclohexyl oxy)-8-trifluoromethyl-naphthalene-2-carbonyl]-9-aza-bicyclo[3.3.1]nonane-3-carboxylic acid;

9-[8-trifluoromethyl-7-(4-trifluoromethyl-cyclohexyloxy)-naphthalene-2-carbonyl]-9-aza-bicyclo[3.3.1]nonane-3-carboxylic acid;

9-[8-(Chloro-7-(4-methyl-cyclohexyloxy)-naphthalen-2-yl-methyl]-9-aza-bicyclo[3.3.1]nonane-3-carboxylic acid;

9-[1-(8-trifluoromethyl-7-(cis-4-methylcyclohexyloxy)-naphthalen-2-yl)ethyl]-9-aza-bicyclo[3.3.1]nonane;

12-(1-(8-trifluoromethyl-7-(cis-4-methylcyclohexyloxy)naphthalene-2-yl)ethyl)-4,6,12-triaza-tricyclo[7.2.1.0(2,7)]dodeca-2(7),3,5-triene;

8-(1-(7-((cis-4-methylcyclohexyl)oxy)-8-(trifluoromethyl)naphthalen-2-yl)propyl)-8-azabicyclo[3.2.1]octane-3-carboxylic acid;

1-(1-(7-((cis-4-methylcyclohexyl)oxy)-8-(trifluoromethyl)naphthalen-2-yl)propyl)piperidine-4-carboxylic acid;

2-((3R)-1-(1-(7-((cis-4-methylcyclohexyl)oxy)-8-(trifluoromethyl)naphthalen-2-yl)propyl)piperidin-3-yl)acetic acid;

((R)-1-{1-[8-trifluoromethyl-7-(4-trifluoromethyl-cyclohexyloxy)-naphthalen-2-yl]-ethyl}-piperidin-3-yl)-acetic acid;

2-((S)-1-((8-(trifluoromethyl)-7-((cis-4-(trifluoromethyl)cyclohexyl)oxy)naphthalen-2-yl)methyl)piperidin-3-yl)acetic acid;

8-(8-(trifluoromethyl)-7-((cis-4-(trifluoromethyl)cyclohexyl)oxy)-2-naphthoyl)-8-azabicyclo[3.2.1]octane-3-carboxylic acid; and 8-[7-(cis-4-methyl-cyclohexyloxy)-8-trifluoromethyl-naphthalene-2-carbonyl]-8-azabicyclo[3.2.1]octane-3-carboxylic acid;

or a pharmaceutically acceptable salt thereof.

The term "bridged ring system," as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system can have more than one bridge within the ring system (e.g., adamantyl). A bridged ring system may have from 6-10 ring members, preferably from 7-10 ring members. Examples of bridged ring systems include adamantyl, 9-azabicyclo[3.3.1]nonan-9-yl, 8-azabicyclo[3.2.1]octanyl, bicyclo[2.2.2]octanyl, 3-azabicyclo[3.1.1]heptanyl, bicyclo[2.2.1]heptanyl, (1R,5S)-bicyclo[3.2.1]octanyl, 3-azabicyclo[3.3.1]nonanyl, and bicyclo[2.2.1]heptanyl. More preferably, the bridged ring system is selected from the group consisting of 9-azabicyclo[3.3.1]nonan-9-yl, 8-azabicyclo[3.2.1]octanyl, and bicyclo[2.2.2]octanyl.

The term "spiro ring system," as used herein, is a ring system that has two rings each of which are independently selected from a carbocyclyl or a heterocyclyl, wherein the two ring structures having one atom in common. Spiro ring systems have from 5 to 14 ring members. Example of spiro ring systems include 2-azaspiro[3.3]heptanyl, spiropentanyl, 2-oxa-6-azaspiro[3.3]heptanyl, 2,7-diazaspiro[3.5]nonanyl, 2-oxa-7-azaspiro[3.5]nonanyl, 6-oxa-9-azaspiro[4.5]decanyl, 6-oxa-2-azaspiro[3.4]octanyl, 5-azaspiro[2.3]hexanyl and 2,8-diazaspiro[4.5]decanyl.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

"Alkylene" refers to a divalent alkyl group. Examples of alkylene groups include methylene, ethylene, propylene, n-butylene, and the like. The alkylene is attached to the rest of the molecule through a single bond and to the radical group through a single bond. The points of attachment of the alkylene to the rest of the molecule and to the radical group can be through one carbon or any two carbons within the carbon chain.

As used herein, the term "haloalkyl" refers to an alkyl, as defined herein, that is substituted by one or more halo groups as defined herein. A haloalkyl can be monohaloalkyl, dihaloalkyl or polyhaloalkyl including perhaloalkyl. A monohaloalkyl can have one iodo, bromo, chloro or fluoro substituent. Dihaloalkyl and polyhaloalkyl groups can be substituted with two or more of the same halo atoms or a combination of different halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. Preferred haloalkyl groups are trifluoromethyl and difluoromethyl.

"Halogen" or "halo" may be fluoro, chloro, bromo or iodo.

"Alkenyl" refers to an unsaturated hydrocarbon group which may be linear or branched and has at least one carbon-carbon double bond. Alkenyl groups with 2-8 carbon atoms can be preferred. The alkenyl group may contain 1, 2 or 3 carbon-carbon double bonds, or more. Examples of alkenyl groups include ethenyl, n-propenyl, isopropenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-8 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6 carbon atoms, more preferably about 1-4 carbon atoms.

As used herein, the term "haloalkoxy" refers to haloalkyl-O—, wherein haloalkyl is defined herein above. Representative example of haloalkoxy groups are trifluoromethoxy, difluoromethoxy, and 1,2-dichloroethoxy. Preferably, haloalkoxy groups have about 1-6 carbon atoms, more preferably about 1-4 carbon atoms.

As used herein, the term "carbocyclyl" refers to saturated or partially unsaturated (but not aromatic) monocyclic, bicyclic or tricyclic hydrocarbon groups of 3-14 carbon atoms, preferably 3-9, or more preferably 3-7 carbon atoms. Carbocyclyls include fused or bridged ring systems. The term "carbocyclyl" encompasses cycloalkyl groups. The term "cycloalkyl" refers to completely saturated monocyclic, bicyclic or tricyclic hydrocarbon groups of 3-12 carbon atoms, preferably 3-9, or more preferably 3-8 carbon atoms. Exemplary monocyclic carbocyclyl groups include, but are not limited to, cyclopropyl, cyclobutyl, cyclopentyl, cyclopentenyl, cyclohexyl or cyclohexenyl. Exemplary bicyclic carbocyclyl groups include bornyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, or bicyclo[2.2.2]octyl. Exemplary tricyclic carbocyclyl groups include adamantyl.

"Cycloalkoxy" refers to cycloalkyl-O—, wherein cycloalkyl is defined herein above.

"Halocycloalkoxy" refers to cycloalkyloxy as defined herein above that is substituted by one or more halo groups.

"Cycloalkenyl" refers to an unsaturated carbocyclic group of 3-12 carbon atoms that has at least one carbon-carbon double bond in the ring.

The term "spirocycloalkyl," as used herein, is a cycloalkyl that has one ring atom in common with the group to which it is attached. Spirocycloalkyl groups may have from 3 to 14 ring members. In a preferred embodiment, the spirocycloalkyl has from 3 to 8 ring carbon atoms and is monocyclic.

The term "aryl" refers to monocyclic, bicyclic or tricyclic aromatic hydrocarbon groups having from 6 to 14 carbon atoms in the ring portion. In one embodiment, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

As used herein, the term "heterocyclyl" refers to a saturated or unsaturated, non-aromatic monocyclic, bicyclic or tricyclic ring system which has from 3- to 15-ring members at least one of which is a heteroatom, and up to 10 of which may be heteroatoms, wherein the heteroatoms are independently selected from O, S and N, and wherein N and S can be optionally oxidized to various oxidation states. In one embodiment, a heterocyclyl is a 3-7-membered monocyclic. In another embodiment, a heterocyclyl is a 6-12-membered bicyclic. In yet another embodiment, a heterocyclyl is a 10-15-membered tricyclic ring system. The heterocyclyl group can be attached at a heteroatom or a carbon atom. Heterocyclyls include fused or bridged ring systems. The term "heterocyclyl" encompasses heterocycloalkyl groups. The term "heterocycloalkyl" refers to completely saturated monocyclic, bicyclic or tricyclic heterocyclyl comprising 3-15 ring members, at least one of which is a heteroatom, and up to 10 of which may be heteroatoms, wherein the heteroatoms are independently selected from O, S and N, and wherein N and S can be optionally oxidized to various oxidation states. Examples of heterocyclyls include dihydrofuranyl, [1,3]dioxolane, 1,4-dioxane, 1,4-dithiane, piperazinyl, 1,3-dioxolane, imidazolidinyl, imidazolinyl, pyrrolidine, dihydropyran, oxathiolane, dithiolane, 1,3-dioxane, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, piperazinyl, azepinyl, oxapinyl, oxazepinyl and diazepinyl.

The term "spiroheterocycloalkyl" as used herein, is a heterocycloalkyl that has one ring atom in common with the group to which it is attached. Spiroheterocycloalkyl groups may have from 3 to 15 ring members. In a preferred embodiment, the spiroheterocycloalkyl has from 3 to 8 ring atoms selected from carbon, nitrogen, sulfur and oxygen and is monocyclic.

As used herein, the term "heteroaryl" refers to a 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic. In one embodiment, the heteroaryl is monocyclic and has 5 or 6 ring members. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. In another embodiment, the heteroaryl is bicyclic and has from 8 to 10 ring members. Examples of bicyclic heteroaryl groups include indolyl, benzofuranyl, quinolyl, isoquinolyl indazolyl, indolinyl, isoindolyl, indolizinyl, benzimidazolyl, quinolinyl, 5,6,7,8-tetrahydroquinoline and 6,7-dihydro-5H-pyrrolo[3,2-d]pyrimidine.

An amino is a group having the formula $NH_2$—. The term N-alkylamino is an amino group in which one of the hydrogen atoms is replaced with an alkyl group. The term N,N-dialkylamino is an amino group in which each hydrogen atoms is replaced with an alkyl group which may be the same or different.

"Alkanoyl" refers to alkyl-C(=O)—, where alkyl is defined herein above.

"Alkoxycarbonyl" refers to alkyl-O—C(=O)—, where alkyl is defined herein above.

"Alkanoyloxy" refers to alkyl-C(=O)—O—, where alkyl is defined herein above.

"Carbamoyl" refers to —C(=O)—$NH_2$. The term N-alkylcarbamoyl refers to a carbamoyl group in which one of the hydrogen atoms is replaced with an alkyl group. The term N,N-dialkylcarbamoyl refers to a carbamoyl group in which each hydrogen atoms is replaced with an alkyl group which may be the same or different.

The number of carbon atoms in a group is specified herein by the prefix "$C_{x-xx}$", wherein x and xx are integers. For example, "$C_{1-4}$alkyl" is an alkyl group which has from 1 to 4 carbon atoms; $C_{1-6}$alkoxy is an alkoxy group having from 1 to 6 carbon atoms; $C_{6-10}$aryl is an aryl group which has from 6 to 10 carbon atoms; $C_{1-4}$haloalkyl is a haloalkyl group which has from 1 to 4 carbon atoms; and N,N-di-$C_{1-6}$alkylamino is a N,N-dialkylamino group in which the nitrogen is substituted with two alkyl groups each of which is independently from 1 to 6 carbon atoms.

The phrase "compound of the invention," as used herein, refers to compounds represented by formulae (I), (Ia), (II), and (III), and any of the specific examples disclosed herein.

The disclosed compounds can contain one or more asymmetric centers in the molecule. In accordance with the present disclosure any structure that does not designate the stereochemistry is to be understood as embracing all the various optical isomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). The compounds can be isotopically-labeled compounds, for example, compounds including various isotopes of hydrogen, carbon, nitrogen, oxygen, phosphorous, fluorine, iodine, or chlorine. The disclosed compounds may exist in tautomeric forms and mixtures and separate individual tautomers are contemplated. In addition, some compounds may exhibit polymorphism.

By way of clarity, compounds of the invention included all isotopes of the atoms present in formulae (I), (Ia), (II), and (III) and any of the examples or embodiments disclosed herein. For example, H (or hydrogen) represents any isotopic form of hydrogen including $^1H$, $^2H$ (D), and $^3H$ (T); C represents any isotopic form of carbon including $^{12}C$, $^{13}C$, and $^{14}C$; O represents any isotopic form of oxygen including $^{16}O$, $^{17}O$ and $^{18}O$; N represents any isotopic form of nitrogen including $^{13}N$, $^{14}N$ and $^{15}N$; P represents any isotopic form of phosphorous including $^{31}P$ and $^{32}P$; S represents any isotopic form of sulfur including $^{32}S$ and $^{35}S$; F represents any isotopic form of fluorine including $^{19}F$ and $^{18}F$; Cl represents any isotopic form of chlorine including $^{35}Cl$, $^{37}Cl$ and $^{36}Cl$; and the like. In a preferred embodiment, compounds represented by formulae (I)-(III) and any of the examples or embodiments disclosed herein comprises isotopes of the atoms therein in their naturally occurring abundance. However, in certain instances, it is desirable to enrich one or more atom in a particular isotope which would normally be present in less abundance. For example, $^1H$ would normally be present in greater than 99.98% abundance; however, a compound of the invention can be enriched in $^2H$ or $^3H$ at one or more positions where H is present. In particular embodiments of the compounds of formulae (I)-(III), when, for example, hydrogen is enriched in the deuterium isotope, the symbol "D" may be used to represent the enrichment in deuterium. In one embodiment, when a compound of the invention is enriched in a radioactive isotope, for example $^3H$ and $^{14}C$, they may be useful in drug and/or substrate tissue distribution assays. It is to be understood that the invention encompasses all such isotopic forms which modulate ATX activity.

Compounds of the invention are ATX modulators, i.e., they modulate the activity of ATX. For example, a compound of the invention can be an ATX inhibitor. A compound of the invention can be a selective ATX modulator. Being selective can mean that the compound binds to ATX preferentially when exposed to a variety of potential binding partners. The compound can have a greater affinity for the ATX, by at by at least 100-fold, by at least 50-fold, by at least 10-fold, by at least 5-fold or by at least 2-fold, than for other binding partners. Affinity can be measured, for example, as a dissociation constant ($K_d$), as an inhibition constant (such as $IC_{50}$), or another measure; provided that affinity is measured in a consistent fashion between ATX and the other binding partners it is compared to.

An inhibitor of ATX mediated activity can block interaction of ATX with its native substrate(s), such as LPC. For example, the inhibitor can show an $IC_{50}$ value of less than 1 µM, less than 750 nM, less than 500 nM, less than 250 nM, less than 100 nM, less than 50 nM, less than 25 nM, or less than 10 nM, when measured in a FRET-based assay using FS-3 substrate (see, e.g., Ferguson, C. G., et al., Org Lett. 2006 May 11; 8(10): 2023-2026, which is incorporated by reference in its entirety).

Some substrates and inhibitors of ATX are described in WO 2011/151461, which is incorporated by reference in its entirety.

Potential uses of an ATX modulating agent include, but are not limited to, prevention or treatment of a pathological condition or symptom in a mammal. The pathological disorder can be an inflammatory disorder, an autoimmune disorder, a fibrosis of the lung, or a malignancy of the lung. Prevention or treatment of the pathological condition or symptom can include administering to the mammal an effective amount of an ATX modulating agent, e.g., an ATX inhibitor, to prevent, treat or reduce symptoms of the inflammatory disorder, autoimmune disorder, the fibrosis of the lung, or the malignancy of the lung. In one embodiment, the inflammatory disorder is rheumatoid arthritis (RA). In another embodiment, the autoimmune disorder is multiple sclerosis (MS). A particular example of lung fibrosis is an interstitial lung disease, for instance, pulmonary fibrosis. See, for example, WO 2011/151461, which is incorporated by reference in its entirety.

In a preferred embodiment, an ATX inhibitor of the present invention can be used to treat or prevent a demyelinating disease or disorder. Demyelinating diseases or disorders include multiple sclerosis, Guillain-Barre Syndrome, chronic inflammatory demyelinating polyneuropathy (CIDP), transverse myelitis, and optic neuritis, spinal cord injury, stroke or other ischemia, cerebral palsy, Charcot-Marie-Tooth disease (CMT), Sjogren-Larsson syndrome, Refsum disease, Krabbe disease, Canavan disease, Alexander disease, nerve damage due to pernicious anemia, progressive multifocal leukoencephalopathy (PML), Lyme disease, tabes dorsalis due to untreated syphilis, demyelination due to exposure to an organophosphates, demyelination due to vitamin B12 deficiency or copper deficiency.

Neurological Disorders

A number of studies have shown that ATX is expressed in non-pathological conditions, throughout development, with high expression levels in the CNS among other tissues. ATX mRNA was identified as highly upregulated during oligodendrocyte differentiation and ATX protein expression is also apparent in maturing ODCs, temporally correlated with the process of myelination. Finally, in the adult brain ATX is expressed in secretory epithelial cells, such as the choroid plexus, ciliary, iris pigment, and retinal pigment epithelial cells, whereas there is evidence for ATX expression in leptomenigncal cells and cells of the CNS vasculature. See, for example, Fuss, B., et al., J Neurosci 17, 9095-9103 (1997); Kawagoe, H., et al. Genomics 30, 380-384 (1995); Lee, H. Y., et al. J Biol Chem 271, 24408-24412 (1996); Narita, M., et al., J Biol Chem 269, 28235-28242 (1994); Bachner, D., et al., Mechanisms of Development 84, 121-125 (1999); Awatramani, R., et al., Nat Genet 35, 70-75 (2003); Li, Y., et al., J Neurol Sci 193, 137-146 (2002); Dugas, J. C., et al., J Neurosci 26, 10967-10983 (2006); Fox, M. A., et al., Molecular and Cellular Neuroscience 27, 140-150 (2004); Hoelzinger, D. B., et al., Neoplasia 7, 7-16 (2005); and Sato, K., et al., J Neurochem 92, 904-914 (2005); each of which is incorporated by reference in its entirety.

Although neurons and astrocytes do not seem to express ATX under physiological conditions, ATX is highly upregulated in astrocytes following brain lesion. Two hallmarks of reactive astrogliosis can be induced by LPA itself: hypertrophy of astrocytes and stress fiber formation. This may indicate an autoregulation loop of astrocytic activation, in which astrocytes upregulate the LPA-generating enzyme ATX and become activated by its metabolite LPA, while increased amounts of the metabolite inhibit the catalytic activity of ATX. See, e.g., Savaskan, N. E., et al., Cell Mol Life Sci 64, 230-243 (2007); Ramakers, G. J, & Moolenaar, W. H., Exp Cell Res 245, 252-262 (1998); and van Meeteren, L. A., et al., J Biol Chem 280, 21155-21161 (2005); each of which is incorporated by reference in its entirety.

ATX expression levels were shown to be elevated in glioblastoma multiform samples, and ATX was shown to augment invasiveness of cells transformed with ras, a key signaling molecule that promotes gliomagenesis. ATX expression was also detected in primary tumor tissues from neuroblastoma patients and retinoic acid induced expression of ATX in N-myc-amplified neuroblastoma cells.

There is significant evidence for ATX signaling in demyelination processes and in other neurodegenerative conditions. As noted above, it has been reported that addition of LPA to dorsal root fibers in ex vivo culture causes demyelination, whereas LPC fails to cause significant demyelination of nerve fibers in ex vivo cultures without further addition of recombinant ATX to the culture. Addition of recombinant ATX caused significant demyelination at equivalent levels to LPA presumable due to conversion of LPC to LPA through the enzymatic activity of ATX. In addition, injury induced demyelination was attenuated by about 50% in atx$^{+/-}$ mice over their wild type counterparts (Nagai, et al., *Molecular Pain* (2010), 6:78).

ATX protein levels were found deregulated in an animal model of MS (experimental autoimmune encephalitis; EAE) at the onset of clinical symptoms. See, e.g., Hoelzinger, D. B., et al. Neoplasia 7, 7-16 (2005); Nam, S. W., et al., Oncogene 19, 241-247 (2000); Kawagoe, H., et al., Cancer Res 57, 2516-2521 (1997); Dufner-Beattie, J., et al., Mol Carcinog 30, 181-189 (2001); Umemura, K., et al., Neuroscience Letters 400, 97-100 (2006); and Fuss, B., et al., J Neurosci 17, 9095-9103 (1997); each of which is incorporated by reference in its entirety. Moreover, significant ATX expression was detected in the cerebrospinal fluid of patients suffering with multiple sclerosis (MS), while completely lacking from the control samples, suggesting a role for ATX in maintenance of cerebrospinal fluid homeostasis during pathological/demyelinating conditions. Hammack, B. N., et al. Proteomic analysis of multiple sclerosis cerebrospinal fluid. Mult Scler 10, 245-260 (2004); and Dennis, J., et al., J Neurosci Res 82, 737-742 (2005); each of which is incorporated by reference in its entirety. Interestingly, ATX mRNA expression was found to be elevated in the frontal cortex of Alzheimer-type dementia patients indicating a potential involvement for ATX signaling in neurodegenerative diseases. LPA receptors are enriched in the CNS and their expression patterns suggest their potential involvement in developmental process including neurogenesis, neuronal migration, axon extension and myelination. Noteworthy, only two receptors have the same spatiotemporal expression as ATX in the CNS (Contos, J. J., et al., Mol Cell Biol 22, 6921-6929 (2002); Jaillard, C, et al, Edg8/S1 P5: an oligodendroglial receptor with dual function on process retraction and cell survival. J Neurosci 25, 1459-1469 (2005); and Saba, J. D. Journal of cellular biochemistry 92, 967-992 (2004); each of which is incorporated by reference in its entirety). LPAi and SIP5 are specific for ODCs, and their expression highly correlates with the process of myelination. LPA1 is expressed in restricted fashion within the neuroblasts of the neuroproliferatve Ventricular Zone (VZ) of the developing cortex, in the dorsal olfactory bulb, along the pial cells of neural crest origin, and in developing facial bone tissue. Expression is observed during E11-E18, corresponding to a time period during which neurogenesis occurs. LPA1 expression is undetectable in the VZ after this point, to reappear during the first postnatal week within ODCs. Notably, Schwann cells (the myelinating cells of the Peripheral Nervous System; PNS) express high levels of LPA1 early in development and persistently throughout life, suggesting an influence of LPA on myelinating processes (Weiner. J. A. & Chun, J., Proc Natl Acad Sci USA 96, 5233-5238 (1999), which is incorporated by reference in its entirety).

The above data strongly support a critical role for ATX and LPA signaling in neuronal development, oligodendrocyte differentiation and myelination, as well as possibly in the autoregulation of astrocyte activation. Moreover, the regulation of ATX and thus LPA production at local sites of CNS injury, inflammatory or autoimmune, could contribute to tissue homeostasis through the numerous effects of LPA. As demyelination and deregulated cerebrospinal fluid homeostasis are the hallmarks of multiple sclerosis, a role of ATX and LPA signaling in the pathophysiology of multiple sclerosis seems very likely.

The ATX inhibitors of the invention can be used to various forms of MS including relapsing-remitting, secondary-progressive, primary-progressive, and progressive-relapsing. In addition, ATX inhibitors of the invention can be used alone or in conjunction with other agents to treat or prevent MS. In a preferred embodiment, the compounds of the invention can be used to treat or prevent MS in combination with an immunomodulating therapy such as corticosteroids, beta interferon-1a (such as Avonex® or Rebif®), beta interferon-1b (Betaseron®), natalizumab (Tysabri®), glatiramer, and mitoxantrone.

Pain Mediation

Pain experienced by mammals can be divided into two main categories: acute pain (or nociceptive) and chronic pain which can be subdivided into chronic inflammatory pain and chronic neuropathic pain. Acute pain is a response to stimulus that causes tissue injury and is a signal to move away from the stimulus to minimize tissue damage. Chronic pain, on the other hand, serves no biological function and develops as a result of inflammation caused by tissue damage (inflammatory pain) or by damage to the nervous system such as demyelination (neuropathic pain). Chronic pain is generally characterized by stimulus-independent, persistent pain or by abnormal pain perception triggered by innocuous stimuli.

LPA has been found to be a mediator of both inflammatory pain and neuropathic pain. The transient receptor potential channel TRPV1 is known to be the originator of inflammatory pain. LPA has been shown to directly activate TRPV1 thereby creating pain stimulus by binding to its intracellular C-terminus (Tigyi, *Nature Chemical Biology* (January 2012), 8:22-23). Thus, compounds which inhibit the formation of LPA by inhibiting the action of ATX would be useful in treating inflammatory pain.

LPA has also been shown to play a role in neuropathic pain. For example, sciatic nerve injury has been shown to induce demyelination, down-regulation of myelin-associated glycoprotein (MAG) and damage to Schwann cell partitioning of C-fiber-containing Remak bundles in the sciatic nerve and dorsal root. However, demyelination, MAG down-regulation and Remak bundle damage in the dorsal root were abolished in $LPA_1$ receptor-deficient (Lpar1$^{-/-}$) mice (Nagai, et al., *Molecular Pain* (2010), 6:78). These results indicate that compounds that inhibit the formation of LPA by inhibiting the action of ATX would decrease dorsal root demyelination following nerve injury and decrease or eliminate neuropathic pain.

Thus the compounds of the invention are useful in treating or preventing chronic pain such as inflammatory pain and neuropathic pain in mammals.

Rheumatoid Arthritis (RA)

Studies in human and animal models of RA suggest that ATX plays a role in the development and progress of the disease. For example, increased ATX mRNA expression was detected in synovial fibroblasts (SFs) from animal models of RA during differential expression profiling, and human RA SFs were shown to express mRNA for both ATX and LPARs (Aidinis, V., et al., PLoS genetics 1, e48 (2005); Zhao, C, et al., Molecular pharmacology 73, 587-600 (2008); each of which is incorporated by reference in its entirety). ATX is overexpressed from activated SFs in arthritic joints, both in animal models and human patients (see WO 2011/151461). ATX expression was shown to be induced from TNF, the major pro-inflammatory factor driving RA.

Disease development was assessed in well established animal models of RA. When ATX expression was conditionally ablated specifically in SFs, the lack of ATX expression in the joints resulted in marked decreased inflammation and synovial hyperplasia. This suggested an active involvement of the ATX-LPA axis in the pathogenesis of the disease. Similar results were also obtained with pharmacologic inhibition of ATX enzymatic activity and LPA signaling. A series of ex vivo experiments on primary SFs revealed that ATX, through LPA production, stimulates rearrangements of the actin cytoskeleton, proliferation and migration to the extracellular matrix (ECM), as well as the secretion of proinflammatory cytokines and matrix metalloproteinases (MMPs). Moreover, the LPA effect was shown to be synergistic with TNF and dependent on the activation of MAPK cellular signaling pathways. See, e.g., Armaka, M., et al., The Journal of experimental medicine 205, 331-337 (2008); which is incorporated by reference in its entirety.

In one embodiment, a method for treating an individual with RA or the individual at risk of suffering thereof comprises administering to said individual an ATX inhibitor of the invention in combination with an anti-TNF antibody for use in the treatment of RA. Examples of suitable anti-TNF antibodies are adalimumab, etanercept, golimumab, and infliximab (Taylor P C, Feldmann M. Anti-TNF biologic agents: still the therapy of choice for rheumatoid arthritis. Nat Rev Rheumatol. 2009 October; 5(10):578-82).

Pulmonary Fibrosis

Evidence also suggests a role for ATX in pulmonary fibrosis. Mice lacking lysophosphatidic acid (LPA) receptor 1 (LPAR1) were protected from Bleomycin (BLM)-induced pulmonary fibrosis and mortality, suggesting a major role for LPA in disease pathophysiology. The majority of circulating LPA is produced by the phospholipase D activity of Autotaxin (ATX) and the hydrolysis of lysophosphatidylcholine (LPC). Increased ATX expression has been previously reported in the hyperplastic epithelium of fibrotic lungs of human patients and animal models.

Therefore, we hypothesized that genetic or pharmacologic inhibition of ATX activity would reduce local or circulating LPA levels and hence attenuate disease pathogenesis.

Lung Cancer

Increased ATX expression has been detected in a large number of malignancies, including mammary, thyroid, hepatocellular and renal cell carcinomas, glioblastoma and neuroblastoma, as well as NSCLC. Strikingly, transgenic overexpression of ATX was shown to induce spontaneous mammary carcinogenesis. In accordance, in vitro ATX overexpression in various cell types promotes proliferation and metastasis while inhibiting apoptosis. LPA's actions are concordant with many of the "hallmarks of cancer", indicating a role for LPA in the initiation or progression of malignant disease. Indeed LPA levels are significantly increased in malignant effusions, and its receptors are aberrantly expressed in several human cancers.

See, for example: Euer, N., et al., Anticancer Res 22, 733-740 (2002); Liu, S., et al., Cancer Cell 15, 539-550 (2009); Zhang, G., et al., Chin Med J (Engl) 112, 330-332 (1999); Stassar, M. J., et al., Br J Cancer 85, 1372-1382 (2001); Kishi, Y., et al., J Biol Chem 281, 17492-17500 (2006); Kawagoe, H., et al., Cancer Res 57, 2516-2521 (1997); Yang, Y., et al., Am J Respir Cell Mol Biol 21, 216-222 (1999); and Toews, M. L., et al. Biochim Biophys Acta 1582, 240-250 (2002); each of which is incorporated by reference in its entirety.

LPA has been shown to be involved in lymphocyte trafficking and helps promote entry of lymphocytes into secondary lymphoid organs (see Kanda, et al., Nat. Immunology (2008), 9:415-423). Therefore the disclosed compounds are expected to be useful for altering lymphocyte trafficking as a method for prolonging allograft survival, for example transplantation including solid organ transplants, treatment of graft vs. host disease, bone marrow transplantation, and the like.

Pharmaceutical compositions can include a compound of the invention, or a pharmaceutically acceptable salt thereof. More particularly, such compounds can be formulated as pharmaceutical compositions using standard pharmaceutically acceptable carriers, fillers, solubilizing agents and stabilizers known to those skilled in the art. For example, a pharmaceutical composition including a compound of the invention, or a salt, analog, derivative, or modification thereof, as described herein, is used to administer the appropriate compound to a subject.

The compounds of the invention, or a pharmaceutically acceptable salt thereof, are useful for treating a disease or disorder associated with ATX activity. In one embodiment, a therapeutically acceptable amount of a compound of the invention, or a pharmaceutically acceptable salt thereof, is administered to a subject in need thereof. In another embodiment, a pharmaceutical composition comprising a therapeutically effective amount of a compound of the invention, or a pharmaceutically acceptable salt thereof, and a pharmaceutically-acceptable carrier is administered to a subject in need thereof.

The compounds of the invention can be used in combination with at least one further active ingredient, such as a medicament used in the treatment of multiple sclerosis such as Tysabri®, dimethyl fumarate, an interferon (such as pegylated or non-pegylated interferons, preferably interferon β-1a or pegylated interferon β-1a), glatiramer acetate, a compound improving vascular function, an immunomodulating agent (such as Fingolimod, cyclosporins, rapamycins or ascomycins, or their immunosuppressive analogs, e.g. cyclosporine A, cyclosporine G, FK-506, ABT-281, ASM981, rapamycin, 40-O-(2-hydroxy)ethyl-rapamycin etc.); corticosteroids; cyclophosphamide; azathioprine; mitoxanthrone, methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone dipropionate; betamethasone phosphate sodique; betamethasone valerate; budesonide; captopril; chlormethine chlorhydrate; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasonephosphate; dexamethasone tebutate; dichlorisone acetate; doxorubicinee chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone; hydrocortisone acetate; hydrocortisone butyrate; hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethansone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD20 (e.g., rituximab and ocrelizumab), CD25, CD28, B7, CD40, CD45, CD56 (e.g., daclizumab), or CD58 or their ligands; or other immunomodulatory compounds, e.g. CTLA41g, or other adhesion molecule inhibitors, e.g. mAbs or low molecular weight inhibitors including Selectin antagonists and VLA-4 antagonists (such as Tysabri®); remyelinating agents such as BHB033. Compounds of the invention can also be used in combination with agents which treat the symptoms of multiple sclerosis such as fampridine.

Axons and dendrites can extend from neurons. The distal tip of an extending axon or neurite can include a specialized region, known as the growth cone. Growth cones can sense the local environment and can guide axonal growth toward a neuron's target cell. Growth cones can respond to environmental cues, for example, surface adhesiveness, growth factors, neurotransmitters and electric fields. The growth cones can advance at a rate of one to two millimeters per day. The growth cone can explore the area ahead of it and on either side, by means of elongations classified as lamellipodia and filopodia. When an elongation contacts an unfavorable surface, it can withdraw. When an elongation contacts a favorable growth surface, it can continue to extend and guides the growth cone in that direction. When the growth cone reaches an appropriate target cell a synaptic connection can be created.

Nerve cell function can be influenced by contact between neurons and other cells in their immediate environment (Rutishauser, et al., 1988, *Physiol. Rev.* 68:819, which is incorporated by reference in its entirety). These cells can include specialized glial cells, oligodendrocytes in the central nervous system (CNS), and Schwann cells in the peripheral nervous system (PNS), which can sheathe the neuronal axon with myelin (Lemke, 1992, in *An Introduction to Molecular Neurobiology*, Z. Hall, Ed., p. 281, Sinauer, each of which is incorporated by reference in its entirety). LPA causes the collapse of the neuron growth cone and tends to inhibit or reverse the morphological differentiation of many neuronal cell lines (see Gendaszewska-Darmach, Acta Biochimica Polonica (2008), 55(2):227-240). Since ATX activity is involved in the generation of LPA, inhibitors of ATX should increase the ability of the nervous system to make synaptic connections. Thus, ATX inhibitors may be useful in treating neurodegenerative disorders such as Alzheimer's disease, Huntington's disease, Parkinson's disease (including Parkinson's dementia), Lewy Body Dementia, amylotrophic lateral sclerosis (ALS), Friedreich's ataxia, spinal muscular atrophy.

CNS neurons can have the inherent potential to regenerate after injury, but they can be inhibited from doing so by inhibitory proteins present in myelin (Brittis et al., 2001, *Neuron* 30:11-14; Jones et al., 2002, *J. Neurosci.* 22:2792-2803; Grimpe et al., 2002, *J. Neurosci.:* 22:3144-3160, each of which is incorporated by reference in its entirety). Such diseases, disorders or injuries can include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, or Bell's palsy. Among these diseases, MS may the most widespread, affecting approximately 2.5 million people worldwide.

MS can begin with a relapsing-remitting pattern of neurologic involvement, which then can progress to a chronic phase with increasing neurological damage. MS can be associated with the destruction of myelin, oligodendrocytes or axons localized to chronic lesions. The demyclination observed in MS may not always permanent and remyelination has been documented in early stages of the disease. Remyelination of neurons can require oligodendrocytes.

Various disease-modifying treatments may be available for MS, including the use of corticosteroids and immunomodulators such as interferon beta or Tysabri®. In addition, because of the central role of oligodendrocytes and myelination in MS, there have been efforts to develop therapies to increase oligodendrocyte numbers or enhance myelination. See, e.g., Cohen et al., U.S. Pat. No. 5,574,009; Chang et al., *N. Engl. Med.* 346: 165-73 (2002), each of which is incorporated by reference in its entirety. However, there remains an urgent need to devise additional therapies for MS and other demyelination and dismyelination disorders.

A compound of the invention, or a pharmaceutically acceptable salt thereof, can promote myelination or remyelination. A method can include administering a compound of the invention, or a pharmaceutically acceptable salt thereof, to cells. A method of promoting oligodendrocyte progenitor cell differentiation can include administering a compound of the invention, or a pharmaceutically acceptable salt thereof, to cells. A method of treating multiple sclerosis can include administering a compound of the invention, or a pharmaceutically acceptable salt thereof, to a subject.

The dose of a compound of the invention, or a pharmaceutically acceptable salt thereof, administered to a subject can be less than 10 µg, less than 25 µg, less than 50 µg, less than 75 µg, less than 0.10 mg, less than 0.25 mg, less than 0.5 mg, less than 1 mg, less than 2.5 mg, less than 5 mg, less than 10 mg, less than 15 mg, less than 20 mg, less than 50 mg, less than 75 mg, less than 100 mg, or less than 500 mg.

Administering can include administering by topical, enteral, parenteral, transdermal, transmucosal, inhalational, intracisternal, epidural, intravaginal, intravenous, intramuscular, subcutaneous, intradermal or intravitreal administration.

The duration of administering can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

Administering the inhibitor or compound can include multiple administrations. The duration between administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

The duration between successive administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours, between 24 hours and 48 hours, between 48 hours and 72 hours, between 72 hours and 1 week or between 1 week and 2 weeks.

Administering an inhibitor or compound to cells can include cells of an in vitro or in vivo system or model. The cells can be part of a cell line. The cell line can be a primary or secondary cell line. The cell line can be an immortal cell line. The cells can be ruptured and be in the form of a cell lysate. The cells can be part of a living organism, i.e., a subject, for example, a mammal. A mammal can include a rat, a mouse, a gerbil, a hamster, a rabbit or a human. The human can be a subject or a patient.

A method can further include monitoring a property of a sample or a subject. A sample can be removed from a subject. For instance, a sample can include a sample of cells or a tissue from a subject. A sample can include blood, plasma, or neuronal tissue including neurons or glial cells. A sample can also remain in the subject. For example, a sample can be a tissue or cells that are observed within the patient.

A method can further include providing untreated control cells, sample or subject and measuring a property of a sample of the untreated control cells, sample or subject.

A property can include the presence or absence of a molecule, the concentration of a molecule, for example myelin basic protein, myelin associated glycoprotein or myelin oligodendrocyte glycoprotein. In some embodiments, determining the presence of a molecule can include determining the concentration of the molecule, determining the purity of the molecule or determining the quantity of the molecule.

A property can be the conductivity of a tissue or cell. A property can be an emission, for example, electromagnetic radiation.

Monitoring a property can include observing the property of the sample or subject alone. Monitoring a property can include monitoring the property before the sample or subject has been administered a compound of the invention, or a pharmaceutically acceptable salt thereof. Monitoring a property can include monitoring the property after the sample or subject has been administered a compound. Monitoring a property can include monitoring a property after the sample or subject has been administered a known concentration of a compound.

Monitoring a property of a sample or subject can include observing the property through a microscope. Monitoring a property of the composition can include measuring the property using a microscope. Monitoring a property of the composition can include monitoring the property using still photography or movies. The photography or movies can be on film media or digital form. Monitoring a property can include taking a scan, for example, an MRI or CT scan.

Promoting myelination, remyelination or oligodendrocyte progenitor cell differentiation can prevent or can treat a pathological condition or symptom in a mammal. A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes dorsalis due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency, and copper deficiency. Some demyclination disorders can have unknown or multiple causes such as trigeminal neuralgia, Marchiafava-Bignami disease and Bell's palsy. In addition, demyelination can contribute to neuropathic pain. Compounds of the invention are expected to be useful in treating demyelination disorders.

Since LPA is a proinflammatory factor reducing the amount of LPA produced by inhibiting ATX is useful for treating inflammatory disorders such as asthma, allergies, arthritis, inflammatory neuropathies, transplantation rejection, Crohn's disease, ulcerative colitis, lupus erythematosis, psoriasis, an inflammatory bowel condition, and diabetes.

LPA has been shown to be involved in wound healing and stimulates the proliferation and migration of endothelial cells promoting processes such as angiogenesis. However, these same processes when deregulated can promote tumor growth and metastasis, and LPA is thought to contribute to the development, progression, and metastasis of several types of cancer including ovarian, prostate, melanoma, breast, head and neck cancers (see Gendaszewska-Darmach, Acta Biochimica Polonica (2008), 55(2):227-240). In addition, since ATX is located outside the cell in circulation, ATX inhibitors are expected to be of most benefit outside the cell. Therefore, ATX inhibitors are expected to be useful in treating cancer, particularly multidrug resistant (MDR) cancers where drug efflux mechanisms are the largest contributor to the drug resistance.

The compound can be administered as a pharmaceutical composition. A pharmaceutical composition can include a compound of the invention, or a pharmaceutically acceptable salt thereof. More particularly, a compound of the invention, or a pharmaceutically acceptable salt thereof can be formulated as pharmaceutical compositions using standard pharmaceutically acceptable carriers, fillers, solubilizing agents and stabilizers known to those skilled in the art. For example, a pharmaceutical composition including a compound of the invention, or a salt, analog, derivative, or modification thereof, as described herein, can be used to administer the appropriate compound to a subject.

A compound of the invention, or a pharmaceutically acceptable salt thereof, can be useful for treating a disease or disorder, for example, in a method including administering to a subject in need thereof of a therapeutically acceptable amount of compound of the invention, or a pharmaceutically acceptable salt thereof, or a pharmaceutical composition comprising a therapeutically effective amount of a compound of the invention, or a pharmaceutically acceptable salt thereof, and a pharmaceutically-acceptable carrier.

In cases where a compound of the invention can be sufficiently basic or acidic to form stable nontoxic acid or base salts, preparation and administration of the compounds as pharmaceutically acceptable salts may be appropriate. Examples of pharmaceutically acceptable salts can be organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included can be amines where the two or three substituents, together with the amino nitrogen, form a heterocyclic or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

A compound of the invention, or a pharmaceutically acceptable salt thereof, formulated as a pharmaceutical composition and administered to a mammalian host, such as a human patient in a variety of forms adapted to the chosen route of administration, e.g., orally or parenterally, as eye-drops, by intravenous, intramuscular, topical or subcutaneous routes. In addition, the term "administer" or "administering" encompasses delivering a compound of the invention as a prodrug which is converted or metabolized in the body of the mammal into a compound of the invention. In one embodiment, a compound of the invention is administered in a non-prodrug form. In another embodiment, the compound is administered as a prodrug which is metabolized to a compound of the invention in the body of a mammal.

Thus, compound of the invention, or a pharmaceutically acceptable salt thereof, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl or propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, or nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, or thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate or gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

For topical administration, a compound of the invention may be applied in pure form, e.g., when they are liquids. However, it can generally be desirable to administer them to the skin as compositions or formulations, in combination with a dermatologically acceptable carrier, which may be a solid or a liquid.

Exemplary solid carriers can include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts or esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference in its entirety.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

Generally, the concentration of the compound(s) of the invention in a liquid composition, such as a lotion, can be from about 0.1 to about 25 weight percent, preferably from about 0.5-10 weight percent. The concentration in a semi-solid or solid composition such as a gel or a powder can be about 0.1-5 wt-%, preferably about 0.5-2.5 weight percent based on the total weight of the composition.

The amount of the compound, or an active salt or derivative thereof, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The compound can be conveniently administered in unit dosage form; for example, containing 0.01 to 10 mg, or 0.05 to 1 mg, of active ingredient per unit dosage form. In some embodiments, a dose of 5 mg/kg or less can be suitable.

The active ingredient can be administered so as to achieve a desired peak plasma concentration of the active compound. The desired peak plasma concentration can be from about 0.5 µM to about 75 µM, preferably, about 1 µM to 50 µM, or about 2 µM to about 30 µM. This may be achieved, for example, by the intravenous injection of a 0.05 to 5% solution of the active ingredient, optionally in saline, or orally administered as a bolus containing between about 1 mg to about 100 mg of the active ingredient.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method can include a kit comprising a compound of the invention and instructional material which can describe administering the compound or a composition comprising the compound to a cell or a subject. This should be construed to include other embodiments of kits that are known to those skilled in the art, such as a kit comprising a (preferably sterile) solvent for dissolving or suspending the compound or composition prior to administering the compound or composition to a cell or a subject. Preferably, the subject can be a human.

In accordance with the disclosed methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

EXAMPLES

In general, a compound of formula (I), or a pharmaceutically acceptable salt thereof, can be prepared according to Scheme 1 (in Scheme 1, "LG" represents a leaving group).

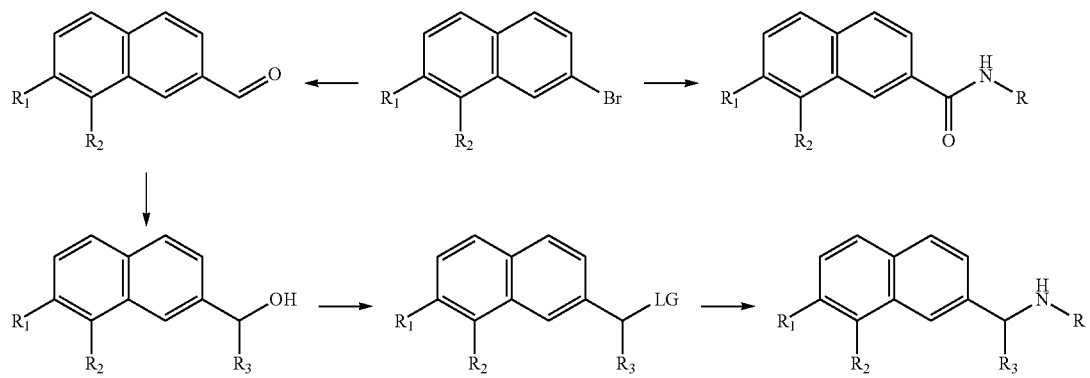

Scheme 1

Example 1: 4-((7-((cis-4-methylcyclohexyl)oxy)-8-(trifluoromethyl)naphthalen-2-yl)methyl)morpholine

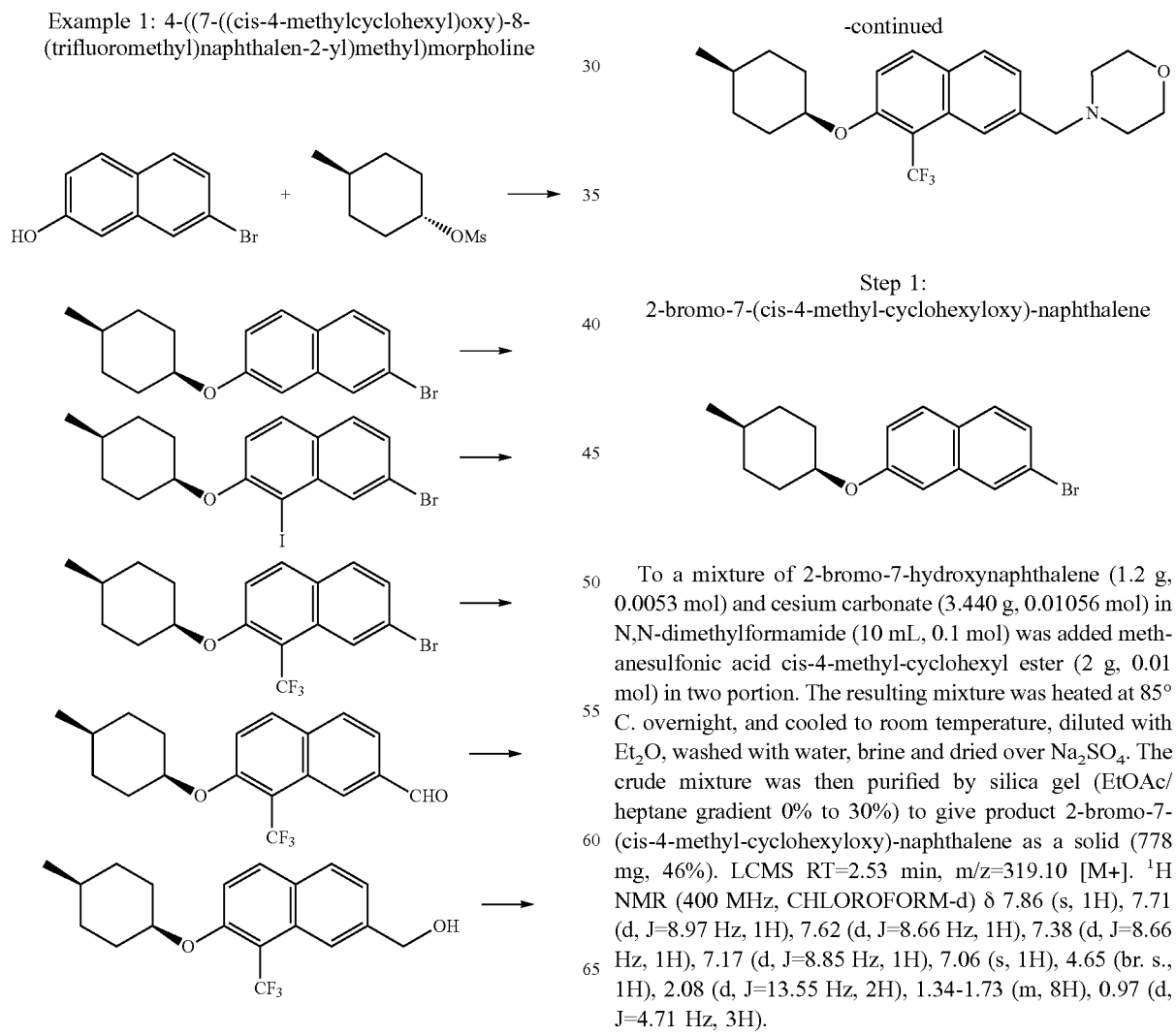

Step 1:
2-bromo-7-(cis-4-methyl-cyclohexyloxy)-naphthalene

To a mixture of 2-bromo-7-hydroxynaphthalene (1.2 g, 0.0053 mol) and cesium carbonate (3.440 g, 0.01056 mol) in N,N-dimethylformamide (10 mL, 0.1 mol) was added methanesulfonic acid cis-4-methyl-cyclohexyl ester (2 g, 0.01 mol) in two portion. The resulting mixture was heated at 85° C. overnight, and cooled to room temperature, diluted with Et$_2$O, washed with water, brine and dried over Na$_2$SO$_4$. The crude mixture was then purified by silica gel (EtOAc/heptane gradient 0% to 30%) to give product 2-bromo-7-(cis-4-methyl-cyclohexyloxy)-naphthalene as a solid (778 mg, 46%). LCMS RT=2.53 min, m/z=319.10 [M+]. $^1$H NMR (400 MHz, CHLOROFORM-d) δ 7.86 (s, 1H), 7.71 (d, J=8.97 Hz, 1H), 7.62 (d, J=8.66 Hz, 1H), 7.38 (d, J=8.66 Hz, 1H), 7.17 (d, J=8.85 Hz, 1H), 7.06 (s, 1H), 4.65 (br. s., 1H), 2.08 (d, J=13.55 Hz, 2H), 1.34-1.73 (m, 8H), 0.97 (d, J=4.71 Hz, 3H).

Step 2: 7-bromo-1-iodo-2-(cis-4-methyl-cyclohexyloxy)-naphthalene

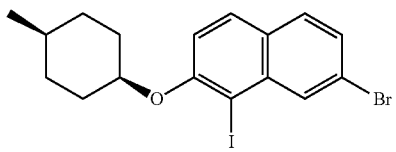 [SMILES: C[C@H]1CC[C@@H](Oc2ccc3ccc(Br)cc3c2I)CC1]

A mixture of 2-bromo-7-(cis-4-methyl-cyclohexyloxy)-naphthalene (0.778 g, 0.00244 mol), N-iodosuccinimide (614 mg, 0.00273 mol) and zirconium tetrachloride (85 mg, 0.00036 mol) in methylene chloride (15.6 mL, 0.244 mol) was heated to reflux under Ar in a vial for 2 h. The precipitate was filtered off and the residue was purified with silica gel column eluted with EtOAc in hexane from 0 to 40% to give the product, 7-bromo-1-iodo-2-(cis-4-methyl-cyclohexyloxy)-naphthalene as a solid (1.03 g, 95%). LCMS Rt=2.76 min, m/z=445.9 [M+]. $^1$H NMR (400 MHz, CHLOROFORM-d) δ 8.35 (s, 1H), 7.73 (d, J=8.91 Hz, 1H), 7.59 (d, J=8.60 Hz, 1H), 7.43 (d, J=10.54 Hz, 1H), 7.17 (d, J=9.04 Hz, 1H), 4.81 (br. s., 1H), 2.07 (d, J=10.42 Hz, 2H), 1.42-1.74 (m, 8H), 1.00 (d, J=5.90 Hz, 3H).

Step 3: 7-Bromo-2-(cis-4-methyl-cyclohexoxy)-1-trifluoromethyl-naphthalene

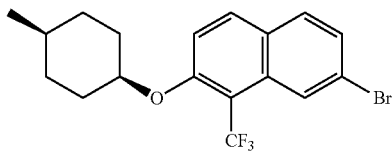 [SMILES: C[C@H]1CC[C@@H](Oc2ccc3ccc(Br)cc3c2C(F)(F)F)CC1]

To a solution of 7-bromo-1-iodo-2-(cis-4-methyl-cyclohexyloxy)-naphthalene (1.03 g, 2.31 mmol), hexamethylphosphoramide (2.0 mL, 12 mmol) and copper(I) iodide (660 mg, 3.5 mmol) in N,N-dimethylformamide (5.37 mL, 69.4 mmol) was added methyl fluorosulphonyldifluoroacetate (1.5 mL, 12 mmol). The mixture was heated at 80° C. overnight. LCMS showed desired product peak Rt=2.62 min, m/z=372.10. The solvent was evaporated and purified on silica gel with EA/HE gave the product, bromo-2-(cis-4-methyl-cyclohexyloxy)-1-trifluoromethyl-naphthalene (848 mg, 95%). $^1$H NMR (400 MHz, CHLOROFORM-d) δ 8.39 (s, 1H), 7.89 (d, J=9.16 Hz, 1H), 7.65 (d, J=8.60 Hz, 1H), 7.48 (d, J=8.66 Hz, 1H), 7.30 (s, 1H), 4.78 (br. s., 1H), 2.07 (d, J=13.11 Hz, 2H), 1.38-1.76 (m, 7H), 0.92-1.05 (m, 3H).

Step 4: 7-(cis-4-methyl-cyclohexyloxy)-8-trifluoromethyl-naphthalene-2-carbaldehyde

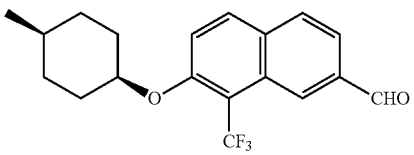 [SMILES: C[C@H]1CC[C@@H](Oc2ccc3ccc(C=O)cc3c2C(F)(F)F)CC1]

7-Bromo-2-(cis-4-methyl-cyclohexyloxy)-1-trifluoromethyl-naphthalene (4.00E2 mg, 1.03 mmol) in tetrahydrofuran (5.03 mL, 62.0 mmol) at −78° C. was added 2.0 M of n-butyllithium in cyclohexane (0.671 mL, 1.34 mmol) and was stirred 15 min. N,N-dimethylformamide (0.400 mL, 5.16 mmol) was added to the above mixture at −78° C. and was stirred for 1 h. After warmed up to rt, water was added and adjusting pH to 3~4 with 1N HCl. The mixture was extracted with EtOAC and organic layer was dried with Na2SO4 to give product, 7-(cis-4-methyl-cyclohexyloxy)-8-trifluoromethyl-naphthalene-2-carbaldehyde as an oil (342 mg, 98%). LCMS: Rt=2.26 min, m/z=337.10.

Step 5: [7-(cis-4-methyl-cyclohexyloxy)-8-trifluoromethyl-naphthalen-2-yl]-methanol

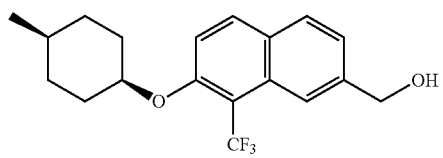 [SMILES: C[C@H]1CC[C@@H](Oc2ccc3ccc(CO)cc3c2C(F)(F)F)CC1]

To a mixture of 7-(cis-4-methyl-cyclohexyloxy)-8-trifluoromethyl-naphthalene-2-carbaldehyde (342 mg, 1.02 mmol) in tetrahydrofuran (16 mL, 2.0E2 mmol) was added 1.00 M of lithium tetrahydroaluminate in tetrahydrofuran (2.542 mL, 2.542 mmol). Gas evolution observed. The reaction was then stirred at rt for 30 min, LCMS showed complete conversion. EtOAc was added and Rochele's salt was added and stirred for 30 min. The organic layer was washed with brine, dried and evaporated, and dried under high vacuum to give desired product, 7-(cis-4-methyl-cyclohexyloxy)-8-trifluoromethyl-naphthalen-2-yl]-methanol (343 mg, 99.7%). LCMS: RT=2.02 min; m/z=338.30; $^1$H NMR (400 MHz, CHLOROFORM-d) δ 8.17 (s, 1H), 7.91 (d, J=9.16 Hz, 1H), 7.79 (d, J=8.41 Hz, 1H), 7.44 (d, J=8.34 Hz, 1H), 7.29 (s, 1H), 4.87 (d, J=5.90 Hz, 2H), 4.77 (br. s., 1H), 1.94-2.18 (m, 2H), 1.78 (t, J=6.05 Hz, 1H), 1.38-1.69 (m, 6H), 0.97 (d, J=4.52 Hz, 3H).

Step 6: Methanesulfonic acid 7-(cis-4-methyl-cyclohexyloxy)-8-trifluoromethyl-naphthalen-2-ylmethyl ester

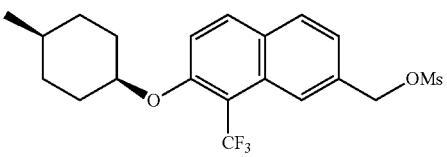 [SMILES: CS(=O)(=O)OCc1ccc2ccc(O[C@H]3CC[C@@H](C)CC3)c(C(F)(F)F)c2c1]

To a solution of [7-(4-methyl-cyclohexyloxy)-8-trifluoromethyl-naphthalen-2-yl]-methanol (343 mg, 1.01 mmol) and N,N-diisopropylethylamine (0.52971 mL, 3.0411 mmol) in methylene chloride (4.7 mL, 73 mmol) was added methanesulfonyl chloride (0.15692 mL, 2.0274 mmol) dropwise. A white precipitate formed. The solution was stirred at rt for 1 h. LCMS showed no starting material left, and complete conversion to 2:1 mixture of RT=2.13 min and 2.41 min. The mixture was diluted with DCM and washed with sodium bicarbonate aq solution and water, dried over MgSO4, filtered, concentrated. The residue (420 mg) was used as in the next step.

Step 7: 4-[7-(cis-4-Methyl-cyclohexyloxy)-8-trifluoromethyl-naphthalen-2-ylmethyl]-morpholine

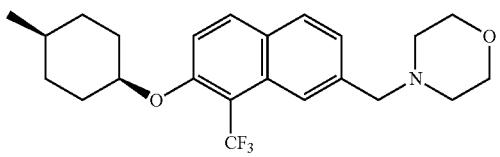 [SMILES: C[C@H]1CC[C@@H](Oc2ccc3ccc(CN4CCOCC4)cc3c2C(F)(F)F)CC1]

To a solution of methanesulfonic acid 7-(cis-4-methylcyclohexyloxy)-8-trifluoromethyl-naphthalen-2-ylmethyl ester (105 mg, 0.252 mmol) in N,N-dimethylformamide (2.9 mL, 38 mmol), morpholine (43.931 mg, 0.50426 mmol) was added, followed by cesium carbonate (246.44 mg, 0.75638 mmol). The reaction was then heated at 80° C. for 1 h. LCMS showed no SM left, and the completion of the reaction. Cooled down, the reaction mixture was filtered through celite and washed with McOH, and purified by HLPC to give the title compound as a white powder (65 mg, 63%). LCMS: RT=1.46 min.; m/z=408.2, MH+; $^1$H NMR (400 MHz, METHANOL-d4) δ 8.35 (s, 1H), 8.15 (d, J=9.41 Hz, 1H), 8.04 (d, J=8.34 Hz, 1H), 7.61 (d, J=9.29 Hz, 1H), 7.55 (d, J=8.35 Hz, 1H), 4.95 (br. s., 1H), 4.57 (s, 2H), 3.40 (br. s., 8H), 2.06 (d, J=15.75 Hz, 2H), 1.28-1.79 (m, 7H), 0.98 (s, 3H). $^{19}$F NMR (376 MHz, METHANOL-d4) δ 53.24 (3F), 77.25 (3F).

Example 2: 9-[7-(cis-4-methyl-cyclohexyloxy)-8-trifluoromethyl-naphthalen-2-ylmethyl]-9-aza-bicyclo[3.3.1]nonane-3-carboxylic acid

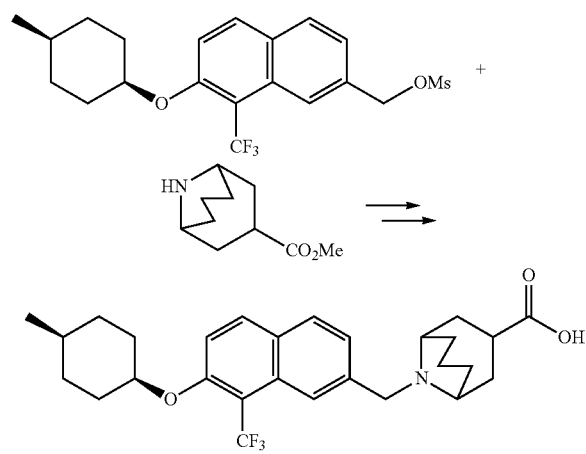

To a solution of methanesulfonic acid 7-(cis-4-methyl-cyclohexyloxy)-8-trifluoromethyl-naphthalen-2-ylmethyl ester (105 mg, 0.252 mmol) in N,N-dimethylformamide (2.9 mL, 38 mmol), 9-Aza-bicyclo[3.3.1]nonane-3-carboxylic acid methyl ester; HCl salt (110.79 mg, 0.50426 mmol) was added, followed by cesium carbonate (246.44 mg, 0.75638 mmol). The reaction was then heated at 80° C. for 1 h. LCMS showed no SM left, and the completion of the reaction (RT 1.60 min.; MH+ 504.3). Cooled down, the reaction mixture was diluted with EtOAc, washed with water (2×). The organic phase was then separated, dried and concentrated. The crude was purified by HPLC, removed the solvent, the ester was then dissolved in tetrahydrofuran (1.2 mL, 14 mmol), treated with 1.0 M of lithium hydroxide in water (1.8 mL, 1.8 mmol) at rt overnight. Acidified with conc. HCl, the organic layer was dried and concentrated (50 mg, 40%). The crude was then purified by HLPC to give the title compound as a white powder. LCMS: RT=1.50 min.; MH+ 490.20; $^1$H NMR (400 MHz, METHANOL-d4) δ 8.42 (br. s., 1H), 8.15 (d, J=9.35 Hz, 1H), 8.04 (d, J=8.41 Hz, 1H), 7.54-7.68 (m, 2H), 4.96 (br. s., 1H), 4.61-4.82 (m, 2H), 3.54-3.74 (m, 2H), 3.43 (br. s., 2H), 1.37-2.71 (m, 18H), 0.97 (d, J=5.77 Hz, 3H).

Example 3: 8-[7-(cis-4-methyl-cyclohexyloxy)-8-trifluoromethyl-naphthalen-2-ylmethyl]-8-aza-bicyclo[3.2.1]octane-3-carboxylic acid

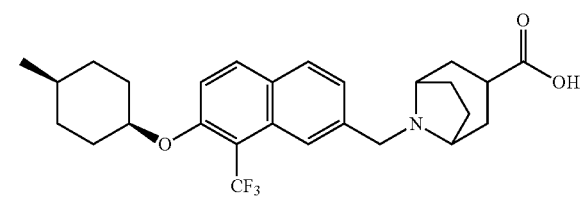 [SMILES: C[C@H]1CC[C@@H](Oc2ccc3ccc(CN4C5CCC4CC(C(=O)O)C5)cc3c2C(F)(F)F)CC1]

To a solution of methanesulfonic acid 7-(cis-4-methyl-cyclohexyloxy)-8-trifluoromethyl-naphthalen-2-ylmethyl ester (105 mg, 0.252 mmol) in N,N-dimethylformamide (2.9 mL, 38 mmol), 8-aza-bicyclo[3.2.1]octane-3-carboxylic acid methyl ester; HCl salt (103.72 mg, 0.50426 mmol) was added, followed by cesium carbonate (246.44 mg, 0.75638 mmol). The reaction was then heated at 80° C. for 1 h. LCMS showed no SM left, and the completion of the reaction (RT 1.56 min.; MH+ 490.3 and 1.49 min, 476.30. Cooled down, the reaction mixture was diluted with EtOAc, washed with water (2×). The organic phase was then separated, dried and concentrated. The crude was purified by HPLC, removed the solvent, the ester was then dissolved in tetrahydrofuran (1.2 mL, 14 mmol), treated with 1.0 M of lithium hydroxide in water (1.8 mL, 1.8 mmol) at rt overnight. Acidified with conc. HCl, the organic layer was dried and concentrated. The crude was then purified by HLPC to give the title compound as a white powder (57.6 mg, 48%). LCMS: RT=1.49 min.; MH+ 476.20; $^1$H NMR (400 MHz, METHANOL-d4) δ 8.36 (s, 1H), 8.15 (d, J=9.29 Hz, 1H), 8.04 (d, J=8.34 Hz, 1H), 7.61 (d, J=9.54 Hz, 1H), 7.57 (d, J=6.78 Hz, 1H), 4.96 (br. s., 1H), 4.41 (s, 2H), 4.02 (br. s., 2H), 2.81-3.09 (m, 2H), 1.44-2.63 (m, 16H), 0.98 (d, J=5.84 Hz, 3H).

Example 4: 1-[7-(cis-4-Methyl-cyclohexyloxy)-8-trifluoromethyl-naphthalen-2-ylmethyl]-piperidine-4-carboxylic acid

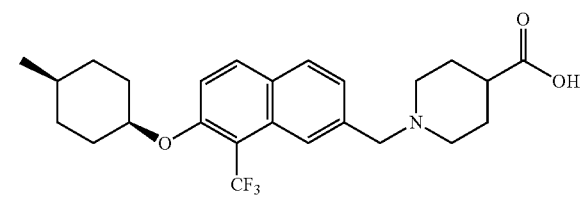 [SMILES: C[C@H]1CC[C@@H](Oc2ccc3ccc(CN4CCC(C(=O)O)CC4)cc3c2C(F)(F)F)CC1]

To a solution of methanesulfonic acid 7-(4-methyl-cyclohexyloxy)-8-trifluoromethyl-naphthalen-2-ylmethyl ester (105 mg, 0.252 mmol) in N,N-dimethylformamide (2.9 mL, 38 mmol), piperidine-4-carboxylic acid ethyl ester, HCl salt; (97.660 mg, 0.50426 mmol) was added, followed by cesium carbonate (246.44 mg, 0.75638 mmol). The reaction was then heated at 80° C. for 1 h. LCMS showed no SM left, and the completion of the reaction (RT=1.58 min.; MH+ 478.3). Cooled down, the reaction mixture was diluted with EtOAc, washed with water (2×). The organic phase was then separated, dried and concentrated. The crude was purified by HPLC, removed the solvent, the ester was then dissolved in tetrahydrofuran (1.2 mL, 14 mmol), treated with 1.0 M of lithium hydroxide in water (1.8 mL, 1.8 mmol) at rt overnight. Acidified with conc. HCl, the organic layer was dried and concentrated. The crude was then purified by HLPC to give the title compound as a white powder (63 mg, 56%). LCMS: RT=1.46 min.; MH+ 450.2; $^1$H NMR (400 MHz, METHANOL-d4) δ 8.33 (s, 1H), 8.15 (d, J=9.29 Hz, 1H), 8.04 (d, J=8.28 Hz, 1H), 7.61 (d, J=9.22 Hz, 1H), 7.54 (d, J=9.79 Hz, 1H), 4.96 (br. s., 1H), 4.52 (s, 2H), 3.46-3.66 (m, 2H), 2.99-3.24 (m, 2H), 2.55-2.74 (m, 1H), 1.37-2.38 (m, 13H), 0.98 (d, J=5.84 Hz, 3H).

Example 5: 9-{1-[7-(cis-4-methyl-cyclohexyloxy)-8-trifluoromethyl-naphthalen-2-yl]-ethyl}-9-azabicyclo[3.3.1]nonane-3-carboxylic acid

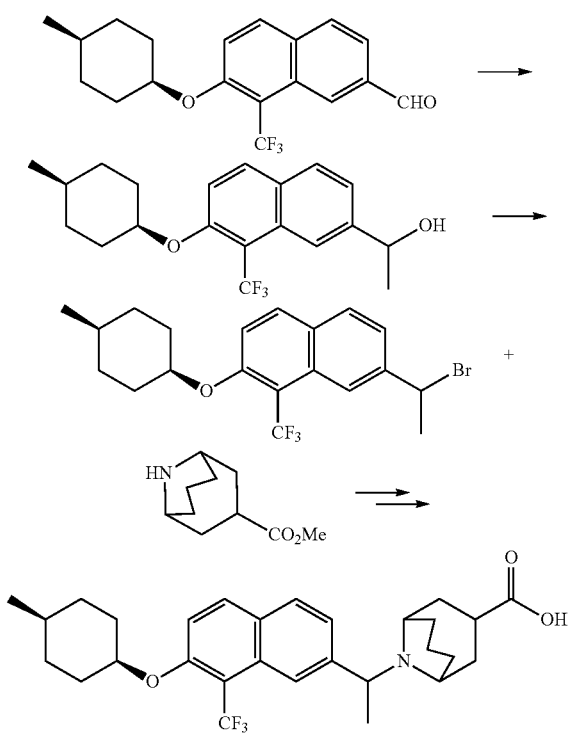

Step 1: 1-[7-(cis-4-Methyl-cyclohexyloxy)-8-trifluoromethyl-naphthalen-2-yl]-ethanol

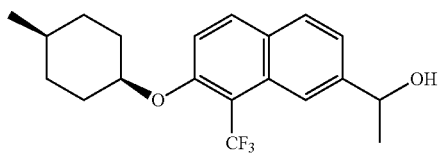

To a solution of 7-(4-methyl-cyclohexyloxy)-8-trifluoromethyl-naphthalene-2-carbaldehyde (134 mg, 0.398 mmol) in dry tetrahydrofuran (2.00 mL, 24.7 mmol) at 0° C.) under N$_2$ was added dropwise a solution of Grinard reagent 1.4 M of methylmagnesium bromide in toluene (0.427 mL, 0.598 mmol). After stirred at rt for 40 min, the reaction was quenched with satd. NH$_4$Cl, extracted with EtOAc. The organic phase was washed with brine, dried, filtered and concentrated. Column purification gave product (129 mg, 92%). LCMS Rt=2.10 min, m/z=335.10 [M−H$_2$O]. $^1$H NMR (400 MHz, CHLOROFORM-d) δ 8.16 (s, 1H), 7.91 (d, J=9.22 Hz, 1H), 7.79 (d, J=8.41 Hz, 1H), 7.47 (d, J=8.41 Hz, 1H), 7.28 (s, 1H), 5.00-5.16 (m, 1H), 4.77 (br. s., 1H), 2.00-2.14 (m, 2H), 1.91 (d, J=3.51 Hz, 1H), 1.60-1.79 (m, 2H), 1.58 (d, J=6.46 Hz, 3H), 1.50 (br. s., 4H), 0.97 (d, J=3.26 Hz, 3H).

Step 2: 7-(1-bromo-ethyl)-2-(cis-4-methyl-cyclohexyloxy)-1-trifluoromethyl-naphthalene

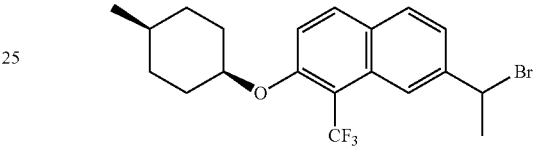

To a solution of 1-[7-(cis-4-methyl-cyclohexyloxy)-8-trifluoromethyl-naphthalen-2-yl]-ethanol (129 mg, 0.366 mmol) in THF under N$_2$ was added 1 M of phosphorus tribromide in methylene chloride dropwise at room temperature. The reaction mixture was stirred at rt for 10 minutes. TLC shows no more starting material, mainly a less polar spot. Worked up with EtOAc and water. The organic phase was dried, filtered and concentrated to give a colorless oil, and used as such for next step directly. $^1$H NMR (400 MHz, CHLOROFORM-d) δ 8.18 (s, 1H), 7.90 (d, J=9.22 Hz, 1H), 7.79 (d, J=8.53 Hz, 1H), 7.54 (d, J=8.53 Hz, 1H), 7.30 (s, 1H), 5.37 (q, J=6.90 Hz, 1H), 4.77 (br. s., 1H), 2.14 (s, 3H), 1.87-2.09 (m, 4H), 1.40-1.72 (m, 5H), 0.97 (d, J=5.21 Hz, 3H).

Step 3: 9-{1-[7-(cis-4-methyl-cyclohexyloxy)-8-trifluoromethyl-naphthalen-2-yl]-ethyl}-9-aza-bicyclo[3.3.1]nonane-3-carboxylic acid

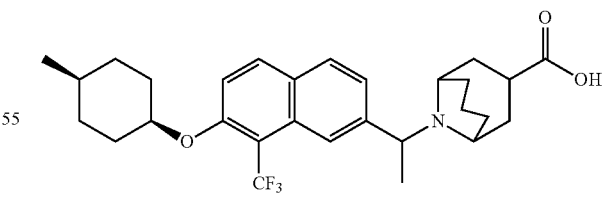

To a mixture of cesium carbonate (179 mg, 0.549 mmol) and 9-aza-bicyclo[3.3.1]nonane-3-carboxylic acid methyl ester; HCl salt (121 mg, 0.549 mmol) was added solution of 7-(1-bromo-ethyl)-2-(cis-4-methyl-cyclohexyloxy)-1-trifluoromethyl-naphthalene (152 mg, 0.366 mmol) in N,N-Dimethylformamide (4 mL, 50 mmol). The reaction mixture was stirred at rt for 30 min. And heated at 50° C. for overnight. LCMS showed fairly clean. LCMS: Rt=1.65 min, m/z=518.3. The mixture was diluted with MeOH, filtered to remove solid, and purified by HPLC (TFA method) to get the ester. The above ester was dissolved in MeOH (0.5 mL) and THF (0.5 mL), added lithium hydroxide (0.0104 mL, 1.10 mmol) and water (0.5 mL) stirred at 50° C. for 1 h. LC-MS shows the reaction was completed. Neutralized with concentrated HCl solution, Prep HPLC gave product as a solid (30.3 mg, 16.4%). LCMS: Rt=1.55 min, m/z=504.2. ¹H NMR (400 MHz, METHANOL-d4) δ 8.41 (s, 0.64H), 8.38 (s, 0.36H), 8.14 (d, J=9.29 Hz, 1H), 8.08 (d, J=8.60 Hz, 1H), 7.66-7.70 (m, 1H), 7.64 (s, 1H), 7.60 (d, J=9.10 Hz, 1H), 5.24-5.34 (m, 0.64H), 5.07-5.16 (m, 0.36H), 4.96 (br. s., 1H), 3.36-3.47 (m, 2H), 1.42-2.64 (m, 23H), 0.98 (d, J=5.77 Hz, 3H).

Example 5a: 9-{(S)-1-[7-(cis-4-methyl-cyclohexyloxy)-8-trifluoromethyl-naphthalen-2-yl]-ethyl}-9-aza-bicyclo[3.3.1]nonane-3-carboxylic acid and Example 5b: 9-{(R)-1-[7-(cis-4-methyl-cyclohexyloxy)-8-trifluoromethyl-naphthalen-2-yl]-ethyl}-9-aza-bicyclo[3.3.1]nonane-3-carboxylic acid

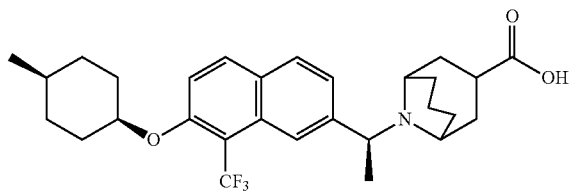

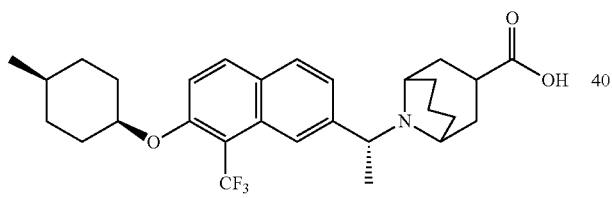

[9-{1-[7-(cis-4-Methyl-cyclohexyloxy)-8-trifluoromethyl-naphthalen-2-yl]-ethyl}-9-aza-bicyclo[3.3.1]nonane-3-carboxylic acid (90 mg, 0.2 mmol) was put under the following SFC separation yielded 15 mg of peak-1 (chemical purity >99%, ee >99%) and 13 mg of peak-2 (chemical purity >99%, ee >99%). IC (2×15 cm), 40% ethanol (0.1% DEA)/CO2, 100 bar; 60 mL/min, 220 nm; inj vol.: 1 mL, 1.5 mg/mL methanol. Peak 1: LCMS m/z=504.10. ¹H NMR (400 MHz, METHANOL-d4) δ 8.27 (br. s., 1H), 8.06 (d, J=9.10 Hz, 1H), 7.93 (d, J=8.41 Hz, 1H), 7.63 (d, J=8.34 Hz, 1H), 7.48 (d, J=9.22 Hz, 1H), 4.90 (br. s., 1H), 4.08-4.83 (m, 1H), 3.34-3.85 (m, 2H), 3.00 (q, J=7.28 Hz, 2H), 1.39-2.62 (m, 21H), 1.29 (t, J=7.28 Hz, 3H), 1.06-1.23 (m, 2H), 0.97 (d, J=5.58 Hz, 3H); Peak 1 was assigned as Example 5a.

Peak 2: LCMS m/z=504.10. ¹H NMR (400 MHz, METHANOL-d4) δ 8.28 (br. s., 1H), 8.07 (s, 1H), 7.95 (s, 1H), 7.65 (s, 1H), 7.50 (s, 1H), 4.90 (br. s., 1H), 3.34-4.86 (m, 3H), 3.01 (q, J=7.28 Hz, 2H), 1.38-2.54 (m, 21H), 1.29 (t, J=7.28 Hz, 3H), 1.04-1.23 (m, 2H), 0.97 (d, J=5.52 Hz, 3H) Peak 2 was assigned as Example 5b.

Example 6: 8-{1-[7-(cis-4-methyl-cyclohexyloxy)-8-trifluoromethyl-naphthalen-2-yl]-ethyl}-8-aza-bicyclo[3.2.1]octane-3-carboxylic acid

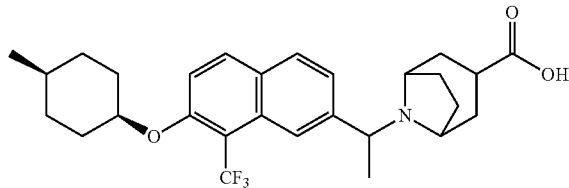 [SMILES: CC(c1ccc2ccc(O[C@H]3CC[C@@H](C)CC3)c(C(F)(F)F)c2c1)N1C2CCC1CC(C(=O)O)C2]

To a mixture of cesium carbonate (179 mg, 0.549 mmol) and 8-aza-bicyclo[3.2.1]octane-3-carboxylic acid methyl ester; HCl salt (113 mg, 0.549 mmol) was added solution of 7-(1-bromo-ethyl)-2-(4-methyl-cyclohexyloxy)-1-trifluoromethyl-naphthalene (152 mg, 0.366 mmol) in N,N-dimethylformamide (4 mL, 50 mmol). The reaction mixture was stirred at rt for 30 min, and heated at 50° C. overnight. LCMS showed fairly clean Rt=1.61 min, m/z=504.3. The mixture was diluted with MeOH, filtered to remove solid, and purified by HPLC (TFA method) to get the ester. The above ester was dissolved in MeOH (0.5 mL) and THF (0.5 mL), added lithium hydroxide (0.0104 mL, 1.10 mmol) and water (0.5 mL) stirred at 50° C. (hot plate) for 1 h. LC-MS shows the reaction was completed. Neutralized with concentrated HCl solution, Prep HPLC gave product as a solid (32.7 mg, 18%). LCMS: Rt=1.54 min, m/z=490.3. ¹H NMR (400 MHz, METHANOL-d4) δ 8.30 (s, 1H), 8.15 (d, J=9.35 Hz, 1H), 8.08 (d, J=8.47 Hz, 1H), 7.53-7.66 (m, 2H), 4.91-5.02 (m, 1H), 4.37-4.60 (m, 1H), 3.39-3.48 (m, 1H), 2.88-3.04 (m, 1H), 1.34-2.66 (m, 21H), 0.98 (s, 3H).

Example 6a: 8-{(R)-1-[7-(cis-4-methyl-cyclohexyloxy)-8-trifluoromethyl-naphthalen-2-yl]-ethyl}-8-aza-bicyclo[3.2.1]octane-3-carboxylic acid and Example 6b: 8-{(S)-1-[7-(cis-4-methyl-cyclohexyloxy)-8-trifluoromethyl-naphthalen-2-yl]-ethyl}-8-aza-bicyclo[3.2.1]octane-3-carboxylic acid

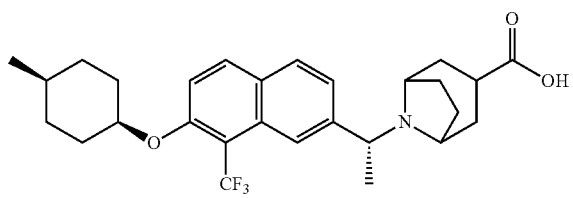

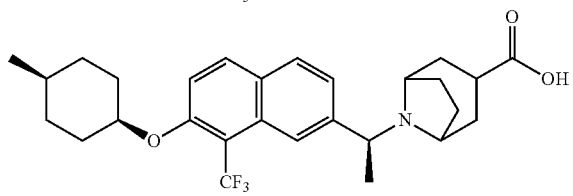

8-{1-[7-(cis-4-methyl-cyclohexyloxy)-8-trifluoromethyl-naphthalen-2-yl]-ethyl}-8-aza-bicyclo[3.2.1]octane-3-carboxylic acid (18 mg, 0.037 mmol) was put under the following SFC separation yielded 10 mg of peak-1 (chemical purity >99%, ee >99%) and 6 mg of peak-2 (chemical purity >99%, ee >99%). IC (2×15 cm), 35% 1:1 heptane:iPOH (0.1% DEA)/CO$_2$, 100 bar; 70 mL/min, 220 nm; inj vol.: 1 mL, 1.5 mg/mL isopropanol. Peak 1: LCMS m/z=490.20. $^1$H NMR (400 MHz, METHANOL-d4) δ 8.29 (s, 1H), 8.12 (d, J=9.35 Hz, 1H), 8.03 (d, J=8.53 Hz, 1H), 7.62 (d, J=8.53 Hz, 1H), 7.57 (d, J=9.22 Hz, 1H), 4.94 (br. s., 1H), 3.85-4.69 (m, 1H), 3.49 (s, 1H), 3.34-3.44 (m, 1H), 3.05 (q, J=7.28 Hz, 2H), 1.81-2.53 (m, 9H), 1.78 (s, 3H), 1.38-1.76 (m, 7H), 1.32 (d, J=3.83 Hz, 3H), 1.08-1.25 (m, 1H), 0.92-1.02 (m, 3H); Peak 1 was assigned as Example 6a.

Peak 2: LCMS m/z=490.20. $^1$H NMR (400 MHz, METHANOL-d4) δ 8.28 (s, 1H), 8.12 (d, J=9.29 Hz, 1H), 8.02 (d, J=8.53 Hz, 1H), 7.61 (d, J=9.98 Hz, 1H), 7.56 (d, J=9.29 Hz, 1H), 4.94 (br. s., 1H), 3.59-4.65 (m, 1H), 3.48 (d, J=4.71 Hz, 1H), 3.36-3.44 (m, 1H), 3.04 (q, J=7.34 Hz, 2H), 1.79-2.75 (m, 9H), 1.76 (d, J=6.59 Hz, 3H), 1.37-1.72 (m, 7H), 1.26-1.35 (m, 3H), 1.08-1.25 (m, 1H), 0.98 (s, 3H). Peak 2 was assigned as Example 6b.

Example 7: 2-((R)-1-((8-(trifluoromethyl)-7-((cis-4-(trifluoromethyl)cyclohexyl)oxy)naphthalen-2-yl)methyl)piperidin-3-yl)acetic acid

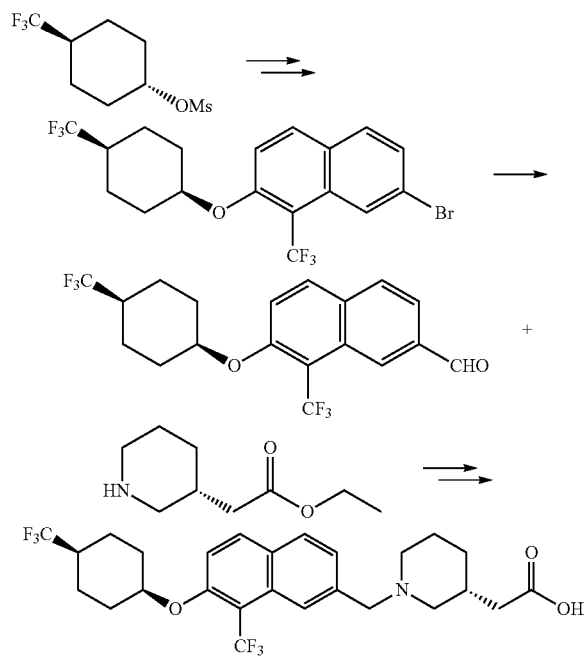

Step 1: 7-bromo-1-(trifluoromethyl)-2-((cis-4-(trifluoromethyl)cyclohexyl)oxy)naphthalene

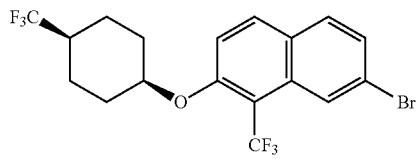 [SMILES: FC(F)(F)c1c(O[C@H]2CC[C@@H](C(F)(F)F)CC2)ccc2ccc(Br)cc12]

The title compound was prepared according to the procedure described for 7-Bromo-2-(cis-4-methyl-cyclohexyloxy)-1-trifluoromethyl-naphthalene from trans-4-(trifluoromethyl)cyclohexyl methanesulfonate and 7-bromo-naphthalen-2-ol in 3 steps.

LCMS m/z 441.00. 1H NMR (400 MHz, CHLOROFORM-d) δ 8.40 (s, 1H), 7.90 (d, J=9.16 Hz, 1H), 7.65 (d, J=8.72 Hz, 1H), 7.49 (dd, J=1.69, 8.66 Hz, 1H), 7.21-7.31 (m, 1H), 4.78-4.92 (m, 1H), 2.22 (d, J=15.18 Hz, 2H), 2.12 (ttd, J=4.06, 8.05, 16.05 Hz, 1H), 1.72-1.96 (m, 4H), 1.53-1.69 (m, 2H).

Step 2: 8-(trifluoromethyl)-7-(((1s,4s)-4-trifluoromethyl)cyclohexyl)oxy)-2-naphthaldehyde

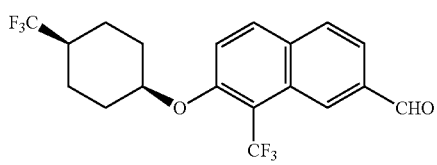 [SMILES: O=Cc1ccc2ccc(O[C@H]3CC[C@@H](C(F)(F)F)CC3)c(C(F)(F)F)c2c1]

To a dry flask was charged with 7-Bromo-1-trifluoromethyl-2-(cis-4-trifluoromethyl-cyclohexyloxy)-naphthalene (1.0 g, 2.27 mmol), N,N,N',N'-tetramethylethylenediamine (0.41 mL, 2.74 mmol) and toluene (5.0 mL, 47 mmol). Degassed with argon. The solution was cooled to −35° C., 2.5 M of n-butyllithium in hexane (1.2 mL, 2.9 mmol) was dropwise added to the mixture while maintaining the temperature at −35° C. The reaction was then stirred at −35° C. for 20 min. A solution of N,N-dimethylformamide (0.2 mL, 2.7 mmol) in toluene (1 ml) was dropwise added. The reaction was then stirred at −35° C. to −25° C. for 20 min. LCMS showed no starting material left and the formation of desired product (RT 2.10 min., MH+ 391.0). The reaction was then quenched with 1N HCl (5 ml) at −20° C. to −10° C. Diluted with EtOAc, the aqueous phase was separated, extracted with EtOAc (2×). The combined organic phase was washed with sat. NaHCO$_3$, and brine. The organic layer was dried and concentrated. The crude was purified by recrystallizations from methanol to give desired product as a white crystal (0.50 g). LCMS: RT 2.11 min.; MH+ 391.0; $^1$H NMR (400 MHz, DMSO-d6) δ 10.19 (s, 1H), 8.66 (s, 1H), 8.33 (d, J=9.29 Hz, 1H), 8.16 (d, J=8.53 Hz, 1H), 7.80-7.91 (m, 2H), 5.14 (br. s., 1H), 2.36-2.46 (m, 1H), 2.06 (d, J=13.05 Hz, 2H), 1.51-1.83 (m, 6H)

Step 3: 2-((R)-1-((8-(trifluoromethyl)-7-((cis-4-(trifluoromethyl)cyclohexyl)oxy)naphthalen-2-yl)methyl)piperidin-3-yl)acetic acid

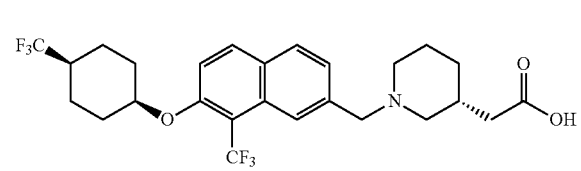 [SMILES: O=C(O)C[C@H]1CCCN(Cc2ccc3ccc(O[C@H]4CC[C@@H](C(F)(F)F)CC4)c(C(F)(F)F)c3c2)C1]

To a mixture of (R)-ethyl 2-(piperidin-3-yl)acetate hydrochloride (64 mg, 0.31 mmol) and 8-trifluoromethyl-7-(cis-4-trifluoromethyl-cyclohexyloxy)-naphthalene-2-carbaldehyde (80.0 mg, 0.205 mmol) in tetrahydrofuran (2.0 mL) was added acetic acid (0.02 mL, 0.41 mmol) and sodium triacetoxyborohydride (87 mg, 0.41 mmol), and the reaction was heated in microwave at 100° C. for 20 min. LCMS showed complete conversion (RT 1.52 min, MH+ 546.0). The reaction was worked up with EtOAc and brine. Dried over MgSO₄ and concentrated. The crude ester intermediate was then dissolved in tetrahydrofuran (1.0 mL, 12 mmol) and methanol (1.0 mL, 25 mmol), treated with 3.0 M of aqueous sodium hydroxide (1.0 mL, 3.0 mmol). The reaction was heated in microwave at 100° C. for 10 min. The crude was neutralized with 2N HCl, purified by HPLC to give the desired product as a white powder (67 mg, TFA salt). LCMS: RT 1.41 min.; MH+ 518.0; 1H NMR (400 MHz, METHANOL-d4) δ 8.23 (s, 1H), 8.06 (d, J=9.04 Hz, 1H), 7.93 (d, J=8.53 Hz, 1H), 7.38-7.58 (m, 2H), 4.93 (br. s., 1H), 4.40 (s, 2H), 3.50 (d, J=11.80 Hz, 1H), 3.40 (d, J=11.55 Hz, 1H), 2.81-2.95 (m, 1H), 2.72 (t, J=11.92 Hz, 1H), 1.96-2.35 (m, 6H), 1.55-1.92 (m, 9H), 1.09-1.29 (m, 1H).

Example 8: 2,2-dimethyl-3-(((8-(trifluoromethyl)-7-((cis-4-(trifluoromethyl)cyclohexyl)oxy)-naphthalen-2-yl)methyl)amino)cyclobutanecarboxylic acid

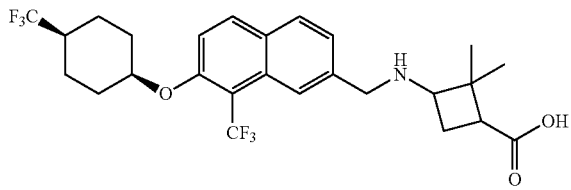 [SMILES: CC1(C)C(NCc2ccc3ccc(O[C@H]4CC[C@@H](C(F)(F)F)CC4)c(C(F)(F)F)c3c2)CC1C(=O)O]

To a mixture of 3-Amino-2,2-dimethyl-cyclobutanecarboxylic acid (44 mg, 0.31 mmol) and 8-trifluoromethyl-7-(4-trifluoromethyl-cyclohexyloxy)-naphthalene-2-carbaldehyde (80.0 mg, 0.205 mmol) in methanol (2.0 mL, 49 mmol) was added acetic acid (0.02 mL, 0.41 mmol), and the reaction was heated in microwave at 100° C. for 10 min. Cooled down, sodium triacetoxyborohydride (87 mg, 0.41 mmol) was then added, and the reaction was stirred at RT for 2 h. The reaction was worked up with EtOAc and brine. Dried over MgSO₄ and concentrated. The crude was purified by HPLC to give the desired product as a white powder (81 mg, TFA salt). LCMS: RT 1.41 min.; MH+ 518.0; 1H NMR (400 MHz, METHANOL-d4) δ 8.33 (s, 1H), 8.15 (d, J=9.29 Hz, 1H), 8.01 (d, J=8.53 Hz, 1H), 7.51-7.63 (m, 2H), 5.02 (br. s., 1H), 4.27-4.43 (m, 2H), 3.56 (t, J=8.91 Hz, 1H), 2.76 (t, J=9.04 Hz, 1H), 2.10-2.45 (m, 5H), 1.66-1.91 (m, 6H), 1.36 (s, 3H), 1.17-1.26 (m, 3H).

Example 9: 9-[8-trifluoromethyl-7-(cis-4-trifluoromethyl-cyclohexyloxy)-naphthalen-2-ylmethyl]-9-azabicyclo[3.3.1]nonane-3-carboxylic acid

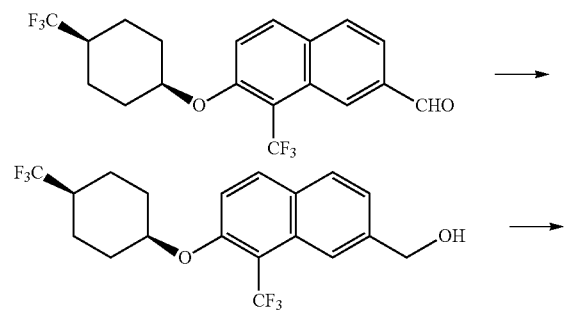

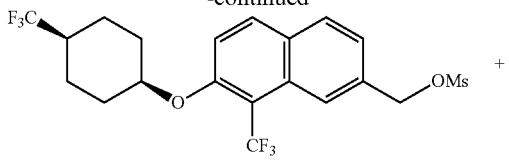

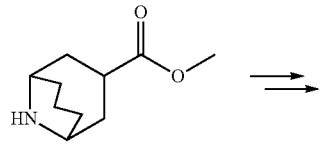

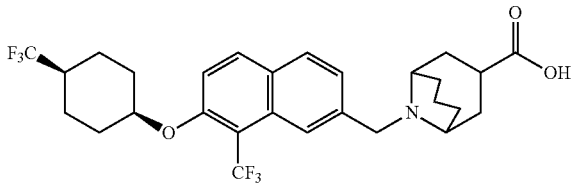

Step 1: [7-(cis-4-trifluoromethyl-cyclohexyloxy)-8-trifluoromethyl-naphthalen-2-yl]-methanol

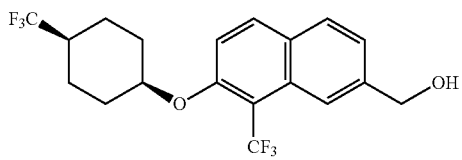

To a mixture of 8-trifluoromethyl-7-(4-trifluoromethyl-cyclohexyloxy)-naphthalene-2-carbaldehyde (115 mg, 0.295 mmol) in tetrahydrofuran (4.6 mL, 57 mmol) was added 1.00 M of lithium tetrahydroaluminate in tetrahydrofuran (0.7366 mL, 0.7366 mmol). Gas evolution observed. The reaction was then stirred at rt for 30 min, LCMS showed complete conversion. EtOAc was added and Rochele's salt was added and stirred for 30 min. The organic layer was washed with brine, dried and evaporated, and dried under high vacuum to give desired product (55.7 mg, 48%). LCMS: RT=1.87 min; m/z=375.10 [M−H2O].

Step 2: methanesulfonic acid 7-(cis-4-trifluoromethyl-cyclohexyloxy)-8-trifluoromethyl-naphthalen-2-ylmethyl ester

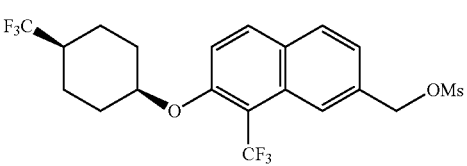 [SMILES: CS(=O)(=O)OCc1ccc2ccc(O[C@H]3CC[C@@H](C(F)(F)F)CC3)c(C(F)(F)F)c2c1]

To a solution of [8-trifluoromethyl-7-(4-trifluoromethyl-cyclohexyloxy)-naphthalen-2-yl]-methanol (55.6 mg, 0.142 mmol) and N,N-diisopropylethylamine (0.074053 mL, 0.42515 mmol) in methylene chloride (0.66 mL, 1.0E1 mmol) was added methanesulfonyl chloride (0.021938 mL, 0.28343 mmol) drop wise. A white precipitate formed. The solution was stirred at rt for 1 h. LCMS showed no starting material left, and complete conversion to 2:1 mixture of RT=1.98 min and 2.26 min. The mixture was diluted with DCM and washed with aq. sodium bicarbonate solution and water, dried over $MgSO_4$, filtered, concentrated. The residue was used as in the next step.

Step 3: 9-[8-trifluoromethyl-7-(cis-4-trifluoromethyl-cyclohexyloxy)-naphthalen-2-ylmethyl]-9-aza-bicyclo[3.3.1]nonane-3-carboxylic acid

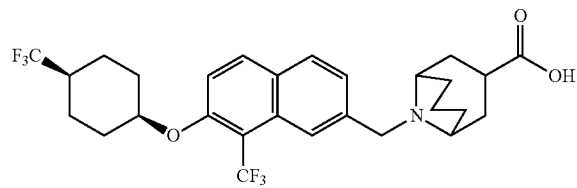 [SMILES: O=C(O)C1CC2CCCC(C1)N2Cc1ccc2ccc(O[C@H]3CC[C@@H](C(F)(F)F)CC3)c(C(F)(F)F)c2c1]

To a solution of methanesulfonic acid 8-trifluoromethyl-7-(4-trifluoromethyl-cyclohexyloxy)-naphthalen-2-ylmethyl ester (92.5 mg, 0.197 mmol) in N,N-dimethylformamide (2.3 mL, 29 mmol), 9-aza-bicyclo[3.3.1]nonane-3-carboxylic acid methyl ester; HCl salt (86.402 mg, 0.39326 mmol) was added, followed by cesium carbonate (192.20 mg, 0.58989 mmol). The reaction was then heated at 50° C. for overnight. After cooled down, the reaction mixture was diluted with MeOH, filtration and purified by HPLC, removed the solvent. The ester was then dissolved in tetrahydrofuran (0.91 mL, 11 mmol), treated with 1.0 M of lithium hydroxide in water (1.4 mL, 1.4 mmol) at 50° C. for 1 h. Acidified with IM HCl, the organic layer was dried and concentrated. The crude was then purified by HLPC to give the title compound as a white powder (40.7 mg, 38%). LCMS: RT=1.43 min.; MH+ 544.20; $^1$H NMR (400 MHz, METHANOL-d4) δ 8.44 (d, J=6.02 Hz, 1H), 8.18 (d, J=9.47 Hz, 1H), 8.06 (d, J=8.28 Hz, 1H), 7.63 (d, J=9.22 Hz, 2H), 5.05 (br. s., 1H), 4.80 (s, 1H), 4.72 (s, 1H), 3.66 (d, J=15.94 Hz, 2H), 3.35-3.49 (m, 2H), 1.60-2.67 (m, 18H).

Example 10: 9-{1-[7-(cis-4-trifluoromethyl-cyclohexyloxy)-8-trifluoromethyl-naphthalen-2-yl]-ethyl}-9-aza-bicyclo[3.3.1]nonane-3-carboxylic acid

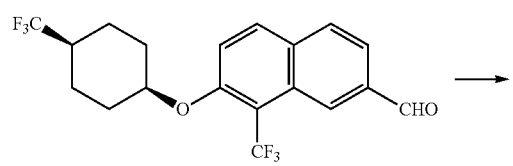

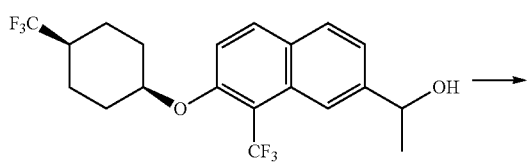

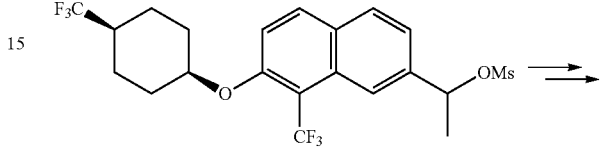

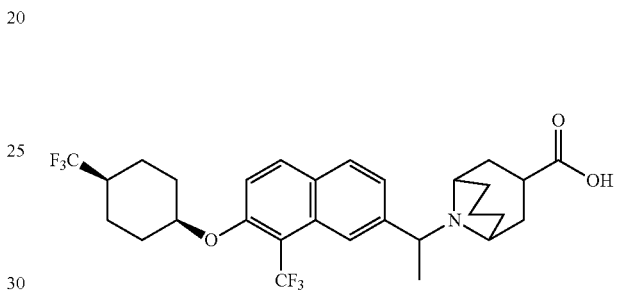

Step 1: 1-[7-(cis-4-trifluoromethyl-cyclohexyloxy)-8-trifluoromethyl-naphthalen-2-yl]-ethanol

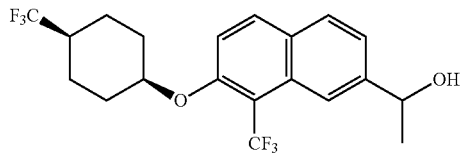 [SMILES: CC(O)c1ccc2ccc(O[C@H]3CC[C@@H](C(F)(F)F)CC3)c(C(F)(F)F)c2c1]

To a solution of 8-trifluoromethyl-7-(4-trifluoromethyl-cyclohexyloxy)-naphthalene-2-carbaldehyde (100 mg, 0.2 mmol) in dry tetrahydrofuran (2.00 mL, 24.7 mmol) at 0° C.) under $N_2$ was added dropwise a solution of Grinard reagent 1.4 M of methylmagnesium bromide in toluene (0.366 mL, 0.512 mmol). After stirred at rt for 40 min, the reaction was quenched with satd. $NH_4Cl$, extracted with EtOAc. The organic phase was washed with brine, dried, filtered and concentrated. Column purification gave the desired product (56.2 mg, 50%). LCMS Rt=1.95 min, m/z=389.10 [M−$H_2O$].

Step 2: 1-(8-(trifluoromethyl)-7-((cis-4-(trifluoromethyl)cyclohexyl)oxy)naphthalen-2-yl)ethyl methanesulfonate

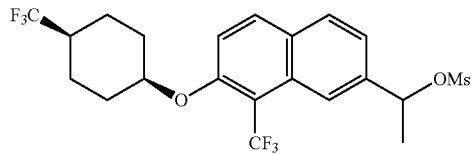 [SMILES: CC(OS(C)(=O)=O)c1ccc2ccc(O[C@H]3CC[C@@H](C(F)(F)F)CC3)c(C(F)(F)F)c2c1]

To a solution of 1-[8-trifluoromethyl-7-(4-trifluoromethyl-cyclohexyloxy)-naphthalen-2-yl]-ethanol (387 mg, 0.952 mmol) and N,N-diisopropylethylamine (0.49765 mL, 2.8570 mmol) in methylene chloride (4.4 mL, 69 mmol) was added methanesulfonyl chloride (0.14742 mL, 1.9047 mmol) dropwise. A white precipitate formed. The solution was stirred at rt for 5 h. LCMS showed no starting material left, and complete conversion to 1:1 mixture of RT=2.26 min and 2.34 min. The mixture was diluted with DCM and washed with sodium bicarbonate aq. solution and water, dried over MgSO$_4$, filtered, concentrated. The residue was used as in the next step.

Step 3: 9-1{-[7-(cis-4-trifluoromethyl-cyclohexyloxy)-8-trifluoromethyl-naphthalen-2-yl]-ethyl}-9-aza-bicyclo[3.3.1]nonane-3-carboxylic acid

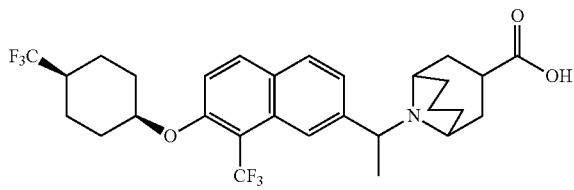 [SMILES: CC(c1ccc2ccc(O[C@H]3CC[C@@H](C(F)(F)F)CC3)c(C(F)(F)F)c2c1)N1C2CCCC1CC(C(=O)O)C2]

To a mixture of cesium carbonate (311 mg, 0.954 mmol) and 9-aza-bicyclo[3.3.1]nonane-3-carboxylic acid methyl ester; HCl salt (1.40E2 mg, 0.636 mmol) was added solution of methanesulfonic acid 1-[8-trifluoromethyl-7-(4-trifluoromethyl-cyclohexyloxy)-naphthalen-2-yl]-ethyl ester (154 mg, 0.318 mmol) in N,N-dimethylformamide (3.69 mL, 47.7 mmol). The reaction mixture was stirred at rt for 30 min, and heated at 50° C. for overnight. LCMS showed fairly clean. The mixture was diluted with McOH, filtered to remove solid, and purified by HPLC (TFA method) to get the ester. LCMS Rt=1.58 min, m/z=572.00. The above ester was dissolved in McOH (0.5 mL) and THF (0.5 mL), added lithium hydroxide (0.0150 mL, 1.59 mmol) and water (0.5 mL) stirred at 50° C. (hot plate) for 1 h. LC-MS shows the reaction was completed. After neutralized with 1N HCl solution, prep HPLC give product as a solid (15 mg, 9%). LCMS Rt=1.48 min, m/z=559.00. $^1$H NMR (400 MHz, METHANOL-d4) δ 8.34-8.47 (m, 1H), 8.17 (d, J=9.22 Hz, 1H), 8.10 (d, J=8.66 Hz, 1H), 7.65-7.77 (m, 1H), 7.62 (s, 1H), 5.09-5.36 (m, 1H), 5.05 (br. s., 1H), 3.35-3.47 (m, 2H), 1.66-3.05 (m, 23H).

Example 11: ((R)-1-{1-[8-trifluoromethyl-7-(4-trifluoromethyl-cyclohexyloxy)-naphthalen-2-yl]-ethyl}-piperidin-3-yl)-acetic acid

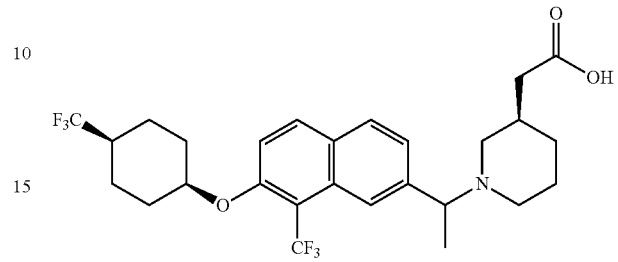

The title compound was prepared according to the procedure of Example 10. LCMS: RT=1.45 min.; MH+ 532.0. $^1$H NMR (400 MHz, METHANOL-d4) δ 8.28 (s, 1H), 8.19 (s, 1H), 8.07 (d, J=8.47 Hz, 1H), 7.63 (d, J=9.22 Hz, 1H), 7.57 (d, J=8.47 Hz, 1H), 5.05 (br. s., 1H), 4.55-4.76 (m, 1H), 3.35-3.45 (m, 2H), 1.13-3.06 (m, 21H).

Example 12: 8-{1-[7-(cis-4-trifluoromethyl-cyclohexyloxy)-8-trifluoromethyl-naphthalen-2-yl]-ethyl}-8-aza-bicyclo[3.2.1]octane-3-carboxylic acid

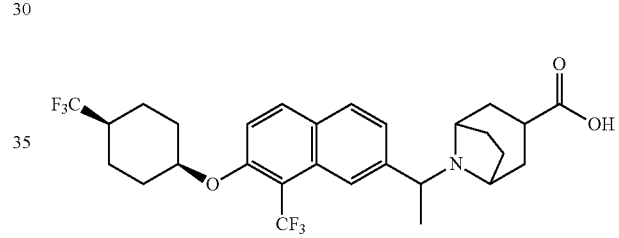

The title compound was prepared according to the procedure described for 9-{1-[7-(cis-4-trifluoromethyl-cyclohexyloxy)-8-trifluoromethyl-naphthalen-2-yl]-ethyl}-9-aza-bicyclo[3.3.1]nonane-3-carboxylic acid from LCMS: RT=1.46 min.; MH+ 544.00. $^1$H NMR (400 MHz, METHANOL-d4) δ 8.32 (s, 1H), 8.18 (d, J=9.41 Hz, 1H), 8.09 (d, J=8.47 Hz, 1H), 7.49-7.73 (m, 2H), 5.05 (br. s., 1H), 4.29-4.67 (m, 1H), 3.39-3.55 (m, 2H), 1.62-3.11 (m, 21H).

Example 12a: 8-{(S)-1-[7-(cis-4-trifluoromethyl-cyclohexyloxy)-8-trifluoromethyl-naphthalen-2-yl]-ethyl}-8-aza-bicyclo[3.2.1]octane-3-carboxylic acid and Example 12b: 8-{(R)-1-[7-(cis-4-trifluoromethyl-cyclohexyloxy)-8-trifluoromethyl-naphthalen-2-yl]-ethyl}-8-aza-bicyclo[3.2.1]octane-3-carboxylic acid

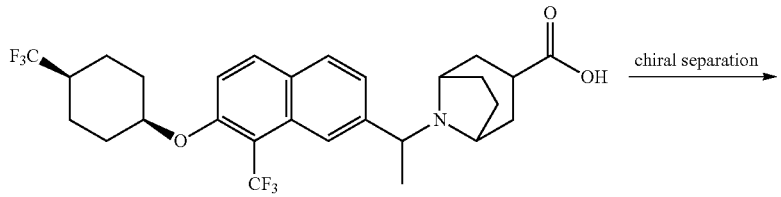

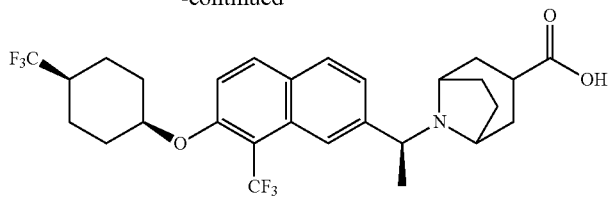

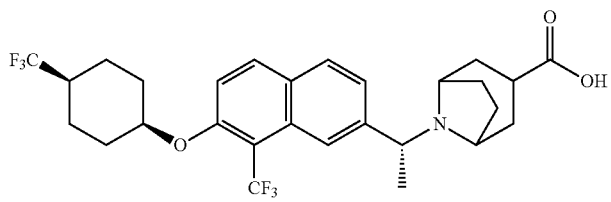

8-{1-[8-Trifluoromethyl-7-(4-trifluoromethyl-cyclohexyloxy)-naphthalen-2-yl]-ethyl}-8-aza-bicyclo[3.2.1]octane-3-carboxylic acid (52 mg, 0.19 mmol) was put under the following SFC separation yielded 16 mg of peak-1 (chemical purity >99%, ee >99%) and 18 mg of peak-2 (chemical purity >99%, ee >99%). LUX2 cellulose (3×15 cm), 35% MeOH (0.1% DEA)/CO2, 100 bar; 60 mL/min, 220 nm; inj vol.: 0.5 mL, 5 mg/mL MeOH.

Isomer I: LCMS m/z=544.00. $^1$H NMR (400 MHz, METHANOL-d4) δ 8.19 (s, 1H), 8.07 (d, J=9.29 Hz, 1H), 7.92 (d, J=8.47 Hz, 1H), 7.61 (d, J=8.47 Hz, 1H), 7.48 (d, J=9.22 Hz, 1H), 4.98 (br. s., 1H), 4.10-4.30 (m, 1H), 3.33-3.80 (m, 2H), 2.96 (q, J=7.26 Hz, 4H), 1.58-2.69 (m, 18H), 1.55 (d, J=6.53 Hz, 3H), 1.18-1.35 (m, 6H);

Isomer II: LCMS m/z=544.00. $^1$H NMR (400 MHz, METHANOL-d4) δ 8.19 (s, 1H), 8.07 (d, J=9.29 Hz, 1H), 7.92 (d, J=8.47 Hz, 1H), 7.61 (d, J=8.47 Hz, 1H), 7.48 (d, J=9.22 Hz, 1H), 4.98 (br. s., 1H), 4.10-4.30 (m, 1H), 3.33-3.80 (m, 2H), 2.96 (q, J=7.26 Hz, 4H), 1.58-2.69 (m, 18H), 1.55 (d, J=6.53 Hz, 3H), 1.18-1.35 (m, 6H)

Example 13: 9-[7-(4-methyl-cyclohexyloxy)-8-trifluoromethyl-naphthalene-2-carbonyl]-9-aza-bicyclo[3.3.1]nonane-3-carboxylic acid

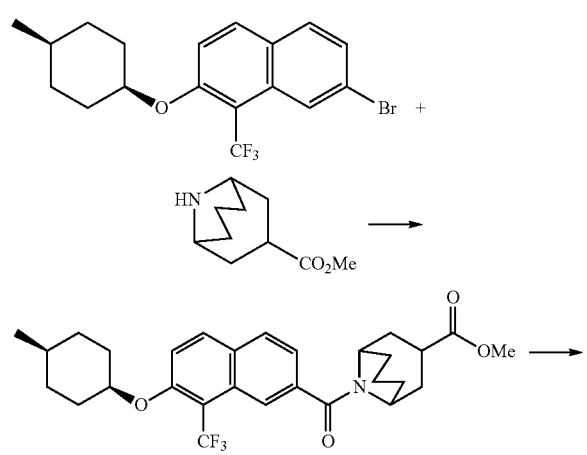

Step 1: 9-[7-(4-methyl-cyclohexyloxy)-8-trifluoromethyl-naphthalene-2-carbonyl]-9-aza-bicyclo[3.3.1]nonane-3-carboxylic acid methyl ester

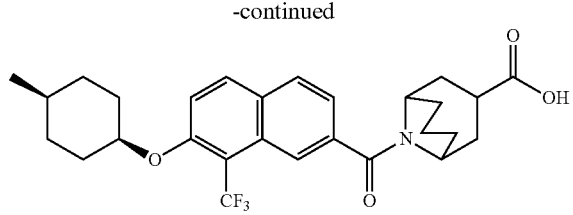

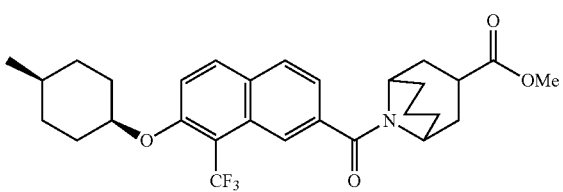 [SMILES: COC(=O)C1CC2CCCC(C1)N2C(=O)c1ccc2ccc(O[C@H]3CC[C@@H](C)CC3)c(C(F)(F)F)c2c1]

A mixture of 7-bromo-2-(4-methyl-cyclohexyloxy)-1-trifluoromethyl-naphthalene (0.200 g, 0.000516 mol), 9-aza-bicyclo[3.3.1]nonane-3-carboxylic acid methyl ester (0.189 g, 1.03 mmol), potassium carbonate (0.21 g, 0.0015 mol), [1,1'-bis(diphenylphosphino) ferrocene]dichloropalladium (II), complex with dichloromethane (1:1) (21.1 mg, 0.0000258 mol) and 1,4-dioxane (2 mL, 0.03 mol) degassed with carbon monoxide. The mixture was then heated at 120° C. under CO (balloon) for overnight. The mixture was filtered through Celite and rinsed with EtOAc. The filtrated was then washed with brine, and then water. The organic phase was dried and concentrated. The crude was purified by ISCO (EtOAc/heptane gradient) to give desired product as a colorless gel (6.5 mg, 2.4%). RT=2.25 min.; MH+ 518.10.

Step 2: 9-[7-(4-methyl-cyclohexyloxy)-8-trifluoromethyl-naphthalene-2-carbonyl]-9-aza-bicyclo[3.3.1]nonane-3-carboxylic acid

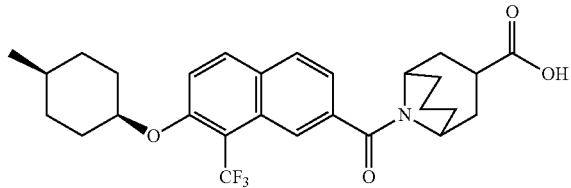 [SMILES: C[C@H]1CC[C@@H](Oc2ccc3ccc(C(=O)N4C5CCCC4CC(C(=O)O)C5)cc3c2C(F)(F)F)CC1]

9-[7-(4-Methyl-cyclohexyloxy)-8-trifluoromethyl-naphthalene-2-carbonyl]-9-aza-bicyclo[3.3.1]nonane-3-carboxylic acid methyl ester (6.5 mg, 0.012 mmol) was then dissolved in tetrahydrofuran (0.5 mL, 6 mmol), methanol (0.5 mL, 10 mmol), water (0.25 mL, 14 mmol), treated with lithium hydroxide (4.6 mg, 0.19 mmol) at rt for 1 h. After acidified with 1N HCl, the crude was then purified by HLPC to give the title compound as a white powder (4.3 mg, 68%). LCMS: RT=1.99 min, MH+ 504.00. $^1$H NMR (400 MHz, METHANOL-d4) δ 8.17 (s, 1H), 8.13 (d, J=9.29 Hz, 1H), 8.00 (d, J=8.28 Hz, 1H), 7.58 (d, J=9.22 Hz, 1H), 7.47 (d, J=8.28 Hz, 1H), 4.94 (br. s., 1H), 3.96 (br. s., 1H), 3.40 (br. s., 1H), 1.37-2.40 (m, 20H), 0.98 (d, J=5.58 Hz, 3H).

Example 14: 9-[8-trifluoromethyl-7-(4-trifluoromethyl-cyclohexyloxy)-naphthalene-2-carbonyl]-9-aza-bicyclo[3.3.1]nonane-3-carboxylic acid

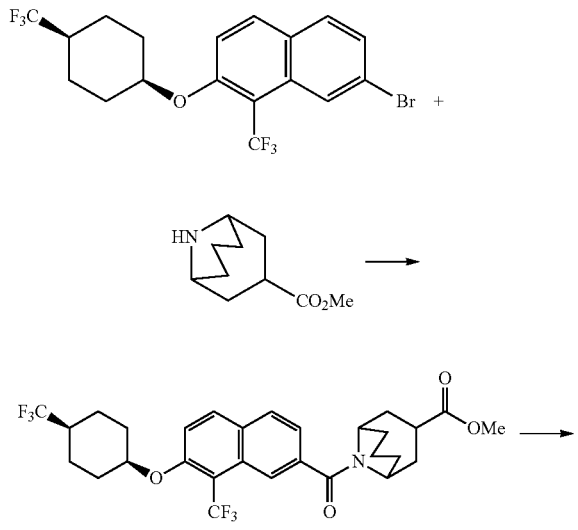

Step 1: 9-[7-(4-trifluoromethyl-cyclohexyloxy)-8-trifluoromethyl-naphthalene-2-carbonyl]-9-aza-bicyclo[3.3.1]nonane-3-carboxylic acid methyl ester

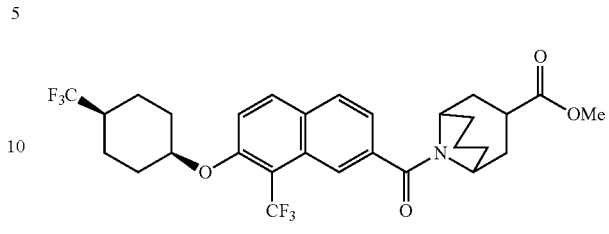

A mixture of 7-bromo-1-trifluoromethyl-2-(4-trifluoromethyl-cyclohexyloxy)-naphthalene (0.200 g, 0.000453 mol), 9-aza-bicyclo[3.3.1]nonane-3-carboxylic acid methyl ester (0.166 g, 0.907 mmol), potassium carbonate (0.19 g, 0.0014 mol), [1,1'-bis(diphenylphosphino)ferrocene]dichloropalladium(II), complex with dichloromethane (1:1) (18.5 mg, 0.0000227 mol) and 1,4-dioxane (2 mL, 0.02 mol) degassed with carbon monoxide. The mixture was then heated at 120° C. under CO (balloon) for 2 h. The mixture was filtered through celite and rinsed with EtOAc. The filtrated was then washed with brine, and then water. The organic phase was dried and concentrated. The crude was purified by ISCO (EtOAc/heptane gradient) to give desired product as a colorless gel (36 mg, 14%). RT=2.09 min.; MH+ 572.00.

Step 2: 9-[8-trifluoromethyl-7-(4-trifluoromethyl-cyclohexyloxy)-naphthalene-2-carbonyl]-9-aza-bicyclo[3.3.1]nonane-3-carboxylic acid

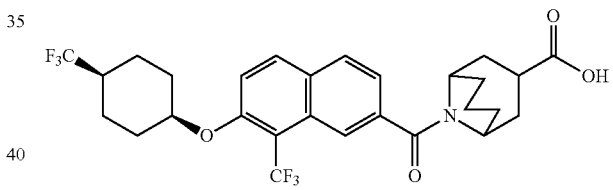

9-[8-Trifluoromethyl-7-(4-trifluoromethyl-cyclohexyloxy)-naphthalene-2-carbonyl]-9-aza-bicyclo[3.3.1]nonane-3-carboxylic acid methyl ester (36 mg, 0.063 mmol) was dissolved in tetrahydrofuran (1 mL, 10 mmol), methanol (1 mL, 20 mmol), water (0.5 mL, 30 mmol), treated with lithium hydroxide (23 mg, 0.96 mmol) at rt for 1 h. After acidified with 1N HCl, the crude was then purified by HLPC to give the title compound as a white powder (27.8 mg, 79%). LCMS: RT=1.85 min.; MH+ 558.00. $^1$H NMR (400 MHz, METHANOL-d4) δ 8.09-8.23 (m, 2H), 8.01 (d, J=8.28 Hz, 1H), 7.59 (d, J=9.16 Hz, 1H), 7.48 (d, J=8.34 Hz, 1H), 5.03 (br. s., 1H), 4.93 (br. s., 1H), 3.95 (br. s., 1H), 1.59-2.39 (m, 20H).

Example 15: 9-[8-Chloro-7-(4-methyl-cyclohexyloxy)-naphthalen-2-ylmethyl]-9-aza-bicyclo[3.3.1]nonane-3-carboxylic acid

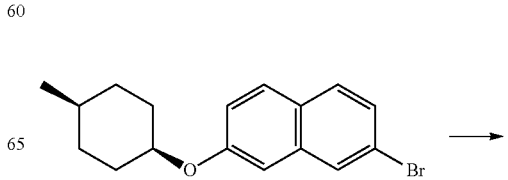

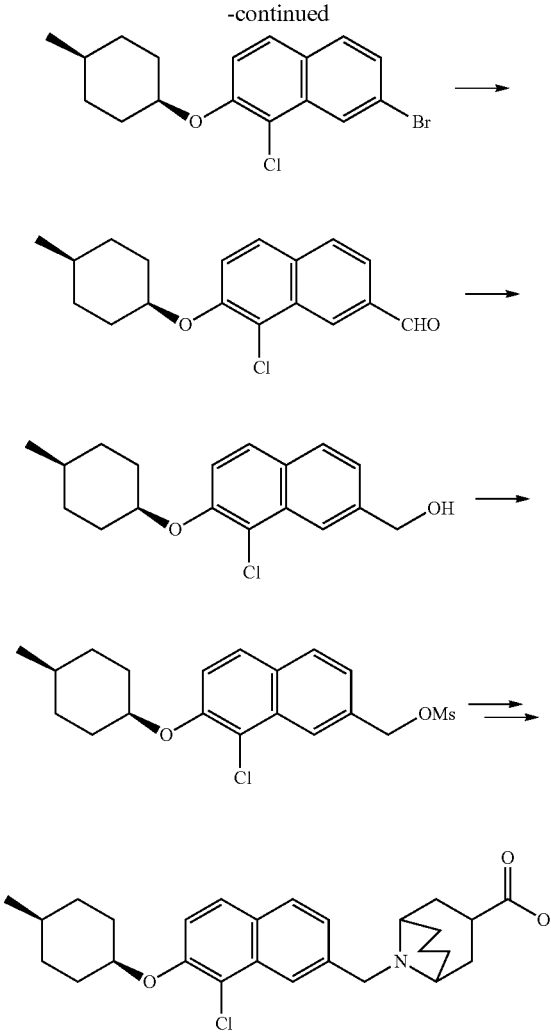

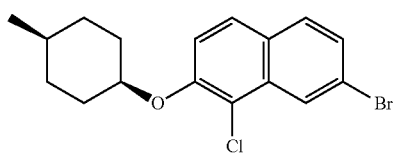 [SMILES: C[C@H]1CC[C@@H](Oc2ccc3ccc(Br)cc3c2Cl)CC1]

Step 1: 7-bromo-1-chloro-2-(4-methyl-cyclohexyloxy)-naphthalene

A mixture of 2-bromo-7-(4-methyl-cyclohexyloxy)-naphthalene (1.00E2 mg, 0.000313 mol), N-chlorosuccinimide (46.8 mg, 0.000351 mol) and zirconium tetrachloride (11 mg, 0.000047 mol) in methylene chloride (2.01 mL, 0.0313 mol) was heated to reflux under Ar in a vial for 2 h. The precipitate was filtered off and the residue was purified with Isco column eluted with EtOAC in hex from 0 to 40% to give the product as a solid (110 mg, 99%). LCMS Rt=2.68 min, m/z=354.10 [M+]. 1H NMR (400 MHz, CHLOROFORM-d) δ 8.40 (s, 1H), 7.64-7.74 (m, 1H), 7.63 (s, 1H), 7.47 (d, J=10.54 Hz, 1H), 7.22-7.36 (m, 1H), 4.73 (br. s., 1H), 2.06 (d, J=11.11 Hz, 2H), 1.16-1.73 (m, 7H), 1.00 (s, 3H).

Step 2: 8-chloro-7-(4-methyl-cyclohexyloxy)-naphthalene-2-carbaldehyde

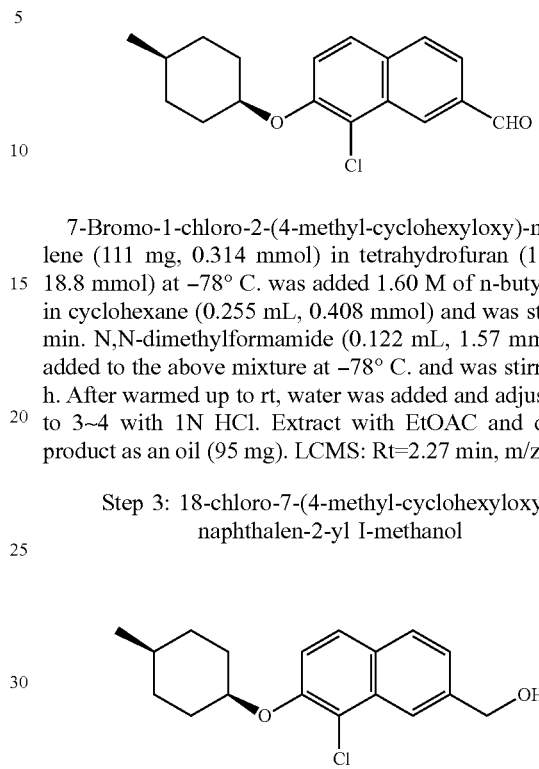

7-Bromo-1-chloro-2-(4-methyl-cyclohexyloxy)-naphthalene (111 mg, 0.314 mmol) in tetrahydrofuran (1.53 mL, 18.8 mmol) at −78° C. was added 1.60 M of n-butyllithium in cyclohexane (0.255 mL, 0.408 mmol) and was stirred 15 min. N,N-dimethylformamide (0.122 mL, 1.57 mmol) was added to the above mixture at −78° C. and was stirred for 1 h. After warmed up to rt, water was added and adjusting pH to 3~4 with 1N HCl. Extract with EtOAC and dry give product as an oil (95 mg). LCMS: Rt=2.27 min, m/z 303.00.

Step 3: 18-chloro-7-(4-methyl-cyclohexyloxy)-naphthalen-2-yl 1-methanol

To a mixture of 8-chloro-7-(4-methyl-cyclohexyloxy)-naphthalene-2-carbaldehyde (95 mg, 0.31 mmol) in tetrahydrofuran (4.9 mL, 61 mmol) was added 1.00 M of lithium tetrahydroaluminate in tetrahydrofuran (0.7844 mL, 0.7844 mmol). Gas evolution observed. The reaction was then stirred at rt for 30 min, LCMS showed complete conversion. EtOAc was added and Rochele's salt was added and stirred for 30 min. The organic layer was washed with brine, dried and evaporated, and dried under high vacuum to give desired product (77 mg, 80%). LCMS: RT=1.99 min; m/z=287.00 [M−H2O];

Step 4: methanesulfonic acid 8-chloro-7-(4-methyl-cyclohexyloxy)-naphthalen-2-ylmethyl ester

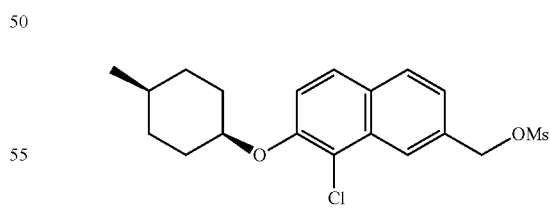

To a solution of [8-chloro-7-(4-methyl-cyclohexyloxy)-naphthalen-2-yl]-methanol (77 mg, 0.25 mmol) and N,N-diisopropylethylamine (0.13200 mL, 0.75785 mmol) in methylene chloride (1.2 mL, 18 mmol) was added methanesulfonyl chloride (0.039105 mL, 0.50523 mmol) dropwise. A white precipitate formed. The solution was stirred at rt for 1 h. LCMS showed no starting material left, and complete conversion to 2:1 mixture of RT 2.12 min and 2.44 min. The mixture was diluted with DCM and washed with sodium Step 5: 9-[8-Chloro-7-(4-methyl-cyclohexyloxy)-naphthalen-2-ylmethyl]-9-aza-bicyclo[3.3.1]nonane-3-carboxylic acid

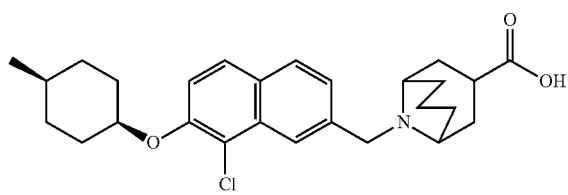 [SMILES: C[C@H]1CC[C@@H](Oc2ccc3ccc(CN4C5CCCC4CC(C(=O)O)C5)cc3c2Cl)CC1]

To a solution of methanesulfonic acid 8-chloro-7-(4-methyl-cyclohexyloxy)-naphthalen-2-ylmethyl ester (97 mg, 0.25 mmol) in N,N-dimethylformamide (2.9 mL, 38 mmol), 9-aza-bicyclo[3.3.1]nonane-3-carboxylic acid methyl ester; HCl salt (111.32 mg, 0.50666 mmol) was added, followed by cesium carbonate (247.62 mg, 0.75998 mmol). The reaction was then heated at 50° C. for overnight. LCMS showed no SM left, and the completion of the reaction (RT=1.61 min.; MH+ 470.0). Cooled down, the reaction mixture was diluted with EtOAc, washed with water, dried and cc with HE/EA to give the ester. The ester was then dissolved in tetrahydrofuran (1.2 mL, 14 mmol), treated with 1.0 M of lithium hydroxide in water (1.8 mL, 1.8 mmol) at 50° C. for 1 h. After acidified with 1N HCl, the organic layer was dried and concentrated. The crude was then purified by HLPC to give the title compound as a white powder (80.7 mg, 70%). LCMS: RT=1.49 min.; MH+ 456.00; 1H NMR (400 MHz, METHANOL-d4) δ 8.32-8.45 (m, 1H), 8.04 (d, J=8.41 Hz, 1H), 7.97 (d, J=9.10 Hz, 1H), 7.57-7.74 (m, 2H), 4.92 (br. s., 1H), 4.59-4.83 (m, 2H), 3.41-3.59 (m, 3H), 1.29-2.48 (m, 20H), 0.92 (d, J=5.90 Hz, 3H).

Example 16: 9-[1-(8-trifluoromethyl-7-(cis-4-methylcyclohexyloxy)-naphthalen-2-yl)ethyl]-9-aza-bicyclo[3.3.1]nonane

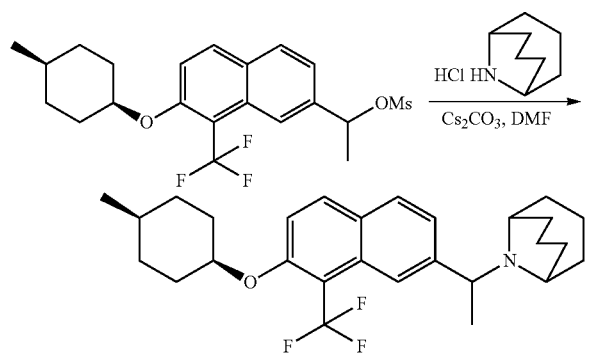

To a solution of methanesulfonic acid 1-[7-(4-methyl-cyclohexyloxy)-8-trifluoromethyl-naphthalen-2-yl]-ethyl ester (0.200 g, 0.464 mmol) in N,N-dimethylformamide (1.7987 mL, 23.230 mmol), 9-azabicyclo[3.3.1]nonane hydrochloride (0.15022 g, 0.92919 mmol) was added, followed by cesium carbonate (0.45412 g, 1.3938 mmol). The reaction was then heated at 60° C. for overnight. Cooled down, the reaction mixture was diluted with EtOAc, washed with water (3×). The organic phase was then separated, dried and concentrated. The crude was purified by prep HPLC to give a solid (45 mg, 22%). LCMS: RT=1.71 min.; m/z=460.30 [MH]+. 1H NMR (400 MHz, METHANOL-d4) δ 8.36 (s, 1H), 8.11 (d, J=9.35 Hz, 1H), 8.04 (d, J=8.53 Hz, 1H), 7.67 (dd, J=1.54, 8.50 Hz, 1H), 7.56 (d, J=9.22 Hz, 1H), 5.22 (q, J=6.69 Hz, 1H), 4.92 (br. s., 1H), 4.06 (br. s., 1H), 3.03 (br. s., 1H), 1.80-2.65 (m, 12H), 1.74 (d, J=6.7 Hz, 3H), 1.33-1.72 (m, 8H), 0.94 (d, J=5.77 Hz, 3H).

Example 17: 12-(1-(8-trifluoromethyl-7-(cis-4-methyl)-4,6,12-triaza-tricyclo[7.2.1.0(2,7)]dodeca-2(7),3,5-triene A solution of methanesulfonic acid 7-(4-methyl-cyclohexyloxy)-8-trifluoromethyl-naphthalen-2-ylmethyl ester (215 mg, 0.516 mmol) and 4,6,12-triaza-tricyclo[7.2.1.0(2,7)]dodeca-2(7),3,5-triene hydrochloride salt (204.1 mg, 1.032 mmol) in N,N-dimethylformamide (2 mL, 20 mmol) was added cesium carbonate (504.6 mg, 1.549 mmol) and heated at 60° C. for overnight. After cooled down to rt, and filtration, and washed with MeOH, the crude was purified with Prep HPLC to give a solid as the product (196 mg, 79%). LCMS: Rt=1.49 min, m/z=482.30 [M+1]. 1H NMR (400 MHz, METHANOL-d4) δ 9.13 (s, 1H), 8.61 (s, 1H), 8.30 (br. s., OH), 8.15 (d, J=9.54 Hz, 1H), 8.05 (d, J=8.28 Hz, 1H), 7.60 (d, J=9.29 Hz, 1H), 7.55 (d, J=8.53 Hz, 1H), 4.94 (br. s., 1H), 4.52-4.73 (m, 2H), 4.47 (t, J=5.40 Hz, 1H), 3.61 (d, J=18.82 Hz, 1H), 1.25-2.82 (m, 15H), 0.95 (d, J=5.77 Hz, 3H)).

Example 18: 8-(1-(7-((cis-4-methylcyclohexyl)oxy)-8-(trifluoromethyl)naphthalen-2-yl)propyl)-8-azabicyclo[3.2.1]octane-3-carboxylic acid The title compound was prepared according to the method of Example 6. 1H NMR (400 MHz, METHANOL-d4) δ 8.25 (br. s., 1H), 8.14 (d, J=9.29 Hz, 1H), 8.07 (d, J=8.53 Hz, 1H), 7.59 (d, J=9.29 Hz, 1H), 7.54 (d, J=8.28 Hz, 1H), 4.95 (br. s., 1H), 4.50-4.63 (m, 1H), 4.15 (dd, J=3.26, 11.55 Hz, 1H), 3.37 (br. s., 1H), 2.87-3.04 (m, 1H), 2.53-2.69 (m, 1H), 1.85-2.46 (m, 11H), 1.70 (t, J=13.18 Hz, 2H), 1.36-1.57 (m, 5H), 0.96 (d, J=5.77 Hz, 3H), 0.78 (t, J=7.28 Hz, 3H), MH+ 504.3

Example 19: 1-(1-(7-((cis-4-methylcyclohexyl)oxy)-8-(trifluoromethyl)naphthalen-2-yl)propyl)piperidine-4-carboxylic acid The title compound was prepared according to the method of Example 6. 1H NMR (400 MHz, METHANOL-d4) δ 8.22 (s, 1H), 8.14 (d, J=9.29 Hz, 1H), 8.06 (d, J=8.53 Hz, 1H), 7.60 (d, J=9.29 Hz, 1H), 7.51 (d, J=8.53 Hz, 1H), 4.95 (br. s., 1H), 4.35-4.56 (m, 1H), 3.90 (d, J=12.05 Hz, 1H), 3.40 (d, J=12.05 Hz, 1H), 2.78-3.06 (m, 2H), 2.46-2.65 (m, 1H), 2.12-2.41 (m, 4H), 1.63-2.10 (m, 6H), 1.36-1.59 (m, 5H), 0.95 (d, J=5.77 Hz, 3H), 0.80 (t, J=7.15 Hz, 3H); MH+ 478.2

Example 20: 2-((3R)-1-(1-(7-((cis-4-methylcyclohexyl)oxy)-8-(trifluoromethyl)naphthalen-2-yl)propyl)piperidin-3-yl)acetic acid The title compound was prepared according to the method of Example 6. 1H NMR (400 MHz, METHANOL-d4) δ 8.21

(s, 1H), 8.14 (d, J=9.29 Hz, 1H), 8.05 (d, J=8.53 Hz, 1H), 7.60 (d, J=9.29 Hz, 1H), 7.51 (d, J=8.53 Hz, 1H), 4.94 (br. s., 1H), 4.40 (dd, J=4.02, 11.55 Hz, 1H), 3.74-3.94 (m, 1H), 3.35-3.50 (m, 1H), 2.49-2.91 (m, 2H), 2.16-2.42 (m, 5H), 1.97-2.12 (m, 2H), 1.65-1.98 (m, 5H), 1.36-1.58 (m, 5H), 1.08-1.27 (m, 1H), 0.96 (d, J=5.52 Hz, 3H), 0.80 (t, J=7.28 Hz, 3H); MH+ 492.3

Example 21: ((R)-1-{1-[8-trifluoromethyl-7-(4-trifluoromethyl-cyclohexyloxy)-naphthalen-2-yl]-ethyl}-piperidin-3-yl)-acetic acid The title compound was prepared according to the method of Example 10. ¹H NMR (400 MHz, METHANOL-d4) δ 8.28 (s, 1H), 8.19 (s, 1H), 8.07 (d, J=8.47 Hz, 1H), 7.63 (d, J=9.22 Hz, 1H), 7.57 (d, J=8.47 Hz, 1H), 5.05 (br. s., 1H), 4.55-4.76 (m, 1H), 3.35-3.45 (m, 2H), 1.13-3.06 (m, 21H); MH+ 532.0

Example 22: 2-((S)-1-((8-(trifluoromethyl)-7-((cis-4-(trifluoromethyl)cyclohexyl)oxy)naphthalen-2-yl)methyl)piperidin-3-yl)acetic acid The title compound was prepared according to the method of Example 7. ¹H NMR (400 MHz, METHANOL-d4) δ 8.32 (s, 1H), 8.16 (d, J=9.29 Hz, 1H), 8.03 (d, J=8.28 Hz, 1H), 7.50-7.66 (m, 2H), 5.02 (br. s., 1H), 4.50 (s, 2H), 3.43-3.68 (m, 2H), 2.97 (t, J=11.67 Hz, 1H), 2.82 (t, J=11.92 Hz, 1H), 2.07-2.46 (m, 6H), 1.67-2.04 (m, 9H), 1.18-1.39 (m, 1H); MH+ 518

Example 23: 8-(8-(trifluoromethyl)-7-((cis-4-(trifluoromethyl)cyclohexyl)oxy)-2-naphthoyl)-8-azabicyclo[3.2.1]octane-3-carboxylic acid The title compound was prepared according to the method of Example 14. ¹H NMR (400 MHz, METHANOL-d4) δ 8.27 (s, 1H), 8.17 (d, J=9.41 Hz, 1H), 8.03 (d, J=8.35 Hz, 1H), 7.62 (d, J=9.29 Hz, 1H), 7.55 (d, J=9.79 Hz, 1H), 5.04 (s, 1H), 3.96-4.24 (m, 1H), 2.91-3.11 (m, 1H), 1.60-2.52 (m, 18H); MH+ 544.0

Example 24: 8-[7-(cis-4-methyl-cyclohexyloxy)-8-trifluoromethyl-naphthalene-2-carbonyl]-8-azabicyclo[3.2.1]octane-3-carboxylic acid The title compound was prepared according to the method of Example 13. ¹H NMR (400 MHz, METHANOL-d4) δ 8.27 (s, 1H), 8.17 (d, J=9.41 Hz, 1H), 8.03 (d, J=8.35 Hz, 1H), 7.62 (d, J=9.29 Hz, 1H), 7.55 (d, J=9.79 Hz, 1H), 5.04 (s, 1H), 3.96-4.24 (m, 1H), 2.91-3.11 (m, 1H), 1.60-2.52 (m, 18H).

Example 25: 1-((8-chloro-7-((cis-4-(trifluoromethyl)cyclohexyl)oxy)naphthalen-2-yl)methyl)piperidine-4-carboxylic acid

Step 1: 2-bromo-7-((cis-4-(trifluoromethyl)cyclohexyl)oxy)naphthalene

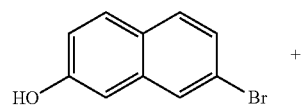

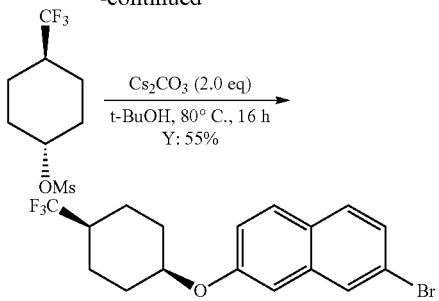

A mixture of 7-bromonaphthalen-2-ol (6.6 g, 30.0 mmol, 1.0 eq), Cs₂CO₃ (19.5 g, 60.0 mmol, 2.0 eq) and cis-4-(trifluoromethyl)cyclohexyl methanesulfonate (11.2 g, 45.0 mmol, 1.5 eq) in DMF (80 mL) was stirred at 80° C. for 16 h and cooled down. The mixture was diluted with EtOAc (200 mL) and washed with water (200 mL×2). The organic layer was dried over Na₂SO₄ and concentrated to yield a crude product, which was purified by column chromatography on silica gel (petroleum ether as eluent) to give 2-bromo-7-((cis-4-(trifluoromethyl)cyclohexyl)oxy)naphthalene (6.5 g, Y: 55%) as yellow solid. 1H NMR (400 MHz, CDCl₃) δ: 7.86 (d, J=1.6 Hz, 1H), 7.71 (d, J=8.8 Hz, 1H), 7.62 (d, J=8.4 Hz, 1H), 7.39 (dd, J=1.6 Hz, 8.4 Hz, 1H), 7.17 (dd, J=2.4 Hz, 8.8 Hz, 1H), 7.04 (d, J=2.4 Hz, 1H), 4.71 (s, 1H), 2.26-2.22 (m, 2H), 2.17-2.07 (m, 1H), 1.87-1.77 (m, 4H), 1.64-1.59 (m, 2H).

Step 2: 7-((cis-4-(trifluoromethyl)cyclohexyl)oxy)-2-naphthaldehyde

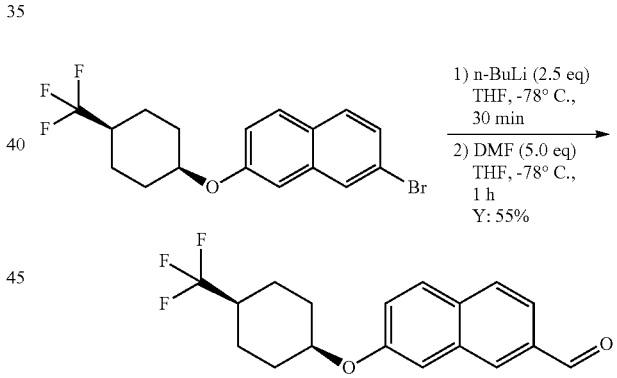

Into a solution of 2-bromo-7-((cis-4-(trifluoromethyl)cyclohexyl)oxy)naphthalene (3.72 g, 10.0 mmol, 1.0 eq) in THF (10 mL) was added n-BuLi (10.0 mL, 2.5M in hexane, 25.0 mmol, 2.5 eq) dropwise at −78° C. After addition, the mixture was stirred at −8° C. for 30 min. DMF (3.65 g, 50.0 mmol, 5.0 eq) was added to the mixture and stirring continued for 1 h at −78° C. The reaction was quenched with aq. NH₄Cl solution (200 mL) and extracted with DCM (200 mL×2). The combined organic layers were washed with water (200 mL×2), brine (200 mL) and concentrated. The residue was purified by column chromatography on silica gel (petroleum ether/EtOAc=50:1) to give 7-((cis-4-(trifluoromethyl)cyclohexyl)oxy)-2-naphthaldehyde (1.6 g, Y: 55%) as yellow solid. ¹H NMR (400 MHz, CDCl₃) δ: 10.14 (s, 1H), 8.21 (s, 1H), 7.88-7.80 (m, 3H), 7.35-7.30 (m, 2H), 4.78-4.77 (m, 1H), 2.29-2.10 (m, 3H), 1.89-1.79 (m, 4H), 1.68-1.59 (m, 2H); ESI-MS (M+H)⁺: 323.1.

Step 3: 8-chloro-7-((cis-4-(trifluoromethyl)cyclohexyl)oxy)-2-naphthaldehyde

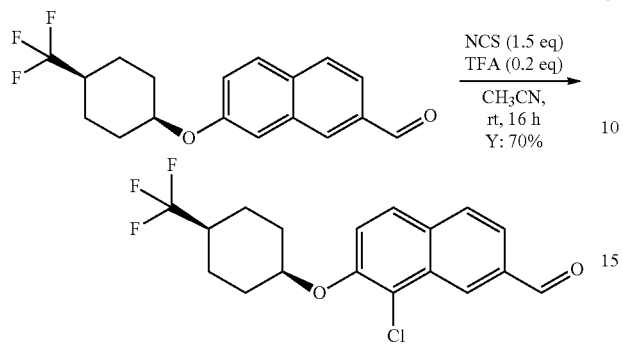

To a mixture of 7-((cis-4-(trifluoromethyl)cyclohexyl)oxy)-2-naphthaldehyde (3.22 g, 10.0 mmol, 1.0 eq) and NCS (2.00 g, 15.0 mmol, 1.5 eq) in CH$_3$CN (30 mL) was added TFA (342 mg, 3.0 mmol, 0.3 eq). The mixture was stirred at rt for 16 h and concentrated. The residue was purified by column chromatography on silica gel (petroleum ether/EtOAc=50:1) to give 8-chloro-7-((cis-4-(trifluoromethyl)cyclohexyl)oxy)-2-naphthaldehyde (2.3 g, Y: 70%) as yellow solid. $^1$H NMR (400 MHz, CDCl$_3$) δ: 10.22 (s, 1H), 8.73 (s, 1H), 7.92-7.87 (m, 2H), 7.81 (d, J=8.8 Hz, 1H), 7.41 (d, J=9.2 Hz, 1H), 4.83 (s, 1H), 2.24-1.94 (m, 5H), 1.82-1.79 (m, 2H) 1.66-1.58 (m, 2H); ESI-MS (M+H)$^+$: 357.1.

Step 4: ethyl 1-((8-chloro-7-((cis-4-(trifluoromethyl)cyclohexyl)oxy)naphthalen-2-yl)methyl)piperidine-4-carboxylate

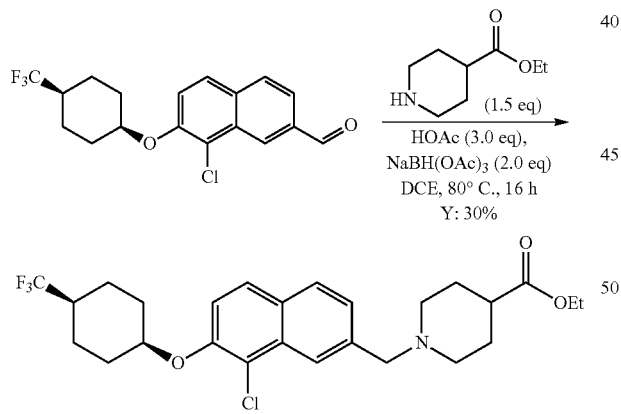

A mixture of 8-chloro-7-((cis-4-(trifluoromethyl)cyclohexyl)oxy)-2-naphthaldehyde (100 mg, 0.3 mmol, 1.0 eq), NaBH(OAc)$_3$ (125 mg, 0.6 mmol, 2.0 eq), HOAc (55 mg, 0.9 mmol, 3.0 eq) and ethyl piperidine-4-carboxylate (75 mg, 0.45 mmol, 1.5 eq) in DCE (2 mL) was stirred at 80° C. for 16 h. The mixture was diluted with water (10 mL) and extracted with DCM (10 mL×2). The combined organic layers were washed with water (10 mL), brine (10 mL), dried over Na$_2$SO$_4$ and concentrated. The residue was purified by pre-TLC on silica gel (petroleum ether/EtOAc=5:1) to give ethyl 1-((8-chloro-7-((cis-4-(trifluoromethyl)cyclohexyl)oxy) naphthalen-2-yl)methyl)piperidine-4-carboxylate (50 mg, Y: 30%) as yellow oil. ESI-MS (M+H)$^+$: 498.2.

Step 5: 1-((8-chloro-7-((cis-4-(trifluoromethyl)cyclohexyl)oxy)naphthalen-2-yl)methyl)piperidine-4-carboxylic acid

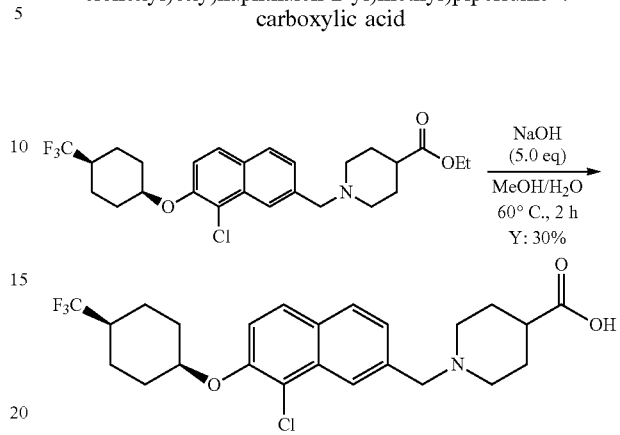

A mixture of ethyl 1-((8-chloro-7-((cis-4-(trifluoromethyl)cyclohexyl)oxy) naphthalen-2-yl)methyl)piperidine-4-carboxylate (30 mg, 0.06 mmol, 1.0 eq) and NaOH (12 mg, 0.30 mmol, 5.0 eq) in MeOH (2 mL) and H$_2$O (0.5 mL) was stirred at 60° C. for 2 h. Then the reaction was cooled to rt and acidified with 1N HCl to pH=6.0. The mixture was purified by reversed phase HPLC (MeCN and H$_2$O as mobile phase) to give 1-((8-chloro-7-((cis-4-(trifluoromethyl)cyclohexyl)oxy)naphthalen-2-yl)methyl)piperidine-4-carboxylic acid as yellow solid (8 mg, Y: 30%). ESI-MS (M+H)$^+$: 470.0. $^1$H NMR (400 MHz, CD$_3$OD) δ: 8.31 (s, 1H), 7.93 (d, J=8.0 Hz, 1H), 7.88 (d, J=9.6 Hz, 1H), 7.51 (d, J=9.2 Hz, 2H), 4.92 (s, 1H), 4.28 (s, 2H), 3.32-3.30 (m, 2H), 2.88-2.82 (m, 2H), 2.38-2.13 (m, 4H), 2.06-1.88 (m, 6H), 1.77-1.67 (m, 4H).

Example 26: 8-((8-chloro-7-((cis-4-(trifluoromethyl)cyclohexyl)oxy)naphthalen-2-yl)methyl)-8-azabicyclo[3.2.1]octane-3-carboxylic acid

Step 1: Isopropyl 8-((8-chloro-7-((cis-4-(trifluoromethyl)cyclohexyl)oxy) naphthalen-2-yl)methyl)-8-azabicyclo[3.2.1]octane-3-carboxylate

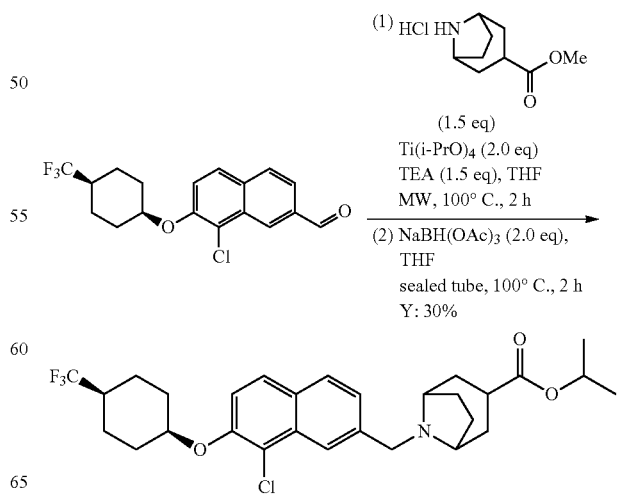

To a mixture of 1-((8-chloro-7-((cis-4-(trifluoromethyl)cyclohexyl)oxy)naphthalen-2-yl)methyl)piperidine-4-carboxylic acid (105 mg, 0.30 mmol, 1.0 eq), TEA (30 mg, 0.30 mmol, 1.0 eq) and methyl 8-azabicyclo[3.2.1]octane-3-carboxylate (75 mg, 0.45 mmol, 1.5 eq) in THF (1 mL) was added Ti(OiPr)$_4$ (175 mg, 0.60 mmol, 2.0 eq). The mixture was stirred at 100° C. for 2 h under microwave condition and cooled to rt. Then NaBH(OAc)$_3$ (140 mg, 0.60 mmol, 2.0 eq) was added. The mixture was stirred at 100° C. for additional 2 h and diluted with water (50 mL). The mixture was extracted with EtOAc (50 mL×2) and the combined organic layers were washed with water (10 mL), brine (10 mL), dried over Na$_2$SO$_4$ and concentrated. The residue was purified by prep-TLC on silica gel (petroleum ether/EtOAc=5:1) to give isopropyl 8-((8-chloro-7-((cis-4-(trifluoromethyl)cyclohexyl)oxy) naphthalen-2-yl)methyl)-8-azabicyclo[3.2.1]octane-3-carboxylate (50 mg, Y: 30%) as yellow solid. ESI-MS (M+H)$^+$: 538.2.

Step 2: 8-((8-chloro-7-((cis-4-(trifluoromethyl)cyclohexyl)oxy)naphthalen-2-yl)methyl)-8-azabicyclo[3.2.1]octane-3-carboxylic acid

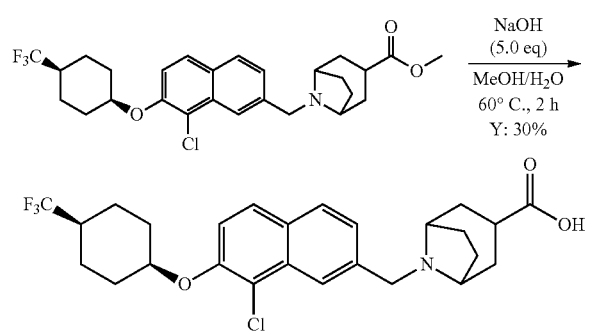

The preparation of 8-((8-chloro-7-((cis-4-(trifluoromethyl)cyclohexyl)oxy)naphthalen-2-yl)methyl)-8-azabicyclo[3.2.1]octane-3-carboxylic acid was the same as 1-((8-chloro-7-((cis-4-ethylcyclohexyl)oxy)naphthalen-2-yl)methyl)piperidine-4-carboxylic acid, weight: 15 mg, yellow oil, Y: 30%. ESI-MS (M+H)$^+$: 496.2. $^1$H NMR (400 MHz, CD$_3$OD) δ: 8.41 (s, 1H), 7.99 (d, J=8.4 Hz, 1H), 7.91 (d, J=9.2 Hz, 1H), 7.59 (d, J=8.0 Hz, 1H), 7.54 (d, J=8.8 Hz, 1H), 4.95 (s, 1H), 4.38 (s, 2H), 3.92-3.88 (m, 2H), 2.73-2.64 (m, 1H), 2.45-2.42 (m, 2H), 2.33-2.04 (m, 7H), 1.99-1.90 (m, 4H), 1.79-1.68 (m, 4H).

Example 27: 9-((8-chloro-7-((cis-4-(trifluoromethyl)cyclohexyl)oxy)naphthalen-2-yl)methyl)-9-azabicyclo[3.3.1]nonane-3-carboxylic acid

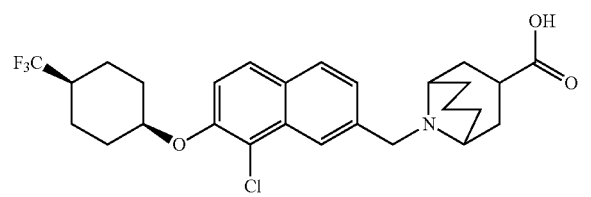 [SMILES: O=C(O)C1CC2CCCC(C1)N2Cc1ccc2ccc(O[C@H]3CC[C@@H](C(F)(F)F)CC3)c(Cl)c2c1]

The title compound was prepared according to the method of Example 26. 20 mg as a yellow solid, Y: 40%. ESI-MS (M+H)$^+$: 510.2. $^1$H NMR (400 MHz, CD$_3$OD) δ: 8.49 (s, 1H), 8.01 (d, J=8.8 Hz, 1H), 7.93 (d, J=8.8 Hz, 1H), 7.62 (d, J=8.4 Hz, 1H), 7.57 (d, J=8.8 Hz, 1H), 4.96 (s, 1H), 4.82-4.75 (m, 2H), 3.68-3.62 (m, 2H), 3.49-3.37 (m, 1H), 2.63-2.57 (m, 2H), 2.30-2.10 (m, 9H), 1.93-1.69 (m, 8H).

Example 28: 1-(1-(8-chloro-7-((cis-4-(trifluoromethyl)cyclohexyl)oxy)naphthalen-2-yl)ethyl)piperidine-4-carboxylic acid Step 1. 1-(8-chloro-7-((cis-4-(trifluoromethyl)cyclohexyl)oxy)naphthalen-2-yl)ethanol

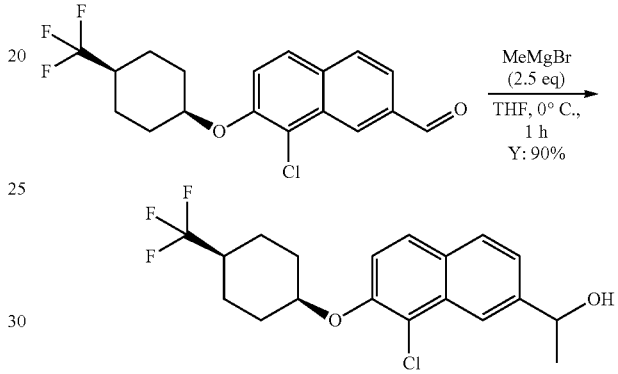

To a solution of 8-chloro-7-((cis-4-(trifluoromethyl)cyclohexyl)oxy)-2-naphthaldehyde (700 mg, 2.0 mmol, 1.0 eq) in THF (2 mL) was slowly added CH$_3$MgBr (3.0M in hexane, 1.7 mL, 2.5 eq) at 0° C. The mixture was stirred at 0° C. for 1 h and quenched with aq. NH$_4$Cl (20 mL). The mixture was extracted with EtOAc (20 mL×3) and the organic phases were dried and concentrated to give 1-(8-chloro-7-((cis-4-(trifluoromethyl)cyclohexyl)oxy)naphthalen-2-yl)ethanol, which was used to the next step without further purification. Weight: 600 mg, yellow oil, Y: 80%. ESI-MS (M-OH)$^+$: 355.2.

Step 2. 1-(8-chloro-7-((cis-4-(trifluoromethyl)cyclohexyl)oxy)naphthalen-2-yl)ethanone A mixture of 1-(8-chloro-7-((cis-4-(trifluoromethyl)cyclohexyl)oxy)naphthalen-2-yl)ethanol (700 mg, 1.6 mmol, 1.0 eq), PCC (700 mg, 3.2 mmol, 2.0 eq) and silica gel (700 mg) in DCM (3 mL) was stirred at rt for 16 h. The mixture was filtered and the filtrate was concentrate to yield a crude product, which was purified by column chromatography on silica gel (petroleum ether/EtOAc=10:1) to give 1-(8-chloro-7-((cis-4-(trifluoromethyl)cyclohexyl)oxy)naphthalen-2-yl)ethanone as yellow solid (480 mg, Y: 70%). ESI-MS (M+H)+: 371.2. $^1$H NMR (400 MHz, CDCl$_3$) δ: 8.84 (s, 1H), 7.97 (d, J=8.4 Hz, 1H), 7.84 (d, J=8.4 Hz, 1H), 7.77 (d, J=8.8 Hz, 1H), 7.37 (d, J=8.8 Hz, 1H), 4.81 (s, 1H), 2.77 (s, 3H), 2.23-1.94 (m, 5H), 1.81-1.58 (m, 4H).

Step 3: Isopropyl 1-(1-(8-chloro-7-((cis-4-(trifluoromethyl)cyclohexyl)oxy)naphthalen-2-yl)ethyl)piperidine-4-carboxylate

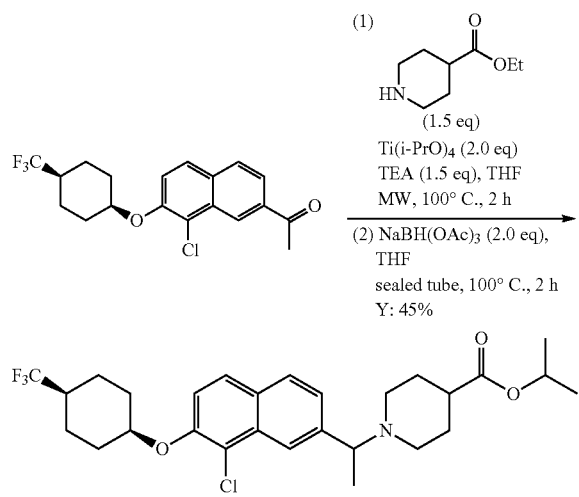

The preparation of isopropyl 1-(1-(8-chloro-7-((cis-4-(trifluoromethyl)cyclohexyl)oxy)naphthalen-2-yl)ethyl)piperidine-4-carboxylate was the same as Example 26. 70 mg as a yellow solid, Y: 45%. ESI-MS (M+H)+: 526.2.

Step 4: 1-(1-(8-chloro-7-((cis-4-(trifluoromethyl)cyclohexyl)oxy)naphthalen-2-yl)ethyl)piperidine-4-carboxylic acid

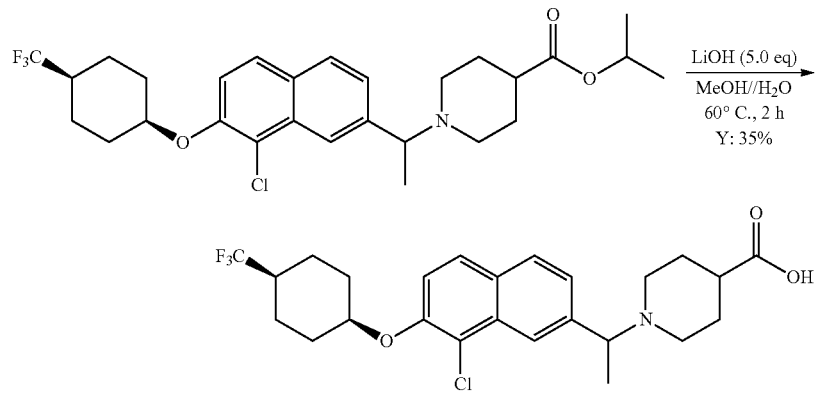

The preparation of 1-(1-(8-chloro-7-((cis-4-(trifluoromethyl)cyclohexyl)oxy)naphthalen-2-yl)ethyl)piperidine-4-carboxylic acid was the same as Example 26. 25 mg as a white solid, Y: 35%. ESI-MS (M+H)+: 484.1. $^1$H NMR (400 MHz, CD$_3$OD) δ: 8.27 (s, 1H), 7.97 (d, J=8.4 Hz, 1H), 7.89 (d, J=8.8 Hz, 1H), 7.54-7.51 (m, 2H), 4.93 (s, 1H), 4.45-4.40 (m, 1H), 3.56-3.54 (m, 1H), 3.20-3.18 (m, 1H), 2.84-2.78 (m, 2H), 2.31-2.14 (m, 4H), 2.08-1.86 (m, 6H), 1.78-1.67 (m, 7H).

Example 29: 8-(1-(8-chloro-7-((cis-4-(trifluoromethyl)cyclohexyl)oxy)naphthalen-2-yl)ethyl)-8-azabicyclo[3.2.1]octane-3-carboxylic acid

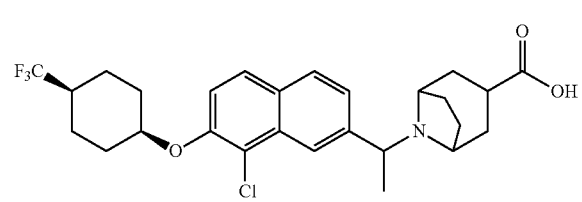 [SMILES: CC(c1ccc2ccc(O[C@H]3CC[C@@H](C(F)(F)F)CC3)c(Cl)c2c1)N1C2CCC1CC(C(=O)O)C2]

The preparation of 8-(1-(8-chloro-7-((cis-4-(trifluoromethyl)cyclohexyl)oxy)naphthalen-2-yl)ethyl)-8-azabicyclo[3.2.1]octane-3-carboxylic acid was the same as Example 26. 25 mg as a white solid, Y: 40%. ESI-MS (M+H)+: 510.1. $^1$H NMR (400 MHz, CD$_3$OD) δ: 8.39 (s, 1H), 8.01 (d, J=8.4 Hz, 1H), 7.91 (d, J=9.2 Hz, 1H), 7.61 (dd, J=1.6 Hz, 8.4 Hz, 1H), 7.54 (d, J=9.6 Hz, 1H), 4.95 (s, 1H), 4.55-4.50 (m, 1H), 4.30-4.26 (m, 1H), 3.55-3.51 (m, 1H), 2.72-2.63 (m, 1H), 2.43-1.68 (m, 20H).

Example 30: 9-(1-(8-chloro-7-((cis-4-(trifluoromethyl)cyclohexyl)oxy)naphthalen-2-yl)ethyl)-9-azabicyclo[3.3.1]nonane-3-carboxylic acid

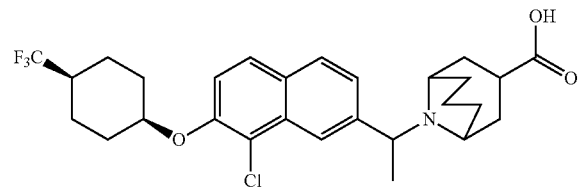 [SMILES: CC(c1ccc2ccc(O[C@H]3CC[C@@H](C(F)(F)F)CC3)c(Cl)c2c1)N1C2CCCC1CC(C(=O)O)C2]

The preparation of 9-(1-(8-chloro-7-((cis-4-(trifluoromethyl)cyclohexyl)oxy)naphthalen-2-yl)ethyl)-9-azabicyclo[3.3.1]nonane-3-carboxylic acid was the same as Example 26. 7 mg as a yellow oil, Y: 25%. ESI-MS (M+H)⁺: 524.2. ¹H NMR (400 MHz, CD₃OD) δ: 8.39 (s, 1H), 7.96 (d, J=8.4 Hz, 1H), 7.87 (d, J=9.2 Hz, 1H), 7.66 (dd, J=1.6 Hz, 8.4 Hz, 1H), 7.50 (d, J=9.2 Hz, 1H), 5.03-4.99 (m, 1H), 4.93 (s, 1H), 3.57-3.51 (m, 1H), 3.10-3.02 (m, 1H), 2.47-2.06 (m, 8H), 2.01-1.91 (m, 4H), 1.78-1.60 (m, 11H).

Example 31: 1-(1-(8-chloro-7-((cis-4-(trifluoromethyl)cyclohexyl)oxy)naphthalen-2-yl)propyl)piperidine-4-carboxylic acid

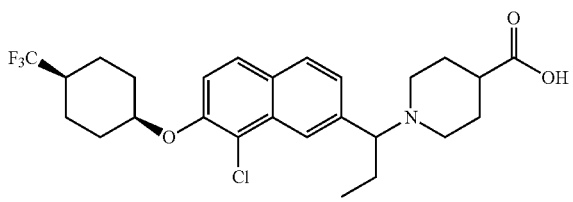 [SMILES: CCC(c1ccc2ccc(O[C@H]3CC[C@@H](C(F)(F)F)CC3)c(Cl)c2c1)N1CCC(C(=O)O)CC1]

The preparation of 1-(1-(8-chloro-7-((cis-4-(trifluoromethyl)cyclohexyl)oxy)naphthalen-2-yl)propyl)piperidine-4-carboxylic acid was the same as Example 28. 11 mg as a yellow oil, Y: 25%. ESI-MS (M+H)⁺: 498.2. ¹H NMR (400 MHz, CD₃OD) δ: 8.32 (s, 1H), 8.05 (d, J=8.8 Hz, 1H), 7.94 (d, J=8.4 Hz, 1H), 7.59-7.53 (m, 2H), 4.96 (s, 1H), 4.53-4.45 (m, 1H), 3.95-3.79 (m, 1H), 3.44-3.36 (m, 1H), 3.01-2.83 (m, 2H), 2.57-2.14 (m, 8H), 2.02-1.69 (m, 8H), 0.82 (t, J=7.2 Hz, 3H).

Example 32: (1R,3S)-3-((1-(8-chloro-7-((cis-4-(trifluoromethyl)cyclohexyl)oxy)naphthalen-2-yl)propyl)amino)-2,2-dimethylcyclobutanecarboxylic acid

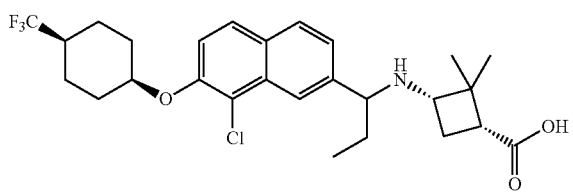 [SMILES: CCC(N[C@H]1C[C@@H](C(=O)O)C1(C)C)c1ccc2ccc(O[C@H]3CC[C@@H](C(F)(F)F)CC3)c(Cl)c2c1]

The preparation of (1R,3S)-3-((1-(8-chloro-7-((cis-4-(trifluoromethyl)cyclohexyl)oxy)naphthalen-2-yl)propyl)amino)-2,2-dimethylcyclobutanecarboxylic acid was the same as Example 28. 18 mg as a white solid, Y: 60%. ESI-MS (M+H)⁺: 512.3. ¹H NMR (400 MHz, CD₃OD, a mixture of diastereomers) δ: 8.08-8.06 (m, 1H), 7.82-7.69 (m, 2H), 7.38-7.30 (m, 2H), 4.75 (s, 1H), 4.09-3.94 (m, 1H), 2.93-2.71 (m, 1H), 2.33-1.50 (m, 14H), 1.15-0.97 (m, 6H), 0.72-0.64 (m, 3H).

Example 33: 1-((8-cyano-7-((cis-4-(trifluoromethyl)cyclohexyl)oxy)naphthalen-2-yl)methyl)piperidine-4-carboxylic acid Step 1: 7-formyl-2-((cis-4-(trifluoromethyl)cyclohexyl)oxy)-1-naphthonitrile

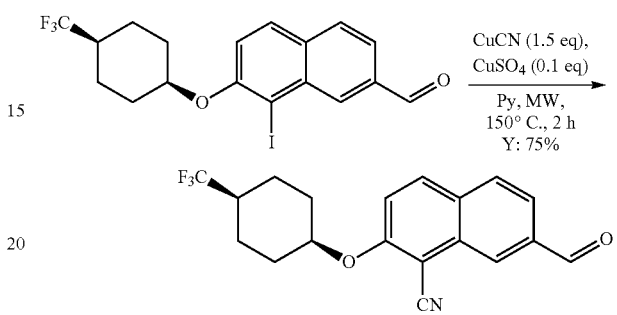

A mixture of 8-iodo-7-((cis-4-(trifluoromethyl)cyclohexyl)oxy)-2-naphthaldehyde (2.0 g, 4.3 mmol, 1.0 eq), CuCN (580 mg, 6.5 mmol, 1.5 eq) and CuSO₄ (65 mg, 0.43 mmol, 0.1 eq) in pyridine (10 mL) was stirred at 150° C. for 2 h under microwave condition. After cooling to rt, the mixture was diluted with EtOAc (30 mL) and washed with H₂O (15 mL×3). The organic phase was dried and concentrated. The residue was purified by column chromatography on silica gel (petroleum ether/EtOAc=10:1) to give 7-formyl-2-((cis-4-(trifluoromethyl)cyclohexyl)oxy)-1-naphthonitrile (1.0 g, Y: 75%) as yellow solid. ESI-MS (M+H)⁺: 348.2.

Step 2: 1-((8-cyano-7-((cis-4-(trifluoromethyl)cyclohexyl)oxy)naphthalen-2-yl)methyl)piperidine-4-carboxylic acid

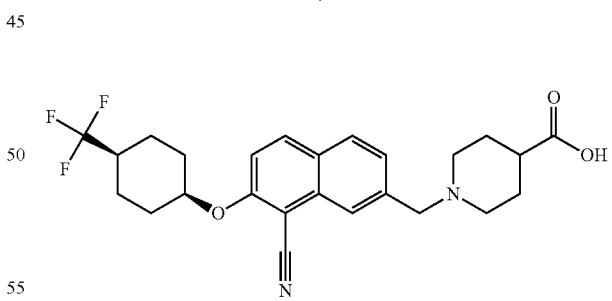

The preparation of 1-((8-cyano-7-((cis-4-(trifluoromethyl)cyclohexyl)oxy)naphthalen-2-yl)methyl)piperidine-4-carboxylic acid was the same as Example 26. 30 mg as a white solid, Y: 44%. ESI-MS (M+H)⁺: 461.2. ¹H NMR (400 MHz, DMSO-d₆) δ: 12.13 (br s, 1H), 8.24 (d, J=9.2 Hz, 1H), 7.98 (d, J=8.4 Hz, 1H), 7.82 (s, 1H), 7.62 (d, J=9.2 Hz, 1H), 7.49 (dd, J=1.2 Hz, 8.4 Hz, 1H), 5.11 (s, 1H), 3.66 (s, 2H), 2.80-2.77 (m, 2H), 2.45-2.40 (m, 1H), 2.25-2.19 (m, 1H), 2.09-2.04 (m, 4H), 1.81-1.53 (m, 10H).

Example 34: 8-((8-cyano-7-((cis-4-(trifluoromethyl)cyclohexyl)oxy)naphthalen-2-yl)methyl)-8-azabicyclo[3.2.1]octane-3-carboxylic acid

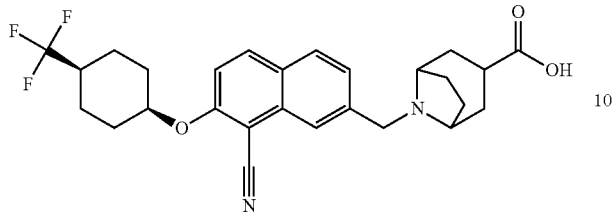

The preparation of 8-((8-cyano-7-((cis-4-(trifluoromethyl)cyclohexyl)oxy)naphthalen-2-yl)methyl)-8-azabicyclo [3.2.1]octane-3-carboxylic acid was the same as Example 26. 40 mg as a white solid, Y: 51%. ESI-MS (M+H)$^+$: 487.2. $^1$H NMR (400 MHz, DMSO-d$_6$) δ: 12.05 (br s, 1H), 8.23 (d, J=9.6 Hz, 1H), 7.97 (d, J=8.4 Hz, 1H), 7.90 (s, 1H), 7.60 (d, J=9.2 Hz, 1H), 7.55 (dd, J=1.2 Hz, 8.4 Hz, 1H), 5.11 (s, 1H), 3.71 (s, 2H), 3.20-3.17 (m, 2H), 2.60-2.54 (m, 1H), 2.44-2.37 (m, 1H), 2.06-2.01 (m, 4H), 1.78-1.72 (m, 8H), 1.62-1.57 (m, 4H).

Example 35: 9-((8-cyano-7-((cis-4-(trifluoromethyl)cyclohexyl)oxy)naphthalen-2-yl)methyl)-9-azabicyclo[3.3.1]nonane-3-carboxylic acid

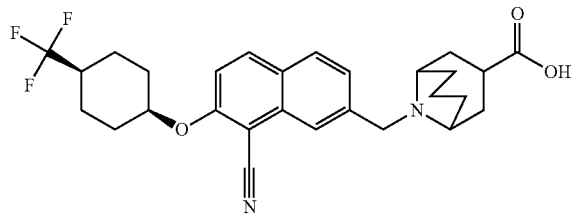 [SMILES: N#Cc1c(O[C@H]2CC[C@@H](C(F)(F)F)CC2)ccc2ccc(CN3C4CCCC3CC(C(=O)O)C4)cc12]

The preparation of 9-((8-cyano-7-((cis-4-(trifluoromethyl)cyclohexyl)oxy)naphthalen-2-yl)methyl)-9-azabicyclo [3.3.1]nonane-3-carboxylic acid was the same as Example 26. 13 mg as a white solid, Y: 16%. ESI-MS (M+H)$^+$: 501.2. $^1$H NMR (400 MHz, DMSO-d$_6$) δ: 8.22 (d, J=9.6 Hz, 1H), 7.96 (d, J=8.4 Hz, 1H), 7.89 (s, 1H), 7.60 (d, J=9.2 Hz, 1H), 7.54 (dd, J=1.2 Hz, 8.4 Hz, 1H), 5.10 (s, 1H), 4.01 (s, 2H), 3.12-3.04 (m, 1H), 2.86-2.84 (m, 2H), 2.45-2.41 (m, 1H), 2.05-1.61 (m, 16H), 1.52-1.47 (m, 2H).

Example 36: 1-(1-(8-cyano-7-((cis-4-(trifluoromethyl)cyclohexyl)oxy)naphthalen-2-yl)ethyl)piperidine-4-carboxylic acid Step 1: 7-(1-hydroxyethyl)-2-((cis-4-(trifluoromethyl)cyclohexyl)oxy)-1-naphthonitrile

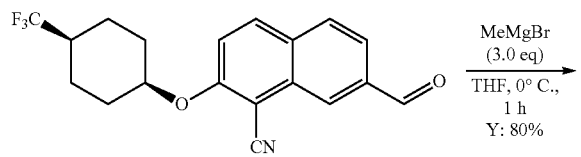

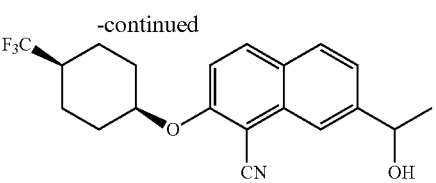

The preparation of 7-(1-hydroxyethyl)-2-((cis-4-(trifluoromethyl)cyclohexyl)oxy)-1-naphthonitrile was the same as 1-(8-chloro-7-((cis-4-(trifluoromethyl)cyclohexyl)oxy)naphthalen-2-yl)ethanol. 250 mg as a colorless oil, Y: 80%. ESI-MS (M-OH)$^+$: 346.2.

Step 2: 1-(1-(8-cyano-7-((cis-4-(trifluoromethyl)cyclohexyl)oxy)naphthalen-2-yl)ethyl)piperidine-4-carboxylic acid

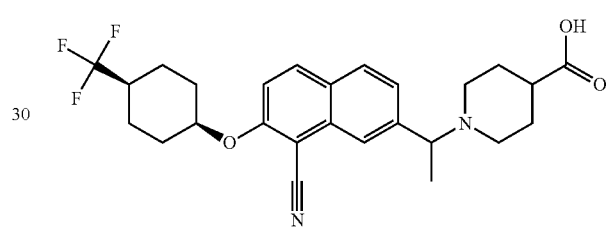

The preparation of 1-(1-(8-cyano-7-((cis-4-(trifluoromethyl)cyclohexyl)oxy)naphthalen-2-yl)ethyl)piperidine-4-carboxylic acid was the same as Example 28. 9 mg as a white solid, Y: 24%. ESI-MS (M+H)$^+$: 475.2. $^1$H NMR (400 MHz, DMSO-d$_6$) δ: 8.23 (d, J=9.2 Hz, 1H), 7.98 (d, J=8.4 Hz, 1H), 7.79 (s, 1H), 7.61 (d, J=9.2 Hz, 1H), 7.53 (dd, J=1.2 Hz, 8.8 Hz, 1H), 5.11 (s, 1H), 3.63 (q, J=6.8 Hz, 1H), 2.97-2.89 (m, 1H), 2.70-2.67 (m, 1H), 2.45-2.39 (m, 1H), 2.16-1.94 (m, 5H), 1.82-1.72 (m, 8H), 1.64-1.45 (m, 2H), 1.35 (d, J=6.8 Hz, 3H).

Example 37: 8-(1-(8-cyano-7-((cis-4-(trifluoromethyl)cyclohexyl)oxy)naphthalen-2-yl)ethyl)-8-azabicyclo[3.2.1]octane-3-carboxylic acid

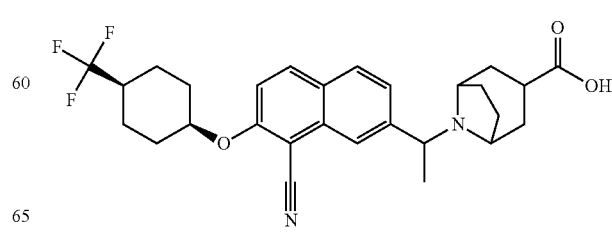

The preparation of 8-(1-(8-cyano-7-((cis-4-(trifluoromethyl)cyclohexyl)oxy)naphthalen-2-yl)ethyl)-8-azabicyclo[3.2.1]octane-3-carboxylic acid was the same as Example 28. 20 mg as a white solid, Y: 53%. ESI-MS (M+H)+: 501.3. $^1$H NMR (400 MHz, DMSO-d$_6$) δ: 8.09-8.06 (m, 2H), 7.94 (d, J=8.0 Hz, 1H), 7.56-7.54 (m, 1H), 7.45 (d, J=9.6 Hz, 1H), 4.94 (s, 1H), 4.37-4.36 (m, 1H), 4.08-4.04 (m, 1H), 3.37-3.35 (m, 1H), 2.56-2.49 (m, 1H), 2.27-2.04 (m, 6H), 1.92-1.62 (m, 14H).

Example 38: 9-(1-(8-cyano-7-((cis-4-(trifluoromethyl)cyclohexyl)oxy)naphthalen-2-yl)ethyl)-9-azabicyclo[3.3.1]nonane-3-carboxylic acid

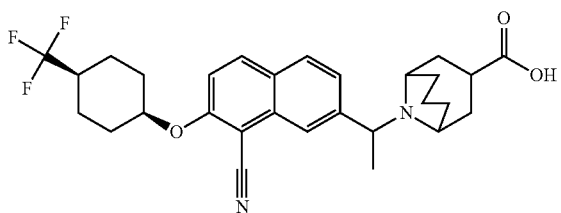

The preparation of 9-(1-(8-cyano-7-((cis-4-(trifluoromethyl)cyclohexyl)oxy)naphthalen-2-yl)ethyl)-9-azabicyclo[3.3.1]nonane-3-carboxylic acid was the same as Example 28. 13 mg as a white solid, Y: 47%. ESI-MS (M+H)+: 515.2. $^1$H NMR (400 MHz, DMSO-d$_6$) δ: 8.21 (d, J=8.8 Hz, 1H), 7.97 (d, J=8.8 Hz, 1H), 7.87 (s, 1H), 7.61-7.56 (m, 2H), 5.10 (s, 1H), 4.27 (q, J=6.8 Hz, 1H), 3.06-2.91 (m, 3H), 2.45-2.40 (m, 1H), 2.06-1.57 (m, 16H), 1.48-1.38 (m, 2H), 1.26 (d, J=6.4 Hz, 3H).

Example 39: 1-(1-(8-cyano-7-((cis-4-(trifluoromethyl)cyclohexyl)oxy)naphthalen-2-yl)propyl)piperidine-4-carboxylic acid

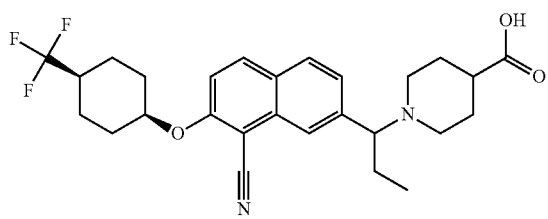 [SMILES: CC(c1ccc2ccc(O[C@H]3CC[C@@H](C(F)(F)F)CC3)c(C#N)c2c1)N1CCC(C(=O)O)CC1]

The preparation of 1-(1-(8-cyano-7-((cis-4-(trifluoromethyl)cyclohexyl)oxy)naphthalen-2-yl)propyl)piperidine-4-carboxylic acid was the same as Example 28. 30 mg as a white solid, Y: 59%. ESI-MS (M+H)+: 489.2. $^1$H NMR (400 MHz, CD$_3$OD) δ: 8.20 (d, J=9.2 Hz, 1H), 8.01 (d, J=8.8 Hz, 1H), 7.37 (s, 1H), 7.57-7.53 (m, 2H), 5.07 (s, 1H), 3.96-3.92 (m, 1H), 3.40-3.37 (m, 1H), 3.08-3.05 (m, 1H), 2.53-1.74 (m, 18H), 0.78 (t, J=7.2 Hz, 3H).

Example 40: 8-(1-(8-cyano-7-((cis-4-(trifluoromethyl)cyclohexyl)oxy)naphthalen-2-yl)propyl)-8-azabicyclo[3.2.1]octane-3-carboxylic acid

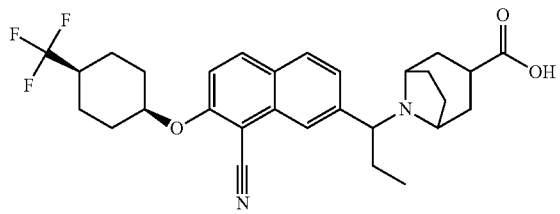 [SMILES: CCC(c1ccc2ccc(O[C@H]3CC[C@@H](C(F)(F)F)CC3)c(C#N)c2c1)N1C2CCC1CC(C(=O)O)C2]

The preparation of 8-(1-(8-cyano-7-((cis-4-(trifluoromethyl)cyclohexyl)oxy)naphthalen-2-yl)propyl)-8-azabicyclo[3.2.1]octane-3-carboxylic acid was the same as Example 28. 30 mg as a white solid, Y: 65%. ESI-MS (M+H)+: 515.2. $^1$H NMR (400 MHz, CD$_3$OD) δ: 8.22 (d, J=9.2 Hz, 1H), 8.13 (s, 1H), 8.06 (d, J=8.4 Hz, 1H), 7.66 (d, J=8.4 Hz, 1H), 7.58 (d, J=9.2 Hz, 1H), 5.08 (s, 1H), 4.17-3.99 (m, 2H), 3.46-3.43 (m, 1H), 2.68-2.62 (m, 1H), 2.33-1.75 (m, 19H), 1.35 (t, J=7.2 Hz, 3H).

Example 41: 9-(1-(8-cyano-7-((cis-4-(trifluoromethyl)cyclohexyl)oxy)naphthalen-2-yl)propyl)-9-azabicyclo[3.3.1]nonane-3-carboxylic acid

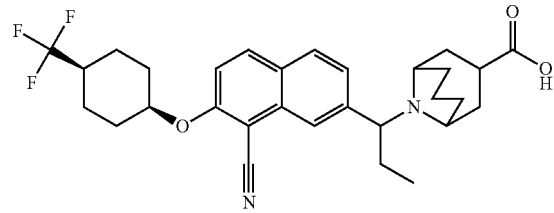 [SMILES: CCC(c1ccc2ccc(O[C@H]3CC[C@@H](C(F)(F)F)CC3)c(C#N)c2c1)N1C2CCCC1CC(C(=O)O)C2]

The preparation of 9-(1-(8-cyano-7-((cis-4-(trifluoromethyl)cyclohexyl)oxy)naphthalen-2-yl)propyl)-9-azabicyclo[3.3.1]nonane-3-carboxylic acid was the same as Example 28. 23 mg as a white solid, Y: 42%. ESI-MS (M+H)+: 529.2. $^1$H NMR (400 MHz, CD$_3$OD) δ: 8.19 (d, J=9.2 Hz, 1H), 8.13 (s, 1H), 8.02 (d, J=8.8 Hz, 1H), 7.69 (d, J=8.0 Hz, 1H), 7.55 (d, J=9.2 Hz, 1H), 5.07 (s, 1H), 4.71-4.65 (m, 1H), 3.52-3.48 (m, 1H), 3.09-3.04 (m, 1H), 2.35-1.66 (m, 22H), 1.35 (t, J=7.2 Hz, 3H).

Example 42: 8-(1-(8-(difluoromethyl)-7-((cis-4-(trifluoromethyl)cyclohexyl)oxy)naphthalen-2-yl)ethyl)-8-azabicyclo[3.2.1]octane-3-carboxylic acid Step 1: 7-bromo-2-((cis-4-(trifluoromethyl)cyclohexyl)oxy)-1-naphthaldehyde

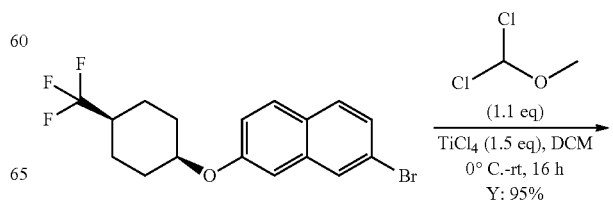

139
-continued

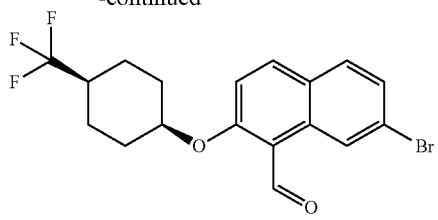

Into a mixture of 2-bromo-7-((cis-4-(trifluoromethyl)cyclohexyl)oxy)naphthalene (372 mg, 1.0 mmol, 1.0 eq) and dichloro(methoxy)methane (140 mg, 1.1 mmol, 1.1 eq) in DCM (3 mL) was added TiCl$_4$ (300 mg, 1.5 mmol, 1.5 eq) dropwised at 0° C. After addition, the mixture was stirred at rt for 16 h. 1N HCl (10 mL) was added and the mixture was extracted with DCM (20 mL×2). The organic layers were dried over Na$_2$SO$_4$, filtered and concentrated to give 7-bromo-2-((cis-4-(trifluoromethyl)cyclohexyl)oxy)-1-naphthaldehyde (380 mg, Y: 95%) as yellow solid, which was used to the next step without further purification. ESI-MS (M+H)$^+$: 401.1. $^1$H NMR (400 MHz, CDCl$_3$) δ: 10.92 (s, 1H), 9.53 (s, 1H), 7.99 (d, J=9.6 Hz, 1H), 7.62 (d, J=8.4 Hz, 1H), 7.52 (d, J=8.8 Hz, 1H), 7.26 (d, J=9.2 Hz, 1H), 4.91 (s, 1H), 2.29-2.11 (m, 3H), 1.89-1.66 (m, 6H).

Step 2: 7-bromo-1-(difluoromethyl)-2-((cis-4-(trifluoromethyl)cyclohexyl)oxy)naphthalene

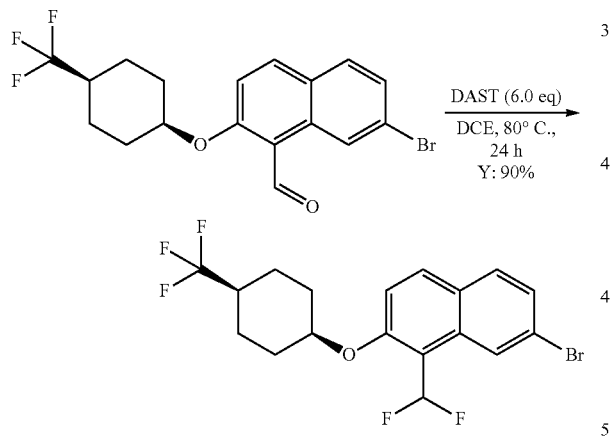

Into a solution of 7-bromo-2-((cis-4-(trifluoromethyl)cyclohexyl)oxy)-1-naphthaldehyde (1.4 g, 3.5 mmol, 1.0 eq) in DCE (10 mL) was added DAST (3.4 g, 21.0 mmol, 6.0 eq) at rt. The mixture was stirred at 80° C. for 24 h and cooled down. Water (50 mL) was added and the mixture was extracted with DCM (50 mL×2). The combined organic layers were washed with aq. NaHCO$_3$ (100 mL), dried over Na$_2$SO$_4$. The organic phase was filtered and concentrated. The residue was purified by column chromatography on silica gel (petroleum ether/EtOAc=50:1) to give 7-bromo-1-(difluoromethyl)-2-((cis-4-(trifluoromethyl)cyclohexyl)oxy)naphthalene (1.3 g, Y: 90%) as yellow solid. $^1$H NMR (400 MHz, CDCl$_3$) δ: 8.52 (s, 1H), 7.86 (d, J=9.2 Hz, 1H), 7.64 (d, J=8.8 Hz, 1H), 7.51 (t, J=54.4 Hz, 1H), 7.49 (dd, J=1.6 Hz, 8.8 Hz, 1H), 7.21 (d, J=9.2 Hz, 1H), 4.80 (s, 1H), 2.12-2.09 (m, 3H), 1.86-1.60 (m, 6H).

140
Step 3: 8-(difluoromethyl)-7-((cis-4-(trifluoromethyl)cyclohexyl)oxy)-2-naphthaldehyde

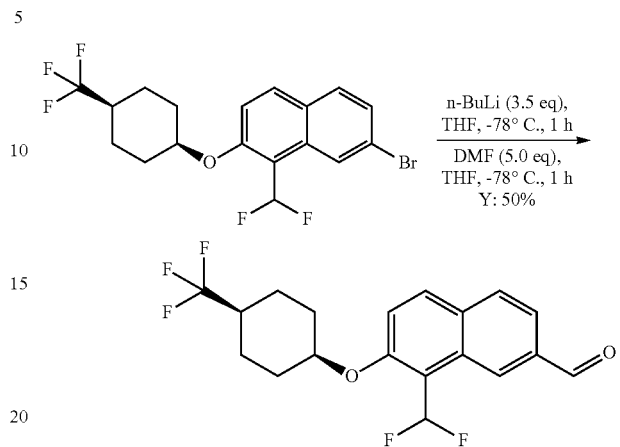

The preparation of 8-(difluoromethyl)-7-((cis-4-(trifluoromethyl)cyclohexyl)oxy)-2-naphthaldehyde was the same as 7-((cis-4-(trifluoromethyl)cyclohexyl)oxy)-2-naphthaldehyde, weight: 540 mg, yellow solid, yield: 50%. ESI-MS (M+H)$^+$: 373.2. $^1$H NMR (400 MHz, CDCl$_3$) δ: 10.19 (s, 1H), 8.85 (s, 1H), 7.97 (d, J=8.8 Hz, 1H), 7.92-7.86 (m, 2H), 7.73 (t, J=54.4 Hz, 1H), 7.37 (d, J=9.2 Hz, 1H), 4.84 (s, 1H), 2.24-2.10 (m, 3H), 1.88-1.65 (m, 6H).

Step 4: 1-(8-(difluoromethyl)-7-((cis-4-(trifluoromethyl)cyclohexyl)oxy)naphthalen-2-yl)ethanol

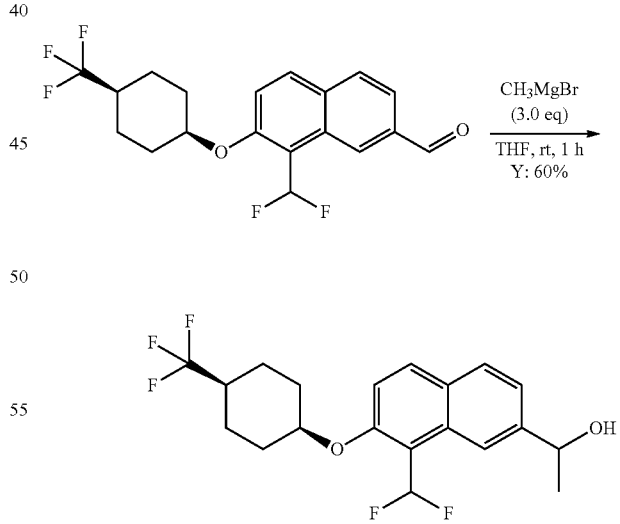

The preparation of 1-(8-(difluoromethyl)-7-((cis-4-(trifluoromethyl)cyclohexyl)oxy)naphthalen-2-yl)ethanol was the same as 1-(8-chloro-7-((cis-4-(trifluoromethyl)cyclohexyl)oxy)naphthalen-2-yl)ethanol. 80 mg as a yellow oil, Y: 60%. ESI-MS (M-OH)$^+$: 371.2.

Step 5: 7-(1-bromoethyl)-1-(difluoromethyl)-2-((cis-4-(trifluoromethyl)cyclohexyl)oxy) naphthalene

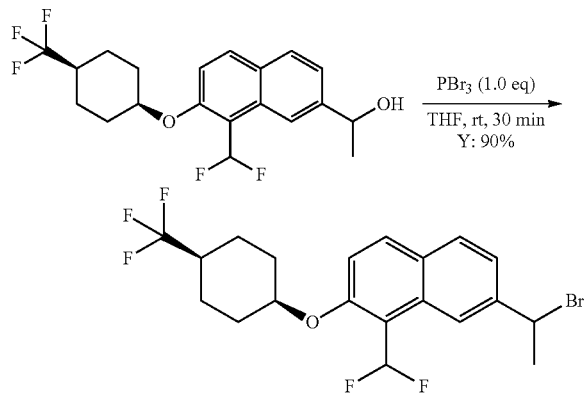

To a solution of 1-(8-(difluoromethyl)-7-((cis-4-(trifluoromethyl)cyclohexyl)oxy)naphthalen-2-yl)ethanol (80 mg, 0.2 mmol, 1.0 eq) in THF (2 mL) under $N_2$ was added $PBr_3$ (0.2 mL, 1M in DCM, 1.0 eq) at rt. The reaction mixture was stirred at rt for 30 minutes and diluted with EtOAc (20 mL). The mixture was washed with water (10 mL×2) and the organic layer was dried, filtered and concentrated to give 7-(1-bromoethyl)-1-(difluoromethyl)-2-((cis-4-(trifluoromethyl)cyclohexyl)oxy)naphthalene (80 mg, Y: 90%) as yellow oil, which was used to the next step immediately.

Step 6: methyl 8-(1-(8-(difluoromethyl)-7-((cis-4-(trifluoromethyl)cyclohexyl)oxy)naphthalen-2-yl)ethyl)-8-azabicyclo[3.2.1]octane-3-carboxylate

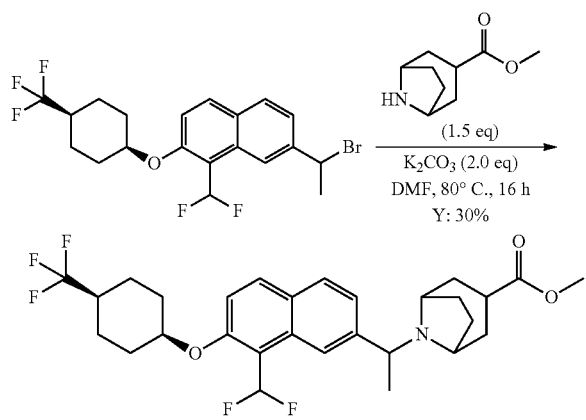

To a mixture of 7-(1-bromoethyl)-1-(difluoromethyl)-2-((cis-4-(trifluoromethyl)cyclohexyl)oxy)naphthalene (80 mg, 0.2 mmol, 1.0 eq) and methyl 8-azabicyclo[3.2.1]octane-3-carboxylate (51 mg, 0.3 mmol, 1.5 eq) in DMF (2 mL) was added $K_2CO_3$ (56 mg, 0.4 mmol, 2.0 eq). The mixture was stirred at 80° C. for 16 h. After cooling to rt, the mixture was purified by pre-TLC on silica gel (petroleum ether/EtOAc=5:1) to give 8-(1-(8-(difluoromethyl)-7-((cis-4-(trifluoromethyl)cyclohexyl)oxy)naphthalen-2-yl)ethyl)-8-azabicyclo[3.2.1]octane-3-carboxylate (30 mg, Y: 30%) as yellow oil. ESI-MS (M+H)$^+$: 540.2.

Step 7: 8-(1-(8-(difluoromethyl)-7-((cis-4-(trifluoromethyl)cyclohexyl)oxy)naphthalen-2-yl)ethyl)-8-azabicyclo[3.2.1]octane-3-carboxylic acid

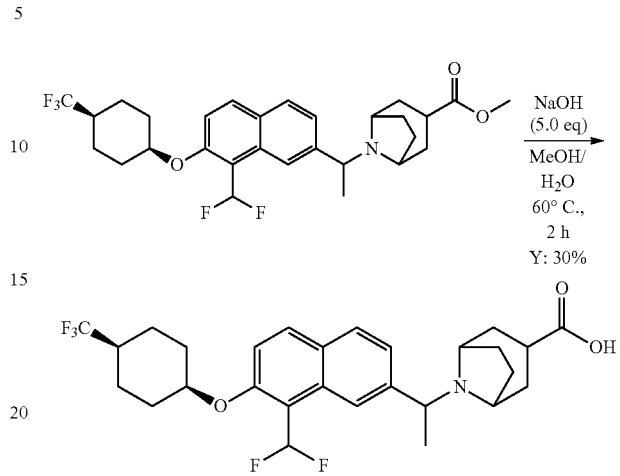

The preparation of 8-(1-(8-(difluoromethyl)-7-((cis-4-(trifluoromethyl)cyclohexyl)oxy)naphthalen-2-yl)ethyl)-8-azabicyclo[3.2.1]octane-3-carboxylic acid was the same as Example 26. 10 mg as a yellow oil, Y: 30%. ESI-MS (M+H)$^+$: 526.2. $^1$H NMR (400 MHz, CD$_3$OD) δ: 8.44 (s, 1H), 8.12-8.06 (m, 2H), 7.63 (t, J=55.2 Hz, 1H), 7.62-7.49 (m, 2H), 5.00 (s, 1H), 4.55-4.44 (m, 2H), 3.47-3.44 (m, 1H), 2.96-2.90 (m, 1H), 2.64-2.58 (m, 1H), 2.36-1.94 (m, 10H), 1.84-1.76 (m, 9H).

Example 43: 1-((8-(trifluoromethyl)-7-((cis-4-(trifluoromethyl)cyclohexyl)oxy)naphthalen-2-yl)methyl)piperidine-4-carboxylic acid Step 1: 8-iodo-7-((cis-4-(trifluoromethyl)cyclohexyl)oxy)-2-naphthaldehyde

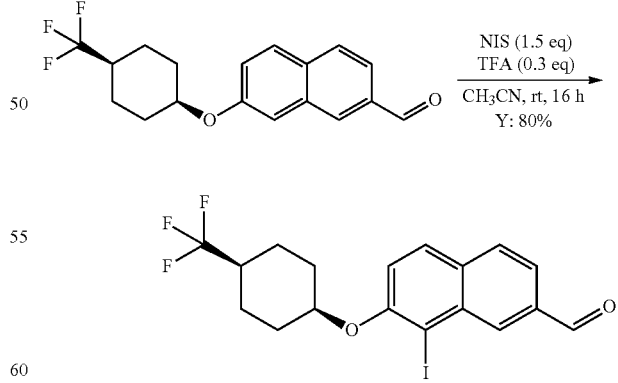

The preparation of 8-iodo-7-((cis-4-(trifluoromethyl)cyclohexyl)oxy)-2-naphthaldehyde was the same as 8-chloro-7-((cis-4-(trifluoromethyl)cyclohexyl)oxy)-2-naphthaldehyde, weight: 1.4 g, yellow solid, Y: 80%. ESI-MS (M+H)$^+$: 449.0.

Step 2: 8-(trifluoromethyl)-7-((cis-4-(trifluoromethyl)cyclohexyl)oxy)-2-naphthaldehyde

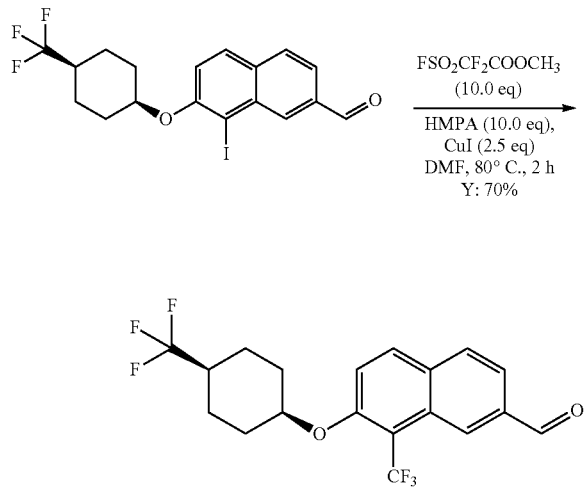

A mixture of 8-iodo-7-((cis-4-(trifluoromethyl)cyclohexyl)oxy)-2-naphthaldehyde (1.4 g, 3.0 mmol, 1.0 eq), FSO$_2$CF$_3$COOCH$_3$ (5.8 g, 30.0 mmol, 10.0 eq), HMPA (5.4 g, 30.0 mmol, 10.0 eq) and CuI (1.4 g, 7.5 mmol, 2.5 eq) in DMF (10 mL) was stirred at 80° C. for 2 h under N$_2$ atmosphere and cooled down. The mixture was diluted with EtOAc (150 mL) and washed with H$_2$O (100 mL×2). The organic layer was dried and concentrated, the residue was purified by column chromatography on silica gel (petroleum ether/EtOAc=20:1) to give 8-(trifluoromethyl)-7-((cis-4-(trifluoromethyl)cyclohexyl)oxy)-2-naphthaldehyde (800 mg, Y: 70%) as yellow solid. ESI-MS (M+H)$^+$: 391.1. $^1$H NMR (400 MHz, CDCl$_3$) δ: 10.17 (s, 1H), 8.72 (s, 1H), 8.03 (d, J=9.2 Hz, 1H), 7.90 (s, 2H), 7.43 (d, 0.1=9.2 Hz, 1H), 4.89 (s, 1H), 2.26-2.08 (m, 3H), 1.94-1.63 (m, 6H).

Step 3: 1-((8-(trifluoromethyl)-7-((cis-4-(trifluoromethyl)cyclohexyl)oxy)naphthalen-2-yl)methyl)piperidine-4-carboxylic acid

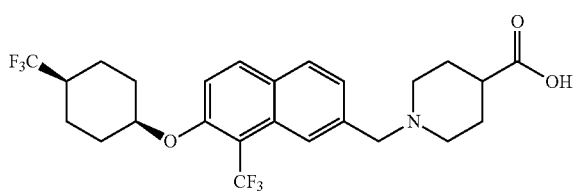 [SMILES: O=C(O)C1CCN(Cc2ccc3ccc(O[C@H]4CC[C@@H](C(F)(F)F)CC4)c(C(F)(F)F)c3c2)CC1]

The preparation of 1-((8-(trifluoromethyl)-7-((cis-4-(trifluoromethyl)cyclohexyl)oxy)naphthalen-2-yl)methyl)piperidine-4-carboxylic acid was the same as Example 26. 27 mg as a white solid, Y: 50%. ESI-MS (M+H)$^+$: 504.2. $^1$H NMR (400 MHz, CD$_3$OD) δ: 7.96 (s, 1H), 7.92 (d, J=9.2 Hz, 1H), 7.82 (d, J=8.4 Hz, 1H), 7.37-7.31 (m, 2H), 4.83 (s, 1H), 3.55 (s, 2H), 2.83-2.80 (m, 2H), 2.18-1.97 (m, 6H), 1.79-1.56 (m, 10H).

Example 44: 1-(1-(8-(trifluoromethyl)-7-((cis-4-(trifluoromethyl)cyclohexyl)oxy) naphthalen-2-yl)ethyl)piperidine-4-carboxylic acid

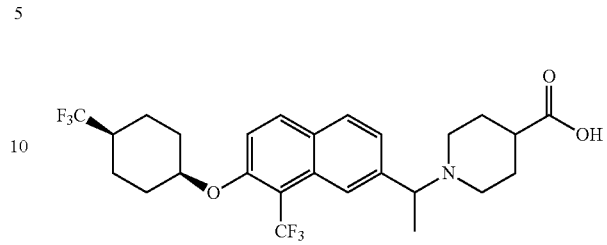

The preparation of 1-(1-(8-(trifluoromethyl)-7-((cis-4-(trifluoromethyl)cyclohexyl)oxy)naphthalen-2-yl)ethyl)piperidine-4-carboxylic acid was the same as Example 28. 40 mg as a yellow oil, yield: 40%. ESI-MS (M+H)$^+$: 518.2. $^1$H NMR (400 MHz, CD$_3$OD) δ: 8.19 (s, 1H), 8.12 (d, J=9.6 Hz, 1H), 7.98 (d, J=8.4 Hz, 1H), 7.57-7.53 (m, 2H), 5.01 (s, 1H), 4.29-4.26 (m, 1H), 3.48-3.44 (m, 1H), 3.13-3.10 (m, 1H), 2.71-2.66 (m, 2H), 2.31-2.16 (m, 4H), 2.02-1.70 (m, 13H).

Example 45: 1-(1-(8-(trifluoromethyl)-7-((cis-4-(trifluoromethyl)cyclohexyl)oxy) naphthalene-2-yl) propyl)piperidine-4-carboxylic acid

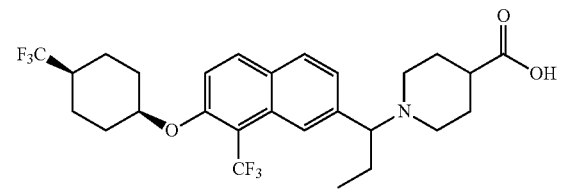 [SMILES: CCC(c1ccc2ccc(O[C@H]3CC[C@@H](C(F)(F)F)CC3)c(C(F)(F)F)c2c1)N1CCC(C(=O)O)CC1]

The preparation of 1-(1-(8-(trifluoromethyl)-7-((cis-4-(trifluoromethyl)cyclohexyl)oxy)naphthalen-2-yl)propyl)piperidine-4-carboxylic acid was the same as Example 28. 25 mg as a white solid, yield: 50%. ESI-MS (M+H)$^+$: 532.2. $^1$H NMR (400 MHz, CD$_3$OD) δ: 7.92 (d, J=9.6 Hz, 1H), 7.86 (s, 1H), 7.73 (d, J=8.8 Hz, 1H), 7.34-7.29 (m, 2H), 4.84 (s, 1H), 3.28-3.24 (m, 1H), 3.01-2.74 (m, 2H), 2.19-1.98 (m, 3H), 1.75-1.54 (m, 15H), 0.61 (t, J=7.2 Hz, 3H).

Example 46: 8-((S)-1-(8-(trifluoromethyl)-7-((cis-4-(trifluoromethyl)cyclohexyl)oxy)naphthalen-2-yl)-2,2,2-trideuteroethyl)-8-azabicyclo[3.2.1]octane-3-carboxylic acid The preparation of 8-((S)-1-(8-(trifluoromethyl)-7-((cis-4-(trifluoromethyl)cyclohexyl)oxy)naphthalen-2-yl) [2,2,2-$^2$H$_3$]ethyl)-8-azabicyclo[3.2.1]octane-3-carboxylic acid was the same as Example 28. White solid (340 mg, Y: 70%). ESI-MS (M+H)$^+$: 547.2. $^1$H NMR (400 MHz, CD$_3$OD) &. 8.31 (s, 1H), 8.15 (d, J=9.6 Hz, 1H), 8.06 (d, J=8.4 Hz, 1H), 7.65 (d, J=8.4 Hz, 1H), 7.60 (d, J=9.2 Hz, 1H), 5.03 (s, 1H), 4.50 (s, 1H), 4.37-4.33 (m, 1H), 3.52-3.46 (m, 1H), 2.76-2.70 (m, 1H), 2.50-2.46 (m, 1H), 2.29-1.71 (m, 16H).

Example 47: 1-((8-chloro-7-((cis-4-ethylcyclohexyl)oxy)naphthalen-2-yl)methyl)piperidine-4-carboxylic acid

Step 1: 2-bromo-7-((cis-4-ethylcyclohexyl)oxy)naphthalene

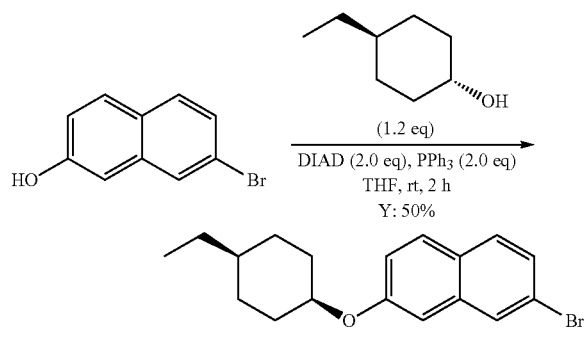

Into a mixture of 7-bromonaphthalen-2-ol (10 g, 45 mmol, 1.0 eq) and trans-4-ethylcyclohexanol (6.92 g, 54 mmol, 1.2 eq) in THF (100 mL) was added PPh$_3$ (23.6 g, 90 mmol, 2.0 eq), followed by DIAD (18.1 g, 90 mmol, 2.0 eq) at rt. The mixture was stirred at rt for 1 h and diluted with petroleum ether (1000 mL). The precipitate was filtered off and the filtrate was concentrated. The residue was purified by column chromatography on silica gel (petroleum ether as eluent) to give 2-bromo-7-((cis-4-ethylcyclohexyl)oxy)naphthalene as white solid (7.5 g, Y: 50%). ESI-MS (M+H)$^+$: 333.1. $^1$H NMR (400 MHz, CDCl$_3$) δ: 7.85 (s, 1H), 7.69 (d, J=9.2 Hz, 1H), 7.60 (d, J=8.4 Hz, 1H), 7.37 (dd, J=2.0 Hz, 8.8 Hz, 1H), 7.16 (dd, J=2.4 Hz, 9.2 Hz, 1H), 7.04 (d, J=2.4 Hz, 1H), 4.65 (s, 1H), 2.08-2.04 (m, 2H), 1.66-1.55 (m, 4H), 1.16-1.30 (m, 5H), 0.90 (t, J=6.8 Hz, 3H).

Step 2: 7-((cis-4-ethylcyclohexyl)oxy)-2-naphthaldehyde

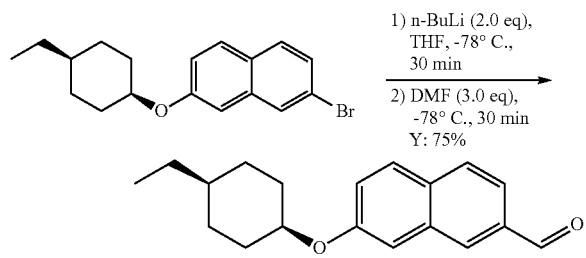

Into a solution of 2-bromo-7-((cis-4-ethylcyclohexyl)oxy)naphthalene (3.32 g, 10 mmol) in THF (10 mL) was added n-BuLi (10 mL, 2.0 M in hexane, 20 mmol, 2.0 eq) dropwise at −78° C. After addition, the mixture was stirred at −78° C. for 30 min. DMF (1.46 g, 30 mmol, 3.0 eq) was added to the mixture and stirring continued for 30 min at −78° C. After the reaction completed, the reaction was quenched with water (200 mL) and extracted with CH$_2$Cl$_2$ (200 mL×2). The combined organic layers were washed with water (200 mL×2), brine (200 mL×2) and concentrated. The residue was purified by column chromatography on silica gel (petroleum ether/EtOAc=30:1) to give 7-((cis-4-ethylcyclohexyl)oxy)-2-naphthaldehyde as a white solid (2.1 g, Y: 75%). ESI-MS (M+H)$^+$: 283.1. $^1$H NMR (400 MHz, CDCl$_3$) δ: 10.13 (s, 1H), 8.20 (s, 1H), 7.86-7.77 (m, 3H), 7.33-7.26 (m, 2H), 4.70 (s, 1H), 2.11-2.07 (m, 2H), 1.67-1.57 (m, 4H) 1.44-1.29 (m, 5H), 0.91 (t, J=6.8 Hz, 3H).

Step 3: 8-chloro-7-((cis-4-ethylcyclohexyl)oxy)-2-naphthaldehyde

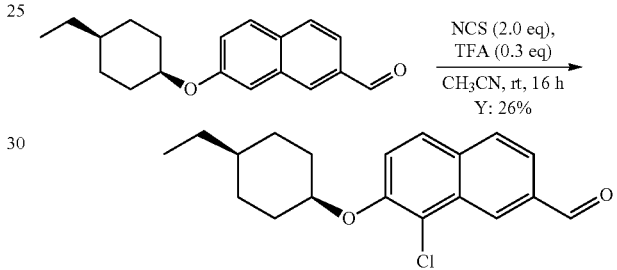

To a mixture of 7-((cis-4-ethylcyclohexyl)oxy)-2-naphthaldehyde (1.20 g, 4.25 mmol, 1.0 eq) and NCS (1.14 g, 8.51 mmol, 2.0 eq) in CH$_3$CN (10 mL) was added TFA (146 mg, 1.27 mmol, 0.3 eq). The mixture was stirred at rt for 16 h and concentrated. The residue was purified by column chromatography on silica gel (petroleum ether/EtOAc=40:1) to give 8-chloro-7-((cis-4-ethylcyclohexyl)oxy)-2-naphthaldehyde as yellow oil (343 mg, Y: 26%). ESI-MS (M+H)$^+$: 317.1. $^1$H NMR (400 MHz, CDCl$_3$) δ: 10.21 (s, 1H), 8.72 (s, 1H), 7.88 (s, 2H), 7.78 (d, J=9.2 Hz, 1H), 7.42 (d, J=9.2 Hz, 1H), 4.78 (s, 1H), 2.09-2.04 (m, 2H), 1.65-1.53 (m, 6H) 1.36-1.26 (m, 3H), 0.92 (t, J=6.8 Hz, 3H).

Step 4: Ethyl 1-((8-chloro-7-((cis-4-ethylcyclohexyl)oxy)naphthalen-2-yl)methyl)piperidine-4-carboxylate

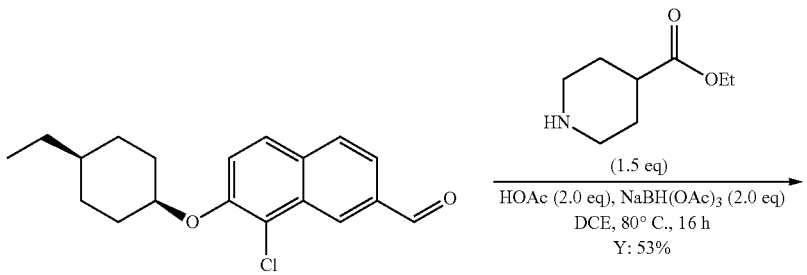

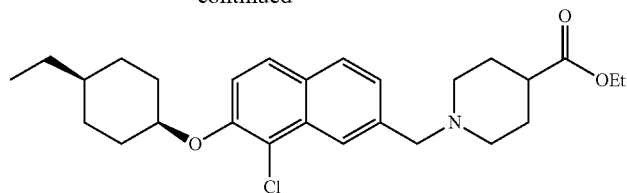

Into a mixture of 8-chloro-7-((cis-4-ethylcyclohexyl)oxy)-2-naphthaldehyde (90 mg, 0.28 mmol) and ethyl piperidine-4-carboxylate (68 mg, 0.43 mmol, 1.5 eq) in DCE (2 mL) was added HOAc (36 mg, 0.57 mmol, 2.0 eq). The mixture was stirred at rt for 10 min and NaBH(OAc)₃ (121 mg, 0.57 mmol, 2.0 eq) was added. The mixture was stirred at 80° C. for 16 h and diluted with water (10 mL). The mixture was extracted with DCM (10 mL×2) and the combined organic layers were washed with water (10 mL), brine (10 mL), dried over Na₂SO₄ and concentrated. The residue was purified by reversed phase HPLC (MeCN/H₂O-0.05% TFA) to give 1-((8-chloro-7-((cis-4-ethylcyclohexyl)oxy)naphthalen-2-yl)methyl)piperidine-4-carboxylate as yellow oil (70 mg, yield: 53%). ESI-MS (M+H)⁺: 458.3.

Step 5: 1-((8-chloro-7-((cis-4-ethylcyclohexyl)oxy)naphthalen-2-yl)methyl)piperidine-4-carboxylic acid

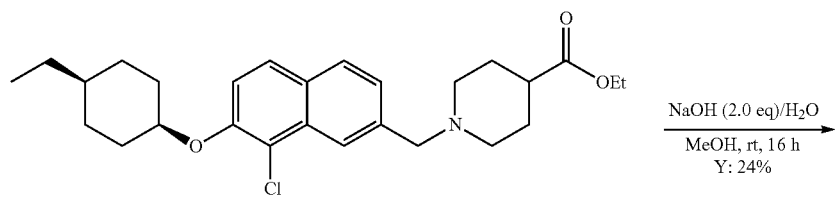

Into a solution of 1-((8-chloro-7-((cis-4-ethylcyclohexyl)oxy)naphthalen-2-yl)methyl)piperidine-4-carboxylate (70 mg, 0.15 mmol) in MeOH (3 mL) was added NaOH (13 mg, 0.30 mmol, 2.0 eq) and H₂O (0.5 mL). The reaction mixture was stirred at rt for 16 h. Then the reaction mixture was acidified with 1N HCl to pH=6 and purified by reversed phase HPLC (MeCN/H₂O) to give 1-((8-chloro-7-((cis-4-ethylcyclohexyl)oxy)naphthalen-2-yl)methyl)piperidine-4-carboxylic acid as a white solid (16 mg, yield: 24%). ESI-MS (M+H)⁺: 430.1. ¹H NMR (400 MHz, CD₃OD) δ: 8.09 (s, 1H), 7.80-7.76 (m, 2H), 7.43 (dd, J=2.0 Hz, 8.8 Hz, 1H), 7.35 (d, J=9.2 Hz, 1H), 4.78 (s, 1H), 3.68 (s, 2H), 2.94-2.91 (m, 2H), 2.13-2.08 (m, 3H), 2.04-2.01 (m, 2H), 1.89-1.85 (m, 2H), 1.78-1.72 (m, 2H), 1.62-1.53 (m, 6H), 1.34-1.27 (m, 3H), 0.93 (t, J=7.2 Hz, 3H).

Example 48: 8-((8-chloro-7-((cis-4-ethylcyclohexyl)oxy)naphthalen-2-yl)methyl)-8-azabicyclo[3.2.1]octane-3-carboxylic acid

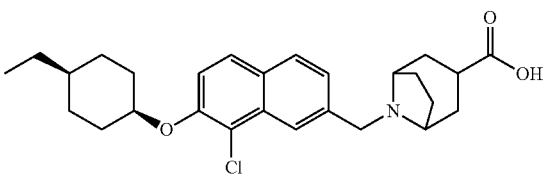 [SMILES: CC[C@H]1CC[C@@H](Oc2ccc3ccc(CN4C5CCC4CC(C(=O)O)C5)cc3c2Cl)CC1]

The preparation of 8-((8-chloro-7-((cis-4-ethylcyclohexyl)oxy)naphthalen-2-yl)methyl)-8-azabicyclo[3.2.1]octane-3-carboxylic acid was the same as Example 26. 30 mg as a white solid, yield: 55%. ESI-MS (M+H)⁺: 456.2. ¹H NMR (400 MHz, CD₃OD) δ: 8.36 (s, 1H), 7.95 (d, J=8.4 Hz, 1H), 7.87 (d, J=9.2 Hz, 1H), 7.56 (dd, J=1.6 Hz, 8.8 Hz, 1H), 7.50 (d, J=9.2 Hz, 1H), 4.87 (s, 1H), 4.30 (s, 2H), 3.82-3.80 (m, 2H), 2.71-2.62 (m, 1H), 2.41-2.38 (m, 2H), 2.07-2.02 (m, 6H), 1.94-1.92 (m, 2H), 1.66-1.36 (m, 6H), 1.36-1.31 (m, 3H), 0.94 (t, J=7.2 Hz, 3H).

Example 49: 9-((8-chloro-7-((cis-4-ethylcyclohexyl)oxy)naphthalen-2-yl)methyl)-9-azabicyclo[3.3.1]nonane-3-carboxylic acid

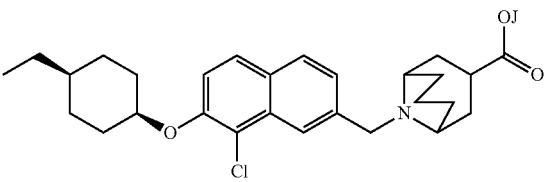

The preparation of 9-((8-chloro-7-((cis-4-ethylcyclohexyl)oxy)naphthalen-2-yl)methyl)-9-azabicyclo[3.3.1]nonane-3-carboxylic acid was the same as Example 26. 30 mg, white solid, yield: 58%. ESI-MS (M+H)+: 470.1. ¹H NMR (400 MHz, CD₃OD) δ: 8.43 (s, 1H), 7.96 (d, J=8.4 Hz, 1H), 7.87 (d, J=9.2 Hz, 1H), 7.60 (dd, J=1.6 Hz, 8.4 Hz, 1H), 7.51 (d, J=8.8 Hz, 1H), 4.88 (s, 1H), 4.70 (s, 2H), 3.56-3.53 (m, 2H), 3.16-3.08 (m, 1H), 2.44-2.35 (m, 4H), 2.11-2.03 (m, 5H), 1.86-1.75 (m, 3H), 1.69-1.52 (m, 6H), 1.37-1.29 (m, 3H), 0.94 (t, J=7.2 Hz, 3H).

Example 50: 1-((7-((cis-4-ethylcyclohexyl)oxy)-8-(trifluoromethyl)naphthalen-2-yl)methyl)piperidine-4-carboxylic acid

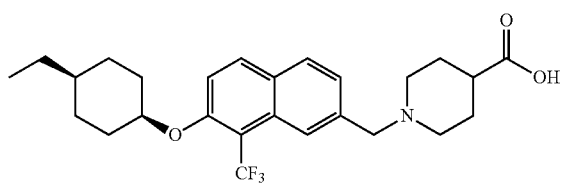 [SMILES: CC[C@H]1CC[C@@H](Oc2ccc3ccc(CN4CCC(C(=O)O)CC4)cc3c2C(F)(F)F)CC1]

The preparation of 1-((7-((cis-4-ethylcyclohexyl)oxy)-8-(trifluoromethyl)naphthalen-2-yl)methyl)piperidine-4-carboxylic acid was the same as Example 43. 60 mg as a white solid, yield: 67%. ESI-MS (M+H)+: 464.1. ¹H NMR (400 MHz, CD₃OD) δ: 8.21 (s, 1H), 8.05 (d, J=9.6 Hz, 1H), 7.91 (d, J=8.4 Hz, 1H), 7.47 (d, J=8.8 Hz, 2H), 4.90 (s, 1H), 4.19 (s, 2H), 3.28-3.25 (m, 2H), 2.81-2.75 (m, 2H), 2.38-2.36 (m, 1H), 2.10-2.01 (m, 4H), 1.89-1.86 (m, 2H), 1.69-1.56 (m, 4H), 1.46-1.40 (m, 2H), 1.33-1.28 (m, 3H), 0.92 (t, J=6.8 Hz, 3H).

Example 51: 8-((7-((cis-4-ethylcyclohexyl)oxy)-8-(trifluoromethyl)naphthalen-2-yl)methyl)-8-azabicyclo[3.2.1]octane-3-carboxylic acid

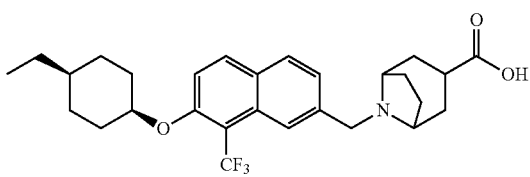 [SMILES: CC[C@H]1CC[C@@H](Oc2ccc3ccc(CN4C5CCC4CC(C(=O)O)C5)cc3c2C(F)(F)F)CC1]

The preparation of 8-((7-((cis-4-ethylcyclohexyl)oxy)-8-(trifluoromethyl)naphthalen-2-yl)methyl)-8-azabicyclo[3.2.1]octane-3-carboxylic acid was the same as Example 26. 30 mg, white solid, yield: 45%. ESI-MS (M+H)+: 490.1. ¹H NMR (400 MHz, CD₃OD) δ: 8.28 (s, 1H), 8.10 (d, J=9.2 Hz, 1H), 7.96 (d, J=8.0 Hz, 1H), 7.58-7.53 (m, 2H), 4.94 (s, 1H), 4.23 (s, 2H), 3.77-3.74 (m, 2H), 2.68-2.62 (m, 1H), 2.36-2.33 (m, 2H), 2.09-1.99 (m, 6H), 1.92-1.88 (m, 2H), 1.72-1.58 (m, 4H), 1.50-1.40 (m, 2H), 1.35-1.30 (m, 3H), 0.94 (t, J=7.2 Hz, 3H).

Example 52: 9-((7-((cis-4-ethylcyclohexyl)oxy)-8-(trifluoromethyl)naphthalen-2-yl)methyl)-9-azabicyclo[3.3.1]nonane-3-carboxylic acid

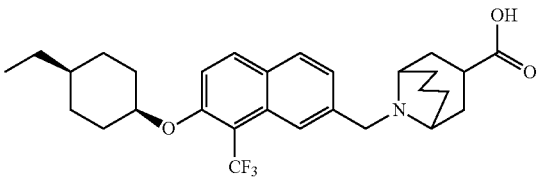 [SMILES: CC[C@H]1CC[C@@H](Oc2ccc3ccc(CN4C5CCCC4CC(C(=O)O)C5)cc3c2C(F)(F)F)CC1]

The preparation of 9-((7-((cis-4-ethylcyclohexyl)oxy)-8-(trifluoromethyl)naphthalen-2-yl)methyl)-9-azabicyclo[3.3.1]nonane-3-carboxylic acid was the same as Example 26. 42 mg as a white solid, yield: 62%. ESI-MS (M+H)+: 504.1. ¹H NMR (400 MHz, CD₃OD) δ: 8.25 (s, 1H), 8.04 (d, J=9.2 Hz, 1H), 7.87 (d, J=8.0 Hz, 1H), 7.57 (d, J=8.4 Hz, 1H), 7.46 (d, J=9.2 Hz, 1H), 4.92 (s, 1H), 4.31 (s, 2H), 3.14-3.08 (m, 3H), 2.35-2.04 (m, 7H), 1.86-1.81 (m, 2H), 1.71-1.57 (m, 7H), 1.51-1.44 (m, 2H), 1.34-1.29 (m, 3H), 0.94 (t, J=7.2 Hz, 3H).

Example 53: 2-((R)-1-((7-((cis-4-ethylcyclohexyl)oxy)-8-(trifluoromethyl)naphthalen-2-yl)methyl)piperidin-3-yl)acetic acid

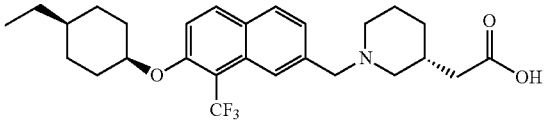 [SMILES: CC[C@H]1CC[C@@H](Oc2ccc3ccc(CN4CCC[C@H](CC(=O)O)C4)cc3c2C(F)(F)F)CC1]

The preparation of 2-((R)-1-((7-((cis-4-ethylcyclohexyl)oxy)-8-(trifluoromethyl)naphthalen-2-yl)methyl)piperidin-3-yl)acetic acid was the same as Example 26. 12 mg as a white solid, yield: 90%. ESI-MS (M+H)+: 478.1. ¹H NMR (400 MHz, CD₃OD) δ: 8.31 (s, 1H), 8.13 (d, J=9.2 Hz, 1H), 8.01 (d, J=8.4 Hz, 1H), 7.59 (d, J=9.6 Hz, 1H), 7.54 (d, J=8.4 Hz, 1H), 4.94 (s, 1H), 4.50 (s, 2H), 3.61-3.58 (m, 1H), 3.51-3.48 (m, 1H), 3.01-2.95 (m, 1H), 2.85-2.79 (m, 1H), 2.38-2.25 (m, 3H), 2.08-1.92 (m, 4H), 1.81-1.58 (m, 5H), 1.49-1.40 (m, 2H), 1.33-1.29 (m, 4H), 0.93 (t, J=7.6 Hz, 3H).

Example 54: 3-(((7-((cis-4-ethylcyclohexyl)oxy)-8-(trifluoromethyl)naphthalen-2-yl)methyl)amino)-2,2-dimethylcyclobutanecarboxylic acid

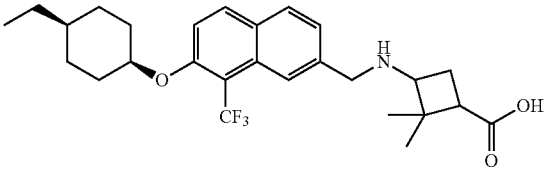 [SMILES: CC[C@H]1CC[C@@H](Oc2ccc3ccc(CNC4CC(C(=O)O)C4(C)C)cc3c2C(F)(F)F)CC1]

The preparation of 3-(((7-((cis-4-ethylcyclohexyl)oxy)-8-(trifluoromethyl)naphthalen-2-yl)methyl)amino)-2,2-dimethylcyclobutanecarboxylic acid was the same as Example 26. 5 mg as a white solid, yield: 29%. ESI-MS (M+H)+:

478.1. ¹H NMR (400 MHz, CD₃OD) δ: 8.30 (s, 1H), 8.11 (d, J=9.2 Hz, 1H), 7.99 (d, J=8.4 Hz, 1H), 7.57-7.53 (m, 2H), 4.99 (s, 1H), 4.23 (AB, 2H), 3.53-3.48 (m, 1H), 2.75-2.70 (m, 1H), 2.35-2.31 (m, 2H), 2.08-2.04 (m, 2H), 1.72-1.57 (m, 4H), 1.18-1.11 (m, 2H), 1.35 (s, 3H), 1.33-1.28 (m, 3H), 1.21 (s, 3H), 0.93 (t, J=7.6 Hz, 3H).

Example 55: 8-(1-(7-((cis-4-ethylcyclohexyl)oxy)-8-(trifluoromethyl)naphthalen-2-yl)ethyl)-8-azabicyclo[3.2.1]octane-3-carboxylic acid

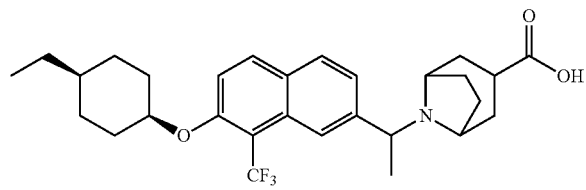 [SMILES: CC[C@H]1CC[C@@H](Oc2ccc3ccc(C(C)N4C5CCC4CC(C(=O)O)C5)cc3c2C(F)(F)F)CC1]

The preparation of 8-(1-(7-((cis-4-ethylcyclohexyl)oxy)-8-(trifluoromethyl)naphthalen-2-yl)ethyl)-8-azabicyclo[3.2.1]octane-3-carboxylic acid was the same as Example 28. 33 mg as a white solid, yield: 67%. ESI-MS (M+H)⁺: 504.3. ¹H NMR (400 MHz, CD₃OD) δ: 8.29 (s, 1H), 8.14 (d, J=9.2 Hz, 1H), 8.06 (d, J=8.4 Hz, 1H), 7.61-7.58 (m, 2H), 4.96 (s, 1H), 4.54-4.45 (m, 2H), 3.44-3.40 (m, 1H), 3.00-2.93 (m, 1H), 2.62-2.56 (m, 1H), 2.30-1.91 (m, 9H), 1.82 (d, J=6.8 Hz, 3H), 1.72-1.66 (m, 2H), 1.61-1.58 (m, 2H), 1.48-1.43 (m, 2H), 1.34-1.29 (m, 3H), 0.93 (t, J=7.2 Hz, 3H).

Example 56: 9-(1-(7-((cis-4-ethylcyclohexyl)oxy)-8-(trifluoromethyl)naphthalen-2-yl)ethyl)-9-azabicyclo[3.3.1]nonane-3-carboxylic acid

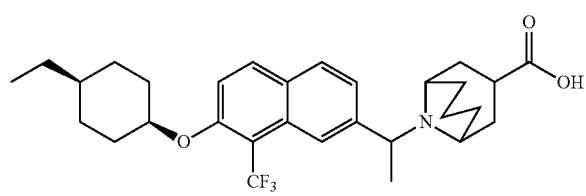 [SMILES: CC[C@H]1CC[C@@H](Oc2ccc3ccc(C(C)N4C5CCCC4CC(C(=O)O)C5)cc3c2C(F)(F)F)CC1]

The preparation of 9-(1-(7-((cis-4-ethylcyclohexyl)oxy)-8-(trifluoromethyl)naphthalen-2-yl)ethyl)-9-azabicyclo[3.3.1]nonane-3-carboxylic acid was the same as Example 28. 10 mg as a white solid, yield: 53%. ESI-MS (M+H)⁺: 518.3. ¹H NMR (400 MHz, CD₃OD) δ: 8.38 (s, 1H), 8.13 (d, J=9.2 Hz, 1H), 8.06 (d, J=8.4 Hz, 1H), 7.67 (d, J=8.0 Hz, 1H), 7.59 (d, J=9.6 Hz, 1H), 5.28-5.09 (m, 1H), 4.96 (s, 1H), 4.23-4.17 (m, 1H), 3.39-3.32 (m, 1H), 3.17-3.14 (m, 1H), 2.46-2.40 (m, 4H), 2.30-2.20 (m, 5H), 1.97-1.91 (m, 2H), 1.77 (d, J=6.8 Hz, 3H), 1.73-1.58 (m, 5H), 1.49-1.40 (m, 2H), 1.34-1.30 (m, 3H), 0.94 (t, J=7.2 Hz, 3H).

Example 57: 1-(1-(7-((cis-4-ethylcyclohexyl)oxy)-8-(trifluoromethyl)naphthalen-2-yl)ethyl)piperidine-4-carboxylic acid

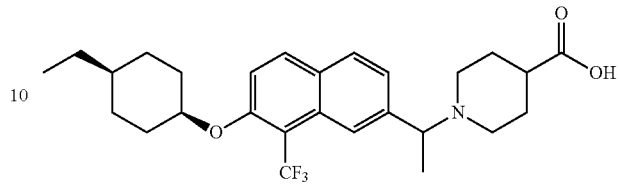

The preparation of 1-(1-(7-((cis-4-ethylcyclohexyl)oxy)-8-(trifluoromethyl)naphthalen-2-yl)ethyl)piperidine-4-carboxylic acid was the same as Example 28. 47 mg as a white solid, yield: 70%. ESI-MS (M+H)⁺: 478.2. ¹H NMR (400 MHz, CD₃OD) δ: 8.26 (s, 1H), 8.14 (d, J=9.2 Hz, 1H), 8.05 (d, J=8.4 Hz, 1H), 7.60 (d, J=9.6 Hz, 1H), 7.54 (d, J=8.8 Hz, 1H), 4.96 (s, 1H), 4.68-4.65 (m, 1H), 4.01-3.68 (m, 1H), 3.32-3.30 (m, 2H), 3.09-3.03 (m, 2H), 2.66-2.54 (m, 1H), 2.18-2.04 (m, 5H), 1.84 (d, J=6.8 Hz, 3H), 1.73-1.66 (m, 2H), 1.61-1.58 (m, 2H), 1.49-1.44 (m, 2H), 1.34-1.30 (m, 3H), 0.94 (t, J=7.2 Hz, 3H).

Example 58: 2-((3R)-1-(1-(7-((cis-4-ethylcyclohexyl)oxy)-8-(trifluoromethyl)naphthalen-2-yl)ethyl)piperidin-3-yl)acetic acid

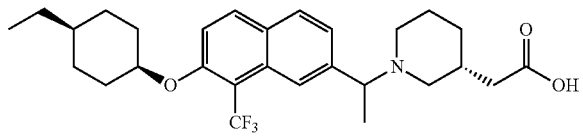 [SMILES: CC[C@H]1CC[C@@H](Oc2ccc3ccc(C(C)N4CCC[C@H](CC(=O)O)C4)cc3c2C(F)(F)F)CC1]

The preparation of 2-((3R)-1-(1-(7-((cis-4-ethylcyclohexyl)oxy)-8-(trifluoromethyl)naphthalen-2-yl)ethyl)piperidin-3-yl)acetic acid was the same as Example 28. 18 mg as a white solid, yield: 78%. ESI-MS (M+H)⁺: 492.3. ¹H NMR (400 MHz, CD₃OD) δ: 8.26 (s, 1H), 8.13 (d, J=8.8 Hz, 1H), 8.04 (d, J=8.4 Hz, 1H), 7.59 (d, J=9.6 Hz, 1H), 7.55 (d, J=8.4 Hz, 1H), 4.96 (s, 1H), 4.69-4.63 (m, 1H), 3.91-3.74 (m, 1H), 3.46-3.26 (m, 1H), 2.94-2.58 (m, 2H), 2.35-2.21 (m, 3H), 2.28-2.00 (m, 3H), 1.95-1.88 (m, 2H), 1.84 (d, J=6.4 Hz, 3H), 1.76-1.66 (m, 2H), 1.62-1.58 (m, 2H), 1.49-1.41 (m, 2H), 1.34-1.20 (m, 4H), 0.94 (t, J=7.2 Hz, 3H).

Example 59: 3-((1-(7-((cis-4-ethylcyclohexyl)oxy)-8-(trifluoromethyl)naphthalen-2-yl)ethyl)amino)-2,2-dimethylcyclobutanecarboxylic acid

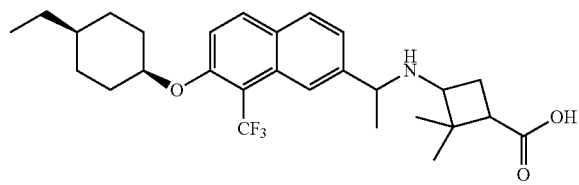 [SMILES: CC[C@H]1CC[C@@H](Oc2ccc3ccc(C(C)NC4CC(C(=O)O)C4(C)C)cc3c2C(F)(F)F)CC1]

The preparation of 3-((1-(7-((cis-4-ethylcyclohexyl)oxy)-8-(trifluoromethyl)naphthalen-2-yl)ethyl)amino)-2,2-dimethylcyclobutanecarboxylic acid was the same as Example 28. 3 mg as a white solid, yield: 10%. ESI-MS (M+H)+: 492.2. ¹H NMR (400 MHz, CD₃OD, a mixture of diastereomers) δ: 8.27-8.23 (m, 1H), 8.12 (d, J=9.2 Hz, 1H), 8.05-8.01 (m, 1H), 7.58-7.54 (m, 2H), 4.95 (s, 1H), 4.59-4.54 (m, 1H), 3.39-3.18 (m, 1H), 2.67-2.55 (m, 1H), 2.09-1.99 (m, 3H), 1.78-1.72 (m, 3H), 1.70-1.65 (m, 2H), 1.63-1.58 (m, 2H), 1.50-1.41 (m, 2H), 1.36-1.30 (m, 6H), 1.23-1.28 (m, 4H), 0.94 (t, J=7.2 Hz, 3H).

Example 60: 1-(1-(7-((cis-4-ethylcyclohexyl)oxy)-8-(trifluoromethyl)naphthalen-2-yl)propyl)piperidine-4-carboxylic acid

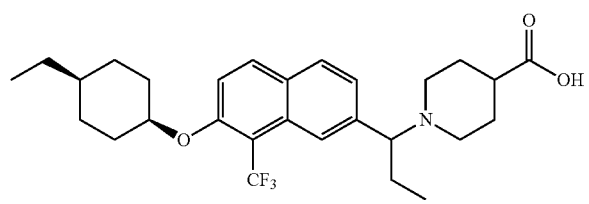 [SMILES: CCC(c1ccc2ccc(O[C@H]3CC[C@@H](CC)CC3)c(C(F)(F)F)c2c1)N1CCC(C(=O)O)CC1]

The preparation of 1-(1-(7-((cis-4-ethylcyclohexyl)oxy)-8-(trifluoromethyl)naphthalen-2-yl)propyl)piperidine-4-carboxylic acid was the same as Example 28: 16 mg as a, white solid, yield: 37%. ESI-MS (M+H)+: 492.2. ¹H NMR (400 MHz, CD₃OD) δ: 8.23 (s, 1H), 8.15 (d, J=9.2 Hz, 1H), 8.06 (d, J=8.8 Hz, 1H), 7.61 (d, J=9.2 Hz, 1H), 7.50 (d, J=8.0 Hz, 1H), 4.97 (s, 1H), 4.45-4.41 (m, 1H), 3.82-3.78 (m, 1H), 3.07-2.83 (m, 2H), 2.62-2.51 (m, 1H), 2.37-2.15 (m, 4H), 2.08-1.94 (m, 4H), 1.73-1.66 (m, 2H), 1.61-1.58 (m, 2H), 1.49-1.42 (m, 3H), 1.34-1.29 (m, 3H), 0.94 (t, J=7.6 Hz, 3H), 0.81 (t, J=7.2 Hz, 3H).

Example 61: 2-((3R)-1-(1-(7-((cis-4-ethylcyclohexyl)oxy)-8-(trifluoromethyl)naphthalen-2-yl)propyl)piperidin-3-yl)acetic acid

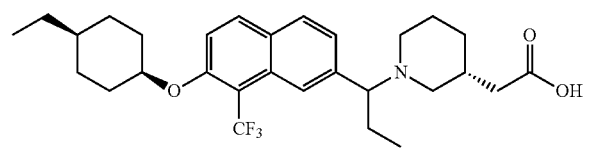 [SMILES: CCC(c1ccc2ccc(O[C@H]3CC[C@@H](CC)CC3)c(C(F)(F)F)c2c1)N1CCC[C@H](CC(=O)O)C1]

The preparation of 2-((3R)-1-(1-(7-((cis-4-ethylcyclohexyl)oxy)-8-(trifluoromethyl)naphthalen-2-yl)propyl)piperidin-3-yl)acetic acid was the same as Example 28. 7 mg as a white solid, yield: 21%. ESI-MS (M+H)+: 506.2. ¹H NMR (400 MHz, CD₃OD) δ: 8.22 (s, 1H), 8.14 (d, J=9.2 Hz, 1H), 8.05 (d, J=8.4 Hz, 1H), 7.60 (d, J=9.6 Hz, 1H), 7.52 (d, J=8.0 Hz, 1H), 4.96 (s, 1H), 4.47-4.42 (m, 1H), 3.89-3.71 (m, 1H), 3.51-3.49 (m, 1H), 2.87-2.62 (m, 2H), 2.35-1.87 (m, 10H), 1.66-1.58 (m, 4H), 1.50-1.41 (m, 2H), 1.34-1.26 (m, 4H), 0.94 (t, 0.1=6.8 Hz, 3H), 0.81 (t, J=7.2 Hz, 3H).

Example 62: 2-((R)-1-((8-chloro-7-((cis-4-ethylcyclohexyl)oxy)naphthalen-2-yl)methyl)piperidin-3-yl)acetic acid

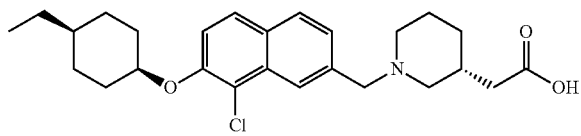 [SMILES: CC[C@H]1CC[C@@H](Oc2ccc3ccc(CN4CCC[C@H](CC(=O)O)C4)cc3c2Cl)CC1]

The preparation of 2-((R)-1-((8-chloro-7-((cis-4-ethylcyclohexyl)oxy)naphthalen-2-yl)methyl)piperidin-3-yl)acetic acid was the same as Example 26. 27 mg as a white solid, yield: 48%. ESI-MS (M+H)+: 444.3. ¹H NMR (400 MHz, CD₃OD) δ: 8.11 (s, 1H), 7.81-7.77 (m, 2H), 7.46 (d, J=8.4 Hz, 1H), 7.38 (d, J=9.2 Hz, 1H), 4.82 (s, 1H), 3.73 (s, 2H), 3.04-3.01 (m, 1H), 2.92-2.90 (m, 1H), 2.11-2.04 (m, 6H), 1.87-1.81 (m, 2H), 1.68-1.56 (m, 8H), 1.37-1.30 (m, 3H), 1.03-0.99 (m, 1H), 0.95 (t, J=6.8 Hz, 3H).

Example 63: 8-(1-(8-(difluoromethyl)-7-((cis-4-ethylcyclohexyl)oxy)naphthalen-2-yl)ethyl)-8-azabicyclo[3.2.1]octane-3-carboxylic acid

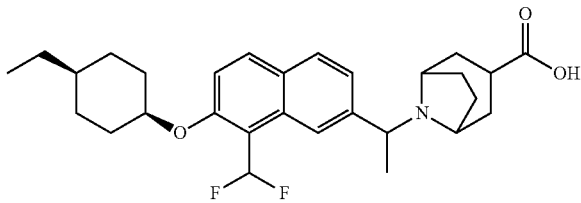 [SMILES: CC[C@H]1CC[C@@H](Oc2ccc3ccc(C(C)N4C5CCC4CC(C(=O)O)C5)cc3c2C(F)F)CC1]

The preparation of 8-(1-(8-(difluoromethyl)-7-((cis-4-ethylcyclohexyl)oxy)naphthalen-2-yl)ethyl)-8-azabicyclo[3.2.1]octane-3-carboxylic acid was the same as Example 42. 26 mg as a white solid, yield: 66%. ESI-MS (M+H)+: 486.2. ¹H NMR (400 MHz, CD₃OD) δ: 8.42 (s, 1H), 8.08-8.03 (m, 2H), 7.62 (t, J=54.8 Hz, 1H), 7.58-7.48 (m, 2H), 4.91 (s, 1H), 4.54-4.41 (m, 2H), 3.48-3.45 (m, 1H), 3.00-2.93 (m, 1H), 2.63-2.55 (m, 1H), 2.34-1.90 (m, 9H), 1.83 (d, J=6.8 Hz, 3H), 1.73-1.64 (m, 4H), 1.39-1.34 (m, 5H), 0.95 (t, J=7.2 Hz, 3H).

Example 64: 1-(1-(8-chloro-7-((cis-4-ethylcyclohexyl)oxy)naphthalen-2-yl)ethyl)piperidine-4-carboxylic acid

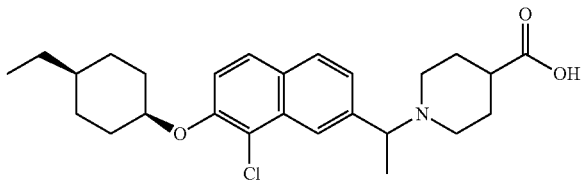 [SMILES: CC[C@H]1CC[C@@H](Oc2ccc3ccc(C(C)N4CCC(C(=O)O)CC4)cc3c2Cl)CC1]

The preparation of 1-(1-(8-chloro-7-((cis-4-ethylcyclohexyl)oxy)naphthalen-2-yl)ethyl)piperidine-4-carboxylic acid was the same as Example 28. 20 mg as a white solid, yield: 35%. ESI-MS (M+H)+: 444.2. ¹H NMR (400 MHz, CD₃OD) δ: 8.28 (s, 1H), 7.97 (d, J=8.8 Hz, 1H), 7.88 (d, J=8.8 Hz, 1H), 7.51 (d, J=8.8 Hz, 2H), 4.92 (s, 1H), 4.52-4.50 (m, 1H), 3.62-3.54 (m, 1H), 3.24-3.21 (m, 1H), 2.89-2.85 (m, 2H), 2.35-2.31 (m, 1H), 2.06-1.86 (m, 6H), 1.79 (d, J=6.4 Hz, 3H), 1.69-1.53 (m, 6H), 1.36-1.30 (m, 3H), 0.94 (t, J=7.2 Hz, 3H).

Example 65: 8-(1-(8-chloro-7-((cis-4-ethylcyclohexyl)oxy)naphthalen-2-yl)ethyl)-8-azabicyclo[3.2.1]octane-3-carboxylic acid

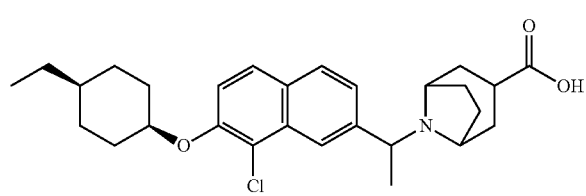 [SMILES: CC[C@H]1CC[C@@H](Oc2ccc3ccc(C(C)N4C5CCC4CC(C(=O)O)C5)cc3c2Cl)CC1]

The preparation of 8-(1-(8-chloro-7-((cis-4-ethylcyclohexyl)oxy)naphthalen-2-yl)ethyl)-8-azabicyclo[3.2.1]octane-3-carboxylic acid was the same as Example 28. 31 mg as a white solid, yield: 39%. ESI-MS (M+H)+: 470.2. ¹H NMR (400 MHz, DMSO-d₆) δ: 12.05 (br s, 1H), 7.98 (s, 1H), 7.89-7.85 (m, 2H), 7.52-7.48 (m, 2H), 4.89 (s, 1H), 3.80-3.78 (m, 1H), 3.15-3.12 (m, 1H), 2.58-2.55 (m, 1H), 1.93-1.67 (m, 6H), 1.60-1.40 (m, 10H), 1.30-1.23 (m, 7H), 0.88 (t, J=7.2 Hz, 3H).

Example 66: 9-(1-(8-chloro-7-((cis-4-ethylcyclohexyl)oxy)naphthalen-2-yl)ethyl)-9-azabicyclo[3.3.1]nonane-3-carboxylic acid

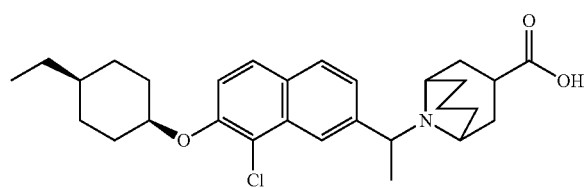 [SMILES: CC[C@H]1CC[C@@H](Oc2ccc3ccc(C(C)N4C5CCCC4CC(C(=O)O)C5)cc3c2Cl)CC1]

The preparation of 9-(1-(8-chloro-7-((cis-4-ethylcyclohexyl)oxy)naphthalen-2-yl)ethyl)-9-azabicyclo[3.3.1]nonane-3-carboxylic acid was the same as Example 28. 31 mg as a white solid, yield: 32%. ESI-MS (M+H)+: 484.3. ¹H NMR (400 MHz, CD₃OD) δ: 8.43 (s, 1H), 7.99 (d, J=8.8 Hz, 1H), 7.87 (d, J=9.2 Hz, 1H), 7.65 (dd, J=1.6 Hz, 8.8 Hz, 1H), 7.50 (d, J=8.8 Hz, 1H), 5.15-5.13 (m, 1H), 4.87 (s, 1H), 3.32-3.30 (m, 2H), 3.05-3.03 (m, 1H), 2.49-1.53 (m, 21H), 1.35-1.31 (m, 3H), 0.94 (t, J=7.2 Hz, 3H).

Example 67: (1R,3S)-3-((1-(8-chloro-7-((cis-4-ethylcyclohexyl)oxy)naphthalen-2-yl)ethyl)amino)-2,2-dimethylcyclobutanecarboxylic acid

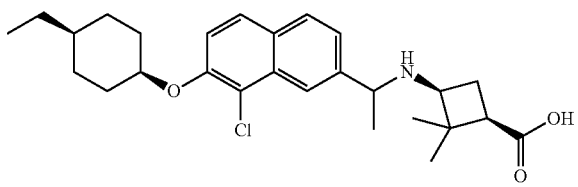 [SMILES: CC[C@H]1CC[C@@H](Oc2ccc3ccc(C(C)N[C@H]4C[C@@H](C(=O)O)C4(C)C)cc3c2Cl)CC1]

The preparation of (1R,3S)-3-((1-(8-chloro-7-((cis-4-ethylcyclohexyl)oxy)naphthalen-2-yl)ethyl)amino)-2,2-dimethylcyclobutanecarboxylic acid was the same as Example 28. 42 mg as a white solid, yield: 43%. ESI-MS (M+H)+: 458.2. ¹H NMR (400 MHz, CD₃OD) δ: 8.25 (d, J=9.2 Hz, 1H), 7.93 (t, J=8.4 Hz, 1H), 7.87-7.83 (m, 1H), 7.54-7.45 (m, 2H), 4.87 (s, 1H), 4.52-4.39 (m, 1H), 3.18-2.97 (m, 1H), 2.51-2.26 (m, 2H), 2.07-2.00 (m, 2H), 1.92-1.81 (m, 1H), 1.73-1.51 (m, 9H), 1.38-1.33 (m, 5H), 1.17-1.15 (m, 4H), 0.94 (t, J=7.2 Hz, 3H).

Example 68: (1R,3S)-3-(((8-chloro-7-((cis-4-ethylcyclohexyl)oxy)naphthalen-2-yl)methyl)amino)-2,2-dimethylcyclobutanecarboxylic acid

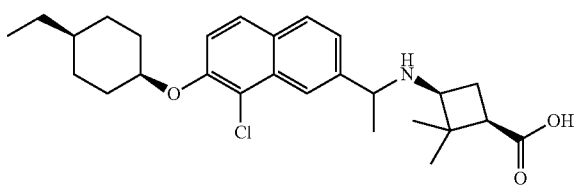 [SMILES: CC[C@H]1CC[C@@H](Oc2ccc3ccc(C(C)N[C@H]4C[C@@H](C(=O)O)C4(C)C)cc3c2Cl)CC1]

The preparation of (1R,3S)-3-(((8-chloro-7-((cis-4-ethylcyclohexyl)oxy)naphthalen-2-yl)methyl)amino)-2,2-dimethylcyclobutanecarboxylic acid was the same as Example 26. 28 mg as a white solid, yield: 29%. ESI-MS (M+H)+: 444.2. ¹H NMR (400 MHz, CD₃OD) δ: 8.32 (s, 1H), 7.94 (d, J=8.4 Hz, 1H), 7.86 (d, J=9.2 Hz, 1H), 7.54-7.48 (m, 2H), 4.87 (s, 1H), 4.29 (AB, 2H), 3.34-3.30 (m, 1H), 2.61-2.57 (m, 1H), 2.42-2.37 (m, 1H), 2.27-2.22 (m, 1H), 2.07-2.04 (m, 2H), 1.70-1.54 (m, 6H), 1.37 (s, 3H), 1.36-1.31 (m, 3H), 1.17 (s, 3H), 0.95 (t, J=7.2 Hz, 3H).

Example 69: 1-((8-cyano-7-((cis-4-ethylcyclohexyl)oxy)naphthalen-2-yl)methyl)piperidine-4-carboxylic acid

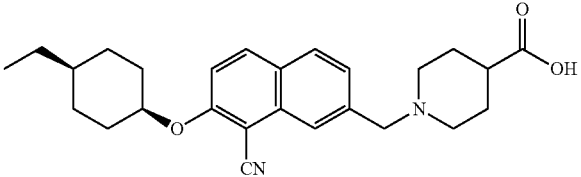 [SMILES: CC[C@H]1CC[C@@H](Oc2ccc3ccc(CN4CCC(C(=O)O)CC4)cc3c2C#N)CC1]

The preparation of 1-((8-cyano-7-((cis-4-ethylcyclohexyl)oxy)naphthalen-2-yl)methyl)piperidine-4-carboxylic acid was the same as Example 33. 20 mg as a white solid, yield: 21%. ESI-MS (M+H)+: 421.2. ¹H NMR (400 MHz, CD₃OD) δ: 8.16 (d, J=9.2 Hz, 1H), 8.06 (s, 1H), 7.96 (d, J=8.0 Hz, 1H), 7.56-7.51 (m, 2H), 5.00 (s, 1H), 4.10 (s, 2H), 3.19-3.16 (m, 2H), 2.65-2.59 (m, 2H), 2.34-2.29 (m, 1H), 2.09-1.83 (m, 6H), 1.74-1.52 (m, 6H), 1.37-1.29 (m, 3H), 0.94 (t, J=7.2 Hz, 3H).

Example 70: 8-((8-cyano-7-((cis-4-ethylcyclohexyl)oxy)naphthalen-2-yl)methyl)-8-azabicyclo[3.2.1]octane-3-carboxylic acid

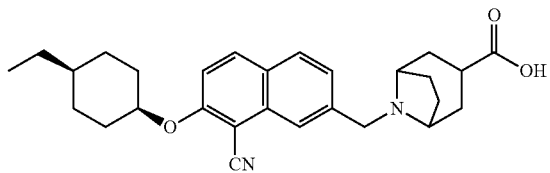 [SMILES: CC[C@H]1CC[C@@H](Oc2ccc3ccc(CN4C5CCC4CC(C(=O)O)C5)cc3c2C#N)CC1]

The preparation of 8-((8-cyano-7-((cis-4-ethylcyclohexyl)oxy)naphthalen-2-yl)methyl)-8-azabicyclo[3.2.1]octane-3-carboxylic acid was the same as Example 26. 26 mg as a white solid, yield: 33%. ESI-MS (M+H)+: 447.2. ¹H NMR (400 MHz, CD₃OD) δ: 9.19 (s, 1H), 8.18 (d, J=9.6 Hz, 1H), 8.02 (d, J=8.0 Hz, 1H), 7.61 (dd, J=1.6 Hz, 8.4 Hz, 1H), 7.54 (d, J=9.2 Hz, 1H), 5.00 (s, 1H), 4.35 (s, 2H), 3.88-3.84 (m, 2H), 2.71-2.65 (m, 1H), 2.43-2.40 (m, 2H), 2.09-1.93 (m, 8H), 1.73-1.49 (m, 6H), 1.36-1.28 (m, 3H), 0.93 (t, J=7.2 Hz, 3H).

Example 71: 9-((8-cyano-7-((cis-4-ethylcyclohexyl)oxy)naphthalen-2-yl)methyl)-9-azabicyclo[3.3.1]nonane-3-carboxylic acid

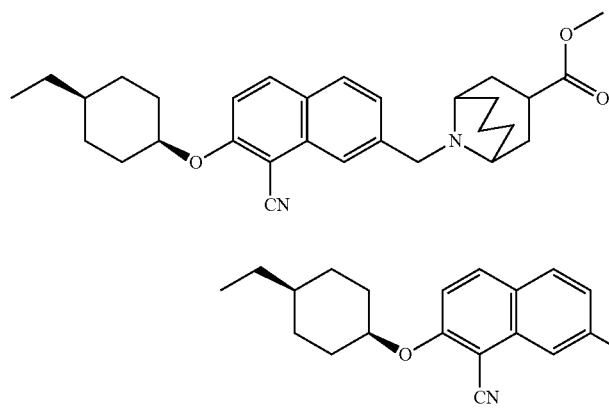

The preparation of 9-((8-cyano-7-((cis-4-ethylcyclohexyl)oxy)naphthalen-2-yl)methyl)-9-azabicyclo[3.3.1]nonane-3-carboxylic acid was the same as Example 26. 8 mg as a white solid, yield: 8%. ESI-MS (M+H)+: 461.2. ¹H NMR (400 MHz, CD₃OD) δ: 8.11 (d, J=9.2 Hz, 1H), 8.08 (s, 1H), 7.89 (d, J=8.4 Hz, 1H), 7.62 (dd, J=1.2 Hz, 8.4 Hz, 1H), 7.45 (d, J=8.8 Hz, 1H), 4.98 (s, 1H), 4.26 (s, 2H), 3.12-3.06 (m, 3H), 2.34-2.06 (m, 7H), 1.80-1.53 (m, 11H), 1.37-1.29 (m, 3H), 0.95 (t, J=7.2 Hz, 3H).

Example 72: 1-(1-(8-cyano-7-((cis-4-ethylcyclohexyl)oxy)naphthalen-2-yl)ethyl)piperidine-4-carboxylic acid

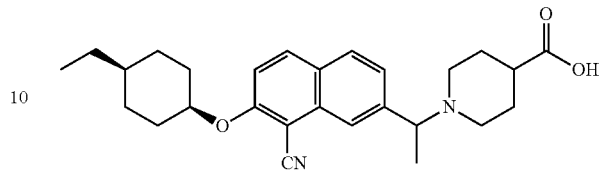

The preparation of 1-(1-(8-cyano-7-((cis-4-ethylcyclohexyl)oxy)naphthalen-2-yl)ethyl)piperidine-4-carboxylic acid was the same as Example 28. 30 mg as a white solid, yield: 32%. ESI-MS (M+H)+: 435.2. ¹H NMR (400 MHz, CD₃OD) δ: 8.14 (d, J=9.2 Hz, 1H), 7.96-7.94 (m, 2H), 7.57 (dd, J=1.6 Hz, 8.8 Hz, 1H), 7.49 (d, J=9.2 Hz, 1H), 5.00 (s, 1H), 3.95-3.93 (m, 1H), 2.96-2.93 (m, 1H), 2.37-2.34 (m, 2H), 2.20-2.07 (m, 3H), 2.00-1.51 (m, 14H), 1.37-1.31 (m, 3H), 0.95 (t, J=7.2 Hz, 3H).

Example 73: 8-(1-(8-cyano-7-((cis-4-ethylcyclohexyl)oxy)naphthalen-2-yl)ethyl)-8-azabicyclo[3.2.1]octane-3-carboxylic acid

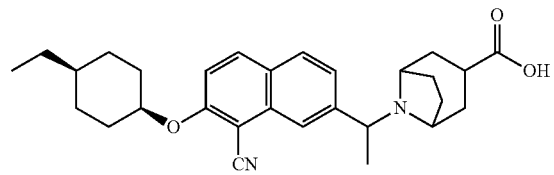 [SMILES: CC[C@H]1CC[C@@H](Oc2ccc3ccc(C(C)N4C5CCC4CC(C(=O)O)C5)cc3c2C#N)CC1]

The preparation of 8-(1-(8-cyano-7-((cis-4-ethylcyclohexyl)oxy)naphthalen-2-yl)ethyl)-8-azabicyclo[3.2.1]octane-3-carboxylic acid was the same as Example 28. 24 mg as a white solid, yield: 45%. ESI-MS (M+H)+: 461.2. ¹H NMR (400 MHz, CD₃OD) δ: 8.16 (d, J=9.2 Hz, 1H), 8.12 (s, 1H), 8.00 (d, J=8.4 Hz, 1H), 7.67 (dd, J=1.2 Hz, 8.4 Hz, 1H), 7.52 (d, J=9.6 Hz, 1H), 5.00 (s, 1H), 4.38-4.36 (m, 1H), 3.93-3.88 (m, 1H), 3.46-3.43 (m, 1H), 2.65-2.60 (m, 1H), 2.27-1.83 (m, 9H), 1.73-1.50 (m, 10H), 1.37-1.29 (m, 3H), 0.94 (t, J=7.2 Hz, 3H).

Example 74: 9-(1-(8-cyano-7-((cis-4-ethylcyclohexyl)oxy)naphthalen-2-yl)ethyl)-9-azabicyclo[3.3.1]nonane-3-carboxylic acid

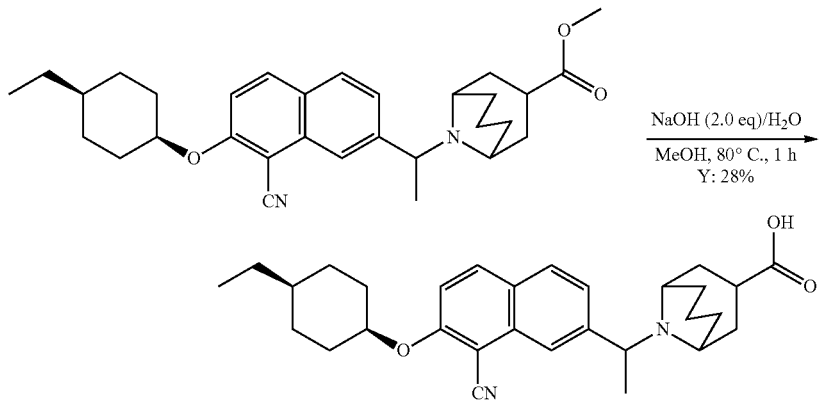

The preparation of 9-(1-(8-cyano-7-((cis-4-ethylcyclohexyl)oxy)naphthalen-2-yl)ethyl)-9-azabicyclo[3.3.1]nonane-3-carboxylic acid was the same as Example 28. 30 mg as a white solid, yield: 28%. ESI-MS (M+H)$^+$+: 475.3. $^1$H NMR (400 MHz, CD$_3$OD) δ: 8.22 (s, 1H), 8.18 (d, J=9.2 Hz, 1H), 8.03 (d, J=8.8 Hz, 1H), 7.72 (dd, J=1.6 Hz, 8.4 Hz, 1H), 7.54 (d, J=9.2 Hz, 1H), 5.06-5.01 (m, 2H), 3.66-3.60 (m, 2H), 3.06-3.02 (m, 1H), 2.44-2.41 (m, 1H), 2.28-1.93 (m, 8H), 1.78-1.49 (m, 12H), 1.37-1.29 (m, 3H), 0.94 (t, J=7.2 Hz, 3H).

Example 75: 1-(1-(8-chloro-7-((cis-4-ethylcyclohexyl)oxy)naphthalen-2-yl)propyl)piperidine-4-carboxylic acid

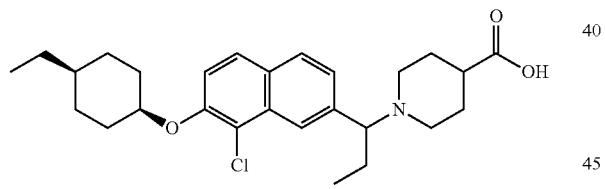

The preparation of 1-(1-(8-chloro-7-((cis-4-ethylcyclohexyl)oxy)naphthalen-2-yl)propyl)piperidine-4-carboxylic acid was the same as Example 28. 36 mg as a white solid, yield: 48%. ESI-MS (M+H)$^+$: 458.2. $^1$H NMR (400 MHz, CD$_3$OD) δ: 8.23 (s, 1H), 7.97 (d, J=8.4 Hz, 1H), 7.88 (d, J=9.2 Hz, 1H), 7.51 (d, J=9.2 Hz, 1H), 7.47 (dd, J=1.6 Hz, 8.8 Hz, 1H), 4.88 (s, 1H), 4.25-4.22 (m, 1H), 3.56-3.53 (m, 1H), 3.25-3.22 (m, 1H), 2.83-2.79 (m, 2H), 2.33-2.25 (m, 3H), 2.06-1.87 (m, 6H), 1.68-1.54 (m, 6H), 1.35-1.30 (m, 3H), 0.94 (t, J=7.2 Hz, 3H), 0.79 (t, J=7.2 Hz, 3H).

Example 76: 1-(1-(8-cyano-7-((cis-4-ethylcyclohexyl)oxy)naphthalen-2-yl)propyl)piperidine-4-carboxylic acid

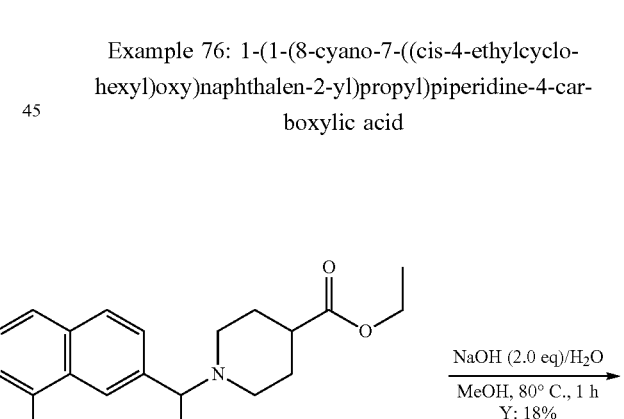

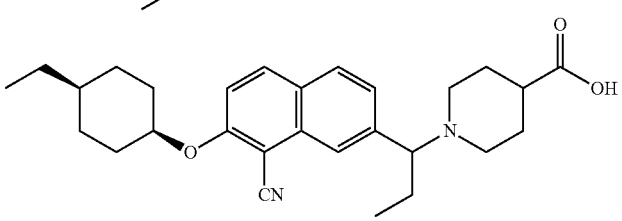

The preparation of 1-(1-(8-cyano-7-((cis-4-ethylcyclohexyl)oxy)naphthalen-2-yl)propyl)piperidine-4-carboxylic acid was the same as Example 28. 33 mg as a white solid, yield: 18%. ESI-MS (M+H)+: 449.3. ¹H NMR (400 MHz, DMSO-d₆) δ: 8.20 (d, J=9.6 Hz, 1H), 7.96 (d, J=8.4 Hz, 1H), 7.68 (s, 1H), 7.58 (d, J=8.8 Hz, 1H), 7.43 (d, J=8.4 Hz, 1H), 5.04 (s, 1H), 3.47-3.44 (m, 1H), 2.94-2.91 (m, 1H), 2.75-2.73 (m, 1H), 2.02-1.85 (m, 5H), 1.75-1.35 (m, 12H), 1.29-1.26 (m, 3H), 0.88 (t, J=6.8 Hz, 3H), 0.72 (t, J=7.2 Hz, 3H).

Example 77: 2-((R)-1-((7-((cis-4-methylcyclohexyl)oxy)-8-(trifluoromethyl)naphthalen-2-yl)methyl)piperidin-3-yl)acetic acid

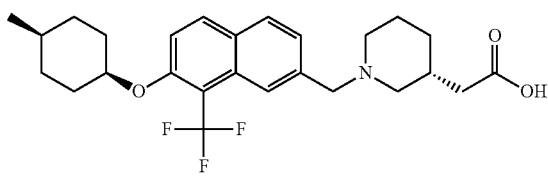 [SMILES: C[C@H]1CC[C@@H](Oc2ccc3ccc(CN4CCC[C@H](CC(=O)O)C4)cc3c2C(F)(F)F)CC1]

The title compound was prepared according to the method of Example 26 as a white solid (30 mg, 21% yield, 2 steps) ESI-MS (M+H)+: 464.3. ¹H NMR (400 MHz, CD₃OD) δ: 8.11 (s, 1H), 7.96 (d, J=9.2 Hz, 1H), 7.81 (d, J=8.4 Hz, 1H), 7.43-7.38 (m, 2H), 4.75 (s, 1H), 4.06 (s, 2H), 3.30-3.27 (m, 1H), 3.17-3.14 (m, 1H), 2.65-2.59 (m, 1H), 2.44-2.39 (m, 1H), 2.12-2.07 (m, 2H), 2.00-1.82 (m, 3H), 1.74-1.47 (m, 5H), 1.41-1.19 (m, 5H), 1.14-1.05 (m, 1H), 0.82 (d, J=6.0 Hz, 3H).

Example 78: 2,2-dimethyl-3-(((7-((cis-4-methylcyclohexyl)oxy)-8-(trifluoromethyl)naphthalen-2-yl)methyl)amino)cyclobutanecarboxylic acid

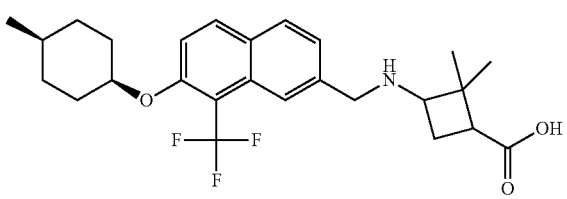 [SMILES: CC1(C)C(NCc2ccc3ccc(O[C@H]4CC[C@@H](C)CC4)c(C(F)(F)F)c3c2)CC1C(=O)O]

The title compound was prepared according to the method of Example 26 as a yellow oil (36 mg: 14% yield, 2 steps). ESI-MS (M+H)+: 464.2. ¹H NMR (400 MHz, CD₃OD) δ: 7.97 (s, 1H), 7.88 (d, J=9.2 Hz, 1H), 7.72 (d, J=8.8 Hz, 1H), 7.35 (d, J=8.8 Hz, 1H), 7.28 (d, J=9.2 Hz, 1H), 4.73 (s, 1H), 3.77 (AB, 2H), 2.78-2.73 (m, 1H), 2.23-2.19 (m, 1H), 2.04-1.77 (m, 4H), 1.56-1.32 (m, 7H), 1.18 (s, 3H), 0.96 (s, 3H), 0.84 (d, J=4.8 Hz, 3H).

Example 79: 1-((8-chloro-7-((cis-4-methylcyclohexyl)oxy)naphthalen-2-yl)methyl)piperidine-4-carboxylic acid

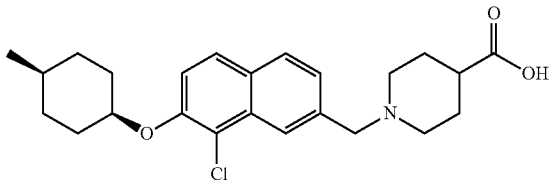 [SMILES: C[C@H]1CC[C@@H](Oc2ccc3ccc(CN4CCC(C(=O)O)CC4)cc3c2Cl)CC1]

The title compound was prepared according to the method of Example 26 as a white solid (35 mg, 47% yield). ESI-MS (M+H)+: 416.2. ¹H NMR (400 MHz, CD₃OD) δ: 8.30 (s, 1H), 7.93 (d, J=8.4 Hz, 1H), 7.87 (d, J=8.4 Hz, 1H), 7.50-7.48 (m, 2H), 4.85 (s, 1H), 4.28 (s, 2H), 3.35-3.30 (m, 2H), 2.85 (m, 2H), 2.40-2.35 (m, 1H), 2.06-1.87 (m, 6H), 1.70-1.54 (m, 7H), 0.98 (d, J=5.2 Hz, 3H).

Example 80: 1-(1-(7-((cis-4-methylcyclohexyl)oxy)-8-(trifluoromethyl)naphthalen-2-yl)ethyl)piperidine-4-carboxylic acid

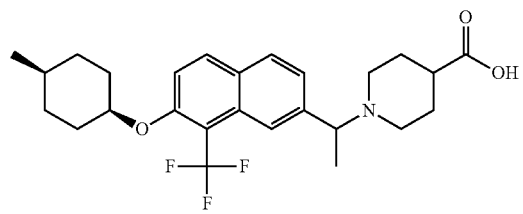 [SMILES: CC(c1ccc2ccc(O[C@H]3CC[C@@H](C)CC3)c(C(F)(F)F)c2c1)N1CCC(C(=O)O)CC1]

The title compound was prepared according to the method of Example 28 as a white solid (10 mg, 43% yield). ESI-MS (M+H)+: 464.3. ¹H NMR (400 MHz, CD₃OD) δ: 8.21 (s, 1H), 8.11 (d, J=9.6 Hz, 1H), 8.00 (d, J=8.4 Hz, 1H), 7.58-7.53 (m, 2H), 4.92 (s, 1H), 4.47-4.46 (m, 1H), 3.56-3.55 (m, 1H), 3.22-3.19 (m, 1H), 2.91-2.86 (m, 2H), 2.37 (m, 1H), 2.11-1.88 (m, 6H), 1.82-1.67 (m, 5H), 1.55-1.40 (m, 5H), 0.96 (d, J=5.6 Hz, 3H).

Example 81: 2-((3R)-1-(1-(7-((cis-4-methylcyclohexyl)oxy)-8-(trifluoromethyl)naphthalen-2-yl)ethyl)piperidin-3-yl)acetic acid

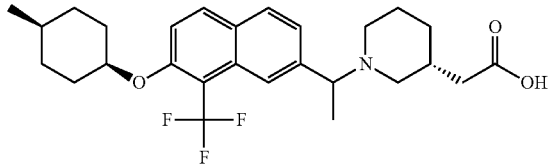 [SMILES: CC(c1ccc2ccc(O[C@H]3CC[C@@H](C)CC3)c(C(F)(F)F)c2c1)N1CCC[C@H](CC(=O)O)C1]

The title compound was prepared according to the method of Example 28 as a white solid (15 mg, 13% yield, 2 steps) ESI-MS (M+H)+: 478.3. ¹H NMR (400 MHz, CD₃OD) δ: 8.18 (s, 1H), 8.09 (d, J=9.6 Hz, 1H), 7.97 (d, J=8.4 Hz, 1H), 7.55-7.52 (m, 2H), 4.91 (s, 1H), 4.37-4.31 (m, 1H), 3.61-3.45 (m, 1H), 3.28-3.06 (m, 1H), 2.68-2.36 (m, 2H), 2.22-

2.04 (m, 5H), 1.93-1.62 (m, 8H), 1.54-1.40 (m, 5H), 1.19-1.09 (m, 1H), 0.96 (d, J=5.6 Hz, 3H).

Example 82: 2,2-dimethyl-3-((1-(7-((cis-4-methyl-cyclohexyl)oxy)-8-(trifluoromethyl)naphthalen-2-yl)ethyl)amino)cyclobutanecarboxylic acid

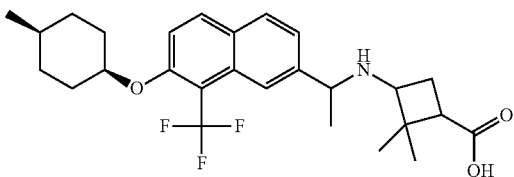 [SMILES: CC(NC1CC(C(=O)O)C1(C)C)c1ccc2ccc(O[C@H]3CC[C@@H](C)CC3)c(C(F)(F)F)c2c1]

The title compound was prepared according to the method of Example 28 as a white solid (5 mg, 20% yield, 2 steps). ESI-MS (M+H)+: 478.1. 1H NMR (400 MHz, CD3OD) δ: 8.14 (s, 1H), 8.09-8.05 (m, 1H), 7.97-7.92 (m, 1H), 7.55-7.48 (m, 2H), 4.95 (s, 1H), 4.35-4.22 (m, 1H), 3.02-2.87 (m, 1H), 2.44-2.15 (m, 2H), 2.07-2.04 (m, 2H), 1.95-1.80 (m, 1H), 1.73-1.64 (m, 3H), 1.59-1.41 (m, 7H), 1.30 (s, 3H), 1.15-1.12 (m, 3H), 0.97 (d, J=5.6 Hz, 3H).

Example 83: 8-((8-chloro-7-((cis-4-methylcyclohexyl)oxy)naphthalen-2-yl)methyl)-8-azabicyclo[3.2.1]octane-3-carboxylic acid

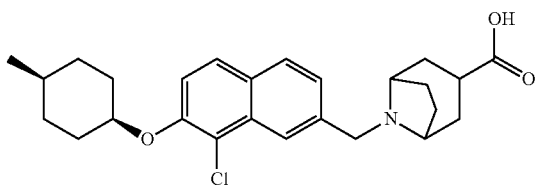 [SMILES: C[C@H]1CC[C@@H](Oc2ccc3ccc(CN4C5CCC4CC(C(=O)O)C5)cc3c2Cl)CC1]

The title compound was prepared according to the method of Example 26 as a white solid (25 mg, 18% yield, 2 steps). ESI-MS (M+H)+: 442.2. 1H NMR (400 MHz, CD3OD) δ: 8.31 (s, 1H), 7.88 (d, J=8.8 Hz, 1H), 7.80 (d, J=8.8 Hz, 1H), 7.48 (dd, J=1.6 Hz, 8.4 Hz, 1H), 7.43 (d, J=9.2 Hz, 1H), 4.78 (s, 1H), 4.29 (s, 2H), 3.82-3.80 (m, 2H), 2.63-2.57 (m, 1H), 2.36-2.34 (m, 2H), 2.02-1.87 (m, 8H), 1.61-1.33 (m, 7H), 0.90 (d, J=4.8 Hz, 3H).

Example 84: 2-((R)-1-((8-chloro-7-((cis-4-methyl-cyclohexyl)oxy)naphthalen-2-yl)methyl)piperidin-3-yl)acetic acid

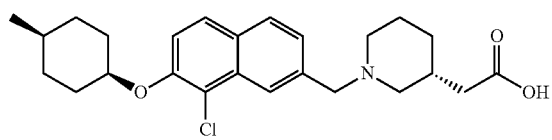 [SMILES: C[C@H]1CC[C@@H](Oc2ccc3ccc(CN4CCC[C@H](CC(=O)O)C4)cc3c2Cl)CC1]

The title compound was prepared according to the method of Example 26 as a white solid (90 mg, 60% yield, 2 steps). ESI-MS (M+H)+: 430.2. 1H NMR (400 MHz, CD3OD) δ: 8.23 (s, 1H), 7.88 (d, J=8.4 Hz, 1H), 7.83 (d, J=9.2 Hz, 1H), 7.50-7.45 (m, 2H), 4.82 (s, 1H), 4.17 (s, 2H), 3.36-3.33 (m, 1H), 3.25-3.23 (m, 1H), 2.69-2.63 (m, 1H), 2.47-2.41 (m, 1H), 2.20-1.98 (m, 5H), 1.86-1.51 (m, 10H), 1.20-1.15 (m, 1H), 0.97 (d, J=5.2 Hz, 3H).

Example 85: 3-(((8-chloro-7-((cis-4-methylcyclohexyl)oxy)naphthalen-2-yl)methyl)amino)-2,2-dimethylcyclobutanecarboxylic acid

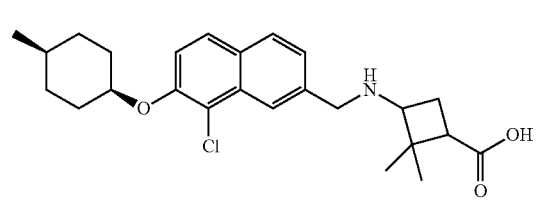 [SMILES: CC1(C)C(NCc2ccc3ccc(O[C@H]4CC[C@@H](C)CC4)c(Cl)c3c2)CC1C(=O)O]

The title compound was prepared according to the method of Example 26 as a white solid (30 mg, 21% yield, 2 steps) ESI-MS (M+H)+: 430.2. 1H NMR (400 MHz, CD3OD) δ: 8.18 (s, 1H), 7.85 (d, J=8.8 Hz, 1H), 7.80 (d, J=8.8 Hz, 1H), 7.47 (d, J=1.2 Hz, 8.4 Hz, 1H), 7.41 (d, J=8.8 Hz, 1H), 4.81 (s, 1H), 4.02 (s, 2H), 3.03-2.99 (m, 1H), 2.42-2.38 (m, 1H), 2.24-2.18 (m, 1H), 2.06-2.01 (m, 3H), 1.69-1.51 (m, 7H), 1.33 (s, 3H), 1.12 (s, 3H), 0.99 (d, J=5.2 Hz, 3H).

Example 86: 9-((8-(difluoromethyl)-7-((cis-4-methylcyclohexyl)oxy)naphthalen-2-yl)methyl)-9-azabicyclo[3.3.1]nonane-3-carboxylic acid

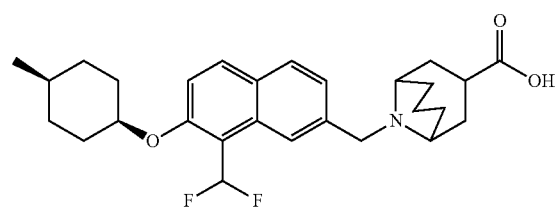 [SMILES: C[C@H]1CC[C@@H](Oc2ccc3ccc(CN4C5CCCC4CC(C(=O)O)C5)cc3c2C(F)F)CC1]

The title compound was prepared according to the method in Example 42 to give a white solid (20 mg, 28% yield, 2 steps). ESI-MS (M+H)+: 472.2. 1H NMR (400 MHz, CD3OD) δ: 8.53 (s, 1H), 8.07 (d, J=9.2 Hz, 1H), 8.01 (d, J=8.4 Hz, 1H), 7.63 (t, J=55.2 Hz, 1H), 7.60 (d, J=8.8 Hz, 1H), 7.53 (d, J=8.8 Hz, 1H), 4.89 (s, 1H), 4.74 (s, 2H), 3.65-3.63 (m, 2H), 3.46-3.41 (m, 1H), 2.59-1.53 (m, 17H), 1.41-1.32 (m, 2H), 0.99 (d, J=6.0 Hz, 3H).

Example 87: 8-(1-(8-(difluoromethyl)-7-((cis-4-methylcyclohexyl)oxy)naphthalen-2-yl)ethyl)-8-azabicyclo[3.2.1]octane-3-carboxylic acid

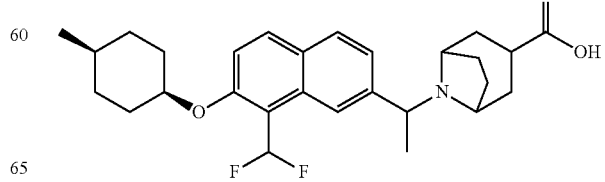

The title compound was obtained according to the method in Example 28 as a white solid (25 mg, 57% yield). ESI-MS (M+H)+: 472.2. ¹H NMR (400 MHz, CD₃OD) δ: 8.42 (s, 1H), 8.06 (d, J=9.2 Hz, 1H), 8.03 (d, J=8.8 Hz, 1H), 7.62 (t, J=54.8 Hz, 1H), 7.59 (dd, J=1.2 Hz, 8.8 Hz, 1H), 7.52 (d, J=9.2 Hz, 1H), 4.89 (s, 1H), 4.55-4.36 (m, 2H), 3.54-3.47 (m, 1H), 2.90-2.75 (m, 1H), 2.52-2.45 (m, 1H), 2.32-1.93 (m, 9H), 1.82 (d, J=6.8 Hz, 3H). 1.75-1.68 (m, 2H), 1.61-1.52 (m, 3H), 1.41-1.30 (m, 2H), 0.99 (d, J=6.0 Hz, 3H).

Example 88: 9-(1-(8-(difluoromethyl)-7-((cis-4-methylcyclohexyl)oxy)naphthalen-2-yl)ethyl)-9-azabicyclo[3.3.1]nonane-3-carboxylic acid

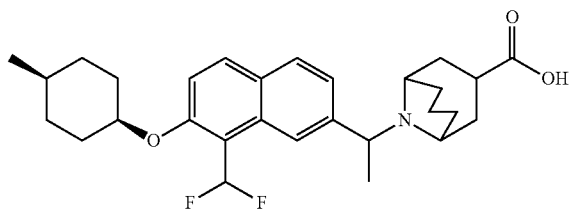 [SMILES: CC(c1ccc2ccc(O[C@H]3CC[C@@H](C)CC3)c(C(F)F)c2c1)N1C2CCCC1CC(C(=O)O)C2]

The title compound is prepared according to the method of example 28 as a white solid (10 mg, 7% yield, 2 steps). ESI-MS (M+H)+: 486.3. ¹H NMR (400 MHz, CD₃OD) δ: 8.39 (s, 1H), 8.01 (d, J=8.8 Hz, 1H), 7.94 (d, J=8.8 Hz, 1H), 7.64 (d, J=8.4 Hz, 1H), 7.60 (t, J=54.8 Hz, 1H), 7.45 (d, J=8.8 Hz, 1H), 4.95 (s, 1H), 4.62-4.60 (m, 2H), 3.14-3.05 (m, 1H), 2.41-1.28 (m, 23H), 0.99 (d, J=6.0 Hz, 3H).

Example 89: 1-(1-(8-chloro-7-((cis-4-methylcyclohexyl)oxy)naphthalen-2-yl)ethyl)piperidine-4-carboxylic acid

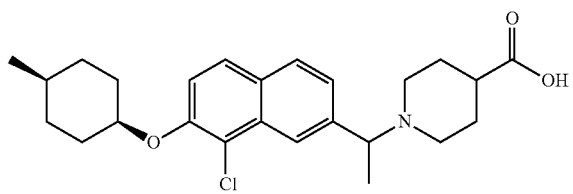 [SMILES: CC(c1ccc2ccc(O[C@H]3CC[C@@H](C)CC3)c(Cl)c2c1)N1CCC(C(=O)O)CC1]

The title compound was prepared according to the method of Example 28 as a white solid (50 mg, 45% yield, 2 steps). ESI-MS (M+H)+: 430.2. ¹H NMR (400 MHz, CD₃OD) δ: 8.01 (s, 1H), 7.75-7.69 (m, 2H), 7.39 (d, J=8.4 Hz, 1H), 7.30 (d, J=9.2 Hz, 1H), 4.72 (s, 1H), 3.65 (q, J=6.4 Hz, 1H), 3.14-3.12 (m, 1H), 2.82-2.79 (m, 1H), 2.14-1.94 (m, 5H), 1.86-1.44 (m, 14H), 0.90 (d, J=6.0 Hz, 3H).

Example 90: 8-(1-(8-chloro-7-((cis-4-methylcyclohexyl)oxy)naphthalen-2-yl)ethyl)-8-azabicyclo[3.2.1]octane-3-carboxylic acid

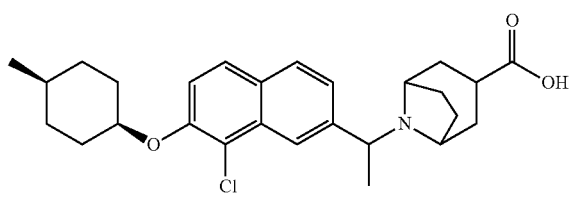 [SMILES: CC(c1ccc2ccc(O[C@H]3CC[C@@H](C)CC3)c(Cl)c2c1)N1C2CCC1CC(C(=O)O)C2]

The title compound was prepared according to the method of Example 28 as a white solid (35 mg, 24% yield, 2 steps). ESI-MS (M+H)+: 456.3. ¹H NMR (400 MHz, CD₃OD) δ: 8.16 (s, 1H), 7.80 (d, J=8.4 Hz, 1H), 7.76 (d, J=9.2 Hz, 1H), 7.59 (dd, J=1.6 Hz, 8.4 Hz, 1H), 7.36 (d, J=9.2 Hz, 1H), 4.79 (s, 1H), 4.11-4.06 (m, 1H), 3.33-3.30 (m, 2H), 2.61-2.53 (m, 1H), 2.14-2.00 (m, 6H), 1.68-1.44 (m, 11H), 1.42 (d, J=6.4 Hz, 3H), 0.98 (d, J=5.6 Hz, 3H).

Example 91: 9-(1-(8-chloro-7-((cis-4-methylcyclohexyl)oxy)naphthalen-2-yl)ethyl)-9-azabicyclo[3.3.1]nonane-3-carboxylic acid

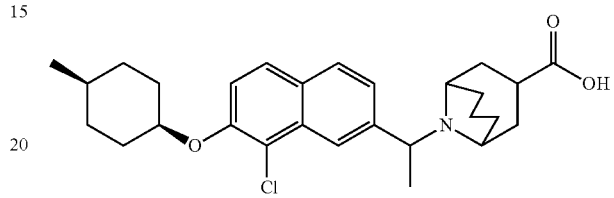

The title compound was prepared according to the method of Example 28 as a white solid (20 mg, 13% yield, 2 steps). ESI-MS (M+H)+: 470.2. ¹H NMR (400 MHz, CD₃OD) δ: 8.32 (s, 1H), 7.91 (d, J=8.0 Hz, 1H), 7.83 (d, J=9.2 Hz, 1H), 7.62 (d, J=8.8 Hz, 1H), 7.44 (d, J=8.8 Hz, 1H), 4.91 (s, 1H), 4.84-4.82 (m, 1H), 3.33-3.30 (m, 2H), 3.07-3.04 (m, 1H), 2.40-1.53 (m, 22H), 0.98 (d, J=4.8 Hz, 3H).

Example 92: 2-((3R)-1-(1-(8-chloro-7-((cis-4-methylcyclohexyl)oxy)naphthalen-2-yl)ethyl)piperidin-3-yl)acetic acid

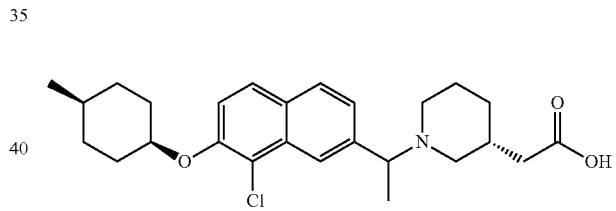

The title compound was prepared according to the method of Example 28 as a white solid (20 mg, 17% yield, 2 steps). ESI-MS (M+H)+: 444.2. ¹H NMR (400 MHz, CD₃OD) δ: 8.70 (s, 1H), 7.82-7.77 (m, 2H), 7.48 (d, J=8.4 Hz, 1H), 7.38 (d, J=8.8 Hz, 1H), 4.80 (s, 1H), 3.73-3.67 (m, 1H), 3.27 (m, 0.5H), 3.14-3.12 (m, 0.5H), 2.98-2.94 (m, 0.5H), 2.82-2.79 (m, 0.5H), 2.17-1.93 (m, 6H), 1.84-1.52 (m, 15H), 0.99-0.91 (d, J=6.4 Hz, 3H).

Example 93: Cis-3-((1-(8-chloro-7-((cis-4-methylcyclohexyl)oxy)naphthalen-2-yl)ethyl)amino)-2,2-dimethylcyclobutanecarboxylic acid

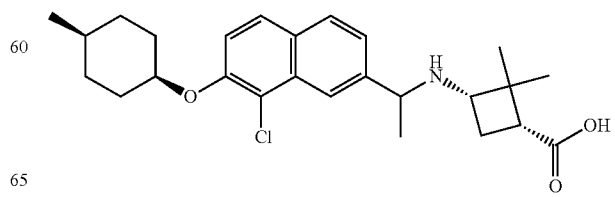

The title compound was prepared according to the method of Example 28 as a white solid (30 mg, 22% yield, 2 steps) ESI-MS (M+H)+: 444.3. ¹H NMR (400 MHz, CD₃OD, a mixture of diastereomers) δ: 8.15 (s, 1H), 7.88-7.79 (m, 2H), 7.51-7.39 (m, 2H), 4.82 (s, 1H), 4.21-4.15 (m, 1H), 2.86-2.80 (m, 1H), 2.35-2.03 (m, 4H), 1.88-1.82 (m, 1H), 1.69-1.49 (m, 10H), 1.29-1.08 (m, 6H), 0.99 (d, J=5.6 Hz, 3H).

Example 94: 1-(1-(8-chloro-7-(cis-4-methylcyclohexyl)oxy)naphthalen-2-yl)propyl)piperidine-4-carboxylic acid

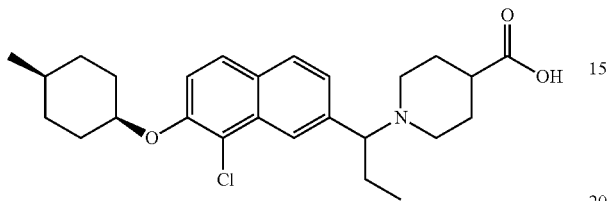

The title compound was prepared according to the method of Example 28 as a white solid (10 mg, 7% yield, 2 steps). ESI-MS (M+H)+: 444.2. ¹H NMR (400 MHz, CD₃OD) δ: 8.17 (s, 1H), 7.93 (d, J=8.8 Hz, 1H), 7.85 (d, J=8.8 Hz, 8.4 Hz, 1H), 7.49-7.44 (m, 2H), 4.85 (s, 1H), 4.02-3.96 (m, 1H), 3.41-3.40 (m, 1H), 3.12-3.10 (m, 1H), 2.63-2.58 (m, 2H), 2.25-1.54 (m, 16H), 0.98 (d, J=5.2 Hz, 3H), 0.78 (t, J=7.2 Hz, 3H).

Example 95: 8-(1-(8-chloro-7-((cis-4-methylcyclohexyl)oxy)naphthalen-2-yl)propyl)-8-azabicyclo[3.2.1]octane-3-carboxylic acid

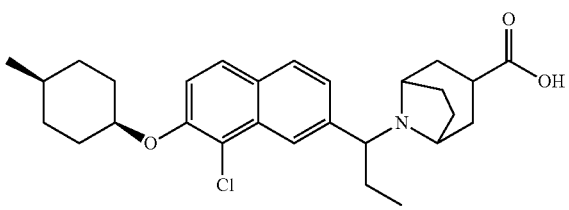 [SMILES: CCC(c1ccc2ccc(O[C@H]3CC[C@@H](C)CC3)c(Cl)c2c1)N1C2CCC1CC(C(=O)O)C2]

The title compound was prepared according to the method of Example 28 as a white solid (12 mg, 7% yield, 2 steps). ESI-MS (M+H)+: 470.2. ¹H NMR (400 MHz, CD₃OD) δ: 8.29 (s, 1H), 7.97 (d, J=8.0 Hz, 1H), 7.87 (d, J=9.2 Hz, 1H), 7.56 (d, J=8.0 Hz, 1H), 7.49 (d, J=9.2 Hz, 1H), 4.92 (s, 1H), 4.15-4.08 (m, 1H), 3.36-3.30 (m, 1H), 2.67-2.62 (m, 1H), 2.33-1.54 (m, 20H), 0.98 (d, J=5.2 Hz, 3H), 0.76 (t, J=7.2 Hz, 3H).

Example 96: 8-((8-cyano-7-((cis-4-methylcyclohexyl)oxy)naphthalen-2-yl)methyl)-8-azabicyclo[3.2.1]octane-3-carboxylic acid

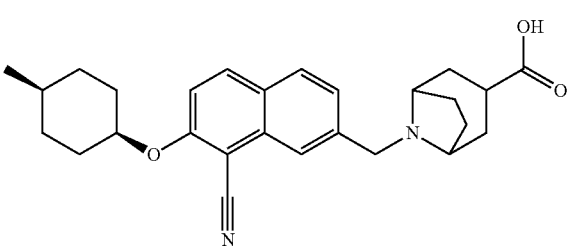 [SMILES: C[C@H]1CC[C@@H](Oc2ccc3ccc(CN4C5CCC4CC(C(=O)O)C5)cc3c2C#N)CC1]

The title compound was obtained according to the method of Example 33 as a white solid (15 mg, 34% yield). ESI-MS (M+H)+: 433.2. ¹H NMR (400 MHz, CD₃OD) δ: 8.21-8.18 (m, 2H), 8.03 (d, J=8.8 Hz, 1H), 7.63 (d, J=8.4 Hz, 1H), 7.56 (d, J=9.2 Hz, 1H), 5.01 (s, 1H), 4.34 (s, 2H), 3.87-3.84 (m, 2H), 2.72-2.65 (m, 1H), 2.43-2.40 (m, 2H), 2.10-2.04 (m, 6H), 1.97-1.94 (m, 2H), 1.76-1.70 (m, 2H), 1.58-1.54 (m, 5H), 1.00 (d, J=5.2 Hz, 3H).

Example 97: 1-((8-cyano-7-((cis-4-methylcyclohexyl)oxy)naphthalen-2-yl)methyl)piperidine-4-carboxylic acid

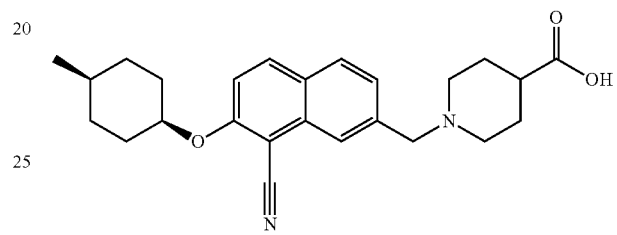

The title compound was prepared according to the method of Example 26 as a white solid (50 mg, 22% yield, 3 steps). ESI-MS (M+H)+: 407.3. ¹H NMR (400 MHz, CD₃OD) δ: 8.17 (d, J=9.2 Hz, 1H), 8.09 (s, 1H), 7.99 (d, J=8.0 Hz, 1H), 7.57-7.52 (m, 2H), 4.99 (s, 1H), 4.20 (s, 2H), 3.26-3.23 (m, 2H), 2.77-2.72 (m, 2H), 2.40-2.35 (m, 1H), 2.08-1.70 (m, 8H), 1.55-1.60 (m, 5H), 0.99 (d, J=5.6 Hz, 3H).

Example 98: 9-((8-cyano-7-((cis-4-methylcyclohexyl)oxy)naphthalen-2-yl)methyl)-9-azabicyclo[3.3.1]nonane-3-carboxylic acid

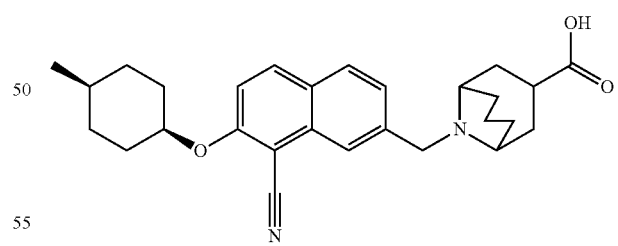

The title compound was prepared according to the method of Example 26 as a white solid (35 mg, 18% yield, 3 steps). ESI-MS (M+H)+: 447.2. ¹H NMR (400 MHz, CD₃OD) δ: 8.20 (s, 1H), 8.16 (d, J=9.6 Hz, 1H), 7.98 (d, J=8.8 Hz, 1H), 7.66 (dd, J=1.2 Hz, 8.4 Hz, 1H), 7.52 (d, J=9.2 Hz, 1H), 4.99 (s, 1H), 4.58 (s, 2H), 3.43-3.39 (m, 2H), 3.13-3.08 (m, 1H), 2.43-1.99 (m, 9H), 1.82-1.69 (m, 5H), 1.57-1.54 (m, 5H), 0.98 (d, J=4.8 Hz, 3H).

Example 99: Cis-3-(((8-cyano-7-((cis-4-methylcyclohexyl)oxy)naphthalen-2-yl)methyl)amino)-2,2-dimethylcyclobutanecarboxylic acid

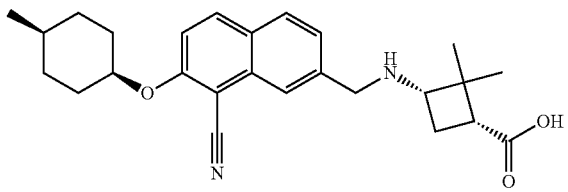 [SMILES: CC1(C)[C@@H](NCc2ccc3ccc(O[C@H]4CC[C@@H](C)CC4)c(C#N)c3c2)C[C@H]1C(=O)O]

The title compound was prepared according to the method of Example 26 as a white solid (40 mg, 26% yield, 2 steps). ESI-MS (M+H)$^+$: 421.3. $^1$H NMR (400 MHz, CD$_3$OD) δ: 8.16 (d, J=9.2 Hz, 1H), 8.09 (s, 1H), 7.98 (d, J=8.4 Hz, 1H), 7.58 (d, J=8.4 Hz, 1H), 7.52 (d, J=9.2 Hz, 1H), 4.99 (s, 1H), 4.23 (AB, 2H), 3.26 (t, J=7.6 Hz, 1H), 2.53 (t, J=8.0 Hz, 1H), 2.38-2.31 (m, 1H), 2.21-2.14 (m, 1H), 2.08-2.04 (m, 2H), 1.75-1.70 (m, 2H), 1.58-1.54 (m, 5H), 1.35 (s, 3H), 1.16 (s, 3H), 0.99 (d, J=5.2 Hz, 3H).

Example 100: 1-(1-(8-cyano-7-((cis-4-methylcyclohexyl)oxy)naphthalen-2-yl)ethyl)piperidine-4-carboxylic acid

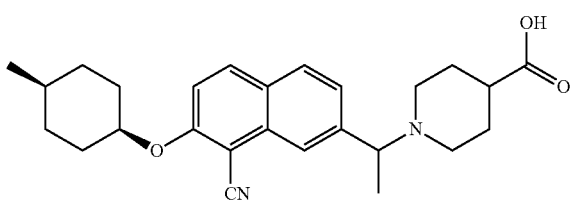 [SMILES: CC(c1ccc2ccc(O[C@H]3CC[C@@H](C)CC3)c(C#N)c2c1)N1CCC(C(=O)O)CC1]

The title compound was prepared according to the method in Example 28 as a white solid (25 mg, 18% yield, 2 steps). ESI-MS (M+H)$^+$: 421.2. $^1$H NMR (400 MHz, CD$_3$OD) δ: 8.16 (d, J=8.8 Hz, 1H), 8.02 (s, 1H), 7.99 (d, J=8.0 Hz, 1H), 7.57 (dd, J=1.6 Hz, 8.4 Hz, 1H), 7.52 (d, J=9.6 Hz, 1H), 5.00 (s, 1H), 4.19-4.17 (m, 1H), 3.43-3.40 (m, 1H), 3.07-3.04 (m, 1H), 2.60-2.58 (m, 2H), 2.28-2.23 (m, 1H), 2.08-1.69 (m, 8H), 1.68 (d, J=6.8 Hz, 3H), 1.56-1.55 (m, 5H), 0.99 (d, J=5.6 Hz, 3H).

Example 101: 8-(1-(8-cyano-7-((cis-4-methylcyclohexyl)oxy)naphthalen-2-yl)ethyl)-8-azabicyclo[3.2.1]octane-3-carboxylic acid

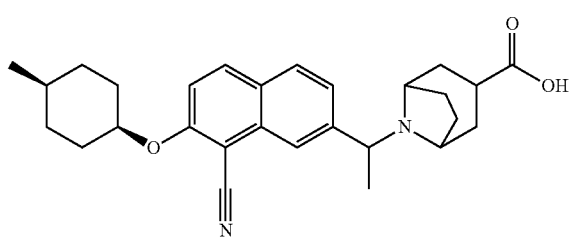 [SMILES: CC(c1ccc2ccc(O[C@H]3CC[C@@H](C)CC3)c(C#N)c2c1)N1C2CCC1CC(C(=O)O)C2]

The title compound was prepared according to the method in Example 28 as a white solid (25 mg, 20% yield, 2 steps). ESI-MS (M+H)$^+$: 447.2. $^1$H NMR (400 MHz, CD$_3$OD) δ: 8.20-8.18 (m, 2H), 8.05 (d, J=8.4 Hz, 1H), 7.67 (dd, J=1.2 Hz, 8.4 Hz, 1H), 7.56 (d, J=9.6 Hz, 1H), 5.01 (s, 1H), 4.50-4.46 (m, 1H), 4.18-4.13 (m, 1H), 3.51-3.46 (m, 1H), 2.70-2.62 (m, 1H), 2.38-2.19 (m, 3H), 2.08-1.70 (m, 12H), 1.58-1.54 (m, 5H), 1.00 (d, J=5.6 Hz, 3H).

Example 102: 9-(1-(8-cyano-7-((cis-4-methylcyclohexyl)oxy)naphthalen-2-yl)ethyl)-9-azabicyclo[3.3.1]nonane-3-carboxylic acid

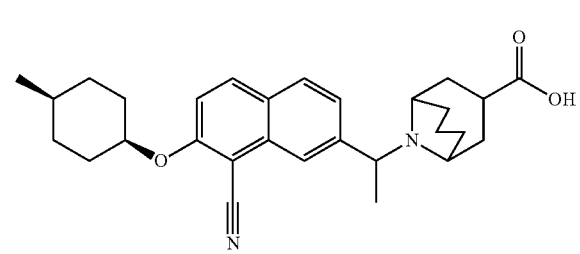 [SMILES: CC(c1ccc2ccc(O[C@H]3CC[C@@H](C)CC3)c(C#N)c2c1)N1C2CCCC1CC(C(=O)O)C2]

The title compound was prepared according to the method in Example 28 as a white solid (30 mg, 23% yield, 2 steps). ESI-MS (M+H)$^+$: 461.3. $^1$H NMR (400 MHz, CD$_3$OD) δ: 8.09 (d, J=9.6 Hz, 1H), 8.00 (s, 1H), 7.86 (d, J=8.4 Hz, 1H), 7.66 (dd, J=1.2 Hz, 8.8 Hz, 1H), 7.41 (d, J=9.2 Hz, 1H), 4.95 (s, 1H), 4.45 (q, J=6.4 Hz, 1H), 3.14-3.06 (m, 2H), 2.92-2.90 (m, 1H), 2.28-2.01 (m, 7H), 1.72-1.50 (m, 12H), 1.35 (d, J=6.8 Hz, 3H), 1.00 (d, J=5.2 Hz, 3H).

Example 103: 1-(1-(8-cyano-7-((cis-4-methylcyclohexyl)oxy)naphthalen-2-yl)propyl)piperidine-4-carboxylic acid

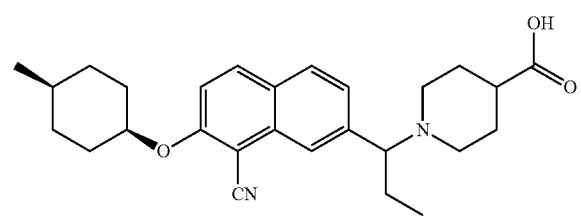 [SMILES: CCC(c1ccc2ccc(O[C@H]3CC[C@@H](C)CC3)c(C#N)c2c1)N1CCC(C(=O)O)CC1]

The title compound was prepared according to the method in Example 28 as a white solid (25 mg, 19% yield). ESI-MS (M+H)$^+$: 435.2. $^1$H NMR (400 MHz, CD$_3$OD) δ: 8.07 (d, J=9.2 Hz, 1H), 7.97-7.87 (m, 2H), 7.44-7.41 (m, 2H), 4.90 (s, 1H), 3.96-3.90 (m, 1H), 3.33-3.30 (m, 1H), 3.02-2.98 (m, 1H), 2.52-2.48 (m, 2H), 2.16-1.57 (m, 11H), 1.45-1.44 (m, 5H), 0.88 (d, J=5.6 Hz, 3H), 0.67 (d, J=7.2 Hz, 3H).

Example 104: 9-(1-(7-((cis-4-methylcyclohexyl)oxy)-8-(trifluoromethyl)naphthalen-2-yl)propyl)-9-azabicyclo[3.3.1]nonane-3-carboxylic acid

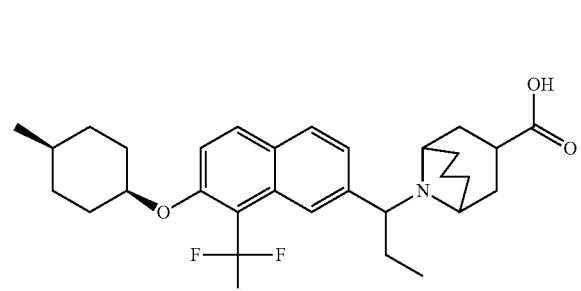

The title compound was prepared according to the method of Example 28 as a white solid (6 mg, 5% yield, 2 steps). ESI-MS (M+H)+: 518.3. ¹H NMR (400 MHz, CD₃OD) δ: 8.19 (s, 1H), 8.00 (d, J=9.2 Hz, 1H), 7.91 (d, J=8.4 Hz, 1H), 7.53 (d, J=8.0 Hz, 1H), 7.44 (d, J=9.2 Hz, 1H), 4.83 (s, 1H), 4.71-4.70 (m, 1H), 2.95-2.92 (m, 1H), 2.30-1.76 (m, 11H), 1.65-1.55 (m, 5H), 1.44-1.30 (m, 6H), 0.88 (d, J=5.6 Hz, 3H), 0.83-0.77 (m, 1H), 0.63 (t, J=7.2 Hz, 3H).

Example 105: 2,2-dimethyl-3-((1-(7-((cis-4-methyl-cyclohexyl)oxy)-8-(trifluoromethyl)naphthalen-2-yl)propyl)amino)cyclobutanecarboxylic acid

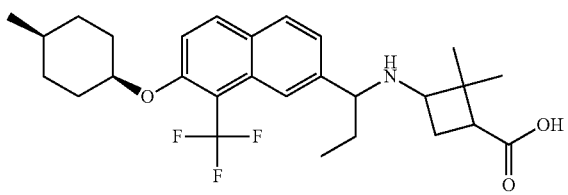 [SMILES: CCC(NC1CC(C(=O)O)C1(C)C)c1ccc2ccc(O[C@H]3CC[C@@H](C)CC3)c(C(F)(F)F)c2c1]

The title compound was prepared according to the method of Example 28 as a white solid (10 mg, 9% yield, 2 steps). ESI-MS (M+H)+: 492.1. ¹H NMR (400 MHz, CD₃OD, a mixture of diastereomers) δ: 8.12-8.07 (m, 2H), 8.00-7.94 (m, 1H), 7.55-7.47 (m, 2H), 4.92 (s, 1H), 4.16-4.00 (m, 1H), 3.01-2.85 (m, 1H), 2.48-1.67 (m, 9H), 1.55-1.41 (m, 5H), 1.29-1.17 (m, 3H), 1.12 (s, 3H), 0.97 (d, J=5.2 Hz, 3H), 0.88-0.81 (m, 3H).

Example 106: 1-((7-((cis-4-isopropylcyclohexyl)oxy)-8-(trifluoromethyl)naphthalen-2-yl)methyl)piperidine-4-carboxylic acid Step 1: 7-((cis-4-isopropylcyclohexyl)oxy)-8-(trifluoromethyl)-2-naphth aldehyde

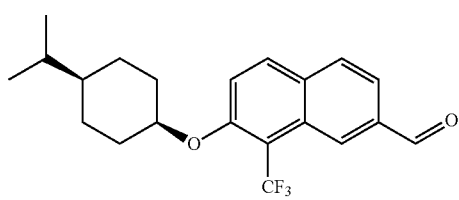 [SMILES: CC(C)[C@H]1CC[C@@H](Oc2ccc3ccc(C=O)cc3c2C(F)(F)F)CC1]

The title compound was prepared according to the method of Example 1 as a yellow oil (680 mg, 63% yield, 3 steps). ESI-MS (M+H)+: 365.2. ¹H NMR (400 MHz, CDCl₃) δ: 10.16 (s, 1H), 8.70 (s, 1H), 7.99 (d, J=9.2 Hz, 1H), 7.87 (s, 2H), 7.44 (d, J=9.2 Hz, 1H), 4.84 (s, 1H), 2.14-2.11 (m, 2H), 1.65-1.48 (m, 7H), 1.20-1.14 (m, 1H), 0.91 (d, J=6.8 Hz, 6H).

Step 2: 1-((7-((cis-4-isopropylcyclohexyl)oxy)-8-(trifluoromethyl)naphthalen-2-yl)methyl)piperidine-4-carboxylic acid

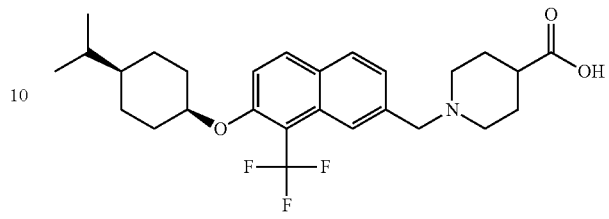

The title compound was prepared according to the method of Example 26 as a white solid (25 mg, 25% yield, 2 steps). ESI-MS (M+H)+: 478.2. ¹H NMR (400 MHz, DMSO-d₆) δ: 8.12 (d, J=9.2 Hz, 1H), 7.97 (s, 1H), 7.90 (d, J=8.4 Hz, 1H), 7.54 (d, J=9.2 Hz, 1H), 7.40 (d, J=8.0 Hz, 1H), 4.99 (s, 1H), 3.59 (s, 2H), 2.77-2.74 (m, 2H), 2.05-1.96 (m, 5H), 1.76-1.73 (m, 2H), 1.61-1.36 (m, 9H), 1.23-1.15 (m, 1H), 0.86 (d, J=6.8 Hz, 6H).

Example 107: 8-((7-((cis-4-isopropylcyclohexyl)oxy)-8-(trifluoromethyl)naphthalen-2-yl)methyl)-8-azabicyclo[3.2.1]octane-3-carboxylic acid

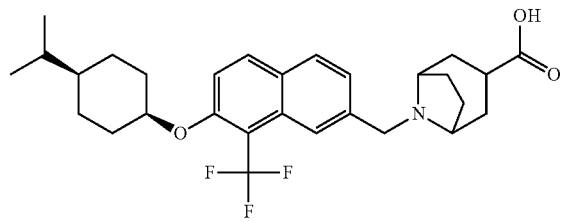 [SMILES: CC(C)[C@H]1CC[C@@H](Oc2ccc3ccc(CN4C5CCC4CC(C(=O)O)C5)cc3c2C(F)(F)F)CC1]

The title compound was prepared according to the method of Example 26 as a white solid (25 mg, 18% yield, 2 steps) ESI-MS (M+H)+: 504.3. ¹H NMR (400 MHz, CD₃OD) δ: 8.10 (s, 1H), 7.96 (d, J=9.2 Hz, 1H), 7.78 (d, J=8.4 Hz, 1H), 7.47 (d, J=8.4 Hz, 1H), 7.37 (d, J=9.2 Hz, 1H), 4.83 (s, 1H), 3.86 (s, 2H), 3.36-3.33 (m, 2H), 2.53-2.46 (m, 1H), 2.11-1.89 (m, 6H), 1.73-1.39 (m, 11H), 1.21-1.13 (m, 1H), 0.84 (d, J=6.8 Hz, 6H).

Example 108: 9-((7-((cis-4-isopropylcyclohexyl)oxy)-8-(trifluoromethyl)naphthalen-2-yl)methyl)-9-azabicyclo[3.3.1]nonane-3-carboxylic acid

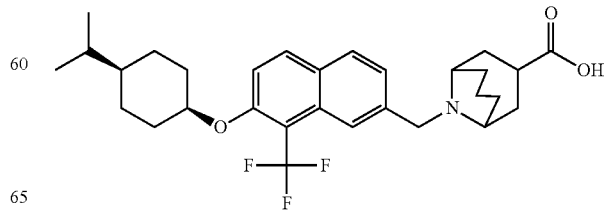

The title compound was prepared according to the method of Example 26 as a white solid (30 mg, 20% yield, 2 steps). ESI-MS (M+H)+: 518.3. ¹H NMR (400 MHz, CD₃OD) δ: 8.37 (s, 1H), 8.12 (d, J=8.4 Hz, 1H), 7.99 (d, J=8.4 Hz, 1H), 7.63 (d, J=8.4 Hz, 1H), 7.57 (d, J=9.2 Hz, 1H), 4.97 (s, 1H), 4.64 (s, 2H), 3.54-3.49 (m, 2H), 3.15-3.09 (m, 1H), 2.44-2.30 (m, 4H), 2.18-2.05 (m, 5H), 1.85-1.48 (m, 10H), 1.31-1.21 (m, 1H), 0.94 (d, J=6.8 Hz, 6H).

Example 109: 3-(((7-((cis-4-isopropylcyclohexyl)oxy)-8-(trifluoromethyl)naphthalen-2-yl)methyl)amino)-2,2-dimethylcyclobutanecarboxylic acid

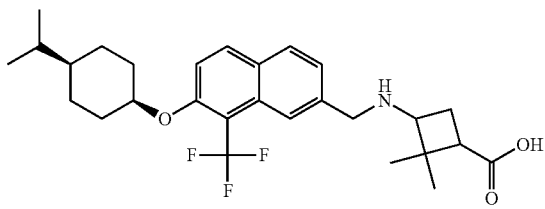 [SMILES: CC(C)[C@H]1CC[C@@H](Oc2ccc3ccc(CNC4CC(C(=O)O)C4(C)C)cc3c2C(F)(F)F)CC1]

The title compound was prepared according to the method of Example 26 as a white solid (20 mg, 15% yield, 2 steps). ESI-MS (M+H)+: 492.3. ¹H NMR (400 MHz, CD₃OD) δ: 8.13 (s, 1H), 7.98 (d, J=9.2 Hz, 1H), 7.85 (d, J=8.8 Hz, 1H), 7.44-7.41 (m, 2H), 4.83 (s, 1H), 4.09 (AB, 2H), 3.21-3.14 (m, 1H), 2.47-2.43 (m, 1H), 2.30-2.23 (m, 1H), 2.11-1.98 (m, 3H), 1.57-1.37 (m, 7H), 1.24 (s, 3H), 1.15-1.08 (m, 1H), 1.05 (s, 3H), 0.82 (d, J=6.8 Hz, 6H).

Example 110: cis-3-((1-(7-((cis-4-methylcyclohexyl)oxy)-8-(trifluoromethyl)naphthalen-2-yl)ethyl)amino)cyclobutanecarboxylic acid

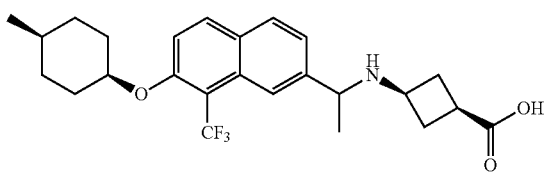 [SMILES: CC(N[C@H]1C[C@@H](C(=O)O)C1)c1ccc2ccc(O[C@H]3CC[C@@H](C)CC3)c(C(F)(F)F)c2c1]

The title compound was prepared according to the method of Example 28 as a white powder (4 mg, 3%). LCMS: MH+ 450.0. ¹H NMR (400 MHz, CD₃OD) δ 8.24 (s, 1H), 8.14 (d, J=9.22 Hz, 1H), 8.04 (d, J=8.47 Hz, 1H), 7.59 (d, J=9.29 Hz, 1H), 7.52 (d, J=8.47 Hz, 1H), 4.95 (br. s., 1H), 4.58 (q, J=6.84 Hz, 1H), 3.52-3.90 (m, 2H), 1.44-3.22 (m, 16H), 0.98 (d, J=5.8 Hz, 3H).

Example 111: trans-3-((1-(7-((cis-4-methylcyclohexyl)oxy)-8-(trifluoromethyl)naphthalen-2-yl)ethyl)amino)cyclobutanecarboxylic acid

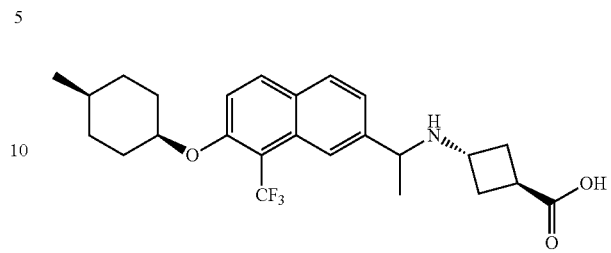

The title compound was prepared according to the method of Example 28 as a white powder (5.9 mg, 4%). LCMS: MH+ 450.00. ¹H NMR (400 MHz, CD₃OD) δ 8.23 (s, 1H), 8.14 (d, J=9.35 Hz, 1H), 8.04 (d, J=8.53 Hz, 1H), 7.59 (d, J=9.29 Hz, 1H), 7.51 (d, J=8.53 Hz, 1H), 4.95 (br. s., 1H), 4.58 (q, J=6.71 Hz, 1H), 3.79-4.04 (m, 2H), 1.36-3.29 (m, 16H), 0.98 (s, 3H).

Example 112: (1S,3R)-2,2-dimethyl-3-((1-(7-((cis-4-methylcyclohexyl)oxy)-8-(trifluoromethyl)naphthalen-2-yl)ethyl)amino)cyclobutanecarboxylic acid

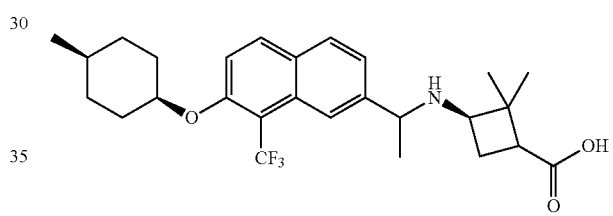

The title compound was prepared according to the method of Example 28 as a white powder (2.0 mg, 1%). LCMS: RT 1.58 min.; MH+ 478.10; ¹H NMR (400 MHz, CD₃OD) δ 8.22-8.37 (m, 1H), 8.14 (d, J=9.41 Hz, 1H), 8.05 (d, J=8.47 Hz, 1H), 7.45-7.66 (m, 2H), 4.95 (br. s., 1H), 4.60 (q, J=6.94 Hz, 1H), 3.43 (d, J=9.85 Hz, 2H), 1.97-2.93 (m, 6H), 1.15-1.86 (m, 16H), 0.98 (d, J=5.71 Hz, 3H).

Example 113: (1R,3S)-2,2-dimethyl-3-((1-(7-((cis-4-methylcyclohexyl)oxy)-8-(trifluoromethyl)naphthalen-2-yl)ethyl)amino)cyclobutanecarboxylic acid

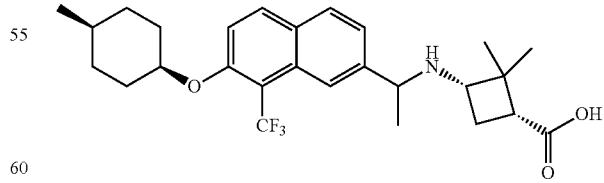

The title compound was prepared according to the method of Example 28 as a white powder (15 mg, 6%). LCMS: RT 1.59 min.; MH+ 478.10. ¹H NMR (400 MHz, CD₃OD) δ 8.22-8.33 (m, 1H), 8.14 (d, J=9.22 Hz, 1H), 8.05 (d, J=8.47 Hz, 1H), 7.37-7.64 (m, 2H), 4.95 (br. s., 1H), 4.60 (q, J=6.76

Hz, 1H), 3.36-3.47 (m, 1H), 1.97-2.93 (m, 5H), 1.42-1.85 (m, 10H), 1.12-1.40 (m, 6H), 0.98 (d, J=5.77 Hz, 3H).

Example 114

Example 114a: (1S,3S)-2,2-dimethyl-3-(((S)-1-(7-((cis-4-methylcyclohexyl)oxy)-8-(trifluoromethyl)naphthalen-2-yl)ethyl)amino)cyclobutanecarboxylic acid Example 114b: (1R,3S)-2,2-dimethyl-3-(((S)-1-(7-((cis-4-methylcyclohexyl)oxy)-8-(trifluoromethyl)naphthalen-2-yl)ethyl)amino)cyclobutanecarboxylic acid Example 114c: (1S,3S)-2,2-dimethyl-3-(((R)-1-(7-((cis-4-methylcyclohexyl)oxy)-8-(trifluoromethyl)naphthalen-2-yl)ethyl)amino)cyclobutanecarboxylic acid and Example 114d: (1R,3S)-2,2-dimethyl-3-(((R)-1-(7-((cis-4-methylcyclohexyl)oxy)-8-(trifluoromethyl)naphthalen-2-yl)ethyl)amino)cyclobutanecarboxylic acid

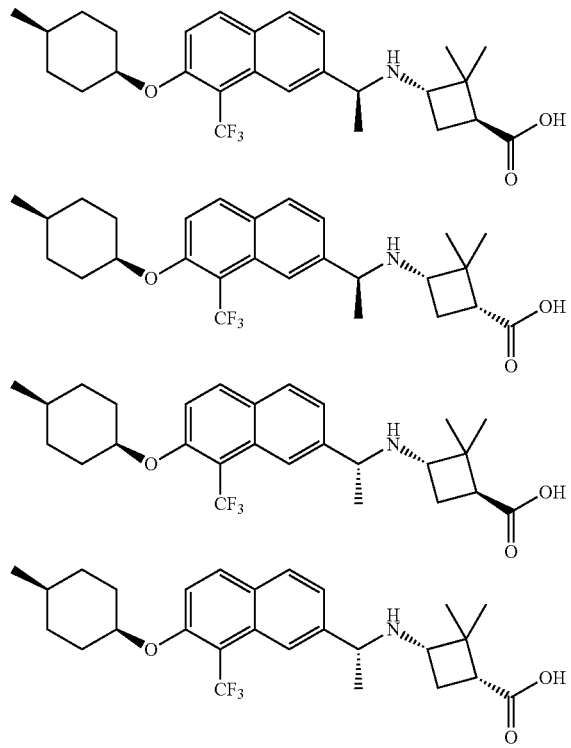

The following SFC separation of (1R,3S)-2,2-dimethyl-3-((1-(7-((cis-4-methylcyclohexyl)oxy)-8-(trifluoromethyl)naphthalen-2-yl)ethyl)amino)cyclobutanecarboxylic acid yielded 7 mg of peak-1 (chemical purity >99%), 10 mg of peak-2 (chemical purity >99%, ee >99%), 5 mg of peak-3 (chemical purity >94%) and 9 mg of peak-4 (chemical purity >99%, ee >99%). Both peaks 2 and 4 were re-worked to obtain the desired ee. Preparative Method: IC (2×15 cm), 12% isopropanol (0.1% DEA)/CO$_2$, 100 bar, 60 mL/min, 220 nm. inj vol.: 0.5 mL, 4 mg/mL methanol. Peak 1: $^1$H NMR (400 MHz, CD$_3$OD) δ 8.18 (s, 1H), 8.08 (d, J=9.16 Hz, 1H), 7.95 (d, J=8.53 Hz, 1H), 7.55 (dd, J=1.44, 8.47 Hz, 1H), 7.51 (d, J=9.22 Hz, 1H), 4.90-4.95 (m, 1H), 4.32 (q, J=6.40 Hz, 1H), 3.05 (q, J=7.32 Hz, 2H), 2.37 (t, J=8.41 Hz, 1H), 2.01-2.14 (m, 2H), 1.83-1.99 (m, 2H), 1.65-1.76 (m, 2H), 1.62 (d, J=6.71 Hz, 3H), 1.42-1.58 (m, 5H), 1.27-1.35 (m, 6H), 1.16 (s, 3H), 0.97 (d, J=5.71 Hz, 3H). LCMS Rt=1.59 min, m/z=478.10.

Peak 2: $^1$H NMR (400 MHz, CD$_3$OD) δ 8.19 (s, 1H), 8.08 (d, J=9.29 Hz, 1H), 7.96 (d, J=8.47 Hz, 1H), 7.55 (dd, J=1.47, 8.50 Hz, 1H), 7.52 (d, J=9.22 Hz, 1H), 4.89-4.95 (m, 1H), 4.31-4.41 (m, 1H), 3.10 (t, J=8.03 Hz, 1H), 2.36-2.44 (m, 1H), 2.06 (dd, J=2.98, 14.09 Hz, 1H), 1.82-2.01 (m, 1H), 1.66-1.76 (m, 2H), 1.64 (d, J=6.71 Hz, 2H), 1.43-1.58 (m, 4H), 1.31 (s, 3H), 1.17 (s, 2H), 0.97 (d, J=5.65 Hz, 2H). LCMS Rt=1.59 min, m/z=478.10.

Peak 3: $^1$H NMR (400 MHz, CD$_3$OD) δ 8.17 (s, 1H), 8.09 (d, J=9.22 Hz, 1H), 7.98 (d, J=8.47 Hz, 1H), 7.48-7.56 (m, 2H), 4.93 (br. s., 1H), 4.43 (q, J=6.96 Hz, 1H), 2.96 (t, J=7.44 Hz, 1H), 2.44-2.52 (m, 1H), 2.19-2.38 (m, 2H), 2.06 (dd, J=3.07, 13.18 Hz, 2H), 1.63-1.77 (m, 6H), 1.43-1.58 (m, 6H), 1.31 (d, J=3.07 Hz, 4H), 1.16 (s, 3H), 1.13 (s, 3H), 0.97 (d, J=5.65 Hz, 3H). LCMS Rt=1.59 min, m/z=478.10.

Peak 4: $^1$H NMR (400 MHz, CD$_3$OD) δ 8.15 (s, 1H), 8.08 (d, J=9.41 Hz, 1H), 7.96 (d, J=8.47 Hz, 1H), 7.47-7.55 (m, 2H), 4.90-4.95 (m, 1H), 4.37 (q, J=6.73 Hz, 1H), 3.04 (q, J=7.30 Hz, 1H), 2.92 (t, J=7.50 Hz, 1H), 2.40-2.48 (m, 1H), 2.14-2.35 (m, 2H), 2.06 (dd, J=3.20, 13.36 Hz, 2H), 1.68-1.76 (m, 2H), 1.66 (d, J=6.71 Hz, 3H), 1.41-1.59 (m, 4H), 1.31 (t, J=7.28 Hz, 2H), 1.13 (d, J=12.05 Hz, 6H), 0.97 (d, J=5.65 Hz, 3H). LCMS Rt=1.59 min, m/z=478.10.

Example: 115: (1S,3R)-3-((1-(7-((cis-4-ethylcyclohexyl)oxy)-8-(trifluoromethyl)naphthalen-2-yl)ethyl)amino)-2,2-dimethylcyclobutanecarboxylic acid

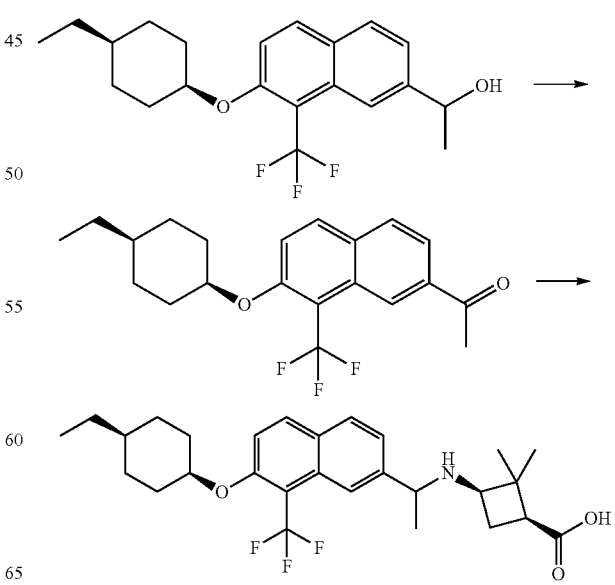

Step 1: 1-(7-((cis-4-ethylcyclohexyl)oxy)-8-(trifluoromethyl)naphthalen-2-yl)ethanone

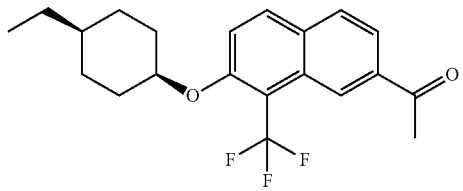 [SMILES: CC[C@H]1CC[C@@H](Oc2ccc3ccc(C(C)=O)cc3c2C(F)(F)F)CC1]

To a solution of 1-[7-(4-Ethyl-cyclohexyloxy)-8-trifluoromethyl-naphthalen-2-yl]-ethanol (2.0 g, 5.4 mmol) in methylene chloride (30.0 mL, 468 mmol) was added Dess-Martin periodinane (2.5 g, 6.0 mmol). After stirred at RT overnight, TLC showed complete conversion, diluted with EtOAc, filtered through celite. The filtrate was load on silica gel and purified by ISCO (EtOPAc/heptane gradient from 5/95 to 50/50) to give desired product as a white solid (1.70 g). LC-MS: RT 2.45 min.; MH+ 365.0; $^1$H NMR (400 MHz, CHLOROFORM-d) δ ppm 0.92 (t, J=7.28 Hz, 3H) 1.21-1.38 (m, 3H) 1.40-1.70 (m, 6H) 2.03-2.15 (m, 2H) 2.74 (s, 3H) 4.82 (br. s., 1H) 7.41 (d, J=9.29 Hz, 1H) 7.85 (d, J=8.53 Hz, 1H) 7.92-8.00 (m, 2H) 8.86 (s, 1H).

Step 2: (1S,3R)-3-((1-(7-((cis-4-ethylcyclohexyl)oxy)-8-(trifluoromethyl)naphthalen-2-yl)ethyl)amino)-2,2-dimethylcyclobutanecarboxylic acid

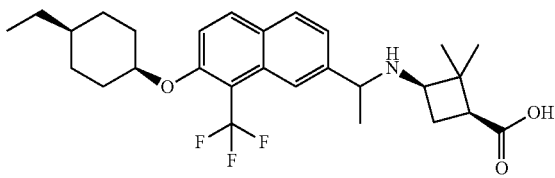 [SMILES: CC[C@H]1CC[C@@H](Oc2ccc3ccc(C(C)N[C@@H]4C[C@H](C(=O)O)C4(C)C)cc3c2C(F)(F)F)CC1]

To a mixture of 1-[7-(4-ethyl-cyclohexyloxy)-8-trifluoromethyl-naphthalen-2-yl]-ethanone (270 mg, 0.73 mmol), (1S,3R)-3-Amino-2,2-dimethyl-cyclobutanecarboxylic acid (157.2 mg, 1.098 mmol), acetic acid (41.61 uL, 0.7318 mmol) and titanium tetraisopropoxide (0.4 mL, 1.46 mmol) in 1,2-dichloroethane (4.0 mL, 51 mmol) was heated in microwave at 130° C. for 1 h. Cooled down, 1.0 M of sodium cyanoborohydride in THF (1.5 mL, 1.46 mmol) was then added. The reaction was stirred at RT overnight. The reaction was diluted with EtOAc, washed with brine, The organic phase was then dried and concentrated. The crude was purified by HPLC to give desired product as a white powder (181 mg). LCMS: RT: 1.68 min., MH+ 492.1; $^1$H NMR (400 MHz CD$_3$OD) δ=8.20-8.31 (m, 1H), 8.12 (d, J=9.3 Hz, 1H), 7.98-8.07 (m, 1H), 7.47-7.62 (m, 2H), 4.94 (br. s., 1H), 4.52-4.64 (m, 1H), 3.40 (dd, J=9.8, 8.0 Hz, 1H), 2.22-2.76 (m, 2H), 1.97-2.13 (m, 2H), 1.53-1.84 (m, 8H), 1.39-1.52 (m, 2H), 1.26-1.37 (m, 5H), 1.13-1.26 (m, 4H), 0.93 ppm (t, J=7.0 Hz, 3H).

Example: 116: ((1R,3S)-3-((1-(7-((cis-4-ethylcyclohexyl)oxy)-8-(trifluoromethyl)naphthalen-2-yl)ethyl)amino)-2,2-dimethylcyclobutanecarboxylic acid

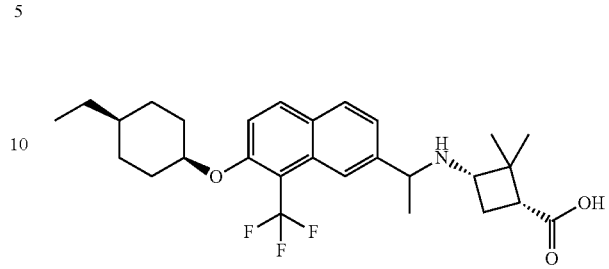

The title compound was prepared according to the method of Example 115 to give a white powder (102 mg). LCMS: RT: 1.67 min., MH+ 492.1; $^1$H NMR (400 MHz, CD$_3$OD) δ ppm 0.93 (t, J=7.03 Hz, 3H) 1.14-1.25 (m, 4H) 1.26-1.37 (m, 5H) 1.38-1.52 (m, 2H) 1.53-1.83 (m, 8H) 1.97-2.12 (m, 2H) 2.23-2.74 (m, 2H) 3.40 (dd, J=9.79, 7.78 Hz, 1H) 4.52-4.65 (m, 1H) 4.95 (br. s., 1H) 7.47-7.62 (m, 2H) 7.98-8.07 (m, 1H) 8.12 (d, J=9.29 Hz, 1H) 8.19-8.31 (m, 1H).

Example: 117

Example 117a: (1R,3R)-3-(((S)-1-(7-((cis-4-ethylcyclohexyl)oxy)-8-(trifluoromethyl)naphthalen-2-yl)ethyl)amino)-2,2-dimethylcyclobutanecarboxylic acid Example 117b: (1S,3R)-3-(((S)-1-(7-((cis-4-ethylcyclohexyl)oxy)-8-(trifluoromethyl)naphthalen-2-yl)ethyl)amino)-2,2-dimethylcyclobutanecarboxylic acid Example 117c: (1R,3R)-3-(((R)-1-(7-((cis-4-ethylcyclohexyl)oxy)-8-(trifluoromethyl)naphthalen-2-yl)ethyl)amino)-2,2-dimethylcyclobutanecarboxylic acid and Example 117d: (1S,3R)-3-(((R)-1-(7-((cis-4-ethylcyclohexyl)oxy)-8-(trifluoromethyl)naphthalen-2-yl)ethyl)amino)-2,2-dimethylcyclobutanecarboxylic acid

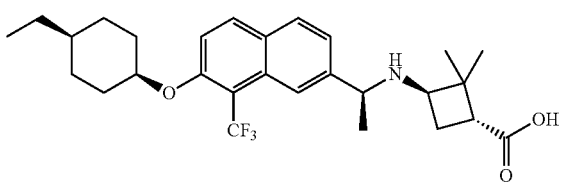

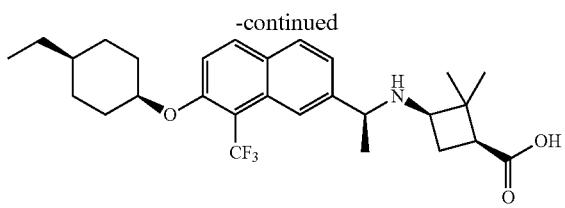

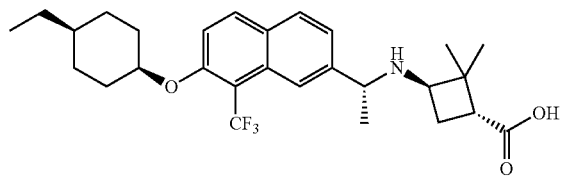 [SMILES: CC[C@H]1CC[C@@H](Oc2ccc3ccc(C(C)N[C@H]4C[C@@H](C(=O)O)C4(C)C)cc3c2C(F)(F)F)CC1]

(1S,3R)-3-((1-(7-((cis-4-ethylcyclohexyl)oxy)-8-(trifluoromethyl)naphthalen-2-yl)ethyl)amino)-2,2-dimethylcyclobutanecarboxylic acid (168 mg, 0.342 mmol) was sent for chiral separation. The chiral separation (conditions: IC (2×15 cm)-(3×15 cm), 20% methanol (0.1% DEA)/CO$_2$, 100 bar; 60 mL/min, 220 nm; inj vol.: 0.6 mL, 10 mg/mL methanol) yielded 77 mg of peak-1 (chemical purity >99%), 10 mg of peak-2 (chemical purity >99%), 85 mg of peak-3 (chemical purity >99%) and 5 mg of peak-4 (chemical purity >99%). The stereo centers were not assigned. Peak#1 (chiral HPLC RT 2.27 min): LCMS: RT 1.67 min. MH+ 492.1; $^1$H NMR (400 MHz, CD$_3$OD) δ ppm 0.93 (t, J=7.15 Hz, 3H) 1.16-1.52 (m, 11H) 1.53-1.84 (m, 8H) 1.97-2.12 (m, 3H) 2.59 (dd, J=10.29, 7.78 Hz, 1H) 3.40 (dd, J=9.79, 8.03 Hz, 1H) 4.58 (q, J=6.78 Hz, 1H) 4.95 (br. s., 1H) 7.52-7.61 (m, 2H) 8.03 (d, J=8.53 Hz, 1H) 8.12 (d, J=9.29 Hz, 1H) 8.27 (s, 1H); Peak#2 (chiral HPLC RT 2.57 min): LCMS: RT 1.67 min. MH+ 492.1; $^1$H NMR (400 MHz CD$_3$OD) δ=8.27 (s, 1H), 8.12 (d, J=9.3 Hz, 1H), 8.03 (d, J=8.5 Hz, 1H), 7.50-7.62 (m, 2H), 4.95 (br. s., 1H), 4.58 (q, J=6.8 Hz, 1H), 3.40 (dd, J=9.8, 7.8 Hz, 1H), 2.60 (dd, J=10.5, 7.8 Hz, 1H), 1.96-2.13 (m, 3H), 1.54-1.83 (m, 8H), 1.38-1.52 (m, 2H), 1.34 (s, 6H), 1.23 (s, 3H), 0.93 ppm (t, J=7.0 Hz, 3H); Peak#3 (chiral HPLC RT 3.02 min): LCMS: RT 1.67 min. MH+ 492.1; $^1$H NMR (400 MHz CD$_3$OD) δ=8.23 (s, 1H), 8.13 (d, J=9.3 Hz, 1H), 8.04 (d, J=8.3 Hz, 1H), 7.58 (d, J=9.3 Hz, 2H), 4.92-4.99 (m, 1H), 4.52-4.62 (m, 1H), 3.19-3.28 (m, 1H), 2.66 (s, 1H), 2.24-2.50 (m, 2H), 1.99-2.13 (m, 2H), 1.54-1.83 (m, 7H), 1.38-1.52 (m, 2H), 1.26-1.38 (m, 3H), 1.19 (d, J=12.0 Hz, 6H), 0.93 ppm (t, J=7.2 Hz, 3H); Peak#4 (chiral HPLC RT 3.59 min): LCMS: RT 1.68 min. MH+ 492.1; $^1$H NMR (400 MHz CD$_3$OD) δ=8.23 (s, 1H), 8.13 (d, J=9.3 Hz, 1H), 8.04 (d, J=8.5 Hz, 1H), 7.47-7.63 (m, 2H), 4.95 (br. s., 1H), 4.57 (q, J=6.8 Hz, 1H), 3.25 (dd, J=9.8, 8.0 Hz, 1H), 2.68 (dd, J=10.3, 7.8 Hz, 1H), 2.25-2.49 (m, 2H), 1.99-2.12 (m, 2H), 1.78 (d, J=6.8 Hz, 3H), 1.69 (t, J=13.4 Hz, 2H), 1.59 (d, J=10.3 Hz, 2H), 1.39-1.51 (m, 2H), 1.30-1.36 (m, 3H), 1.19 (d, J=11.3 Hz, 6H), 0.93 ppm (t, J=7.2 Hz, 3H).

Example: 118

Example 118a: (1S,3S)-3-(((S)-1-(7-((cis-4-ethylcyclohexyl)oxy)-8-(trifluoromethyl)naphthalen-2-yl)ethyl)amino)-2,2-dimethylcyclobutanecarboxylic acid Example 118b: (1R,3S)-3-(((S)-1-(7-((cis-4-ethylcyclohexyl)oxy)-8-(trifluoromethyl)naphthalen-2-yl)ethyl)amino)-2,2-dimethylcyclobutanecarboxylic acid Example 118c: (1S,3S)-3-(((R)-1-(7-((cis-4-ethylcyclohexyl)oxy)-8-(trifluoromethyl)naphthalen-2-yl)ethyl)amino)-2,2-dimethylcyclobutanecarboxylic acid and Example 118d: (1R,3S)-3-(((R)-1-(7-((cis-4-ethylcyclohexyl)oxy)-8-(trifluoromethyl)naphthalen-2-yl)ethyl)amino)-2,2-dimethylcyclobutanecarboxylic acid

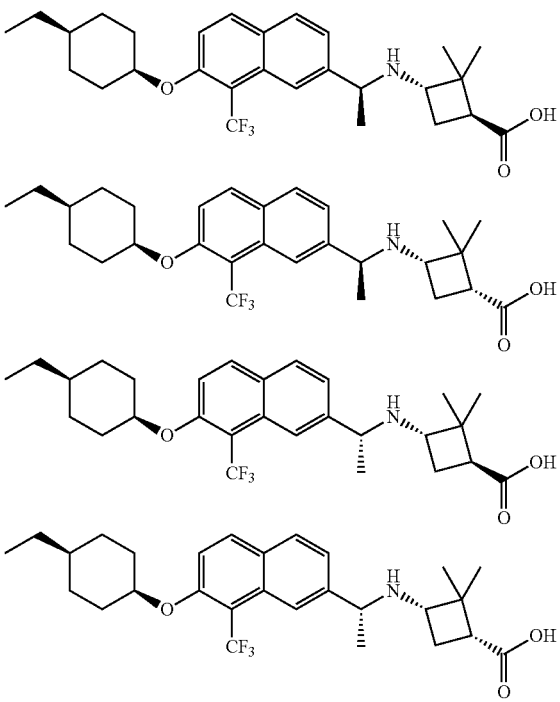

(1R,3S)-3-((1-(7-((cis-4-ethylcyclohexyl)oxy)-8-(trifluoromethyl) naphthalen-2-yl)ethyl)amino)-2,2-dimethylcyclobutanecarboxylic acid (92 mg, 0.19 mmol) was sent for chiral separation. The chiral separation (method: IC (2×15 cm)-(3×15 cm), 20% methanol (0.1% DEA)/CO$_2$, 100 bar; 60 mL/min, 220 nm; inj vol.: 0.5 mL, 9 mg/mL methanol) yielded 9 mg of peak-1 (chemical purity >99%), 41 mg of peak-2 (chemical purity >99%), 8 mg of peak-3 (chemical purity >99%) and 20 mg of peak-4 (chemical purity >99%). The stereo centers were not assigned. Peak#1 (chiral HPLC RT 3.24 min): LCMS: RT 1.66 min.; MH+ 492.1; $^1$H NMR (400 MHz, CD$_3$OD) δ 8.20 (s, 1H), 8.08 (d, J=9.29 Hz, 1H), 7.96 (d, J=8.28 Hz, 1H), 7.53 (t, J=8.91 Hz, 2H), 4.92 (br. s., 1H), 4.40 (q, J=6.53 Hz, 1H), 3.15 (t, J=8.03 Hz, 1H), 2.43 (t, J=8.03 Hz, 1H), 1.77-2.13 (m, 4H), 1.53-1.74 (m, 7H), 1.38-1.52 (m, 2H), 1.24-1.37 (m, 6H), 1.17 (s, 3H), 0.90-0.98 (m, 3H); Peak#2 (chiral HPLC RT 3.68 min): LCMS: RT 1.66 min.; MH+ 492.1; $^1$H NMR (400 MHz, CD$_3$OD) δ 8.27 (s, 1H), 8.12 (d, J=9.29 Hz, 1H), 8.03 (d, J=8.53 Hz, 1H), 7.49-7.62 (m, 2H), 4.95 (br. s., 1H), 4.58 (q, J=6.78 Hz, 1H), 3.40 (dd, J=8.03, 9.79 Hz, 1H), 2.59 (dd, J=7.78, 10.54 Hz, 1H), 1.96-2.13 (m, 3H), 1.53-1.83 (m, 8H), 1.38-1.52 (m, 2H), 1.15-1.37 (m, 9H), 0.93 (d, J=14.31 Hz, 3H); Peak#3 (chiral HPLC RT 4.53 min): LCMS: RT 1.67 min.; MH+ 492.1; $^1$H NMR (400 MHz, CD$_3$OD) δ 8.18 (s, 1H), 8.10 (d, J=9.29 Hz, 1H), 7.99 (d, J=8.53 Hz, 1H), 7.44-7.59 (m, 2H), 4.94 (br. s., 1H), 4.48 (q, J=6.53 Hz, 1H), 3.03 (t, J=7.53 Hz, 1H), 2.54 (br. s., 1H), 2.31 (br. s., 2H), 1.98-2.13 (m, 2H), 1.54-1.77 (m, 7H), 1.39-1.52 (m, 2H), 1.24-1.38 (m, 3H), 1.15 (br. s., 6H), 0.93 (t, J=7.15 Hz, 3H); Peak#4 (chiral HPLC RT 5.44 min): LCMS: RT 1.66 min.; MH+ 492.1; 1H NMR (400 MHz, CD$_3$OD) δ 8.23 (s, 1H), 8.13 (d, J=9.29 Hz, 1H), 8.04 (d, J=8.53 Hz, 1H), 7.45-7.63 (m, 2H), 4.95 (br. s., 1H), 4.57 (q, J=6.78 Hz, 1H), 3.25 (dd, J=8.03, 9.79 Hz, 1H), 2.63-2.72 (m, 1H), 2.25-2.49 (m, 2H), 1.99-2.12 (m, 2H), 1.53-1.84 (m, 7H), 1.10-1.52 (m, 11H), 0.93 (t, J=7.15 Hz, 3H).

Example: 119: (1S,3R)-2,2-dimethyl-3-((1-(8-(trifluoromethyl)-7-((cis-4-(trifluoromethyl) cyclohexyl) oxy)naphthalen-2-yl)ethyl)amino)cyclobutanecarboxylic acid

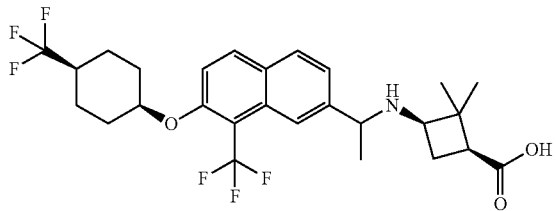 [SMILES: CC(N[C@@H]1C[C@H](C(=O)O)C1(C)C)c1ccc2ccc(O[C@H]3CC[C@@H](C(F)(F)F)CC3)c(C(F)(F)F)c2c1]

The title compound was prepared according to the method of Example 115 to give a white powder (198 mg, 30%). LCMS: RT: 1.52 min., MH+ 532.0; $^1$H NMR (400 MHz CD$_3$OD) δ=8.22-8.32 (m, 1H), 8.15 (d, J=9.3 Hz, 1H), 8.00-8.09 (m, 1H), 7.48-7.65 (m, 2H), 5.03 (br. s., 1H), 4.52-4.65 (m, 1H), 3.41 (dd, J=9.8, 7.8 Hz, 1H), 2.54-2.72 (m, 1H), 2.18 (d, J=12.5 Hz, 4H), 1.55-1.90 (m, 10H), 1.34 (s, 2H), 1.13-1.27 ppm (m, 4H).

Example: 120: (1R,3S)-2,2-dimethyl-3-((1-(8-(trifluoromethyl)-7-((cis-4-(trifluoromethyl) cyclohexyl) oxy)naphthalen-2-yl)ethyl)amino)cyclobutanecarboxylic acid

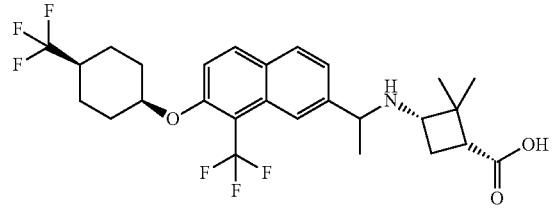

The title compound was prepared according to the method of Example 114 to give a white powder (210 mg, 53%). LCMS: RT: 1.52 min., MH+ 532.0; $^1$H NMR (400 MHz CD$_3$OD) δ=8.22-8.33 (m, 1H), 8.15 (d, J=9.3 Hz, 1H), 8.00-8.08 (m, 1H), 7.50-7.63 (m, 2H), 5.02 (br. s., 1H), 4.51-4.65 (m, 1H), 3.41 (dd, J=9.8, 7.8 Hz, 1H), 2.53-2.74 (m, 1H), 1.96-2.50 (m, 4H), 1.55-1.91 (m, 10H), 1.34 (s, 2H), 1.12-1.27 ppm (m, 4H).

Example: 121

Example 121a: (1R,3R)-2,2-dimethyl-3-(((S)-1-(8-(trifluoromethyl)-7-((cis-4-(trifluoromethyl)cyclohexyl)oxy)naphthalen-2-yl)ethyl)amino)cyclobutanecarboxylic acid Example 121b: (1S,3R)-2,2-dimethyl-3-(((S)-1-(8-(trifluoromethyl)-7-((cis-4-(trifluoromethyl)cyclohexyl)oxy)naphthalen-2-yl)ethyl)amino)cyclobutanecarboxylic acid Example 121c: (1R,3R)-2,2-dimethyl-3-(((R)-1-(8-(trifluoromethyl)-7-((cis-4-(trifluoromethyl)cyclohexyl)oxy)naphthalen-2-yl)ethyl)amino)cyclobutanecarboxylic acid and Example 121d: (1S,3R)-2,2-dimethyl-3-(((R)-1-(8-(trifluoromethyl)-7-((cis-4-(trifluoromethyl)cyclohexyl)oxy)naphthalen-2-yl)ethyl)amino)cyclobutanecarboxylic acid

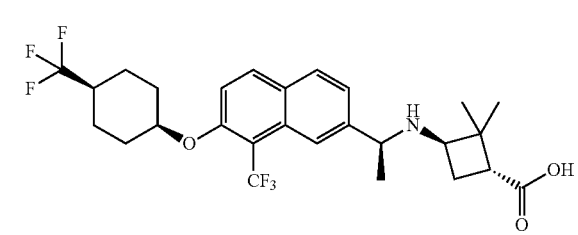

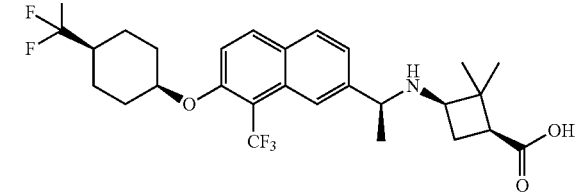

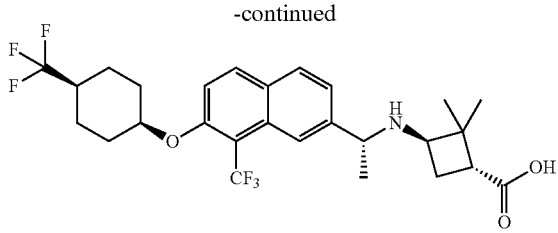

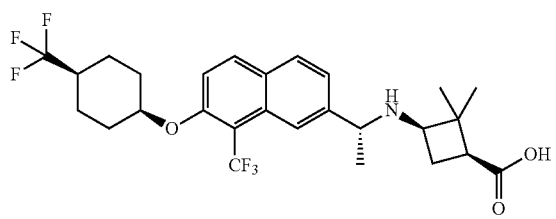

(1S,3R)-2,2-Dimethyl-3-{1-[8-trifluoromethyl-7-(4-trifluoromethyl-cyclohexyloxy)-naphthalen-2-yl]-ethylamino}-cyclobutanecarboxylic acid (183 mg, 0.344 mmol) was sent for chiral separation. The chiral separation yielded 75 mg of peak-1 (chemical purity >99%), 12 mg of peak-2 (chemical purity >99%), 39 mg of peak-3 (chemical purity >99%) and 8 mg of peak-4 (chemical purity >98%). Chiral method: Step 1: separation of Peaks 1+2 from Peaks 3+4, analytical method: IC (25×0.46 cm), 20% methanol (DEA)/CO2, 100 bar, 3.0 mL/min, 220 and 254 nm, prep method: IC (2×15 cm)-(3×15 cm), 15% methanol (0.1% DEA)/CO2, 100 bar, 60 mL/min, 220 nm; Step 2: Isolation of Peak 1 and Peak 2, analytical method: IC (15×0.46 cm), 15% isopropanol (DEA)/CO2, 100 bar, 3.0 mL/min, 220 and 254 nm, prep method: IC (2×15 cm)-(3×15 cm), 20% isopropanol (0.1% DEA)/CO2, 100 bar, 70 ml/min, 220 nm; Step 3: Isolation of Peak 3 and Peak 4, analytical method: IC (15×0.46 cm), 20% methanol (DEA)/CO2, 100 bar, 3.0 mL/min, 220 and 254 nm, prep method: IC (2×15 cm)-(3×15 cm), 12% methanol (0.1% DEA)/CO2, 100 bar, 70 mL/min, 220 nm. The stereo centers were not assigned. Peak#1: LCMS: RT 1.52 min. MH+ 532.0; $^1$H NMR (400 MHz, CD$_3$OD) δ 8.29 (s, 1H), 8.15 (d, J=9.29 Hz, 1H), 8.05 (d, J=8.53 Hz, 1H), 7.51-7.64 (m, 2H), 5.03 (br. s., 1H), 4.59 (q, J=6.78 Hz, 1H), 3.41 (dd, J=7.78, 9.79 Hz, 1H), 2.60 (dd, J=7.78, 10.54 Hz, 1H), 2.11-2.38 (m, 3H), 2.03 (q, J=10.54 Hz, 1H), 1.55-1.91 (m, 10H), 1.34 (s, 3H), 1.23 (s, 3H); Peak#2: LCMS: RT 1.52 min. MH+ 532.0; $^1$H NMR (400 MHz, CD$_3$OD) δ 8.30 (s, 1H), 8.15 (d, J=9.29 Hz, 1H), 8.05 (d, J=8.53 Hz, 1H), 7.51-7.65 (m, 2H), 5.03 (br. s., 1H), 4.59 (q, J=6.78 Hz, 1H), 3.41 (dd, J=8.03, 9.79 Hz, 1H), 2.60 (dd, J=7.78, 10.54 Hz, 1H), 2.12-2.38 (m, 3H), 1.97-2.10 (m, 1H), 1.57-1.89 (m, 10H), 1.32-1.38 (m, 3H), 1.23 (s, 3H); Peak#3: LCMS: RT 1.52 min. MH+ 532.0; $^1$H NMR (400 MHz, CD$_3$OD) δ 8.26 (s, 1H), 8.16 (d, J=9.29 Hz, 1H), 8.06 (d, J=8.53 Hz, 1H), 7.49-7.65 (m, 2H), 5.03 (br. s., 1H), 4.58 (q, J=6.78 Hz, 1H), 3.25 (dd, J=8.03, 9.54 Hz, 1H), 2.68 (dd, J=7.91, 10.16 Hz, 1H), 2.11-2.50 (m, 5H), 1.67-1.90 (m, 9H), 1.20 (d, J=10.79 Hz, 6H); Peak#4: LCMS: RT 1.51 min. MH+ 532.0; $^1$H NMR (400 MHz, CD$_3$OD) δ ppm 1.20 (d, J=11.29 Hz, 6H), 1.68-1.89 (m, 9H), 2.10-2.50 (m, 5H), 2.68 (dd, J=10.29, 7.78 Hz, 1H), 3.25 (dd, J=9.79, 8.03 Hz, 1H), 4.58 (q, J=6.61 Hz, 1H), 5.03 (br. s., 1H), 7.48-7.66 (m, 2H), 8.06 (d, J=8.53 Hz, 1H), 8.16 (d, J=9.29 Hz, 1H), 8.25 (s, 1H).

Example: 122

Example 122a: (1R,3R)-2,2-dimethyl-3-(((S)-1-(8-(trifluoromethyl)-7-((cis-4-(trifluoromethyl)cyclohexyl)oxy)naphthalen-2-yl)ethyl)amino)cyclobutanecarboxylic acid Example 122b: (1S,3R)-2,2-dimethyl-3-(((S)-1-(8-(trifluoroethyl)-7-cis-4-(trifluoromethyl)cyclohexyl)oxy)naphthalen-2-yl)ethyl)amino)cyclobutanecarboxylic acid Example 122c: (1R,3R)-2,2-dimethyl-3-(((R)-1-(8-(trifluoromethyl)-7-((cis-4-(trifluoromethyl)cyclohexyl)oxy)naphthalen-2-yl)ethyl)amino)cyclobutanecarboxylic acid and Example 122d: (1S,3R)-2,2-dimethyl-3-(((R)-1-(8-(trifluoromethyl)-7-((cis-4-(trifluoromethyl)cyclohexyl)oxy)naphthalen-2-yl)ethyl)amino)cyclobutanecarboxylic acid

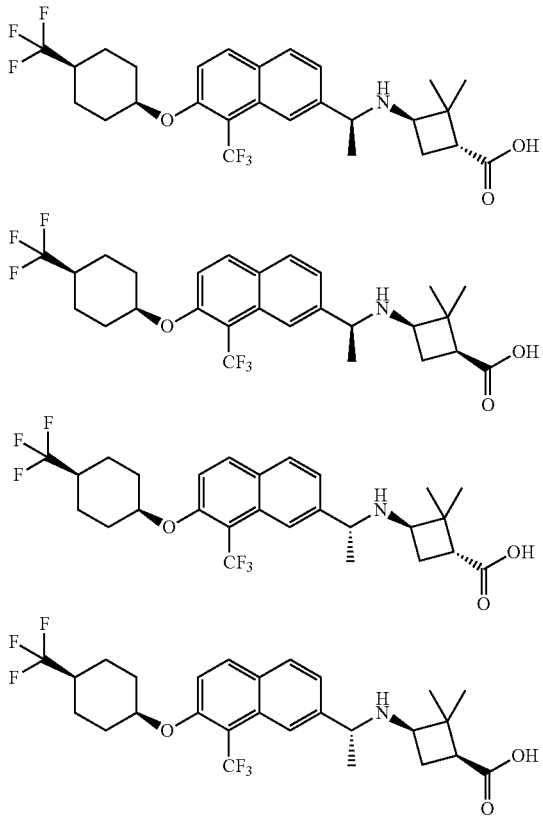

(1R,3S)-2,2-Dimethyl-3-{1-[8-trifluoromethyl-7-(4-trifluoromethyl-cyclohexyloxy)-naphthalen-2-yl]-ethylamino}-cyclobutanecarboxylic acid (205 mg, 0.39 mmol) was sent for chiral separation. The chiral separation yielded 20 mg of peak-1 (chemical purity >99%), 82 mg of peak-2 (chemical purity >99%), 12 mg of peak-3 (chemical purity >99%) and 38 mg of peak-4 (chemical purity >99%). The chiral method: Step 1: Separation of Peaks 1, 2, 3 and 4, IC (2×15 cm)-(3×15 cm), 15% methanol (0.1% DEA)/CO$_2$, 100 bar, 65 mL/min, 220 nm; Step 2: Re-purification of peak-2: IC (2×15 cm)-(3×15 cm), 15% isopropanol (0.1% DEA)/CO$_2$, 100 bar, 70 mL/min, 220 nm; Step 3: Re-purification of peak-3 and peak-4, IC (2×15 cm)-(3×15 cm), 15% methanol (0.1% DEA)/CO2, 100 bar, 65 mL/min, 220 nm. The stereo centers were not assigned. Peak#1 LCMS: RT 1.52 min.; MH+ 532.0; $^1$H NMR (400 MHz CD$_3$OD) δ=8.30 (s, 1H), 8.15 (d, J=9.3 Hz, 1H), 8.05 (d, J=8.5 Hz, 1H), 7.51-7.64 (m, 2H), 5.03 (br. s., 1H), 4.59 (q, J=6.8 Hz, 1H), 3.41 (dd, J=9.7, 7.9 Hz, 1H), 2.60 (dd, J=10.5, 7.8 Hz, 1H), 2.11-2.37 (m, 3H), 1.97-2.09 (m, 1H), 1.56-1.91 (m, 10H), 1.34 (s, 3H), 1.23 ppm (s, 3H); Peak#2: LCMS: RT 1.51 min.; MH+ 532.0; $^1$H NMR (400 MHz CD$_3$OD) δ=8.29 (s, 1H), 8.15 (d, J=9.3 Hz, 1H), 8.04 (d, J=8.5 Hz, 1H), 7.52-7.64 (m, 2H), 5.02 (br. s., 1H), 4.59 (q, J=6.8 Hz, 1H), 3.41 (dd, J=9.8, 8.0 Hz, 1H), 2.59 (dd, J=10.3, 7.8 Hz, 1H), 2.11-2.39 (m, 3H), 1.97-2.10 (m, 1H), 1.68-1.90 (m, 9H), 1.63 (dt, J=11.8, 7.8 Hz, 1H), 1.34 (s, 3H), 1.23 ppm (s, 3H); Peak#3: LCMS: RT 1.52 min.; MH+ 532.0; $^1$H NMR (400 MHz CD$_3$OD) δ=8.22-8.32 (m, 1H), 8.16 (d, J=9.3 Hz, 1H), 8.01-8.10 (m, 1H), 7.48-7.66 (m, 2H), 5.03 (br. s., 1H), 4.58 (q, J=6.7 Hz, 1H), 3.20-3.27 (m, 1H), 2.68 (dd, J=10.2, 7.9 Hz, 1H), 2.10-2.49 (m, 5H), 1.67-1.90 (m, 9H), 1.12-1.26 ppm (m, 6H); Peak#4: LCMS: RT 1.52 min.; MH+ 532.0; $^1$H NMR (400 MHz CD$_3$OD) δ=8.26 (s, 1H), 8.16 (d, J=9.3 Hz, 1H), 8.06 (d, J=8.5 Hz, 1H), 7.61 (d, J=9.3 Hz, 1H), 7.53 (dd, J=8.5, 1.0 Hz, 1H), 5.03 (br. s., 1H), 4.58 (q, J=6.8 Hz, 1H), 3.25 (dd, J=9.8, 8.0 Hz, 1H), 2.68 (dd, J=10.2, 7.9 Hz, 1H), 2.09-2.50 (m, 5H), 1.67-1.91 (m, 9H), 1.20 ppm (d, J=10.8 Hz, 6H).

Example 123: 1-((8-(trifluoromethyl)-7-((cis-4-(trifluoromethyl)cyclohexyl)oxy) naphthalen-2-yl)methyl)azepane-4-carboxylic acid

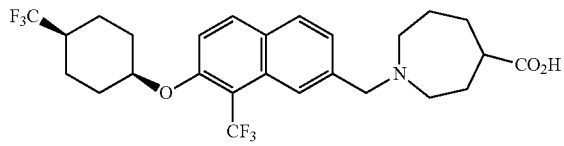 [SMILES: O=C(O)C1CCCN(Cc2ccc3ccc(O[C@H]4CC[C@@H](C(F)(F)F)CC4)c(C(F)(F)F)c3c2)CC1]

The title compound was prepared according to the method of Example 7. $^1$H NMR (400 MHz, CD$_3$OD) δ 8.34 (s, 1H), 8.16 (d, J=9.29 Hz, 1H), 8.03 (d, J=8.53 Hz, 1H), 7.46-7.68 (m, 2H), 5.03 (br. s., 1H), 4.56 (s, 2H), 3.21-3.65 (m, 4H), 2.77 (br. s., 1H), 1.63-2.40 (m, 15H); LCMS m/z 518.0 [M+H]$^+$ Example 124: cis-4-(((8-(trifluoromethyl)-7-((cis-4-(trifluoromethyl) cyclohexyl)oxy)naphthalen-2-yl)methyl)amino)cyclohexanecarboxylic acid

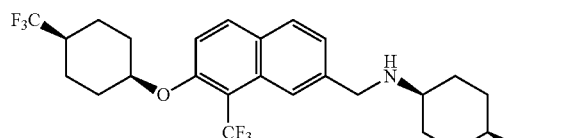

The title compound was prepared according to the method of Example 7. $^1$H NMR (400 MHz, CD$_3$OD) δ 8.31 (s, 1H), 8.13 (d, J=9.29 Hz, 1H), 8.00 (d, J=8.53 Hz, 1H), 7.47-7.64 (m, 2H), 5.01 (br. s., 1H), 4.40 (s, 2H), 3.18-3.32 (m, 1H), 2.71 (d, J=3.26 Hz, 1H), 2.06-2.37 (m, 7H), 1.57-1.89 (m, 10H); LCMS m/z 518.0 [M+H]$^+$ Example 125: trans-4-(((8-(trifluoromethyl)-7-((cis-4-(trifluoromethyl) cyclohexyl)oxy)naphthalen-2-yl)methyl)amino)cyclohexanecarboxylic acid

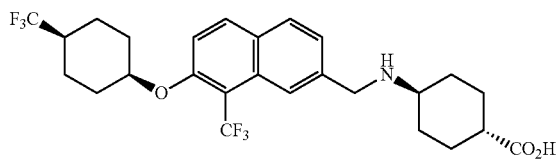 [SMILES: O=C(O)[C@H]1CC[C@H](NCc2ccc3ccc(O[C@H]4CC[C@@H](C(F)(F)F)CC4)c(C(F)(F)F)c3c2)CC1]

The title compound was prepared according to the method of Example 7. $^1$H NMR (400 MHz, CD$_3$OD) δ 8.32 (s, 1H), 8.14 (d, J=9.29 Hz, 1H), 8.01 (d, J=8.53 Hz, 1H), 7.45-7.66 (m, 2H), 5.02 (br. s., 1H), 4.42 (s, 2H), 3.16-3.32 (m, 1H), 1.38-2.41 (m, 18H); LCMS m/z 518.0 [M+H]$^+$ Example 126: 2-(4-(((8-(trifluoromethyl)-7-((cis-4-(trifluoromethyl) cyclohexyl)oxy)naphthalen-2-yl)methyl)amino)cyclohexyl)acetic acid

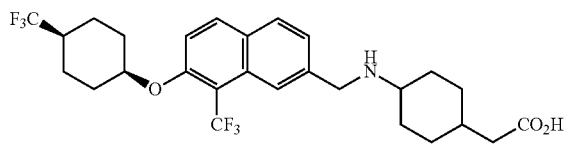 [SMILES: O=C(O)CC1CCC(NCc2ccc3ccc(O[C@H]4CC[C@@H](C(F)(F)F)CC4)c(C(F)(F)F)c3c2)CC1]

The title compound was prepared according to the method of Example 7. $^1$H NMR (400 MHz, CD$_3$OD) δ 8.31 (s, 1H), 8.14 (d, J=9.29 Hz, 1H), 8.01 (d, J=8.28 Hz, 1H), 7.44-7.64 (m, 2H), 5.02 (br. s., 1H), 4.41 (s, 2H), 3.06-3.23 (m, 1H), 2.11-2.35 (m, 6H), 1.98 (d, J=12.30 Hz, 2H), 1.65-1.87 (m, 7H), 1.42-1.60 (m, 2H), 1.03-1.25 (m, 2H); LCMS m/z 532.0 [M+H]$^+$ Example 127: 3-(((8-(trifluoromethyl)-7-((cis-4-(trifluoromethyl)cyclohexyl) oxy)naphthalen-2-yl)methyl)amino)cyclopentanecarboxylic acid

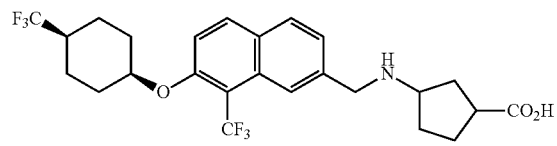 [SMILES: O=C(O)C1CCC(NCc2ccc3ccc(O[C@H]4CC[C@@H](C(F)(F)F)CC4)c(C(F)(F)F)c3c2)C1]

The title compound was prepared according to the method of Example 7. $^1$H NMR (400 MHz, CD$_3$OD) δ 8.32 (s, 1H), 8.14 (d, J=9.29 Hz, 1H), 8.01 (d, J=8.53 Hz, 1H), 7.56 (dd, J=8.78, 19.33 Hz, 2H), 5.02 (br. s., 1H), 4.34-4.50 (m, 2H), 3.73 (quin, J=7.53 Hz, 1H), 2.97 (quin, J=7.91 Hz, 1H), 2.35-2.53 (m, 1H), 1.66-2.33 (m, 14H); LCMS m/z 504.0 [M+H]$^+$ Example 128: 3-(((8-(trifluoromethyl)-7-((cis-4-(trifluoromethyl)cyclohexyl) oxy)naphthalen-2-yl)methyl)amino)cyclobutanecarboxylic acid

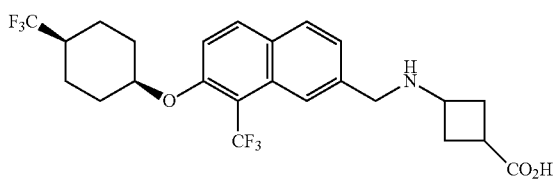 [SMILES: O=C(O)C1CC(NCc2ccc3ccc(O[C@H]4CC[C@@H](C(F)(F)F)CC4)c(C(F)(F)F)c3c2)C1]

The title compound was prepared according to the method of Example 7. $^1$H NMR (400 MHz, CD$_3$OD) δ 8.29 (s, 1H), 8.14 (d, J=9.29 Hz, 1H), 8.01 (d, J=8.53 Hz, 1H), 7.41-7.64 (m, 2H), 5.02 (br. s., 1H), 4.31 (s, 2H), 3.81 (quin, J=8.28 Hz, 1H), 2.96-3.09 (m, 1H), 2.62 (dtd, J=2.76, 7.78, 10.04 Hz, 2H), 2.36-2.48 (m, 2H), 2.08-2.33 (m, 3H), 1.65-1.92 (m, 6H); LCMS m/z 490.0.0 [M+H]$^+$ Example 129: cis-4-((1-(8-(trifluoromethyl)-7-((cis-4-(trifluoromethyl)cyclohexyl) oxy)naphthalen-2-yl)ethyl)amino)cyclohexanecarboxylic acid

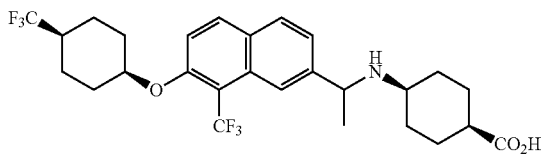 [SMILES: CC(N[C@H]1CC[C@@H](C(=O)O)CC1)c1ccc2ccc(O[C@H]3CC[C@@H](C(F)(F)F)CC3)c(C(F)(F)F)c2c1]

The title compound was prepared according to the method of Example 28 as a white powder after lyophilization (443 mg, yield 84%). $^1$H NMR (400 MHz, CD$_3$OD) δ: 8.27 (s, 1H), 8.16 (d, J=9.2 Hz, 1H), 8.05 (d, J=8.4 Hz, 1H), 7.61 (d, J=9.2 Hz, 1H), 7.55 (dd, J=1.6 Hz, 8.8 Hz, 1H), 5.04 (s, 1H), 4.79 (q, J=6.8 Hz, 1H), 2.91-2.86 (m, 1H), 2.64-2.60 (m, 1H), 2.30-2.11 (m, 6H), 1.93-1.44 (m, 14H). LCMS m/z 532.2 [M+H]$^+$ Example 130: 4-((1-(7-((cis-4-ethylcyclohexyl)oxy)-8-(trifluoromethyl) naphthalen-2-yl)ethyl)amino)bicyclo[2.2.1]heptane-1-carboxylic acid

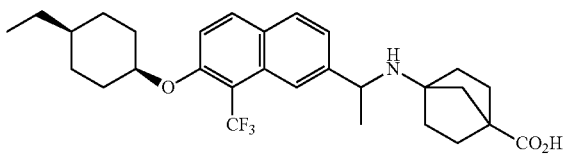 [SMILES: CC[C@H]1CC[C@@H](Oc2ccc3ccc(C(C)NC45CCC(C(=O)O)(CC4)C5)cc3c2C(F)(F)F)CC1]

The title compound was prepared according to the method of Example 28. $^1$H NMR (400 MHz, CD$_3$OD) δ 8.26 (s, 1H), 8.11 (d, J=9.29 Hz, 1H), 8.02 (d, J=8.53 Hz, 1H), 7.48-7.63 (m, 2H), 4.94 (br. s., 1H), 4.70-4.80 (m, 1H), 1.90-2.22 (m, 7H), 1.53-1.88 (m, 11H), 1.10-1.52 (m, 6H), 0.93 (t, J=7.15 Hz, 3H); LCMS m/z 504.1 [M+H]$^+$ Example 131: 3-((1-(7-((cis-4-ethylcyclohexyl)oxy)-8-(trifluoromethyl)naphthalen-2-yl)ethyl)amino)cyclopentanecarboxylic acid

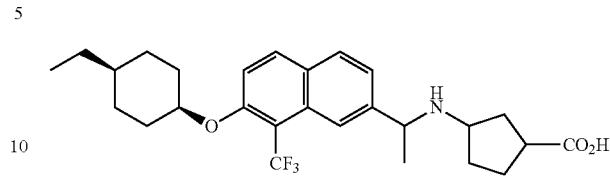

The title compound was prepared according to the method of Example 28. $^1$H NMR (400 MHz, CD$_3$OD) δ 8.25 (br. s., 1H), 8.12 (d, J=9.29 Hz, 1H), 8.03 (d, J=8.28 Hz, 1H), 7.54 (dd, J=8.91, 19.95 Hz, 2H), 4.94 (br. s., 1H), 4.52-4.74 (m, 1H), 3.36-3.53 (m, 1H), 2.71-2.92 (m, 1H), 1.52-2.47 (m, 15H), 1.37-1.50 (m, 2H), 1.24-1.36 (m, 3H), 0.93 (t, J=7.15 Hz, 3H); LCMS m/z 478.1 [M+H]$^+$ Example 132: methyl 9-(1-(7-((cis-4-ethylcyclohexyl)oxy)-8-(trifluoromethyl)naphthalen-2-yl)ethyl)-9-azabicyclo[3.3.1]nonane-3-carboxylate

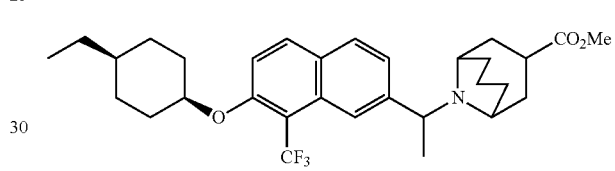

The title compound was prepared according to the method of Example 5. $^1$H NMR (400 MHz, DMSO-d$_6$) δ 8.11 (d, J=9.29 Hz, 1H), 8.04 (br. s., 1H), 7.90 (d, J=8.53 Hz, 1H), 7.34-7.59 (m, 2H), 4.97 (br. s., 1H), 4.18 (q, J=6.02 Hz, 1H), 3.62 (s, 3H), 3.14 (qd, J=6.14, 12.20 Hz, 1H), 2.85-3.00 (m, 2H), 1.10-2.11 (m, 24H), 0.87 (t, J=7.03 Hz, 3H); LCMS m/z 532.1 [M+H]$^+$ Example 133

Example 133a: 9-((S)-1-(7-((cis-4-ethylcyclohexyl)oxy)-8-(trifluoromethyl)naphthalen-2-yl)ethyl)-9-azabicyclo[3.3.1]nonane-3-carboxylic acid and Example 133b: 9-((R)-1-(7-((cis-4-ethylcyclohexyl)oxy)-8-(trifluoromethyl)naphthalen-2-yl)ethyl)-9-azabicyclo[3.3.1]nonane-3-carboxylic acid

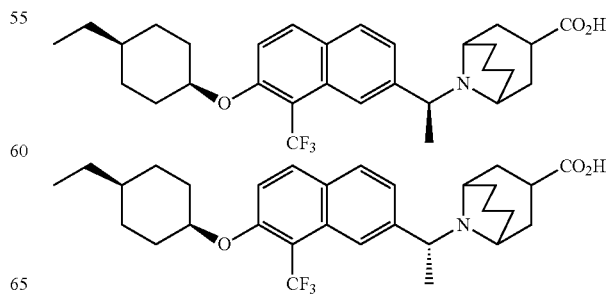

Methyl 9-(1-(7-((cis-4-ethylcyclohexyl)oxy)-8-(trifluoromethyl)naphthalen-2-yl)ethyl)-9-azabicyclo[3.3.1]nonane-3-carboxylate (265 mg) was put under the following SFC separation yielded 120 mg of peak-1 (chemical purity >99%, ee >99%) and 127 mg of peak-2 (chemical purity >99%, ee >99%). IC (2×15 cm); 35% methanol (0.1% DEA)/$CO_2$, 100 bar; 60 mL/min, 220 nm; inj vol.: 1 mL, 9 mg/mL 1:2 DCM:methanol. Isomers from peak-1 and peak-2 were hydrolyzed separately.

Peak-1: $^1$H NMR (400 MHz, $CD_3OD$) δ 8.37 (d, J=9.54 Hz, 1H), 7.97-8.18 (m, 2H), 7.51-7.76 (m, 2H), 5.03-5.35 (m, 1H), 4.95 (br. s., 1H), 4.18 (d, J=13.55 Hz, 1H), 3.36-3.44 (m, 1H), 3.05-3.20 (m, 1H), 1.82-2.64 (m, 11H), 1.53-1.80 (m, 8H), 1.38-1.51 (m, 2H), 1.20-1.37 (m, 3H), 0.93 (t, J=7.15 Hz, 3H); LCMS m/z 518.1 $[M+H]^+$ Peak-2: $^1$H NMR (400 MHz, $CD_3OD$) δ 8.37 (d, J=9.54 Hz, 1H), 7.97-8.18 (m, 2H), 7.51-7.76 (m, 2H), 5.03-5.35 (m, 1H), 4.95 (br. s., 1H), 4.18 (d, J=13.55 Hz, 1H), 3.36-3.44 (m, 1H), 3.05-3.20 (m, 1H), 1.82-2.64 (m, 11H), 1.53-1.80 (m, 8H), 1.38-1.51 (m, 2H), 1.20-1.37 (m, 3H), 0.93 (t, J=7.15 Hz, 3H); LCMS m/z 518.1 $[M+H]^+$

Example 134: cis-4-((1-(7-((cis-4-ethylcyclohexyl)oxy)-8-(trifluoromethyl)naphthalen-2-yl)ethyl)amino)cyclohexanecarboxylic acid

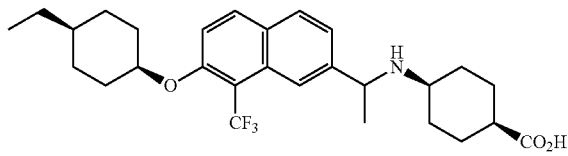

The title compound was prepared according to the method of Example 28. $^1$H NMR (400 MHz, $CD_3OD$) δ 8.24 (s, 1H), 8.12 (d, J=9.29 Hz, 1H), 8.02 (d, J=8.53 Hz, 1H), 7.41-7.62 (m, 2H), 4.95 (br. s., 1H), 4.68-4.81 (m, 1H), 2.87 (tt, J=3.92, 11.14 Hz, 1H), 2.61 (br. s., 1H), 1.99-2.32 (m, 5H), 1.83-1.97 (m, 1H), 1.38-1.77 (m, 13H), 1.15-1.37 (m, 3H), 0.93 (t, J=7.15 Hz, 3H); LCMS m/z 492.1 $[M+H]^+$

Example 135: cis-4-(((S)-1-(7-((cis-4-ethylcyclohexyl)oxy)-8-(trifluoromethyl)naphthalen-2-yl)ethyl)amino)cyclohexanecarboxylic acid and cis-4-(((R)-1-(7-((cis-4-ethylcyclohexyl)oxy)-8-(trifluoromethyl)naphthalen-2-yl)ethyl)amino)cyclohexanecarboxylic acid

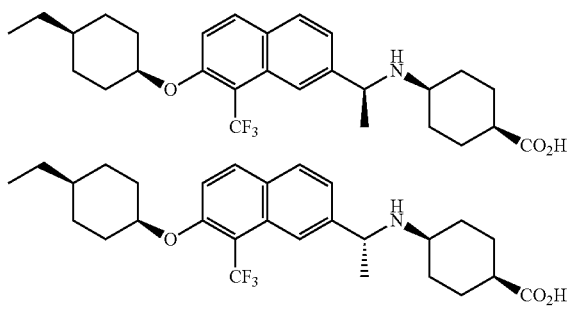

cis-4-((1-(7-((cis-4-Ethylcyclohexyl)oxy)-8-(trifluoromethyl)naphthalen-2-yl)ethyl)amino)cyclohexanecarboxylic acid (89 mg) was put under the following SFC separation yielded 31 mg of peak-1 (chemical purity >99%, ee >99%) and 23 mg of peak-2 (chemical purity >99%, ee >98%). OJ-H (2×15 cm); 15% isopropanol (0.1% DEA)/$CO_2$, 100 bar; 80 mL/min, 220 nm; inj vol.: 0.5 mL, 4.4 mg/mL 2:1 DCM:isopropanol.

Peak-1: $^1$H NMR (400 MHz, $CD_3OD$) δ 8.24 (s, 1H), 8.12 (d, J=9.29 Hz, 1H), 8.02 (d, J=8.53 Hz, 1H), 7.41-7.62 (m, 2H), 4.95 (br. s., 1H), 4.68-4.81 (m, 1H), 2.87 (tt, J=3.92, 11.14 Hz, 1H), 2.61 (br. s., 1H), 1.99-2.32 (m, 5H), 1.83-1.97 (m, 1H), 1.38-1.77 (m, 13H), 1.15-1.37 (m, 3H), 0.93 (t, J=7.15 Hz, 3H); LCMS m/z 492.1 $[M+H]^+$ Peak-2: $^1$H NMR (400 MHz, $CD_3OD$) δ 8.24 (s, 1H), 8.12 (d, J=9.29 Hz, 1H), 8.02 (d, J=8.53 Hz, 1H), 7.41-7.62 (m, 2H), 4.95 (br. s., 1H), 4.68-4.81 (m, 1H), 2.87 (tt, J=3.92, 11.14 Hz, 1H), 2.61 (br. s., 1H), 1.99-2.32 (m, 5H), 1.83-1.97 (m, 1H), 1.38-1.77 (m, 13H), 1.15-1.37 (m, 3H), 0.93 (t, J=7.15 Hz, 3H); LCMS m/z 492.1 $[M+H]^+$

Example 136: cis-4-(((S)-1-(8-(trifluoromethyl)-7-((cis-4-(trifluoromethyl) cyclohexyl)oxy)naphthalen-2-yl)ethyl)amino)cyclohexanecarboxylic acid and cis-4-(((R)-1-(8-(trifluoromethyl)-7-((cis-4-(trifluoromethyl) cyclohexyl)oxy)naphthalen-2-yl)ethyl)amino)cyclohexanecarboxylic acid

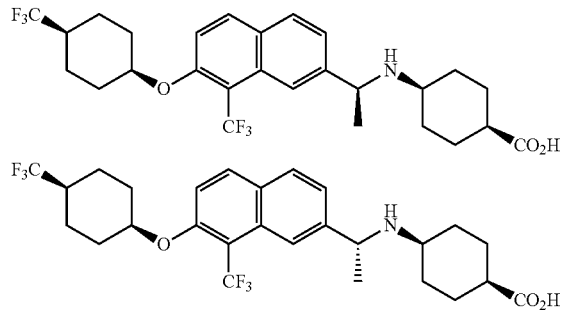

cis-4-((1-(8-(Trifluoromethyl)-7-((cis-4-(trifluoromethyl) cyclohexyl)oxy) naphthalen-2-yl)ethyl)amino)cyclohexanecarboxylic acid (340 mg) was put under the following SFC separation yielded 141 mg of peak-1 (chemical purity >99%, ee >99%) and 162 mg of peak-2 (chemical purity >99%, ee >98%). OJ-H (2×15 cm); 15% ethanol (0.1% DEA)/$CO_2$, 100 bar; 60 mL/min, 220 nm; inj vol.: 0.25 mL, 14 mg/mL 1:2 DCM:methanol.

Peak-1: $^1$H NMR (400 MHz, $CD_3OD$) δ 8.26 (s, 1H), 8.14 (d, J=9.29 Hz, 1H), 8.04 (d, J=8.53 Hz, 1H), 7.46-7.67 (m, 2H), 5.02 (br. s., 1H), 4.69-4.80 (m, 1H), 2.78-2.96 (m, 1H), 2.61 (br. s., 1H), 2.03-2.37 (m, 6H), 1.41-1.95 (m, 14H); LCMS m/z 532.0 $[M+H]^+$ Peak-2: $^1$H NMR (400 MHz, $CD_3OD$) δ 8.26 (s, 1H), 8.14 (d, J=9.29 Hz, 1H), 8.04 (d, J=8.53 Hz, 1H), 7.46-7.67 (m, 2H), 5.02 (br. s., 1H), 4.69-4.80 (m, 1H), 2.78-2.96 (m, 1H), 2.61 (br. s., 1H), 2.03-2.37 (m, 6H), 1.41-1.95 (m, 14H); LCMS m/z 532.0 $[M+H]^+$ Example 137: 9-((S)-1-(8-(trifluoromethyl)-7-((cis-4-(trifluoromethyl) cyclohexyl)oxy)naphthalen-2-yl)ethyl)-9-azabicyclo[3.3.1]nonane-3-carboxylic acid and 9-((R)-1-(8-(trifluoromethyl)-7-((cis-4-(trifluoromethyl) cyclohexyl)oxy)naphthalen-2-yl)ethyl)-9-azabicyclo[3.3.1]nonane-3-carboxylic acid

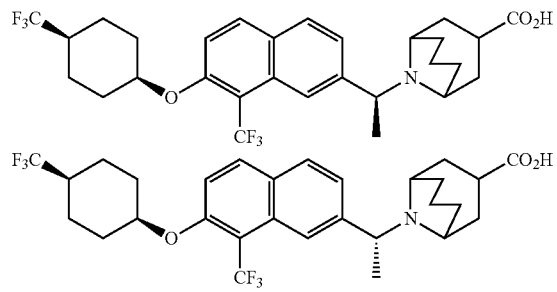

Isopropyl 9-(1-(8-(trifluoromethyl)-7-((cis-4-(trifluoromethyl)cyclohexyl) oxy)naphthalen-2-yl)ethyl)-9-azabicyclo[3.3.1]nonane-3-carboxylate (330 mg) was put under the following SFC separation yielded 99 mg of peak-1 (chemical purity >99%, ee >99%) and 99 mg of peak-2 (chemical purity >99%, ee >99%). IC (2×15 cm); 25% methanol (0.1% DEA)/CO$_2$, 100 bar; 60 mL/min, 220 nm; inj vol.: 0.7 mL, 9 mg/mL methanol. Isomers from peak-1 and peak-2 were hydrolyzed separately.

The isomer hydrolyzed from peak-1: $^1$H NMR (400 MHz, CD$_3$OD) δ 8.34 (d, J=8.78 Hz, 1H), 8.15 (d, J=9.29 Hz, 1H), 8.03 (s, 1H), 7.69 (d, J=9.04 Hz, 1H), 7.62 (d, J=9.29 Hz, 1H), 5.03 (br. s., 1H), 4.58 (d, J=6.02 Hz, 1H), 4.09 (dd, J=2.89, 11.42 Hz, 1H), 3.41 (d, J=2.76 Hz, 1H), 2.86-3.03 (m, 1H), 1.65-2.62 (m, 19H), 0.78 (t, J=7.28 Hz, 3H); LCMS m/z 558.0 [M+H]$^+$ The isomer hydrolyzed from peak-2: $^1$H NMR (400 MHz, CD$_3$OD) δ 8.34 (d, J=8.78 Hz, 1H), 8.15 (d, J=9.29 Hz, 1H), 8.03 (s, 1H), 7.69 (d, J=9.04 Hz, 1H), 7.62 (d, J=9.29 Hz, 1H), 5.03 (br. s., 1H), 4.58 (d, J=6.02 Hz, 1H), 4.09 (dd, J=2.89, 11.42 Hz, 1H), 3.41 (d, J=2.76 Hz, 1H), 2.86-3.03 (m, 1H), 1.65-2.62 (m, 19H), 0.78 (t, J=7.28 Hz, 3H); LCMS m/z 558.0 [M+H]$^+$ Example 138: 9-((3-fluoro-7-((cis-4-methylcyclohexyl)oxy)-8-(trifluoro methyl)naphthalen-2-yl)methyl)-9-azabicyclo[3.3.1]nonane-3-carboxylic acid

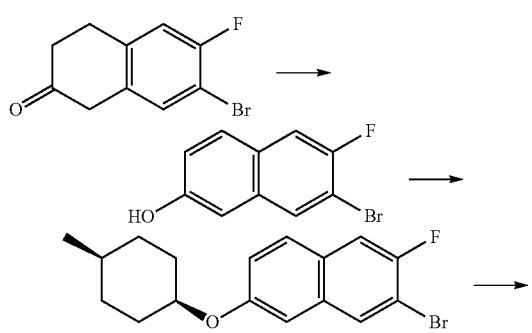

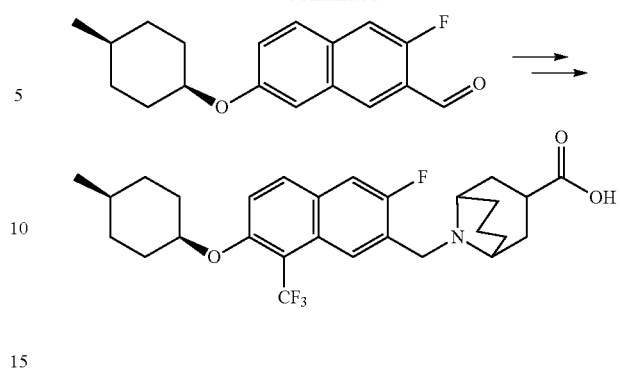

Step 1: 7-bromo-6-fluoronaphthalen-2-ol

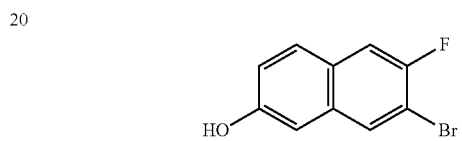

To a stirred solution of 7-bromo-6-fluoro-3,4-dihydronaphthalen-2(1H)-one (2.0 g, 8.26 mmol, 1.0 eq) and NBS (1.6 g, 9.02 mmol, 1.1 eq) in MeCN (50 mL) was added TMSOTf (92 mg, 0.41 mmol, 0.05 eq). The mixture was stirred at rt for 16 h and diluted with EtOAc (150 mL). The mixture was washed with H$_2$O (100 mL), dried over Na$_2$SO$_4$ and concentrated under reduced pressure. The crude product was purified by reversed phase HPLC to give 7-bromo-6-fluoronaphthalen-2-ol as a brown solid (466 mg, yield: 23%). $^1$H NMR (400 MHz, CDCl$_3$) δ: 7.90 (d, J=6.8 Hz, 1H), 7.66 (d, J=8.8 Hz, 1H), 7.45 (d, J=9.2 Hz, 1H), 7.13 (dd, J=2.0 Hz, 8.8 Hz, 1H), 7.07 (d, J=2.0 Hz, 1H).

Step 2: 3-bromo-2-fluoro-6-((cis-4-methylcyclohexyl)oxy)naphthalene

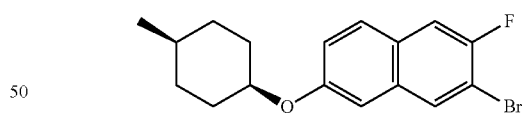

To a solution of 7-bromo-6-fluoronaphthalen-2-ol (466 mg, 1.94 mmol) and (cis)-1-methyl-4-(methylsulfonyl)cyclohexane (560 mg, 1.5 eq) in t-BuOH (10 mL) was added Cs$_2$CO$_3$ (1.26 g, 3.88 mmol, 2.0 eq). The mixture was stirred at 100° C. for 16 h. After the reaction completed, the mixture was filtered and the filtrate was concentrated. The residue was purified by column chromatography on silica gel (petroleum ether:EtOAc=40:1) to give 3-bromo-2-fluoro-6-(((cis)-4-methylcyclohexyl)oxy)naphthalene as a white solid (360 mg, yield: 55%). $^1$H NMR (400 MHz, CDCl$_3$) δ: 7.90 (d, J=6.8 Hz, 1H), 7.63 (d, J=9.2 Hz, 1H), 7.42 (d, J=9.2 Hz, 1H), 7.19 (dd, J=2.0 Hz, 8.4 Hz, 1H), 7.04 (d, J=2.0 Hz, 1H), 4.61-4.58 (m, 1H), 2.06-2.02 (m, 2H), 1.64-1.30 (m, 7H), 0.95 (d, J=6.0 Hz, 3H).

Step 3: 3-fluoro-7-((cis-4-methylcyclohexyl)oxy)-2-naphthaldehyde

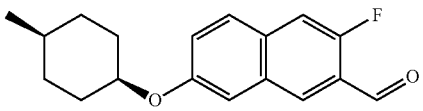 [SMILES: C[C@H]1CC[C@@H](Oc2ccc3cc(F)c(C=O)cc3c2)CC1]

To a solution of 3-bromo-2-fluoro-6-((cis-4-methylcyclohexyl)oxy) naphthalene (95 mg, 0.28 mmol, 1.0 eq) in dry THF (4 mL) was added n-BuLi (2.5 M, 0.23 mL, 2.0 eq) dropwise at −78° C. under $N_2$ atmosphere. The mixture was stirred for 1 h at −78° C. Then DMF (41 mg, 0.56 mmol, 2.0 eq) was added and the mixture was stirred for another 1 h at −78° C. The reaction was quenched with aq. $NH_4Cl$ (10 mL) and extracted with ethyl acetate (3×10 mL). The combined organic layers were washed with brine (20 mL), dried over $Na_2SO_4$ and concentrated to give crude product. The crude product was purified by TLC on silica gel (petroleum ether:EtOAc=20:1) to give 3-fluoro-7-(((cis)-4-methylcyclohexyl)oxy)-2-naphthaldehyde as a yellow oil (50 mg, yield: 62%). $^1$H NMR (400 MHz, $CDCl_3$) δ: 7.90 (d, J=6.8 Hz, 1H), 7.63 (d, J=9.2 Hz, 1H), 7.42 (d, J=9.2 Hz, 1H), 7.19 (dd, J=2.0 Hz, 8.4 Hz, 1H), 7.04 (d, J=2.0 Hz, 1H), 4.61-4.58 (m, 1H), 2.06-2.02 (m, 2H), 1.64-1.30 (m, 7H), 0.95 (d, J=6.0 Hz, 3H). LCMS m/z 287.1 [M+H]$^+$ Step 4: 9-((3-fluoro-7-((cis-4-methylcyclohexyl)oxy)-8-(trifluoro methyl)naphthalen-2-yl)methyl)-9-azabicyclo[3.3.1]nonane-3-carboxylic acid

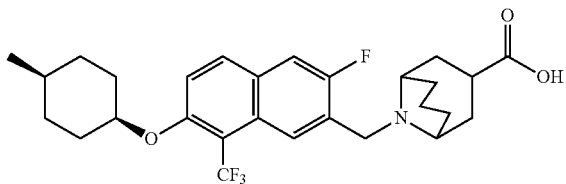 [SMILES: C[C@H]1CC[C@@H](Oc2ccc3cc(F)c(CN4C5CCCC4CC(C(=O)O)C5)cc3c2C(F)(F)F)CC1]

The title compound was prepared according to the method of Example 7. $^1$H NMR (400 MHz, $CD_3OD$) δ: 8.49 (d, J=7.2 Hz, 1H), 8.12 (d, J=9.2 Hz, 1H), 7.79 (d, J=10.8 Hz, 1H), 7.65 (d, J=9.6 Hz, 1H), 4.94 (s, 1H), 4.81 (s, 2H), 3.75 (s, 2H), 3.45-3.40 (m, 1H), 2.60-2.02 (m, 11H), 1.87-1.67 (m, 3H), 155-1.41 (m, 5H), 0.96 (d, J=7.2 Hz, 3H). LCMS m/z 508.1 [M+H]$^+$ Example 139: 8-(1-(3-fluoro-7-((cis-4-methylcyclohexyl)oxy)-8-(trifluoromethyl)naphthalen-2-yl)ethyl)-8-azabicyclo[3.2.1]octane-3-carboxylic acid

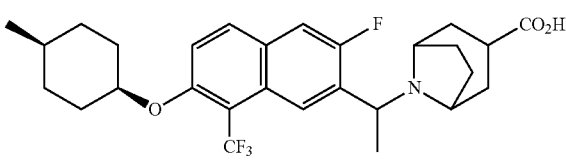 [SMILES: CC(c1cc2c(C(F)(F)F)c(O[C@H]3CC[C@@H](C)CC3)ccc2cc1F)N1C2CCC1CC(C(=O)O)C2]

The title compound was prepared according to the method of Example 5. $^1$H NMR (400 MHz, $CD_3OD$) δ: 8.43 (d, J=6.8 Hz, 1H), 8.12 (d, J=9.2 Hz, 1H), 7.81 (d, J=11.2 Hz, 1H), 7.65 (d, J=9.6 Hz, 1H), 4.94 (s, 1H), 4.74-4.69 (m, 1H), 4.56-4.51 (m, 1H), 3.68-3.62 (m, 1H), 3.01-2.95 (m, 1H), 2.51-2.48 (m, 1H), 2.39-2.34 (m, 1H), 2.19-2.02 (m, 8H), 1.85 (d, J=6.8 Hz, 3H), 1.74-1.68 (m, 2H), 1.55-1.43 (m, 5H), 0.96 (d, J=6.0 Hz, 3H). LCMS m/z 508.3 [M+H]$^+$ Example 140: 8-(1-(3-fluoro-8-(trifluoromethyl)-7-((cis-4-(trifluoromethyl) cyclohexyl)oxy)naphthalen-2-yl)ethyl)-8-azabicyclo[3.2.1]octane-3-carboxylic acid

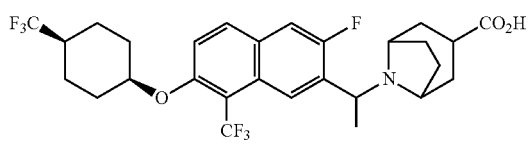 [SMILES: CC(c1cc2c(C(F)(F)F)c(O[C@H]3CC[C@@H](C(F)(F)F)CC3)ccc2cc1F)N1C2CCC1CC(C(=O)O)C2]

The title compound was prepared according to the method of Example 5. $^1$H NMR (400 MHz, $CD_3OD$) δ: 8.45 (d, J=6.8 Hz, 1H), 8.15 (d, J=9.6 Hz, 1H), 7.82 (d, J=10.8 Hz, 1H), 7.67 (d, J=9.6 Hz, 1H), 5.03 (s, 1H), 4.72-4.71 (m, 1H), 4.56-4.55 (m, 1H), 3.66-3.61 (m, 1H), 2.99-2.96 (m, 1H), 2.60-2.58 (m, 1H), 2.37-1.97 (m, 10H), 1.85 (d, J=6.8 Hz, 3H), 1.80-1.72 (m, 6H). LCMS m/z 562.2 [M+H]$^+$ Example 141: 8-((3-fluoro-8-(trifluoromethyl)-7-((cis-4-(trifluoromethyl) cyclohexyl)oxy)naphthalen-2-yl)methyl)-8-azabicyclo[3.2.1]octane-3-carboxylic acid

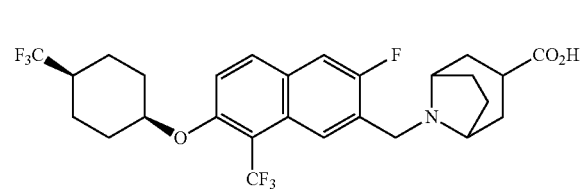 [SMILES: O=C(O)C1CC2CCC(C1)N2Cc1cc2c(C(F)(F)F)c(O[C@H]3CC[C@@H](C(F)(F)F)CC3)ccc2cc1F]

The title compound was prepared according to the method of Example 7. $^1$H NMR (400 MHz, $CD_3OD$) δ: 8.49 (d, J=6.8 Hz, 1H), 8.15 (d, J=9.2 Hz, 1H), 7.81 (d, J=10.4 Hz, 1H), 7.68 (d, J=9.6 Hz, 1H), 5.03 (s, 1H), 4.50 (s, 2H), 4.11 (s, 2H), 3.01-2.97 (m, 1H), 2.58-2.53 (m, 2H), 2.30-2.11 (m, 9H), 1.84-1.72 (m, 6H). LCMS m/z 548.2 [M+H]$^+$ Example 142: cis-4-((1-(7-((cis-4-methylcyclohexyl)oxy)-8-(trifluoromethyl)naphthalen-2-yl)ethyl)amino)cyclohexanecarboxylic acid

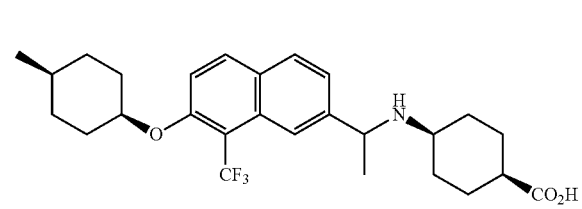 [SMILES: CC(N[C@H]1CC[C@@H](C(=O)O)CC1)c1ccc2ccc(O[C@H]3CC[C@@H](C)CC3)c(C(F)(F)F)c2c1]

The title compound was prepared according to the method of Example 28. $^1$H NMR (400 MHz, $CD_3OD$) δ: 8.25 (s, 1H), 8.13 (d, J=9.2 Hz, 1H), 8.04 (d, J=8.4 Hz, 1H), 7.58 (d, J=8.8 Hz, 1H), 7.53 (dd, J=1.2 Hz, 8.8 Hz, 1H), 4.95 (s, 1H), 4.78 (q, J=6.8 Hz, 1H), 2.91-2.85 (m, 1H), 2.65-2.61 (m, 1H), 2.26-2.04 (m, 5H), 1.92-1.89 (m, 1H), 1.74-1.44 (m, 14H), 0.97 (d, J=6.4 Hz, 3H); LCMS m/z 478.3 [M+H]+

Example 143: trans-4-((1-(8-(trifluoromethyl)-7-((cis-4-(trifluoromethyl) cyclohexyl)oxy)naphthalen-2-yl)ethyl)amino)cyclohexanecarboxylic acid

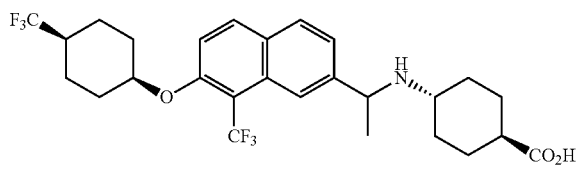 [SMILES: CC(N[C@H]1CC[C@H](C(=O)O)CC1)c1ccc2ccc(O[C@H]3CC[C@@H](C(F)(F)F)CC3)c(C(F)(F)F)c2c1]

The title compound was prepared according to the method of Example 28. ¹H NMR (400 MHz, CD₃OD) δ: 8.28 (s, 1H), 8.16 (d, J=9.6 Hz, 1H), 8.06 (d, J=8.4 Hz, 1H), 7.61 (d, J=9.2 Hz, 1H), 7.57 (dd, J=1.6 Hz, 8.8 Hz, 1H), 5.04 (s, 1H), 4.80 (q, J=6.8 Hz, 1H), 2.93-2.88 (m, 1H), 2.33-2.08 (m, 8H), 1.89-1.72 (m, 9H), 1.52-1.34 (m, 4H); LCMS m/z 532.2 [M+H]+

Example 144: 8-((S)-1-(7-((cis-4-ethylcyclohexyl)oxy)-8-(trifluoromethyl)naphthalen-2-yl)ethyl)-8-azabicyclo[3.2.1]octane-3-carboxylic acid and 8-((R)-1-(7-((cis-4-ethylcyclohexyl)oxy)-8-(trifluoromethyl)naphthalen-2-yl)ethyl)-8-azabicyclo[3.2.1]octane-3-carboxylic acid

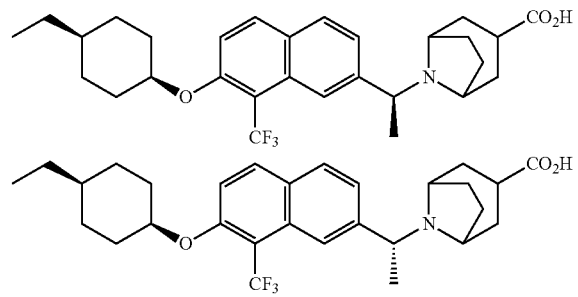

Methyl 8-(1-(7-((cis-4-ethylcyclohexyl)oxy)-8-(trifluoromethyl)naphthalen-2-yl)ethyl)-8-azabicyclo[3.2.1]octane-3-carboxylate was put under the following SFC separation yielded peak-1 and peak-2. OZ-H (3×25 cm); 35% methanol/CO₂, 100 bar; 80 mL/min, 220 nm; inj vol.: 3.5 mL, 5.4 mg/mL methanol. Isomers from peak-1 and peak-2 were hydrolyzed separately.

The isomer hydrolyzed from peak-1: ¹H NMR (400 MHz, CD₃OD) δ: 8.29 (s, 1H), 8.14 (d, J=9.2 Hz, 1H), 8.06 (d, J=8.4 Hz, 1H), 7.59 (d, J=8.8 Hz, 2H), 4.97 (s, 1H), 4.56-4.54 (m, 1H), 4.49-4.44 (m, 1H), 3.44-3.43 (m, 1H), 3.01-2.95 (m, 1H), 2.60-2.56 (m, 1H), 2.30-1.91 (m, 9H), 1.82 (d, J=6.8 Hz, 3H), 1.73-1.30 (m, 9H), 0.94 (t, J=7.2 Hz, 3H). LCMS m/z 504.2 [M+H]+

The isomer hydrolyzed from peak-2: ¹H NMR (400 MHz, CD₃OD) δ: 8.28 (s, 1H), 8.11 (d, J=9.6 Hz, 1H), 8.03 (d, J=8.4 Hz, 1H), 7.62-7.60 (m, 1H), 7.56 (d, J=9.6 Hz, 1H), 4.94 (s, 1H), 4.50-4.46 (m, 1H), 4.30-4.26 (m, 1H), 3.50-3.25 (m, 1H), 2.71-2.62 (m, 1H), 2.47-2.42 (m, 1H), 2.26-1.92 (m, 8H), 1.85-1.77 (m, 4H), 1.70-1.56 (m, 4H), 1.47-1.30 (m, 5H), 0.93 (t, J=6.8 Hz, 3H). LCMS m/z 504.2 [M+H]+

Example 145: cis-4-((1-(7-((cis-4-ethylcyclohexyl)oxy)-8-(trifluoromethyl)naphthalen-2-yl)propyl)amino)cyclohexanecarboxylic acid

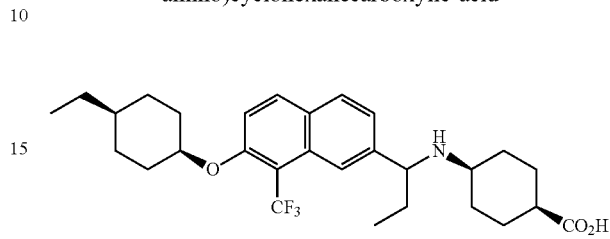

The title compound was prepared according to the method of Example 28. ¹H NMR (400 MHz, CD₃OD) δ: 8.22 (s, 1H), 8.14 (d, J=9.2 Hz, 1H), 8.05 (d, J=8.8 Hz, 1H), 7.59 (d, J=8.8 Hz, 1H), 7.49 (d, J=8.4 Hz, 1H), 4.96 (s, 1H), 4.53-4.49 (m, 1H), 2.85-2.79 (m, 1H), 2.62-2.58 (m, 1H), 2.25-2.03 (m, 7H), 1.88-1.85 (m, 1H), 1.73-1.59 (m, 6H), 1.50-1.33 (m, 7H), 0.94 (t, J=6.8 Hz, 3H), 0.84 (t, J=6.8 Hz, 3H). LCMS m/z 506.2 [M+H]+

Example 146: cis-4-((1-(7-((cis-4-methylcyclohexyl)oxy)-8-(trifluoromethyl)naphthalen-2-yl)propyl)amino)cyclohexanecarboxylic acid

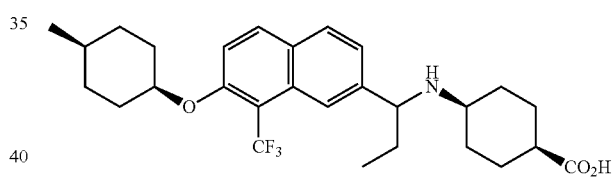

The title compound was prepared according to the method of Example 28. ¹H NMR (400 MHz, CD₃OD) δ: 8.22 (s, 1H), 8.13 (d, J=9.2 Hz, 1H), 8.05 (d, J=8.4 Hz, 1H), 7.59 (d, J=8.4 Hz, 1H), 7.49 (d, J=8.8 Hz, 1H), 4.96 (s, 1H), 4.53-4.49 (m, 1H), 2.84-2.78 (m, 1H), 2.63-2.60 (m, 1H), 2.25-2.00 (m, 7H), 1.88-1.84 (m, 1H), 1.74-1.43 (m, 11H), 0.97 (d, J=5.2 Hz, 3H), 0.83 (t, J=7.2 Hz, 3H). LCMS m/z 492.2 [M+H]+

Example 147: cis-4-((1-(8-(trifluoromethyl)-7-((cis-4-(trifluoromethyl) cyclohexyl)oxy)naphthalen-2-yl)propyl)amino)cyclohexanecarboxylic acid

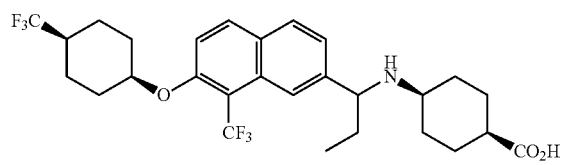 [SMILES: CCC(N[C@H]1CC[C@@H](C(=O)O)CC1)c1ccc2ccc(O[C@H]3CC[C@@H](C(F)(F)F)CC3)c(C(F)(F)F)c2c1]

The title compound was prepared according to the method of Example P. ¹H NMR (400 MHz, CD₃OD) δ: 8.24 (s, 1H), 8.17 (d, J=9.2 Hz, 1H), 8.07 (d, J=8.4 Hz, 1H), 7.61 (d, J=9.2

Hz, 1H), 7.51 (dd, J=1.2 Hz, 8.4 Hz, 1H), 5.04 (s, 1H), 4.54-4.50 (m, 1H), 2.85-2.79 (m, 1H), 2.63-2.60 (m, 1H), 2.30-2.02 (m, 8H), 1.88-1.72 (m, 7H), 1.69-1.59 (m, 2H), 1.51-1.41 (m, 2H), 0.83 (t, J=7.2 Hz, 3H). LCMS m/z 546.2 [M+H]⁺

Example 148: 3-((trans-4-(tert-butyl)cyclohexyl)amino) isoquinoline-6-carboxylic acid

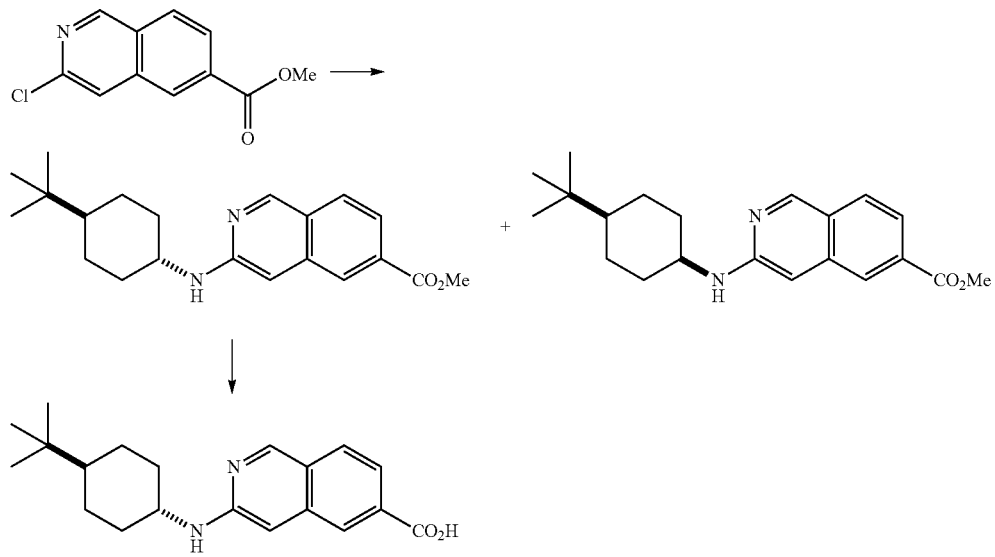

Step 1: Methyl 3-((trans-4-(tert-butyl)cyclohexyl)amino)isoquinoline-6-carboxylate and Methyl 3-((cis-4-(tert-butyl)cyclohexyl)amino)isoquinoline-6-carboxylate

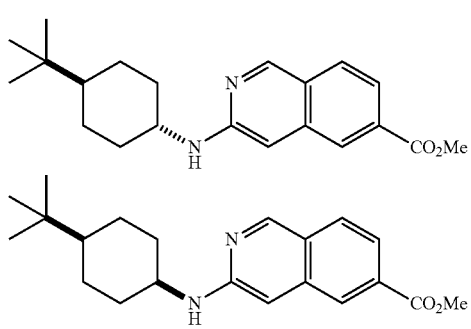

To a mixture of methyl 3-chloroisoquinoline-6-carboxylate (500 mg, 2.26 mmol, 1.0 eq.) in dioxane (25 mL) was added amine (700.6 mg, 4.52 mmol, 2.0 eq.), Cs₂CO₃ (1.1 g, 3.39 mmol, 1.5 eq.), Pd₂(dba)₃ (62.1 mg, 0.068 mmol, 0.03 eq.) and Xantphos (78.4 mg, 0.136 mmol, 0.06 eq.) under N₂. The reaction was set in 9 batches in parallel. Then the reaction mixtures were stirred in sealed tube at 110° C. overnight. The mixture was cooled, combined and filtered. The filtrate was concentrated and purified by chromatography on silica gel with PE/EA (40/1 to 20/1) to give two mixed isomers. The mixed isomers were purified by prep-HPLC then prep-TLC to provide trans-isomer (1.11 g, 16.0% yield) and cis isomer (1.05 g, 15.2% yield), both as yellow solids.

Trans isomer: ¹HNMR (400 MHz, Methanol-d4) δ: 8.86 (s, 1H), 8.29 (s, 1H), 7.86 (d, J=8.8 Hz, 1H), 7.69 (d, J=8.8 Hz, 1H), 6.77 (s, 1H), 3.97 (s, 3H), 3.92 (br, 1H), 2.09-2.03 (m, 2H), 1.69-1.62 (m, 4H), 1.43-1.14 (m, 3H), 0.92 (s, 9H).

Cis isomer: ¹HNMR (400 MHz, Methanol-d4) δ: 8.85 (s, 1H), 8.28 (s, 1H), 7.85 (d, J=8.8 Hz, 1H), 7.68 (d, J=8.8 Hz, 1H), 6.75 (s, 1H), 3.97 (s, 3H), 3.51 (br, 1H), 2.21-2.20 (m, 2H), 1.92-1.90 (m, 2H), 1.30-1.12 (m, 6H), 0.93 (s, 9H).

Step 2: 3-((trans-4-(tert-butyl)cyclohexyl)amino) isoquinoline-6-carboxylic acid

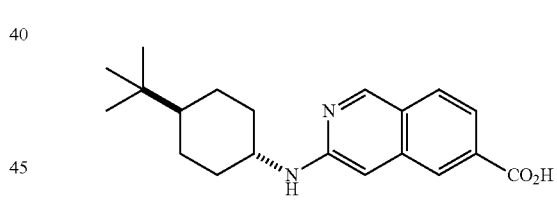

To the mixture of methyl 3-((trans-4-(tert-butyl)cyclohexyl)amino)isoquinoline-6-carboxylate (500 mg, 1.47 mmol, 1.0 eq.) in MeOH (6 mL) and water (1.5 mL) was added NaOH (235.2 mg, 5.88 mmol, 4.0 eq.) at room temperature, and the mixture was stirred under reflux overnight until the ester was consumed completely. The mixture was concentrated in vacuum and the residue dissolved into water and acidified with 2 N HCl to pH=2. The suspension was filtered and washed with a little EA, dried in vacuum to afford 3-((trans-4-(tert-butyl)cyclohexyl)amino)isoquinoline-6-carboxylic acid as a yellow solid (460 mg, yield 96%). ¹HNMR (400 MHz, DMSO) δ: 8.90 (s, 1H), 8.17 (s, 1H), 7.83 (d, J=9.2 Hz, 1H), 7.53-(d, J=9.2 Hz, 1H), 6.73 (s, 1H), 6.40 (br, 1H), 3.46 (br, 1H), 2.06-2.04 (m, 2H), 1.78-1.75 (m, 2H), 1.21-1.00 (m, 5H), 0.85 (s, 9H). LCMS m/z 327.2 [M+H]⁺

Example 149: Methyl 3-(3-((trans-4-(tert-butyl)cyclohexyl)amino)isoquinoline-6-carboxamido)cyclohexanecarboxylate

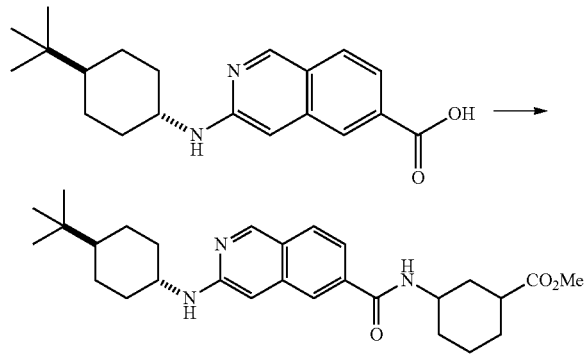

A mixture of 3-(((trans)-4-(tert-butyl)cyclohexyl)amino)isoquinoline-6-carboxylic acid (32 mg, 0.1 mmol, 1.0 eq.), methyl 3-aminocyclohexanecarboxylate (24 mg, 0.15 mmol, 1.5 eq.), HATU (34 mg, 0.12 mmol, 1.2 eq.) and DIEA (39 mg, 0.3 mmol, 3.0 eq.) in DMF (1 mL) was stirred at 35° C. overnight. Ethyl acetate (10 mL) was added and the mixture, washed with brine (10 mL). The organic phase was dried over Na$_2$SO$_4$, filtered and dried to give the crude, which was purified by prep-HPLC to provide methyl 3-(3-((trans-4-(tert-butyl)cyclohexyl)amino)isoquinoline-6-carboxamido)cyclohexane carboxylate as a green oil. $^1$H NMR (400 MHz, CD$_3$OD) δ: 8.82 (s, 1H), 7.99 (s, 1H), 7.84 (d, J=8.8 Hz, 1H), 7.51 (dd, J=8.8 Hz, &1.6 Hz, 1H), 6.72 (s, 1H), 3.97-3.96 (m, 1H), 3.69 (s, 3H), 3.51-3.50 (m, 1H), 2.55-2.53 (m, 1H), 2.23-2.20 (m, 3H), 2.00-1.91 (m, 5H), 1.52-1.11 (m, 9H), 0.93 (s, 9H). LCMS m/z 466.3 [M+H]$^+$

Example 150: 3-(3-((trans-4-(tert-butyl)cyclohexyl)amino)isoquinoline-6-carboxamido)cyclohexanecarboxylic acid

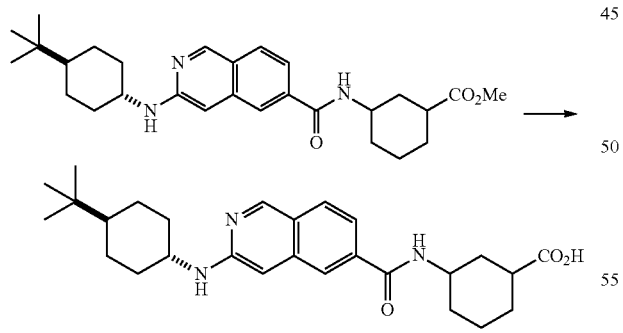

A mixture of methyl 3-(3-((trans-4-(tert-butyl)cyclohexyl)amino)isoquinoline-6-carboxamido)cyclohexanecarboxylate (180 mg, 0.4 mmol, 1.0 eq.) and NaOH (69 mg, 1.7 mmol, 4.0 eq.) in MeOH/H$_2$O (1 mL) was stirred at 35° C. overnight. The solvent was removed in vacuum and the residue was dissolved in water. The aqueous phase was washed with EA (10 mL) and the pH of aqueous phase was adjusted to about 1. The precipitate was collected by filtration and dried to give the crude which was purified by prep-HPLC to give the target compound as a green solid (30 mg, 16.6% yield). $^1$H NMR (400 MHz, CD$_3$OD) δ: 8.83 (s, 1H), 8.00 (s, 1H), 7.85 (d, J=8.4 Hz, 1H), 7.51 (d, J=8.4 Hz, 1H), 6.74 (s, 1H), 3.98-3.97 (m, 1H), 3.50-3.54 (m, 1H), 2.53-2.50 (m, 1H), 2.22-2.20 (m, 3H), 2.03-1.93 (m, 5H), 1.53-1.13 (m, 9H), 0.94 (s, 9H). LCMS m/z 452.2 [M+H]$^+$

Example 151: 3-((trans-4-(tert-butyl)cyclohexyl)amino)-N-cyclohexyl isoquinoline-6-carboxamide

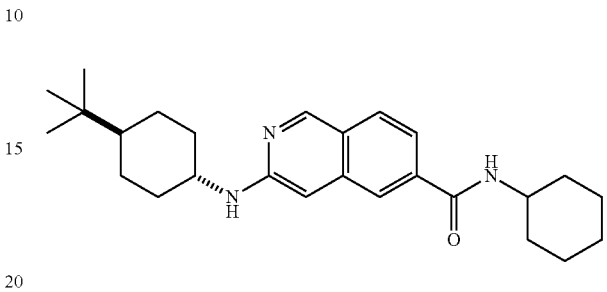

The title compound was prepared according to the method of Example 149. $^1$HNMR (400 MHz, CD$_3$OD) δ: 8.82 (s, 1H), 7.98 (s, 1H), 7.84 (d, J=8.4 Hz, 1H), 7.50 (dd, J=8.4 Hz&1.6 Hz, 1H), 6.72 (s, 1H), 3.93-3.88 (m, 1H), 3.50 (br, 1H), 2.20 (br, 2H), 2.03-1.99 (m, 6H), 1.84-1.83 (m, 1H), 1.43-1.12 (m, 11H), 0.93 (s, 9H). LCMS m/z 408.4 [M+H]$^+$

Example 152: 4-(3-((trans-4-(tert-butyl)cyclohexyl)amino)isoquinoline-6-carboxamido)bicyclo[2.2.2]octane-1-carboxylic acid

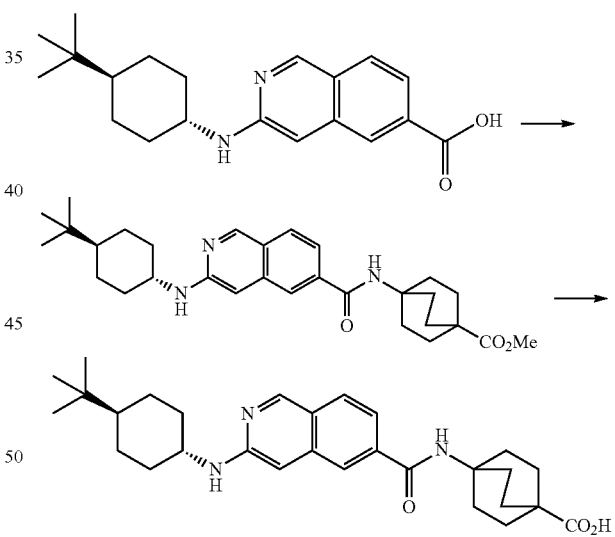

Step 1: methyl 4-(3-((trans-4-(tert-butyl)cyclohexyl)amino)isoquinoline-6-carboxamido)bicyclo[2.2.2]octane-1-carboxylate

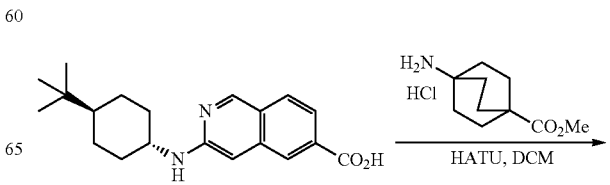

-continued

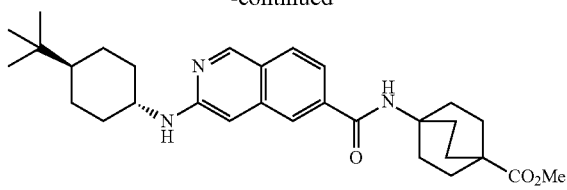

To a suspension of 3-((trans-4-(tert-butyl)cyclohexyl)amino)isoquinoline-6-carboxylic acid (80 mg, 0.245 mmol, 1 eq) and methyl 4-aminobicyclo[2.2.2]octane-1-carboxylate hydrochloride (81 mg, 0.368 mmol, 1.5 eq) in DCM (30 mL) was added DIEA (95 mg, 0.735 mmol, 3 mmol) and HATU (140 mg, 0.368 mmol, 1.5 eq) at room temperature. The reaction mixture was stirred at room temperature for 16 h. The reaction mixture was concentrated in vacuum to give the crude product. The crude product was purified by Pre-HPLC to give methyl 4-(3-((trans-4-(tert-butyl)cyclohexyl)amino)isoquinoline-6-carboxamido)bicyclo[2.2.2]octane-1-carboxylate (73 mg, 61%) as a yellow solid. $^1$HNMR (400 MHz, CDCl$_3$) δ: 8.64 (s, 1H), 7.92 (s, 1H), 7.80 (d, J=8.4 Hz, 1H), 7.52 (d, J=8.4 Hz, 1H), 6.86 (s, 1H), 6.02 (s, 1H), 3.69 (s, 3H), 3.32-3.34 (m, 1H), 2.21-2.24 (m, 2H), 2.08-2.12 (m, 6H), 1.91-2.01 (m, 8H), 1.40-1.43 (m, 2H), 1.14-1.20 (m, 3H), 0.91 (s, 9H).

Step 2: 4-(3-((trans-4-(tert-butyl)cyclohexyl) amino) isoquinoline-6-carboxamido)bicyclo[2.2.2]octane-1-carboxylic acid

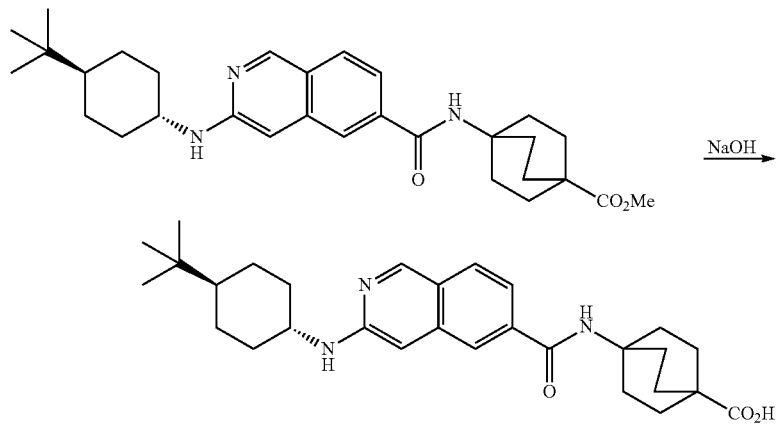

To a solution of methyl 4-(3-(((trans)-4-(tert-butyl)cyclohexyl)amino) isoquinoline-6-carboxamido)bicyclo[2.2.2]octane-1-carboxylate (70 mg, 0.142 mmol, 1 eq) in a mixture of methanol (5 mL) and THF (10 mL) was added a solution of sodium hydroxide (17 mg, 0.427 mmol, 3 eq) in water (5 mL) at room temperature. The reaction mixture was stirred at room temperature for 16 h. The mixture was concentrated in vacuum to give crude product. The crude product was poured into 6 mL of water. The suspension was filtered and the filter cake was dried to give 4-(3-((trans-4-(tert-butyl)cyclohexyl) amino)isoquinoline-6-carboxamido)bicyclo[2.2.2]octane-1-carboxylic acid (55 mg, 82%) as a yellow solid. $^1$HNMR (400 MHz, DMSO-d6) δ: 8.84 (s, 1H), 7.90 (s, 1H), 7.80 (s, 1H), 7.76 (d, J=8.0 Hz, 1H), 7.38 (d, J=8.0 Hz, 1H), 6.62 (s, 1H), 6.34 (d, J=8.0 Hz, 1H), 3.43-3.45 (m, 1H), 2.03-2.06 (m, 2H), 1.94-1.98 (m, 6H), 1.76-1.80 (m, 8H), 1.00-1.20 (m, 5H), 0.85 (s, 9H). LCMS m/z 478.2 [M+H]$^+$ Example 153: 8-(3-((trans-4-(tert-butyl)cyclohexyl) amino)isoquinoline-6-carbonyl)-8-azabicyclo[3.2.1] octane-3-carboxylic acid

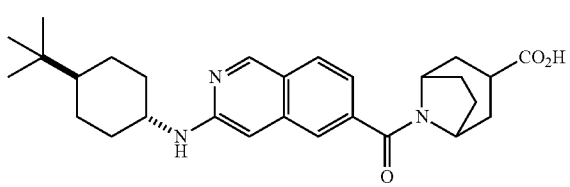 [SMILES: CC(C)(C)[C@H]1CC[C@H](Nc2cc3cc(C(=O)N4C5CCC4CC(C(=O)O)C5)ccc3cn2)CC1]

The title compound was prepared according to the method of Example 152. $^1$H NMR (400 MHz, CD$_3$OD) δ: 8.97 (s, 1H), 8.05 (d, J=8.8 Hz, 1H), 7.82 (s, 1H), 7.38 (dd, J=1.2 Hz, 8.8 Hz, 1H), 7.33 (s, 1H), 4.84 (s, 1H), 4.12-4.10 (m, 1H), 3.57-3.51 (m, 1H), 3.04-2.99 (m, 1H), 2.22-1.84 (m, 12H), 1.39-1.24 (m, 4H), 1.17-1.11 (m, 1H), 0.92 (s, 9H). LCMS m/z 464.2 [M+H]$^+$ Example 154: cis-4-(3-((trans-4-(tert-butyl)cyclohexyl)amino)isoquinoline-6-carboxamido)cyclohexane carboxylic acid

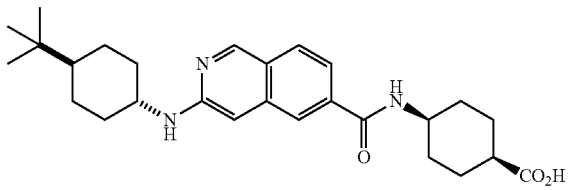 [SMILES: CC(C)(C)[C@H]1CC[C@H](Nc2cc3cc(C(=O)N[C@H]4CC[C@@H](C(=O)O)CC4)ccc3cn2)CC1]

The title compound was prepared according to the method of Example 52. ¹H NMR (400 MHz, CD₃OD) δ: 8.85 (s, 1H), 7.98 (s, 1H), 7.89 (d, J=8.8 Hz, 1H), 7.53 (dd, J=2.0 Hz, 8.8 Hz, 1H), 7.20 (s, 1H), 3.90 (s, 1H), 3.45-3.40 (m, 1H), 2.50-2.49 (m, 1H), 2.11-2.01 (m, 4H), 1.85-1.57 (m, 8H), 1.31-1.14 (m, 4H), 1.06-1.01 (m, 1H), 0.82 (s, 9H). LCMS m/z 452.2 [M+H]⁺

Example 155: trans-4-(3-((trans-4-(tert-butyl)cyclohexyl)amino) isoquinoline-6-carboxamido)cyclohexanecarboxylic acid

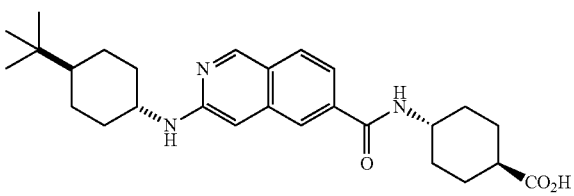 [SMILES: CC(C)(C)[C@H]1CC[C@H](Nc2cc3cc(C(=O)N[C@H]4CC[C@H](C(=O)O)CC4)ccc3cn2)CC1]

The title compound was prepared according to the method of Example 152. ¹H NMR (400 MHz, CD₃OD) δ: 8.96 (s, 1H), 8.09 (s, 1H), 8.00 (d, J=8.8 Hz, 1H), 7.65 (dd, J=1.2 Hz, 8.4 Hz, 1H), 7.28 (s, 1H), 3.93-3.89 (m, 1H), 3.56-3.51 (m, 1H), 2.34-1.93 (m, 9H), 1.64-1.14 (m, 9H), 0.94 (s, 9H). LCMS m/z 452.2 [M+H]⁺

Example 156: 1-(3-((trans-4-(tert-butyl)cyclohexyl)amino)isoquinoline-6-carbonyl)piperidine-4-carboxylic acid

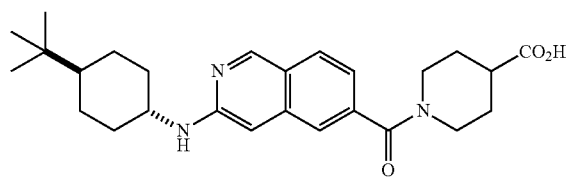 [SMILES: CC(C)(C)[C@H]1CC[C@H](Nc2cc3cc(C(=O)N4CCC(C(=O)O)CC4)ccc3cn2)CC1]

The title compound was prepared according to the method of Example 152. ¹H NMR (400 MHz, CD₃OD) δ: 8.83 (s, 1H), 7.88 (d, J=8.4 Hz, 1H), 7.59 (s, 1H), 7.14 (dd, J=8.4 Hz&1.6 Hz, 1H), 6.73 (s, 1H), 4.53-4.50 (m, 1H), 3.72-3.68 (m, 1H), 3.51-3.50 (m, 1H), 3.33-3.32 (m, 2H), 2.68-2.67 (m, 1H), 2.22-2.20 (m, 3H), 1.92-1.90 (m, 3H), 1.85-1.70 (m, 2H), 1.30-1.12 (m, 5H), 0.93 (s, 9H). LCMS m/z 438.2 [M+H]⁺

Example 157: 2-(1-(3-((trans-4-(tert-butyl)cyclohexyl)amino)isoquinoline-6-carbonyl)piperidin-4-yl)acetic acid

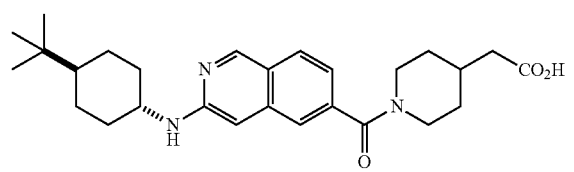 [SMILES: CC(C)(C)[C@H]1CC[C@H](Nc2cc3cc(C(=O)N4CCC(CC(=O)O)CC4)ccc3cn2)CC1]

The title compound was prepared according to the method of Example 152. ¹H NMR (400 MHz, CD₃OD) δ: 8.82 (s, 1H), 7.87 (d, J=8.0 Hz, 1H), 7.57 (s, 1H), 7.14 (d, J=8.0 Hz, 1H), 6.70 (s, 1H), 4.69-4.66 (m, 1H), 3.76-3.73 (m, 1H), 3.50-3.49 (m, 1H), 3.18-3.10 (m, 1H), 2.95-2.80 (m, 1H), 2.33-1.72 (m, 8H), 1.36-1.12 (m, 8H), 0.93 (s, 9H). LCMS m/z 452.2 [M+H]⁺

Example 158: (1r,4r)-4-(3-(((1r,4r)-4-(tert-butyl)cyclohexyl)amino)isoquinoline-6-carboxamido)cyclohexane-1-carboxylic acid

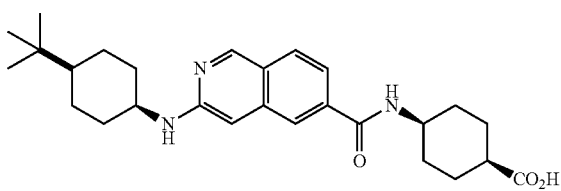 [SMILES: CC(C)(C)[C@H]1CC[C@@H](Nc2cc3cc(C(=O)N[C@H]4CC[C@@H](C(=O)O)CC4)ccc3cn2)CC1]

The title compound was prepared according to the method of Example 152. ¹H NMR (400 MHz, CD₃OD) δ: 9.04 (s, 1H), 8.12-8.02 (m, 2H), 7.67 (d, J=8.4 Hz, 1H), 7.45 (s, 1H), 3.99 (br, 2H), 2.64 (br, 1H), 2.15-2.02 (m, 4H), 1.86-1.75 (m, 9H), 1.39-1.15 (m, 4H), 0.93 (s, 9H). LCMS m/z 452.2 [M+H]⁺

Example 159: cis-4-(3-((trans-4-(tert-butyl)cyclohexyl)amino)-4-chloroisoquinoline-6-carboxamido)cyclohexanecarboxylic acid

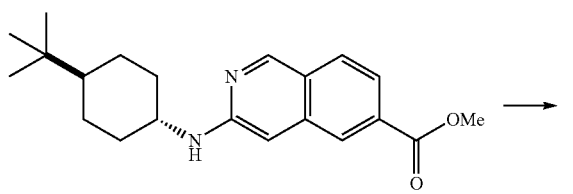

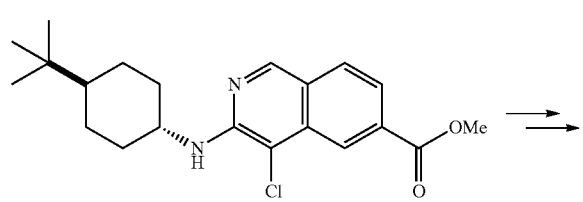

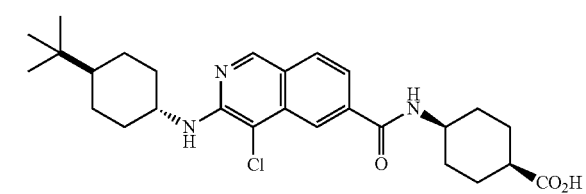

Step 1: Methyl 3-((trans-4-(tert-butyl)cyclohexyl)amino)-4-chloroisoquinoline-6-carboxylate

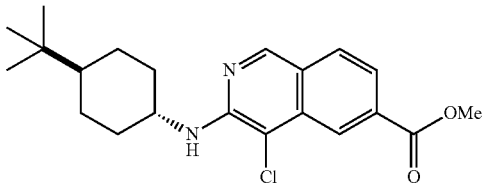 [SMILES: COC(=O)c1ccc2cnc(N[C@H]3CC[C@H](C(C)(C)C)CC3)c(Cl)c2c1]

To a solution of methyl 3-((trans-4-(tert-butyl)cyclohexyl)amino)isoquinoline-6-carboxylate (290 mg, 0.853 mmol, 1.0 eq.) in DCM (10 mL) was added NCS (136.7 mg, 1.024 mmol, 1.2 eq.) at room temperature and stirred overnight. TLC showed the starting material was consumed completely. The mixture was washed with water (10 mL), brine (10 mL), dried over $Na_2SO_4$, and concentrated in vacuum to afford methyl 3-((trans-4-(tert-butyl)cyclohexyl)amino)-4-chloroisoquinoline-6-carboxylate as a yellow oil (330 mg, yield 100%).

Step 1: 3-((trans-4-(tert-butyl)cyclohexyl)amino)-4-chloroisoquinoline-6-carboxylic acid

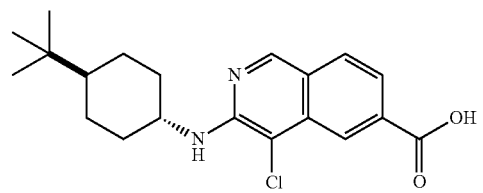 [SMILES: CC(C)(C)[C@H]1CC[C@H](Nc2ncc3ccc(C(=O)O)cc3c2Cl)CC1]

To a mixture of methyl 3-((trans-4-(tert-butyl)cyclohexyl)amino)-4-chloroisoquinoline-6-carboxylate (320 mg, 0.86 mmol, 1.0 eq.) in MeOH (3.5 mL) was added 3N NaOH aq. (1.15 mL, 4.0 eq.) and stirred at room temperature overnight, followed by heating at 80° C. for 3 h, and TLC showed the reaction was complete. The solvent was removed in vacuum and the residue was dissolved in water. The aqueous phase was washed with EA (10 mL×2) and the aqueous phase was acidified with 2 N HCl to about pH 2. The precipitate was collected by filtration and dried to give 3-((trans-4-(tert-butyl)cyclohexyl)amino)-4-chloroisoquinoline-6-carboxylic acid as a yellow solid (210 mg, yield 68%). LCMS m/z 361.0 [M+H]$^+$

Step 2: cis-4-(3-((trans-4-(tert-butyl)cyclohexyl)amino)-4-chloroisoquinoline-6-carboxamido)cyclohexanecarboxylic acid

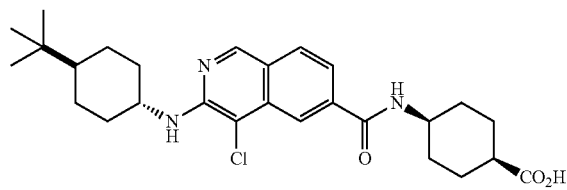 [SMILES: CC(C)(C)[C@H]1CC[C@H](Nc2ncc3ccc(C(=O)N[C@H]4CC[C@@H](C(=O)O)CC4)cc3c2Cl)CC1]

The title compound was prepared according to the method of Example 152. $^1$H NMR (400 MHz, $CD_3OD$) δ: 8.91 (s, 1H), 8.30 (s, 1H), 7.96 (d, J=8.8 Hz, 1H), 7.61 (d, J=8.0 Hz, 1H), 4.03-3.96 (m, 2H), 2.63 (br, 1H), 2.18-2.16 (m, 4H), 2.05-1.88 (m, 4H), 1.76-1.74 (m, 4H), 1.41-1.14 (m, 5H), 0.93 (s, 9H). LCMS m/z 486.2 [M+H]$^+$

Example 160: Activity Measurements

ATX (Autotaxin) is a 125 KDa glycoprotein with lysophospholipase D (LPLD) activity that generates the bioactive lipid lysophosphatidic acid (LPA) from lysophosphatidylcholine (LPC). The ATX biochemical assay utilizes a FRET (fluorescence resonance energy transfer) technology platform. The fluorescence signal of FRET substrate FS-3 is quenched due to intra-molecular FRET of a fluorophore to a non-fluorescing quencher (Ferguson, C. G., et al., Org Lett. 2006 May 11; 8(10): 2023-2026, which is incorporated by reference in its entirety). ATX catalyzes the hydrolysis of the substrate which separates the dabsyl quencher from the fluorescein reporter, which becomes fluorescent. The reaction is monitored by a SpectraMax M5 (Molecular Devices, Sunnyvale, Calif.) with at excitation wavelength 485 nm and emission wavelength 535 nm.

Reagents

Fatty acid free-BSA (Sigma A8806): 10 mg/mL in $H_2O$, stored at 4° C.

2×ATX assay buffer: 100 mM Tris, 280 mM NaCl, 10 mM KCl, 2 mM $CaCl_2$, 2 mM $MgCl_2$, pH 7.4.

Human ATX protein: expressed and purified in house. Stored at −80° C.

Substrate FS-3 (Echelon, L-2000): 100 μg in 77.74 μL $H_2O$ (1 mM stock), stored at −20° C.

384-well flat bottom plates—Corning #3575.

Assay

Compound dilution—All compounds were provided at 10 mM in 100% DMSO. In the first well, 2 μL of 10 mM compound was added to 78 μL of DMSO (1:40 dilution). In subsequent wells 3-fold dilution (total 10 dilutions) were performed.

1×ATX assay buffer was made up with a final concentration of 1 mg/mL fatty acid free-BSA using 2×ATX assay buffer, 10 mg/ml fatty acid free-BSA and dd$H_2O$.

ATX protein was diluted with 1×ATX assay buffer to a concentration of 1.32 μg/mL (1.32×). 38 μL was added per well to the assay plate. The final concentration of ATX in the reaction as 1.0 μg/mL.

2 μL per well of compounds was transferred to provide the desired concentration. The plate was centrifuged, then incubated at room temperature for 30 minutes on the shaker.

FS-3 was diluted with 1×ATX assay buffer to a concentration of FS-3 of 10 μM (5×). Then, 10 μL was added per well to the assay plate. The final concentration of FS-3 in the reaction was 2 μM. The plate was centrifuged. The plate was kept shaking at room temperature for 2 hours. Because FS-3 substrate is light sensitive, plates were kept covered and protected from light.

Fluorescence was measured using SpectraMax M5 (excitation at 485 nm/emission at 538 nm, top read).

The compounds of examples 2, 3, 5, 5b, 6, 6a, 7, 10, 12, 12b 14, 15, 27, 37, 38, 42, 44, 46, 48, 49, 51, 52, 55, 56, 57, 59, 63, 70, 71, 73, 74, 82, 86, 87, 88, 98, 101, 102, 105, 107, 108, 112, 113, 114b, 114c, 115, 116, 117b, 117c, 118b, 119, 120, 121b, 121c, 122b, 122c, 129, 131, 133a, 134, 135a, 136a, 137a, 137b, 139, 140, 141, 142, 145, 144b, 147, 152, 154 and 155 had an $IC_{50}$ of no greater than 100 nM.

The compounds of examples 6b, 8, 18, 21, 23, 24, 26, 29, 30, 34, 35, 41, 45, 58, 60, 61, 65, 66, 67, 78, 80, 81, 83, 90, 91, 93, 96, 99, 104, 118c, 123, 124, 130, 132, 133b, 135b, 136b, 138, 146 and 150 had an $IC_{50}$ of no greater than 250 nM.

The compounds of examples 7, 12a, 13, 32, 40, 43, 50, 53, 54, 72, 95, 106, 110, 114d, 118a, 118d, 125, 126, 127, 143 and 144a had an $IC_{50}$ of no greater than 500 nM.

OPC Differentiation Assay

Enriched populations of oligodendrocytes were grown from post-natal day 2 (P2) female Sprague Dawley rats. The forebrain was dissected out and placed in Hank's buffered saline solution (HBSS; Invitrogen, Grand Island, N.Y.). The tissue was cut into 1 mm fragments and incubated at 37° C. for 15 minutes in 0.01% trypsin and 10 µg/mL DNase. Dissociated cells were plated on poly-L-lysine-coated T75 tissue culture flasks and grown at 37° C. for 10 days in Dulbecco's modified Eagle's medium (DMEM) with 20% fetal calf serum (Invitrogen). $A2B5^+$ OPCs were collected by shaking the flask overnight at 200 rpm and 37° C., resulting in a 95% pure population.

For the differentiation assay, 2 µM and 20 µM antagonist or the same concentrations of vehicle (DMSO) were applied to OPCs cultured in CNTF/T3 containing media. After a 3-day incubation, cells were lysed in 80 µL lysis buffer (50 mM HEPES [4-(2-hydroxyethyl)-1-piperazineethanesulfonic acid], pH 7.5, 150 mM NaCl, 1.5 mM $MgCl_2$, 1 mM ethylene glycol tetraacetic acid [EGTA], 1% Triton X-100 and 10% glycerol) for 30 minutes at 4° C. After centrifugation at 14,000 g for 15 minutes, the supernatants were boiled in Laemmli sample buffer, subjected to 4-20% SDS-PAGE, and analyzed by Western blotting with anti-MBP, anti-myelin-associated glycoprotein (MAG), or anti-beta actin antibodies. The secondary antibodies used were anti-mouse IgG-HRP (horseradish peroxidase) and anti-rabbit IgG-HRP respectively.

DRG-OPC Myelination Assay

Embryonic neocortical neurons are dissected from embryonic day 18 (E18) Sprague Dawley rats, and then plated on poly-D-lysine (100 µg/mL)-coated cover slips and grown in neurobasal medium supplemented with B27 (Invitrogen) for one week. $A2B5^+$ OPCs are prepared as described above and then added into the cultured neocortical neurons. One day later, different concentrations of an ATX inhibitor and control reagents are applied into the co-cultures. Fresh media containing the different concentrations of an ATX inhibitor or control compounds are supplied every three days. After ten days, co-cultures are subjected to sodium dodecyl sulfate polyacrylamide gel electrophoresis (SDS-PAGE)/Western blot analyses to quantify MAG, MBP, and MOG.

Remyelination Assay in Brain Slice Culture

Approximately three to four consecutive 300 µm slices are taken from the junction of the corpus callosum to the hippocampus in post-natal, day 17 Sprague Dawley rats (Charles River, Willmington, Mass.). Slices are cultured in basal DMEM supplemented with 25% horse serum for three days, before being treated with 6 mg/mL LPC (Sigma L-4129) for a further three days. The medium is then changed, and slices incubated with medium containing an ATX inhibitor or vehicle control for a final period of three days, after which myelination is visualized by black gold staining (Millipore, Bedford, Mass.) following the manufacture's protocol. Images are acquired using a Leica M420 microscope (Bannockburn, Ill.) and the staining intensity of corpus callosum is analyzed using Metamorph software (Molecular Devices, Downingtown, Pa.). Three or four brain slices are used for each treatment group.

Lysolecithin Demyelination Model

Adult Sprague Dawley rats (220-260 g) are anesthetized by intraperitoneal injection of a cocktail, consisting of Ketamine (35 mg/kg), Xylazine (6 mg/kg) and Acepromazine (1 mg/kg). The back of the animal is shaved from the lower thoracic to the lumbar region, subsequently sanitized with 70% isopropanol, Betadine Scrub solution, and 70% isopropanol again. The animal is then placed onto stereotaxic frame.

After ensuring an adequate anesthetic level, the skin is incised along the midline over the thoracic region. The dorsal fascia is incised and the paraspinal muscles separated from the spinous processes of the thoracic vertebrae T-9 through T-11. The T-10 vertebra is demolished, and the lamina removed with micro-rongeurs. Once the dorsal spinal cord region is exposed, a microcapillary glass needle is inserted into the dorsal column to a depth of 0.6 mm. The demyelinating reagent, 1.5 µL of 1% Lysolecithin (LPC, Sigma# L1381) in saline is injected with the infusion rate of 2 nL/sec controlled by a micro-pump (World Precision Instrument #micro4). Once the injection is completed, the needle is placed for additional 1 min before removal. The paraspinal muscles and the lumbar fascia are closed with suture (#5, silk). The skin incision is closed with wound clips. Animals are allowed to recover from the anesthesia and are observed in the humidified incubator.

Buprenorphine (0.05 mg/kg) is administrated subcutaneously (s.c.) twice a day for additional two days following operation.

Three days following the primary surgery, treatments with an ATX inhibitor (30 pmol), LPA (30 pmol) or control (0.1% DMSO in saline) are injected at the primary injection region in a volume of 1.5 µL with the same infusion speed as indicated above. Nine days following the primary surgery, the animals are anesthetized and perfused trans-cardially with heparin (10 iu/mL) in saline followed by 4% PFA in PBS. The spinal cords are removed and post fixed in PFA overnight. Then the cords are cut into 100 µM thickness longitudinally and then 1% loxuol fast blue is stained and histological evaluation for remyelination and repair is assessed under microscope.

For systemic treatment, the animals are administered once daily intraperitoneally with either an ATX inhibitor (10 mg/kg) or control (15% HPCD (hydroxypropyl-β-cyclodextrin)) 2 days following the primary surgery. Nine days after the primary surgery, animals are sacrificed and the spinal cords were processed as indicated above.

CFA Inflammatory Pain Model

In the CFA (complete Freund's adjuvant) model, adult male SD (250-300 g) rats are anesthetized with isoflurane inhalation (4.5% induction/2.0% maintenance). Heat-killed M. Tuberculosis H37 RA (non-viable) suspended at a concentration of 1.0 mg/ml in incomplete Freund's adjuvant is used (Chondrex Inc., catalog#7008). At day 0, intradermal injection (i.d.) of 100 µl of CFA (1:1 oil/saline) is slowly perfused into the right footpad of the rats. At day 1, baseline tactile allodynia test are conducted: rats that develop sensitive painful response are enrolled to the study. At day 2, rats are orally dosed once with either vehicle or ATX inhibitor, then at 2 hrs, 4 hrs, 6 hrs and 24 hrs after dosage, all rats are tested for mechanical allodynia response.

Tactile allodynia is tested as follows. A rat is placed in an elevated Plexiglas observation chamber (approximately 4'×6"×10") having a wire grid (1 $cm^2$ spacing) mesh floor under polycarbonate cages. The rat is left to acclimate to the experimental conditions for 20 minutes before testing begins. After the rat is calm, tactile allodynia is assessed using a series of von Frey filaments ranging from 2.04-28.84 g (Stoelting, Wood Dale, Ill.). Graded pressure is presented to a localized area on the plantar surface of the paw via the use of Von Frey hairs (monofilaments which are calibrated to bend at a known pressure). A response to the VonFrey hair is recorded as the rat withdrawing the tested paw and is usually followed by lifting and licking. A series of filaments are used to determine the threshold response using the established "Up-Down" method. Each paw is tested 4-6 times repeatedly with 1-2 seconds (modified from Seltzer et al., 1991) in between each probe to accurately assess the behavior. A sharp lifting of the paw is scored as a positive response.

Rat Model of Neuropathic Pain

Chronic Constriction Injury (CCI) Surgery: In the CCI model (Bennett and Xie, *Pain,* 1989, which is incorporated by reference in its entirety), adult male SD (250-275 g) rats are anesthetized with isoflurane inhalation (4.5% induction/ 2.0% maintenance). The surgery is performed under aseptic conditions and involves exposing the sciatic nerve at the mid-thigh level. Ocular lubricant is used as needed to prevent corneal drying. After shaving and disinfecting the skin (betadine followed by 70% ethanol), a small incision is made just caudal to the biceps femoris. Care is taken to not disturb the sciatic nerve. The nerve is slightly elevated, and 4 loose ligatures of 4-0 chromic gut suture are inserted under the nerve, and then are loosely tied around it. The sutures constrict the nerve but do not strangle it. Prior to inserting the chromic gut, it is rinsed twice in sterile saline. The incision is closed with wound clips, and rats are allowed to recover from anesthesia on a circulating water heating pad before being returned to their home cages. In the sham controls the skin is opened, and the sciatic nerve is identified and elevated, but no sutures are tied around the nerve. All rats are screened for pain response around post-surgery day 7 and only rats with sensitive pain response are enrolled to the study.

Animals are orally dosed twice/day for 3 times/week with either vehicle or ATX inhibitor post-surgery at days 10, 12, 14, 17, 19 and 21, and animals are also tested at the same schedule for three types of neuropathic pain: thermal hyperalgesia, tactile allodynia and incapacitance.

(1) Plantar thermal hyperalgesia: Rats are tested for hyperalgesia using a plantar device (Ugo Basile Inc., Cat.#37370). After acclimation to the testing room, rats are placed on an elevated glass floor beneath inverted clear plastic cages, and a radiant heat source beneath the glass is aimed at the mid-plantar surface of the hindpaw after they have ceased all exploratory behavior. The onset of light activates a timer, which is terminated by a hindpaw withdrawal response. A cutoff time of 30 seconds is used to avoid tissue damage in the absence of a response. The average withdrawal latency value of three trials from the ipsilateral hindpaw is measured with at least 5-10 minutes between each trial to avoid any tissue damage.

(2) Tactile allodynia is tested as described above.

(3) Incapacitance: The incapacitance test measures the weight the rat places on each of its hindpaws. The rat is placed in a small, clear Plexiglas box (6" long×3" wide×4" tall). The box is tilted up and opens in the front. The rat is placed in the box so that its hindpaws are at the back (lower) portion of the box, and the forepaws are at the front (raised) part of the box. The rat's head is at the opening in the front of the box. The box is placed on a divided scale such that each of the rat's hindpaws is on one of the two weighing pans of the scale. The weight that the rat placed on each hindpaw is then measured. The procedure is rapid (about 10 sec) and does not cause the animal any pain.

Other embodiments are within the scope of the following claims.

What is claimed is:
1. A compound represented by formula (I):

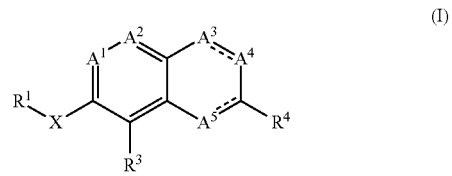

or a pharmaceutically acceptable salt thereof, wherein
X is O, S(O)$_r$, NR$^{12}$, C(O) or CH$_2$;
A$^1$ is N;
A$^2$ is CR$^2$;
A$^3$, A$^4$ and A$^5$ are each independently CR$^2$ or N, provided that at least three of A$^1$, A$^2$, A$^3$, A$^4$, and A$^5$ are independently CR$^2$;
"------" indicates a double bond;
R$^1$ is a C$_{6-20}$alkyl, a C$_{3-14}$carbocyclyl, a 3- to 15-membered heterocyclyl, a C$_{6-10}$aryl, or a five- to 14-membered heteroaryl, wherein the heterocyclyl and the heteroaryl comprise from 1 to 10 heteroatoms independently selected from N, S or O, and wherein R$^1$ is optionally substituted with from one to six independently selected R$^6$;
R$^2$, for each occurrence, is independently selected from the group consisting of hydrogen, halo, hydroxyl, nitro, cyano, carboxy, C$_{1-6}$alkyl, C$_{1-6}$haloalkyl, C$_{3-8}$cycloalkyl, C$_{3-8}$halocycloalkyl, C$_{1-6}$alkoxy, C$_{1-6}$haloalkoxy, C$_{3-8}$cycloalkoxy, C$_{3-8}$halocycloalkoxy, C$_{1-6}$alkanoyl, amino, N—(C$_{1-6}$alkyl)amino, N,N-di-(C$_{1-6}$alkyl)amino, C$_{1-6}$alkoxycarbonyl, C$_{1-6}$alkanoyloxy, carbamoyl, N—(C$_{1-6}$alkyl)carbamoyl, N,N-di-(C$_{1-6}$alkyl)carbamoyl, C$_{1-6}$alkylamido, mercapto, C$_{1-6}$alkylthio, C$_{1-6}$alkylsulfonyl, sulfamoyl, N—(C$_{1-6}$alkyl)sulfamoyl, N,N-di-(C$_{1-6}$alkyl)sulfamoyl, and C$_{1-6}$alkylsulfonamido;
R$^3$ is hydrogen, a halo, C$_{1-6}$haloalkyl or cyano, provided that when R$^3$ is hydrogen, R$^1$ is a C$_{3-8}$cycloalkyl which is optionally substituted with from 1 to 6 independently selected R$^6$;
R$^4$ is a carboxylic acid or a group represented by the following formula:

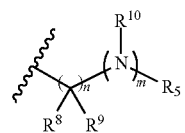

wherein ⌇ represents the point of attachment; provided that when R$^4$ is a carboxylic acid, A$^1$ is N and R$^1$ is a C$_{3-8}$cycloalkyl which is optionally substituted with from 1 to 6 independently selected R$^6$;
R$^5$ is a C$_{3-8}$carbocyclyl, a 3- to 8-membered heterocyclyl, C$_{6-10}$aryl, a 5- to 10-membered heteroaryl, a bridged ring system comprising from 6 to 12 ring members, a spiro ring system comprising from 5-14 ring members, or a bicyclic ring system represented by the following formula:

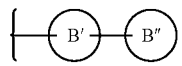

wherein B' and B" are independently selected from the group consisting of monocyclic $C_{3-8}$carbocyclyl, a monocyclic 3- to 8-membered heterocyclyl, phenyl or a 5- to 6-membered heteroaryl; wherein $R^5$ is optionally substituted with from 1 to 4 independently selected $R^{11}$;

$R^6$, for each occurrence, is independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom form $C_{3-8}$spirocycloalkyl or 3- to 8-membered spiroheterocycloalkyl;

$R^7$ is —OH, —C(O)OR$^{15}$, —C(O)N(R$^{16}$)$_2$, —C(O)N(R$^{15}$)—S(O)$_2$R$^{15}$, —S(O)$_2$OR$^{15}$, —C(O)NHC(O)R$^{15}$, —Si(O)OH, —B(OH)$_2$, —N(R$^{15}$)S(O)$_2$R$^{15}$, —S(O)$_2$N(R$^{15}$)$_2$, —O—P(O)(OR$^{15}$)$_2$, —P(O)(OR$^{15}$)$_2$, —CN, —S(O)$_2$NHC(O)R$^{15}$, —C(O)NHS(O)$_2$R$^{15}$, —C(O)NHOH, —C(O)NHCN, or a heteroaryl or a heterocyclyl selected from the group consisting of formulae (a)-(i'):

(a) 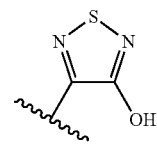

(b) 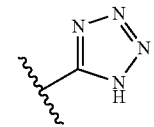

(c) 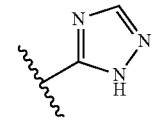

(d) 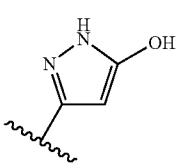

(e) 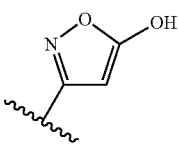

(f) 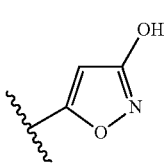

-continued (g) 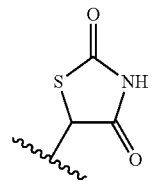

(h) 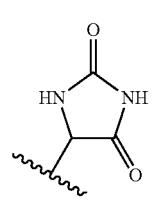

(i) 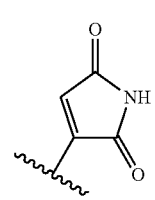

(j) 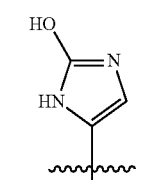

(k) 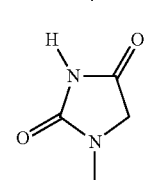

(l) 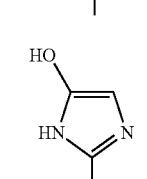

(m) 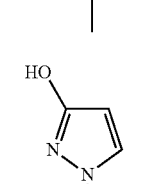

(n) 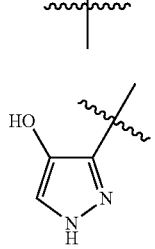

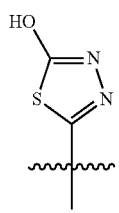 (o)
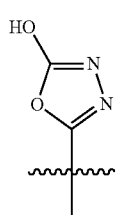 (p)
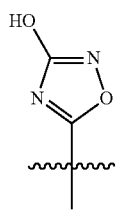 (q)
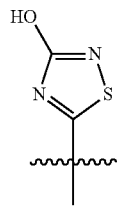 (r)
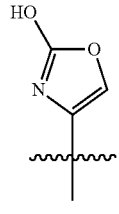 (s)
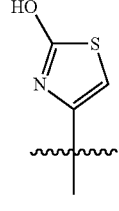 (t)
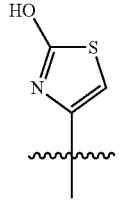 (u)
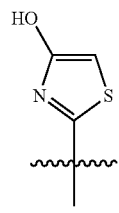 (v)
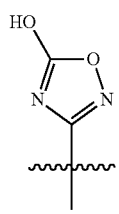 (w)
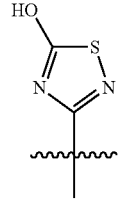 (x)
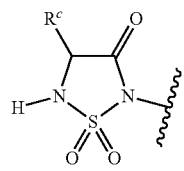 (y)
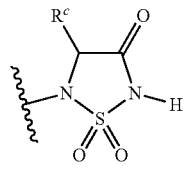 (z)
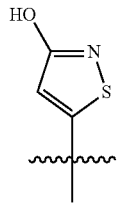 (a')
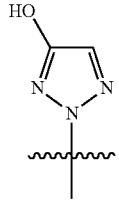 (b')
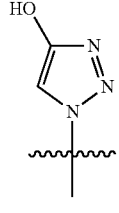 (c')

-continued

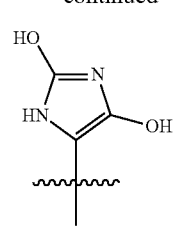
(d')

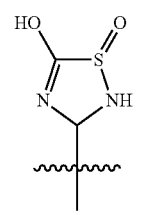
(e')

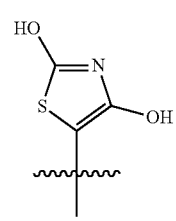
(f')

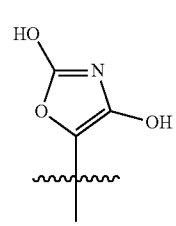
(g')

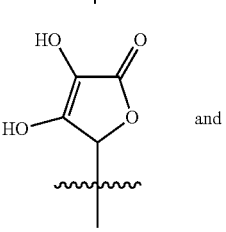
(h')
and

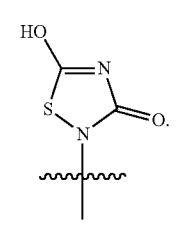
(i')

$R^8$ and $R^9$ are each independently be hydrogen, a carboxy, $C_{1-6}$alkyl, or a $C_{2-6}$alkenyl; or $R^8$ and $R^9$ together with the carbon to which they are attached can be —C(=O)—, a $C_{3-8}$spirocycloalkyl, or a 3- to 8-membered spiroheterocycloalkyl;

$R^{10}$ and $R^{12}$ are each independently be hydrogen or a $C_{1-6}$alkyl;

$R^{11}$, for each occurrence, is independently halo, hydroxyl, nitro, cyano, $C_{1-6}$alkyl, $C_{1-6}$haloalkyl, $C_{1-6}$alkoxy, $(CR^{17}R^{18})_p$—$R^7$, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —NR$^a$R$^b$, —C(O)NR$^a$R$^b$, —N(R$^a$)C(O)R$^b$, —C(O)R$^a$, —S(O)$_r$R$^a$, or —N(R$^a$)S(O)$_2$R$^b$;

$R^{15}$ for each occurrence is independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ is optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl;

$R^{16}$ is $R^{15}$; or two $R^{16}$ together with the nitrogen atom to which they are attached can form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl;

$R^{17}$ and $R^{18}$, for each occurrence, are each independently hydrogen, a halo, or a $C_{1-4}$haloalkyl;

$R^a$ and $R^b$, for each occurrence, are independently hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl;

$R^c$ is hydrogen or a $C_{1-4}$alkyl;

m is 0 or 1, provided that when m is 0, $R^5$ comprises at least one nitrogen;

n is an integer from 1 to 6;

p is 0 or an integer from 1 to 6;

r, for each occurrence, is independently 0, 1, or 2, provided that the compound is not 3-(1,4-dioxaspiro[4.5]decan-8-ylamino)-8-methylisoquinoline-6-carboxylic acid.

2. The compound according to claim 1, or a pharmaceutically acceptable salt thereof, wherein the compound is represented by structural formula (Ia):

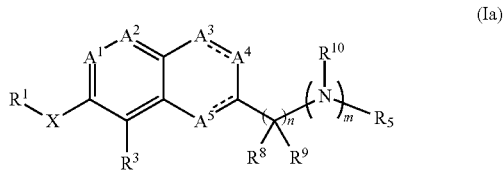
(Ia)

wherein:

X is O, S(O)$_r$, NR$^{12}$, C(O) or CH$_2$;

$A^1$ is N;

$A^2$ is CR$^2$;

$A^3$, $A^4$ and $A^5$ are each independently CR$^2$ or N, provided that at least three of $A^1$, $A^2$, $A^3$, $A^4$, and $A^5$ are independently CR$^2$;

"------" indicates a double bond;

$R^1$ is a $C_{6-20}$alkyl, a $C_{3-14}$carbocyclyl, a 3- to 15-membered heterocyclyl, a $C_{6-10}$aryl, or a five- to 14-membered heteroaryl, wherein the heterocyclyl and the heteroaryl comprise from 1 to 10 heteroatoms independently selected from N, S or O, and wherein $R^1$ is optionally substituted with from one to six independently selected $R^6$;

$R^2$, for each occurrence, is independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido;

$R^3$ is a halo, $C_{1-6}$haloalkyl or cyano;

$R^5$ is a $C_{3-8}$carbocyclyl, a 3- to 8-membered heterocyclyl, $C_{6-10}$aryl, a 5- to 10-membered heteroaryl, a bridged ring system comprising from 6 to 12 ring members, a spiro ring system comprising from 5-14 ring members, or a bicyclic ring system represented by the following formula:

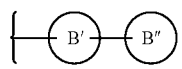

wherein B' and B" are independently selected from the group consisting of monocyclic $C_{3-8}$carbocyclyl, a monocyclic 3- to 8-membered heterocyclyl, phenyl or a 5- to 6-membered heteroaryl; wherein $R^5$ is optionally substituted with from 1 to 4 independently selected $R^{11}$;

$R^6$, for each occurrence, is independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom can form $C_{3-8}$spirocycloalkyl or 3- to 8-membered spiroheterocycloalkyl;

$R^7$ is —OH, —C(O)OR$^{15}$, —C(O)N($R^{16}$)$_2$, —C(O)N($R^{15}$)—S(O)$_2$R$^{15}$, —S(O)$_2$OR$^{15}$, —C(O)NHC(O)R$^{15}$, —Si(O)OH, —B(OH)$_2$, —N($R^{15}$)S(O)$_2$R$^{15}$, —S(O)$_2$N($R^{15}$)$_2$, —O—P(O)(OR$^{15}$)$_2$, —P(O)(OR$^{15}$)$_2$, —CN, —S(O)$_2$NHC(O)R$^{15}$, —C(O)NHS(O)$_2$R$^{15}$, —C(O)NHOH, —C(O)NHCN, or a heteroaryl or a heterocyclyl selected from the group consisting of formulae (a)-(i'):

(a) 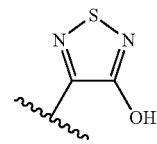

(b) 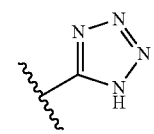

(c) 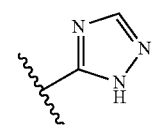

(d) 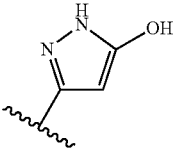

(e) 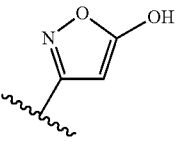

(f) 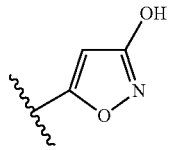

(g) 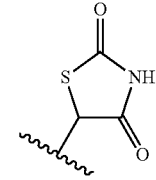

(h) 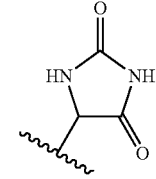

(i) 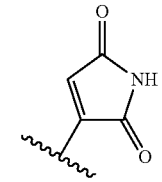

(j) 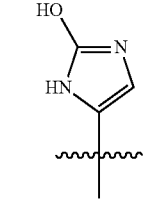

(k) 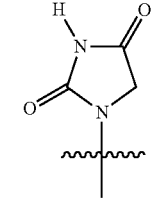

-continued
(l) 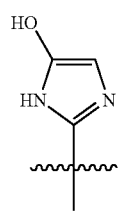
(m) 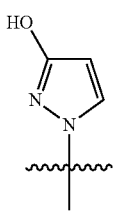
(n) 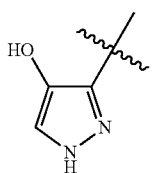
(o) 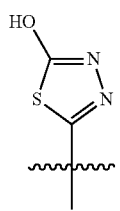
(p) 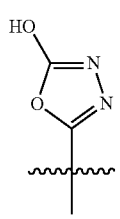
(q) 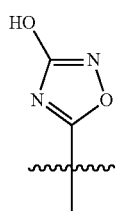
(r) 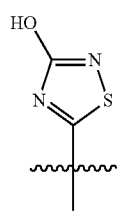
-continued
(s) 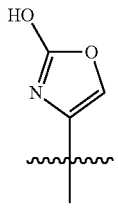
(t) 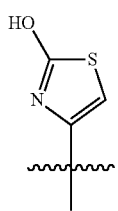
(u) 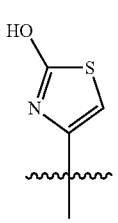
(v) 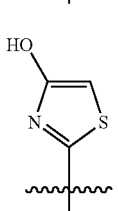
(w) 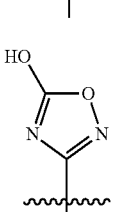
(x) 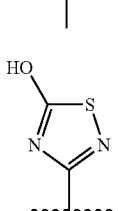
(y) 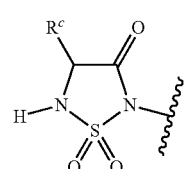
(z) 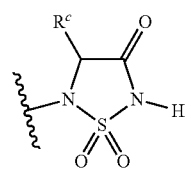

(a') 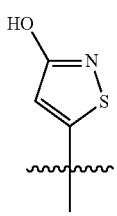

(b') 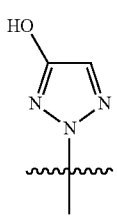

(c') 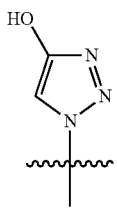

(d') 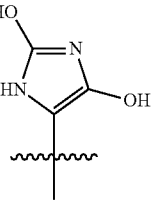

(e') 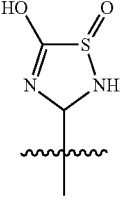

(f') 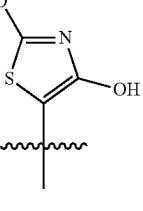

(g') 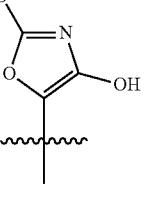

(h') 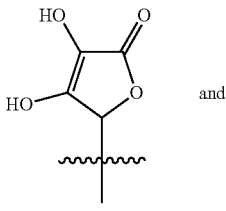

and (i') 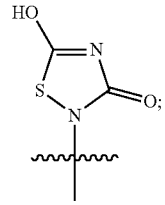

$R^8$ and $R^9$ are each independently hydrogen, a carboxy, $C_{1-6}$alkyl, or a $C_{2-6}$alkenyl; or $R^8$ and $R^9$ together with the carbon to which they are attached are —C(=O)—, a $C_{3-8}$spirocycloalkyl, or a 3- to 8-membered spiroheterocycloalkyl;

$R^{10}$ and $R^{12}$ are each, independently, hydrogen or a $C_{1-6}$alkyl;

$R^{11}$, for each occurrence, is independently halo, hydroxyl, nitro, cyano, $C_{1-6}$alkyl, $C_{1-6}$haloalkyl, $C_{1-6}$alkoxy, $(CR^{17}R^{18})_p$—$R^7$, $C_{1-4}$haloalkoxy, $C_{2-6}$alkenyl, $C_{2-6}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —C(O)$NR^aR^b$, —N($R^a$)C(O)$R^b$, —C(O)$R^a$, —S(O)$_r R^a$, or —N($R^a$)S(O)$_2 R^b$;

$R^{15}$ for each occurrence is independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ is optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl;

$R^{16}$ is $R^{15}$; or two $R^{16}$ together with the nitrogen atom to which they are attached form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl;

$R^{17}$ and $R^{18}$, for each occurrence, are each independently hydrogen, a halo, or a $C_{1-4}$haloalkyl;

$R^a$ and $R^b$, for each occurrence, are independently hydrogen, $C_{1-6}$alkyl, $C_{2-6}$alkenyl, $C_{2-6}$alkynyl, $C_{3-8}$cycloalkyl, $C_{6-10}$aryl, or $C_{3-8}$halocycloalkyl;

$R^c$ is hydrogen or a $C_{1-4}$alkyl;

m is 0 or 1, provided that when m is 0, $R^5$ comprises at least one nitrogen;

n is an integer from 1 to 6;

p is 0 or an integer from 1 to 6; and r, for each occurrence, is independently 0, 1, or 2.

3. The compound of claim 1, or a pharmaceutically acceptable salt thereof, wherein:

m is 0; and $R^5$ is selected from the group consisting of:

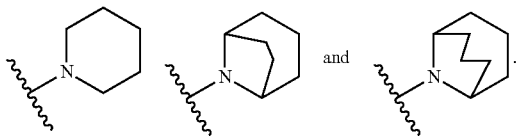

4. The compound of claim 1, or a pharmaceutically acceptable salt thereof, wherein:

m is 1; and $R^5$ is cyclobutyl, cyclopentyl, or cyclohexyl, each of which may be optionally substituted with from 1 to 3 independently selected $R^{11}$.

5. The compound of claim 1, or a pharmaceutically acceptable salt thereof, wherein $R^7$ is —COOH.

6. The compound of claim 1, or a pharmaceutically acceptable salt thereof, wherein n is 1.

7. The compound of claim 6, or a pharmaceutically acceptable salt thereof, wherein $R^8$ is hydrogen, and $R^9$ is $C_{1-6}$alkyl; or $R^8$ and $R^9$ together with the carbon to which they are attached are —C(=O)—.

8. The compound of claim 6, or a pharmaceutically acceptable salt thereof, wherein $R^8$ and $R^9$ are each independently hydrogen.

9. The compound of claim 1, or a pharmaceutically acceptable salt thereof, wherein $R^6$ is $C_{1-6}$alkyl.

10. The compound of claim 1, or a pharmaceutically acceptable salt thereof, wherein $R^1$ is

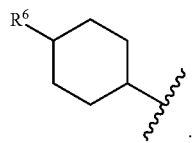

11. The compound of claim 10, or a pharmaceutically acceptable salt thereof, wherein $R^6$ is t-butyl.

12. The compound according to claim 1, or a pharmaceutically acceptable salt thereof, wherein: X is NH.

13. The compound according to claim 1, or a pharmaceutically acceptable salt thereof, wherein: $R^8$ and $R^9$ together with the carbon to which they are attached are —C(=O)—.

14. The compound of claim 1, wherein the compound is selected from the group consisting of:

Methyl 3-(3-((trans-4-(tert-butyl)cyclohexyl)amino)isoquinoline-6-carboxamido)cyclohexanecarboxylate;

3-(3-((trans-4-(tert-butyl)cyclohexyl)amino)isoquinoline-6-carboxamido)cyclohexanecarboxylic acid;

3-((trans-4-(tert-butyl)cyclohexyl)amino)-N-cyclohexyl isoquinoline-6-carboxamide;

4-(3-((trans-4-(tert-butyl)cyclohexyl) amino)isoquinoline-6-carboxamido)bicyclo[2.2.2]octane-1-carboxylic acid;

8-(3-((trans-4-(tert-butyl)cyclohexyl)amino)isoquinoline-6-carbonyl)-8-azabicyclo[3.2.1]octane-3-carboxylic acid;

cis-4-(3-((trans-4-(tert-butyl)cyclohexyl)amino)isoquinoline-6-carboxamido)cyclohexanecarboxylic acid;

trans-4-(3-((trans-4-(tert-butyl)cyclohexyl)amino) isoquinoline-6-carboxamido)cyclohexanecarboxylic acid;

1-(3-((trans-4-(tert-butyl)cyclohexyl)amino)isoquinoline-6-carbonyl)piperidine-4-carboxylic acid;

(1r,4r)-4-(3-(((1r,4r)-4-(tert-butyl)cyclohexyl)amino)isoquinoline-6-carboxamido)cyclohexane-1-carboxylic acid;

2-(1-(3-((trans-4-(tert-butyl)cyclohexyl)amino)isoquinoline-6-carbonyl)piperidin-4-yl)acetic acid; or cis-4-(3-((trans-4-(tert-butyl)cyclohexyl)amino)-4-chloroisoquinoline-6-carboxamido)cyclohexanecarboxylic acid, or a pharmaceutically acceptable salt thereof.

15. A pharmaceutical composition comprising a pharmaceutically acceptable carrier or excipient and a compound according to claim 1, or a pharmaceutically acceptable salt thereof.

16. A method of treating or reducing symptoms of a condition in a mammal comprising administering to said mammal an effective amount of a compound according to claim 1, or a pharmaceutically acceptable salt thereof, wherein the condition is selected from the group consisting of rheumatoid arthritis and multiple sclerosis.

17. The method of claim 16, wherein the condition is rheumatoid arthritis.

18. The method of claim 16, wherein the condition is multiple sclerosis.

19. The method of claim 16, further comprising administering to said mammal an effective amount of one or more drugs selected from the group consisting of: a corticosteroid, a bronchodilator, an antiasthmatic, an antiinflammatory, an antirheumatic, an immunosuppressant, an antimetabolite, an immunomodulator, an antipsoriatic, and an antidiabetic.

20. A method of treating, or reducing chronic pain in a mammal comprising treating said mammal with an effective amount of a compound according to claim 1 or a pharmaceutically acceptable salt thereof.

21. The method of claim 20, wherein the chronic pain is inflammatory pain or neuropathic pain.

* * * * *